(12) United States Patent
Guzi et al.

(10) Patent No.: US 7,605,155 B2
(45) Date of Patent: *Oct. 20, 2009

(54) SUBSTITUTED PYRAZOLO[1,5-A]PYRIMIDINES AS PROTEIN KINASE INHIBITORS

(75) Inventors: Timothy J. Guzi, Chatham, NJ (US); Kamil Paruch, Garwood, NJ (US); Michael P. Dwyer, Scotch Plains, NJ (US); Marc Labroli, Mount Laurel, NJ (US); Kartik M. Keertikar, East Windsor, NJ (US)

(73) Assignee: Schering Corporation, Kenilworth, NJ (US)

( * ) Notice: Subject to any disclaimer, the term of this patent is extended or adjusted under 35 U.S.C. 154(b) by 105 days.

This patent is subject to a terminal disclaimer.

(21) Appl. No.: 11/542,920

(22) Filed: Oct. 4, 2006

(65) Prior Publication Data

US 2007/0072881 A1    Mar. 29, 2007

Related U.S. Application Data

(63) Continuation-in-part of application No. 11/245,401, filed on Oct. 6, 2005, now Pat. No. 7,196,078, which is a continuation-in-part of application No. 10/776,988, filed on Feb. 11, 2004, now Pat. No. 7,119,200, which is a continuation-in-part of application No. 10/654,546, filed on Sep. 3, 2003, now Pat. No. 7,161,003.

(60) Provisional application No. 60/408,027, filed on Sep. 4, 2002, provisional application No. 60/421,959, filed on Oct. 29, 2002.

(51) Int. Cl.
| C07D 487/04 | (2006.01) |
|---|---|
| C07D 413/06 | (2006.01) |
| C07D 417/04 | (2006.01) |
| C07D 243/08 | (2006.01) |
| A61K 31/519 | (2006.01) |
| A61K 31/551 | (2006.01) |
| A61K 31/497 | (2006.01) |
| A61K 31/541 | (2006.01) |
| A61K 31/5355 | (2006.01) |
| A61P 35/04 | (2006.01) |

(52) U.S. Cl. .............. 514/218; 514/259.3; 514/252.16; 514/228.5; 514/234.2; 514/255.05; 544/218; 544/230; 544/117; 544/58.2; 540/575

(58) Field of Classification Search ................ 544/281; 514/259.3

See application file for complete search history.

(56) References Cited

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Vippagunta et. al., Advanced Drug Delivery, 2001,, 48, 3-26.*

* cited by examiner

*Primary Examiner*—Brenda L Coleman
*Assistant Examiner*—Susanna Moore
(74) *Attorney, Agent, or Firm*—Palaiyur S. Kalyanaraman

(57) ABSTRACT

In its many embodiments, the present invention provides a class of pyrazolo[1,5-a]pyrimidine compounds as inhibitors of cyclin dependent kinases (CDKs), methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions. All illustrative compound is shown below:

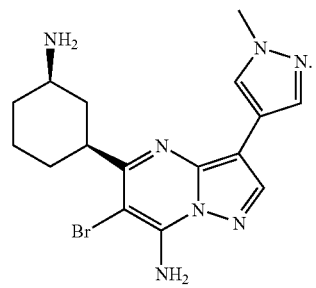

14 Claims, No Drawings

SUBSTITUTED PYRAZOLO[1,5-A]PYRIMIDINES AS PROTEIN KINASE INHIBITORS

REFERENCE TO RELATED APPLICATIONS

This application is a Continuation-in-Part of U.S. patent application, Ser. No. 11/245,401, filed Oct. 6, 2005 (which published as US 2006/0128725 on Jun. 15, 2006), which is a Continuation-in-Part of U.S. patent application, Ser. No. 10/776,988, filed Feb. 11, 2004 (which published as US 2004/0209878 on Oct. 21, 2004), which is a Continuation-in-Part of U.S. patent application, Ser. No. 10/654,546 filed Sep. 3, 2003, which claims priority to U.S. provisional patent applications, Ser. Nos. 60/408,027 filed Sep. 4, 2002 and 60/421,959 filed Oct. 29, 2002.

FIELD OF THE INVENTION

The present invention relates to pyrazolo[1,5-a]pyrimidine compounds useful as protein kinase inhibitors (such as for example, the inhibitors of the cyclin-dependent kinases, mitogen-activated protein kinase (MAPK/ERK), glycogen synthase kinase 3(GSK3beta) and the like), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. This application claims benefit of priority from U.S. provisional patent applications, Ser. No. 60/408,027 filed Sep. 4, 2002, and Ser. No. 60/421,959 filed Oct. 29, 2002.

BACKGROUND OF THE INVENTION

Protein kinase inhibitors include kinases such as, for example, the inhibitors of the cyclin-dependent kinases (CDKs), mitogen activated protein kinase (MAPK/ERK), glycogen synthase kinase 3(GSK3beta), and the like. Protein kinase inhibitors are described, for example, by M. Hale et al in WO02/22610 A1 and by Y. Mettey et al in *J. Med. Chem.*, (2003) 46 222-236. The cyclin-dependent kinases are serine/threonine protein kinases, which are the driving force behind the cell cycle and cell proliferation. Individual CDK's, such as, CDK1, CDK2, CDK3, CDK4, CDK5, CDK6 and CDK7, CDK8, CDK9 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986-2999.

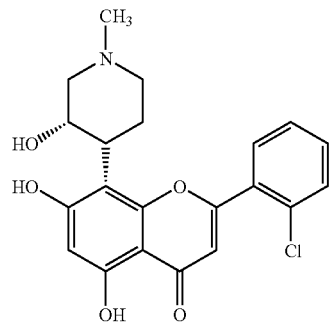

Formula I

Other known inhibitors of the CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b] pyridine compounds as CDK inhibitors. An illustrative compound from the '305 patent has the Formula II:

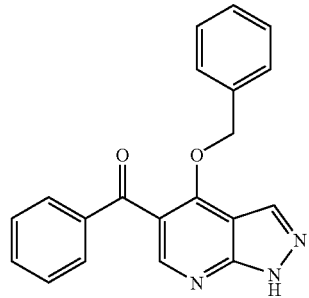

Formula II

K. S. Kim et al, *J. Med. Chem.* 45 (2002) 3905-3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. Other publications of interest are: WO 03/101993 (published Dec. 11, 2003), WO 03/091256 (published Nov. 6, 2003), and DE 10223917 (published Dec. 11, 2003). The string of parent cases for this present application, Ser. No. 11/245,401, filed Oct. 6, 2005 (which published as US2006/0128725 on Jun. 15, 2006), Ser. No. 10/776,988, filed Feb. 11, 2004 (which published as US2004/0209878 on Oct. 21, 2004), and Ser. No. 10/654,546 filed Sep. 3, 2003 (which published as WO2004/022561 on Mar. 18, 2004) should be considered as part of this invention.

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, U.S. patent application, Ser. No. 11/245,401, filed Oct. 6, 2005 (which published as US2006/0128725 on Jun. 15, 2006) referred to herein provides a novel class of pyrazolo[1,5-a]pyrimidine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the afore-mentioned U.S. patent application, Ser. No. 11/245,401 discloses a compound, or pharmaceutically acceptable salts, solvates, esters or prodrugs of said compound, said compound having the general structure shown in Formula III:

Formula III

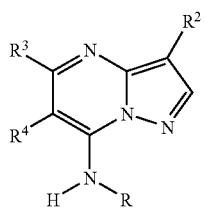

wherein:

R is H, alkyl, alkenyl, alkynyl, arylalkyl, arylalkenyl, cycloalkyl, cycloalkylalkyl, alkenylalkyl, alkynylalkyl, heterocyclyl, heterocyclylalkyl, heteroarylalkyl (including N-oxide of said heteroaryl), —(CHR$^5$)$_n$-aryl, —(CHR$^5$)$_n$— heteroaryl,

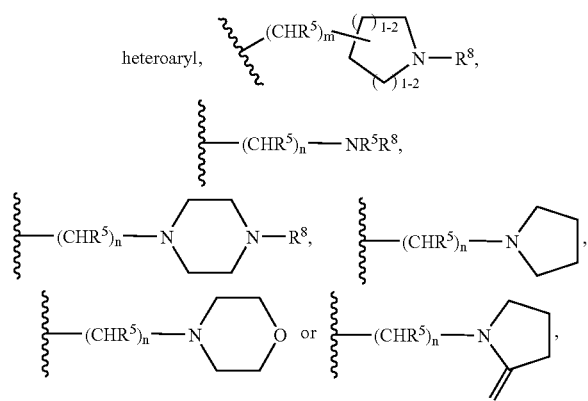

wherein each of said alkyl, alkenyl, alkynyl, aryl, cycloalkyl, heterocyclyl, and heteroaryl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^5$R$^{10}$, —C(R$^4$R$^5$)$_p$—R$^9$, —N(R$^5$)Boc, —(CR$^4$R$^5$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$$^{10}$, R$^2$ is selected from the group consisting of H, R$^9$, alkyl, alkenyl, alkynyl, CF$_3$, heterocyclyl, heterocyclylalkyl, halogen, haloalkyl, aryl, arylalkyl, heteroarylalkyl, alkynylalkyl, cycloalkyl, heteroaryl, alkyl substituted with 1-6 R$^9$ groups which can be the same or different and are independently selected from the list of R$^9$ shown below, aryl substituted with 1-3 aryl or heteroaryl groups which can be the same or different and are independently selected from phenyl, pyridyl, thiophenyl, furanyl and thiazolo groups, aryl fused with an aryl or heteroaryl group, heteroaryl substituted with 1-3 aryl or heteroaryl groups which can be the same or different and are independently selected from phenyl, pyridyl, thiophenyl, furanyl and thiazolo groups, heteroaryl fused with an aryl or heteroaryl group,

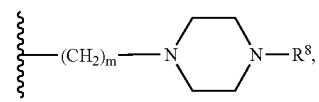

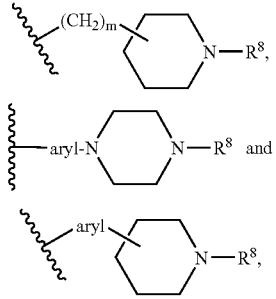

wherein one or more of the aryl and/or one or more of the heteroaryl in the above-noted definitions for R$^2$ can be unsubstituted or optionally substituted with one or more moieties which can be the same or different, each moiety being independently selected from the group consisting of halogen, —CN, —OR$^5$, —SR$^5$, —S(O$_2$)R$^6$, —S(O$_2$)NR$^5$R$^6$, —NR$^5$R$^6$, —C(O)NR$^5$R$^6$, CF$_3$, alkyl, aryl and OCF$_3$;

R$^3$ is selected from the group consisting of H, halogen, —NR$^5$R$^6$, —OR$^6$, —SR$^6$, —C(O)N(R$^5$R$^6$), alkyl, alkynyl, cycloalkyl, aryl, arylalkyl, heterocyclyl, heterocyclylalkyl, heteroaryl and heteroarylalkyl,

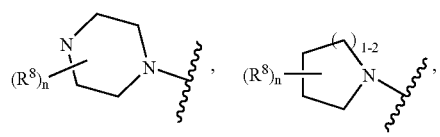

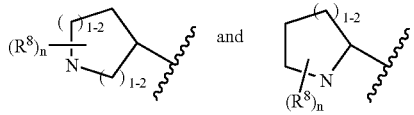

wherein each of said alkyl, cycloalkyl, aryl, arylalkyl, heterocyclyl, heterocyclylalkyl, heteroaryl and heteroarylalkyl for $R^3$ and the heterocyclyl moieties whose structures are shown immediately above for $R^3$ can be unsubstituted or optionally independently substituted with one or more moieties which can be the same or different, each moiety being independently selected from the group consisting of halogen, alkyl, aryl, cycloalkyl, $CF_3$, CN, $-OCF_3$, $-(CR^4R^5)_pOR^5$, $-OR^5$, $-NR^5R^6$, $-(CR^4R^5)_pNR^5R^6$, $-C(O_2)R^5$, $-C(O)R^5$, $-C(O)NR^5R^6$, $-SR^6$, $-S(O_2)R^6$, $-S(O_2)NR^5R^6$, $-N(R^5)S(O_2)R^7$, $-N(R^5)C(O)R^7$, $-N(R^5)C(R^4R^5)_nN(R^5R^6)$ and $-N(R^5)C(O)NR^5R^6$, with the proviso that no carbon adjacent to a nitrogen atom on a heterocyclyl ring carries a $-OR^5$ moiety;

$R^4$ is H, halo or alkyl;

$R^5$ is H, alkyl, aryl, heteroaryl or cycloalkyl;

$R^6$ is selected from the group consisting of H, Boc, alkyl, alkenyl, aryl, arylalkyl, arylalkenyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, $-OR^5$, $-NR^5R^{10}$, $-C(R^4R^5)_p-R^9$, $-N(R^5)Boc$, $-(CR^4R^5)_pOR^5$, $-C(O_2)R^5$, $-C(O)R^5$, $-C(O)NR^5R^{10}$, $-SO_3H$, $-SR^{10}$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

$R^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, $CF_3$, $OCF_3$, CN, $-OR^5$, $-NR^4R^5$, $-C(R^4R^5)_p-R^9$, $-N(R^5)Boc$, $-(CR^4R^5)_pOR^5$, $-C(O_2)R^5$, $-C(O)NR^4R^5$, $-C(O)R^5$, $-SO_3H$, $-SR^5$, $-S(O_2)R^7$, $-S(O_2)NR^4R^5$, $-N(R^5)S(O_2)R^7$, $-N(R^5)C(O)R^7$ and $-N(R^5)C(O)NR^4R^5$;

or optionally (i) $R^5$ and $R^{10}$ in the moiety $-NR^5R^{10}$, or (ii) $R^5$ and $R^6$ in the moiety $-NR^5R^6$, may be joined together to form a cycloalkyl or heterocyclyl moiety, with each of said cycloalkyl or heterocyclyl moiety being unsubstituted or optionally independently being substituted with one or more $R^9$ groups;

$R^7$ is selected from the group consisting of alkyl, cycloalkyl, aryl, arylalkenyl, heteroaryl, arylalkyl, heteroarylalkyl, heteroarylalkenyl, and heterocyclyl, wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, $CF_3$, $OCF_3$, CN, $-OR^5$, $-NR^5R^{10}$, $-CH_2OR^5$, $-C(O_2)R^5$, $-C(O)NR^5R^{10}$, $-C(O)R^5$, $-SR^{10}$, $-S(O_2)R^{10}$, $-S(O_2)NR^5R^{10}$, $-N(R^5)S(O_2)R^{10}$, $-N(R^5)C(O)R^{10}$ and $-N(R^5)C(O)NR^5R^{10}$;

$R^8$ is selected from the group consisting of $R^6$, $-OR^6$, $-C(O)NR^5R^{10}$, $-S(O_2)NR^5R^{10}$, $-C(O)R^7$, $-C(=N-CN)-NH_2$, $-C(=NH)-NHR^5$, heterocyclyl, and $-S(O_2)R^7$;

$R^9$ is selected from the group consisting of halogen, $-CN$, $-NR^5R^{10}$, $-SCN$, $-NO_2$, $-C(O)R^5$, $-C(O_2)R^6$, $-C(O)NR^5R^{10}$, $-OR^6$, $-SR^6$, $-S(O_2)R^7$, $-S(O_2)NR^5R^{10}$, $-N(R^5)S(O_2)R^7$, $-N(R^5)C(O)R^7$ and $-N(R^5)C(O)NR^5R^{10}$;

m is 0 to 4;

n is 1 to 4; and p is 1 to 4, with the proviso that when $R^2$ is phenyl, $R^3$ is not alkyl, alkynyl or halogen, and that when $R^2$ is aryl, R is not

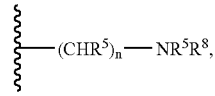

and with the further proviso that when R is arylalkyl, then any heteroaryl substituent on the aryl of said arylalkyl contains at least three heteroatoms.

The present invention discloses the following compounds shown in Table 1, or a pharmaceutically acceptable salt, solvate, ester or prodrug thereof.

The compounds of the invention can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses pyrazolo[1,5-a]pyrimidine compounds, or a pharmaceutically acceptable salt, solvate, ester or prodrug thereof.

In another embodiment, this invention discloses the inventive compounds shown in Table 1, which exhibited CDK2 inhibitory activity of about 0.0001 µM to > about 5 µM. The assay methods are described later in this application.

TABLE 1
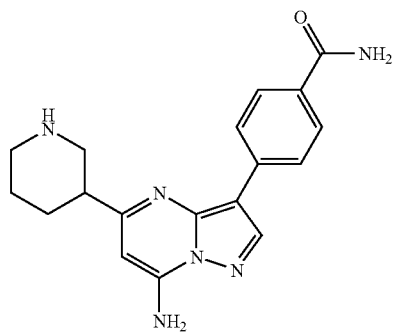 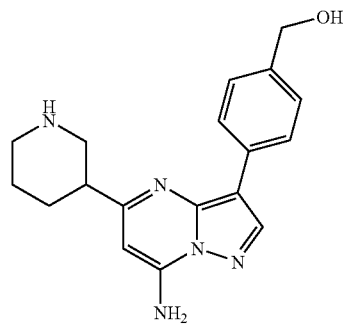
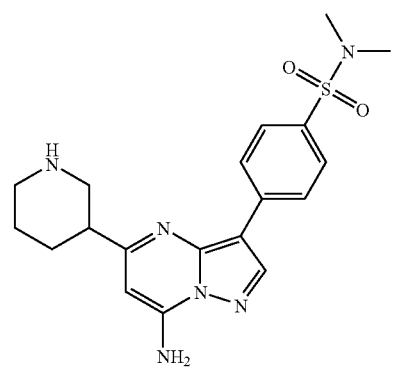 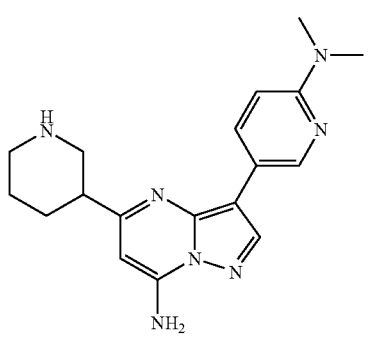
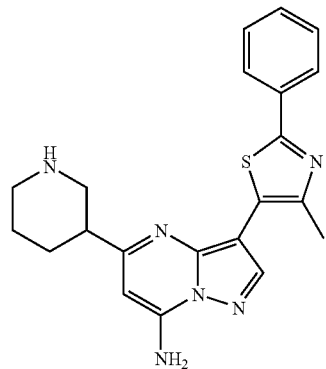 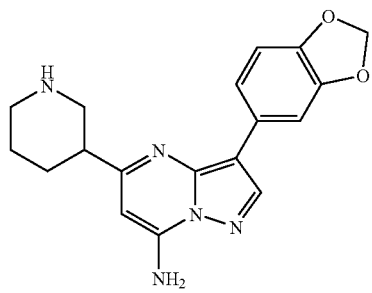
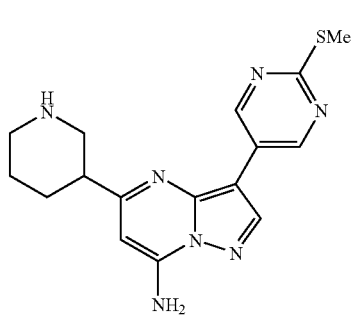 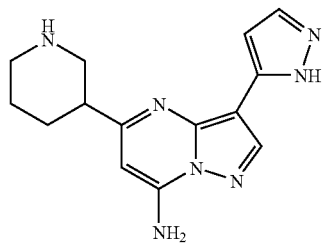

TABLE 1-continued
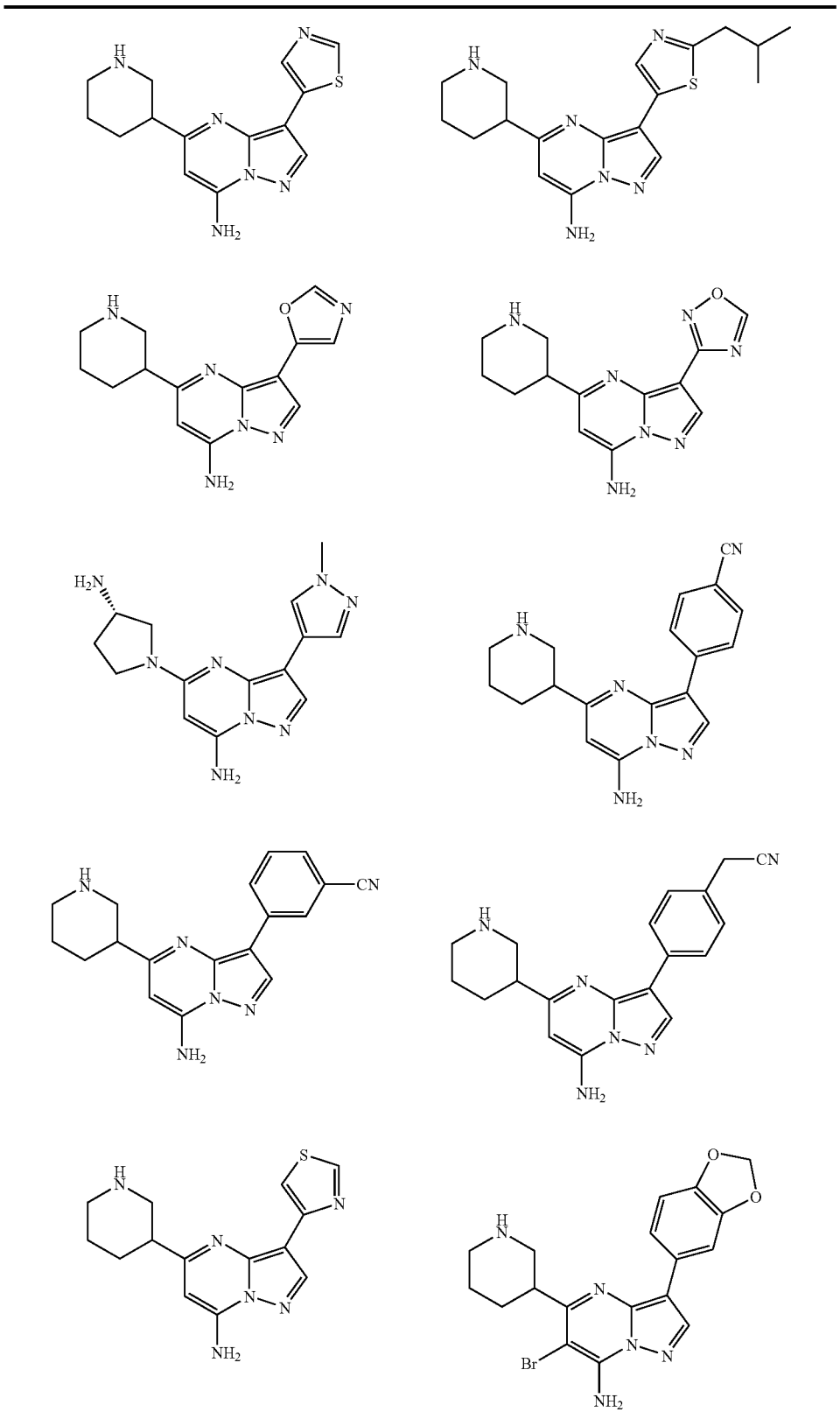

TABLE 1-continued
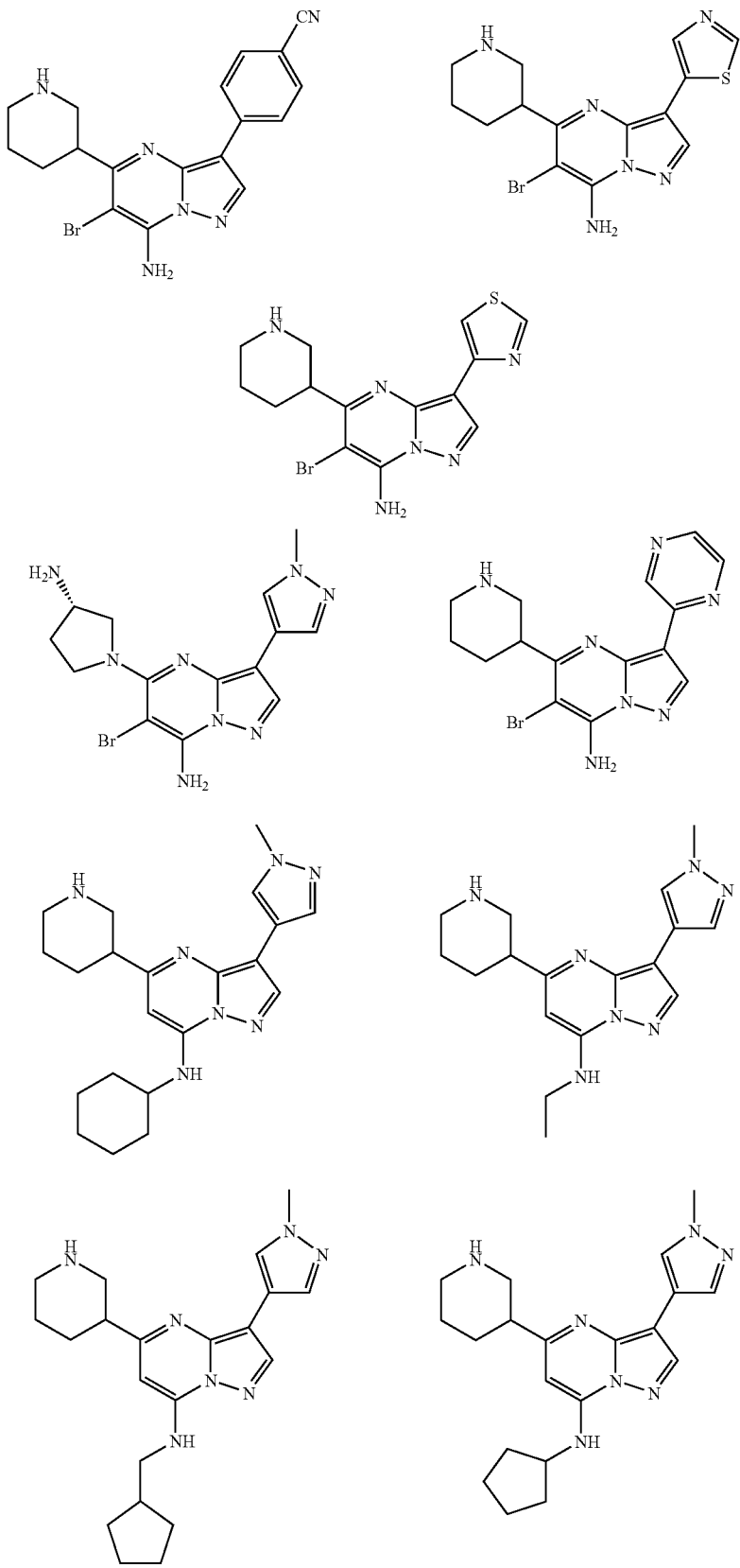

TABLE 1-continued
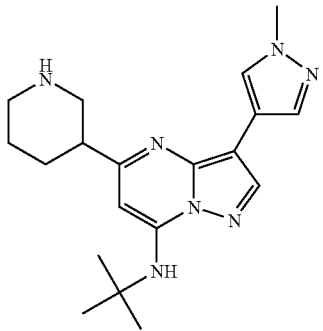 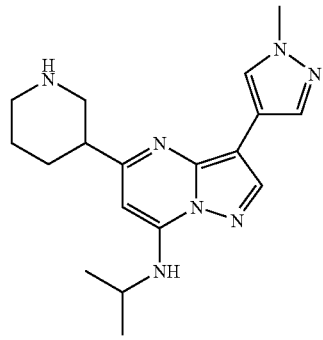
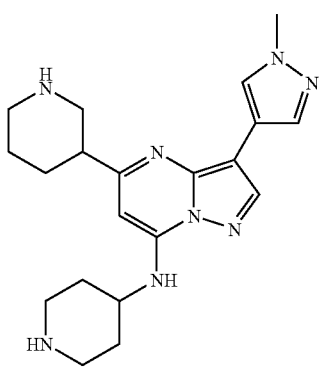 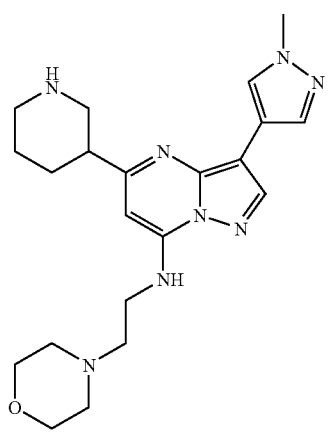
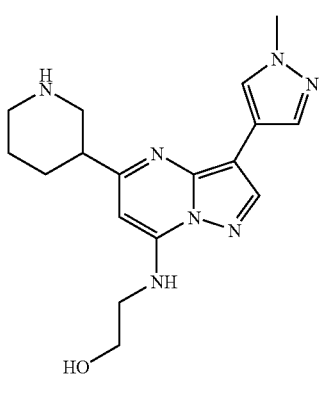 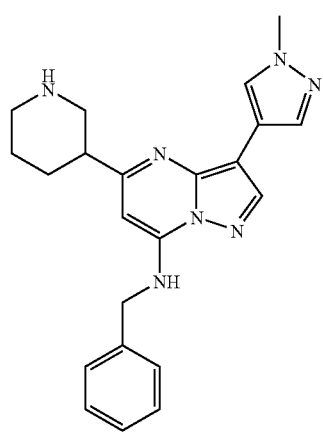
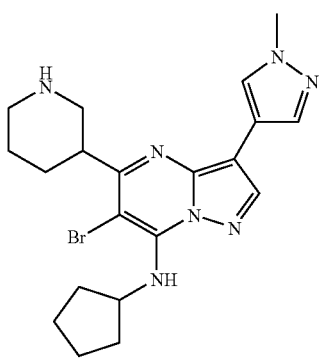 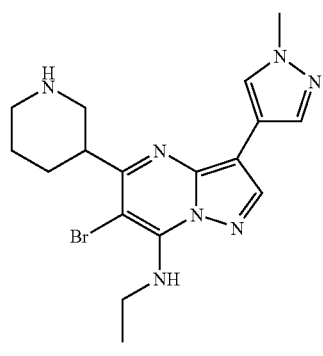

TABLE 1-continued
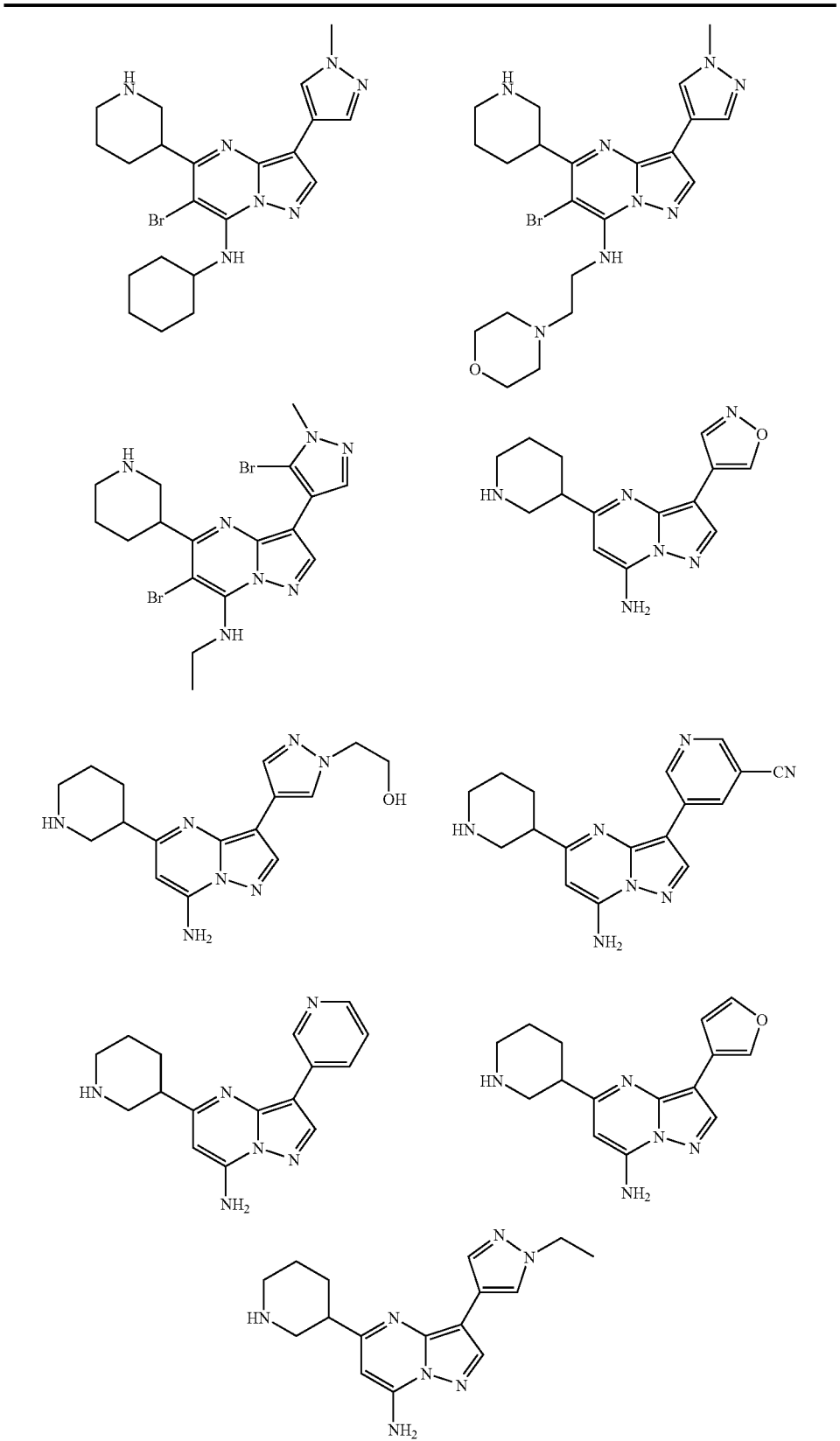

TABLE 1-continued
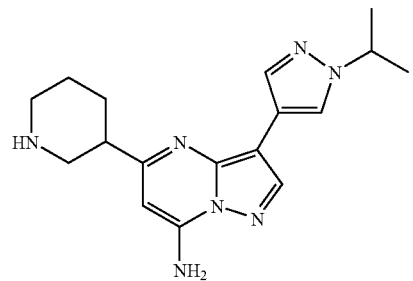
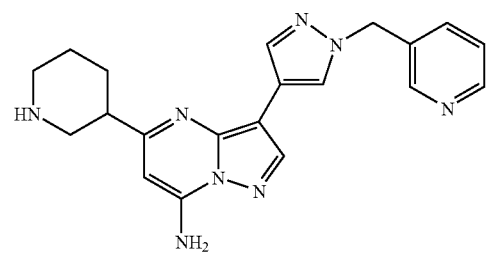
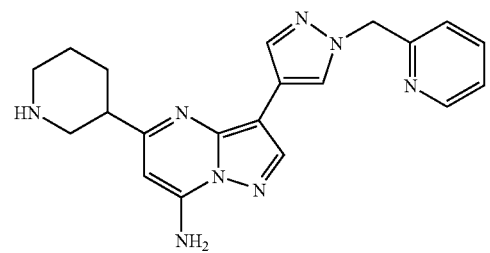
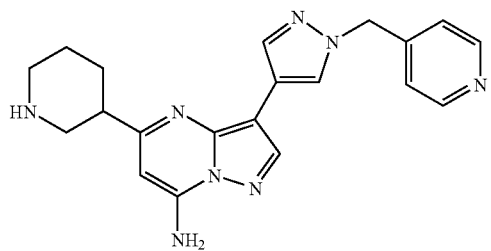
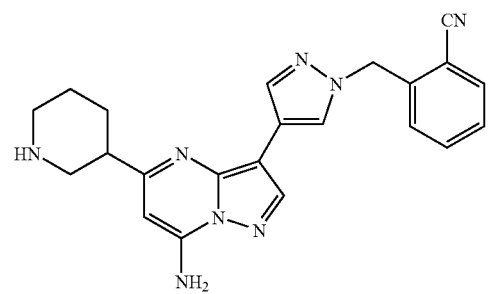

TABLE 1-continued
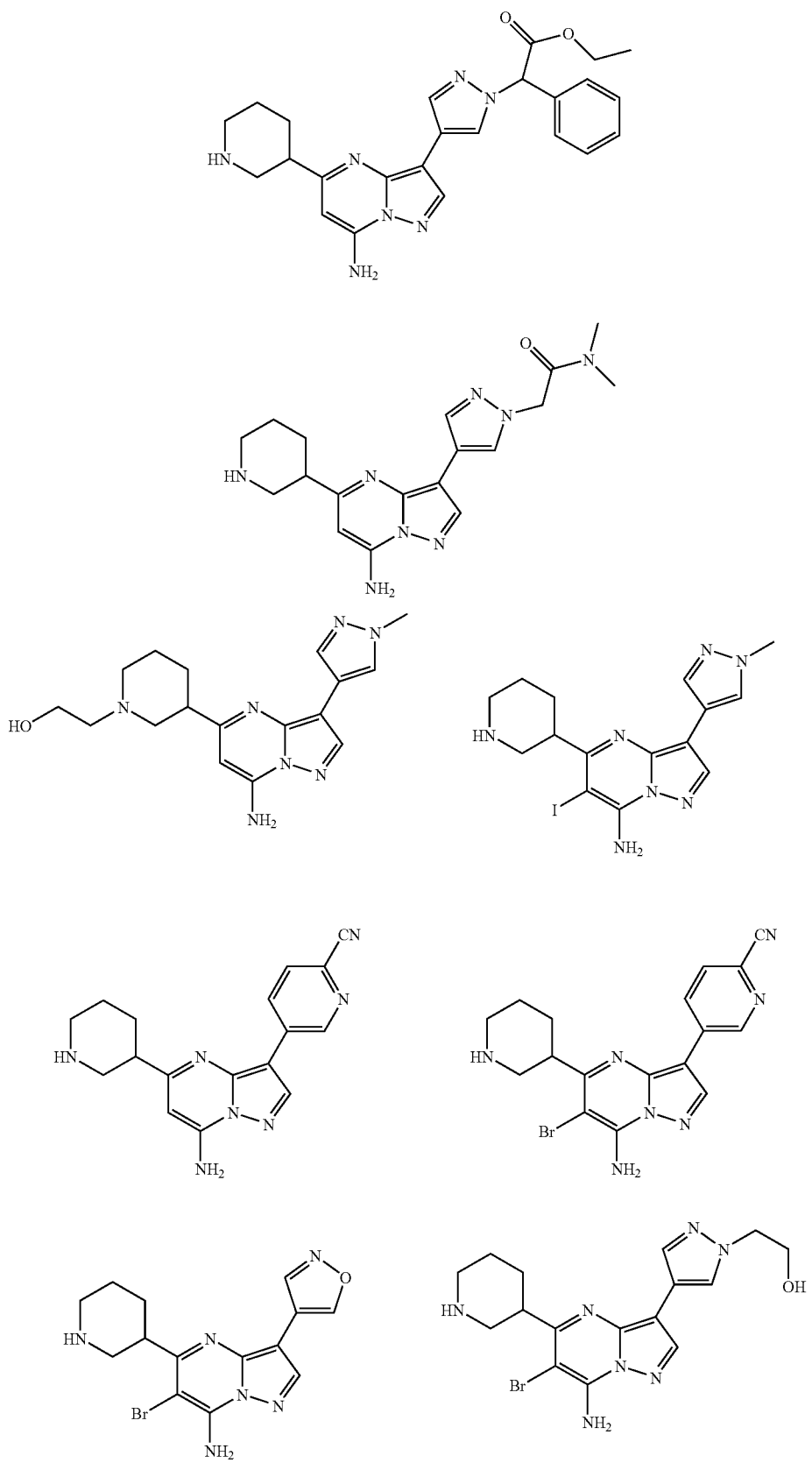

TABLE 1-continued
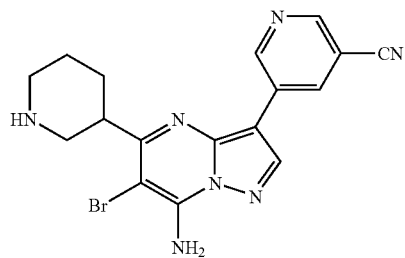 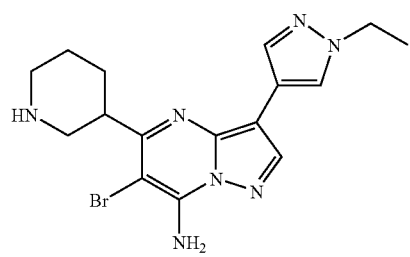
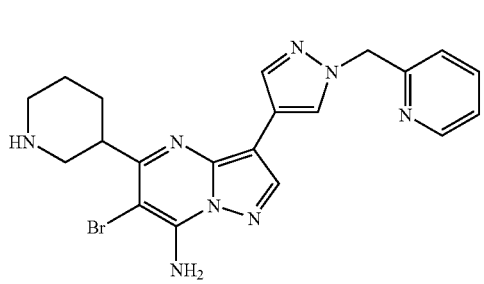 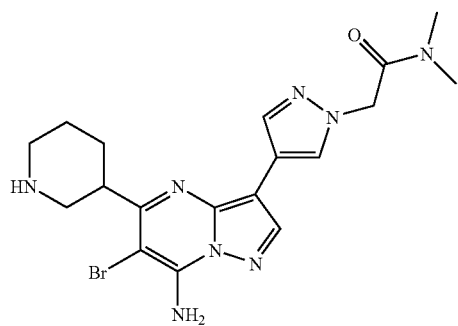
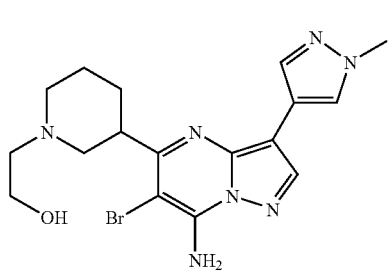 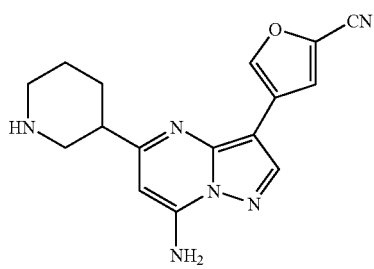
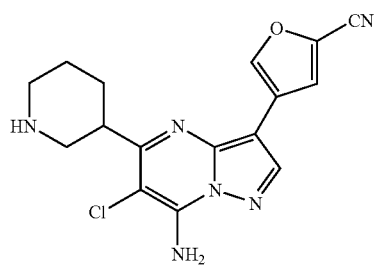
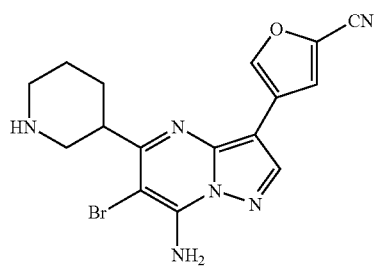 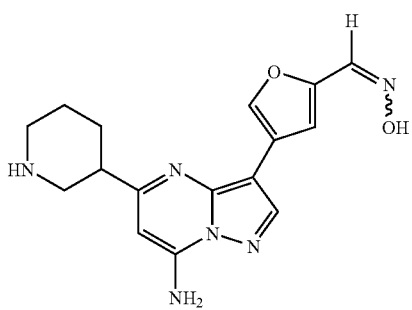

TABLE 1-continued
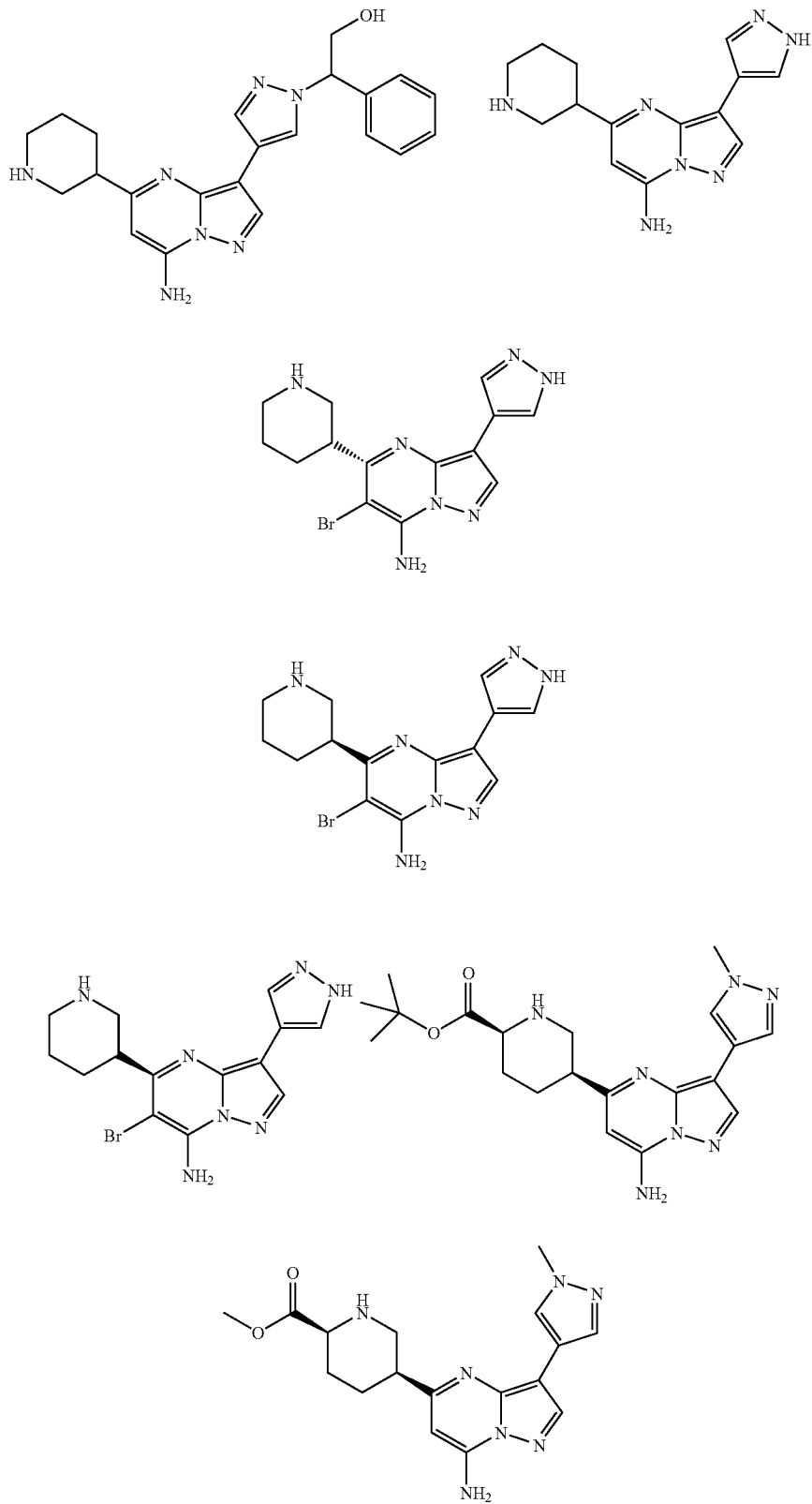

TABLE 1-continued
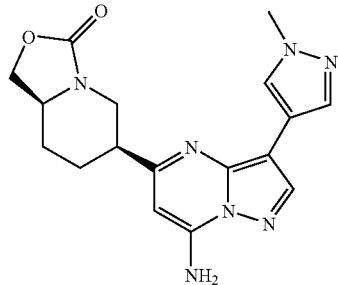
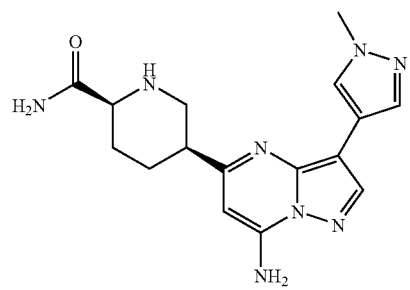
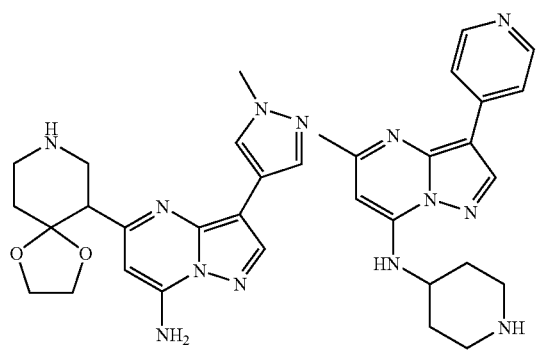
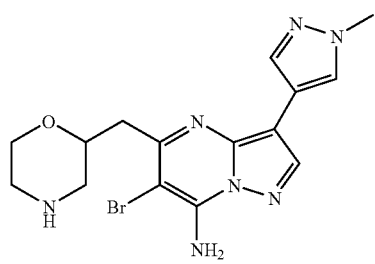
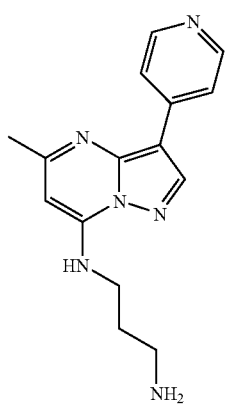

TABLE 1-continued
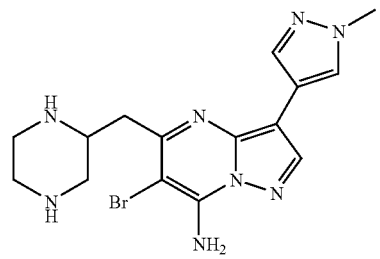
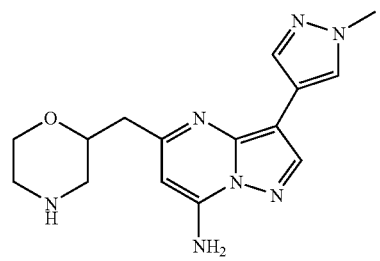
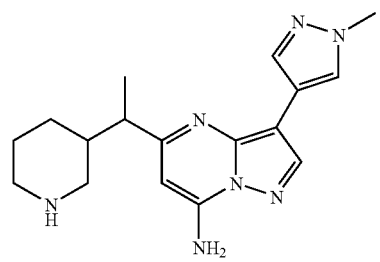
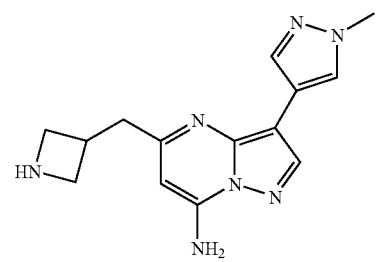
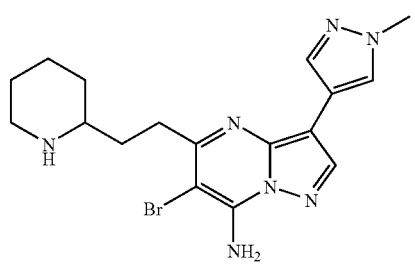
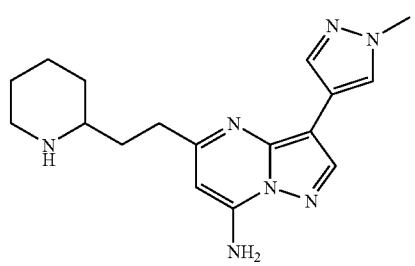

TABLE 1-continued
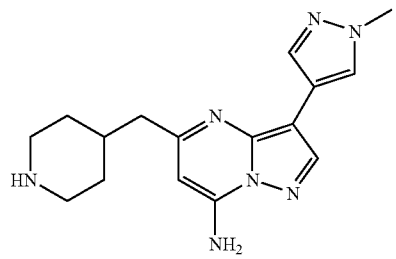
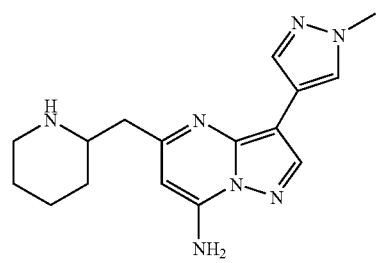
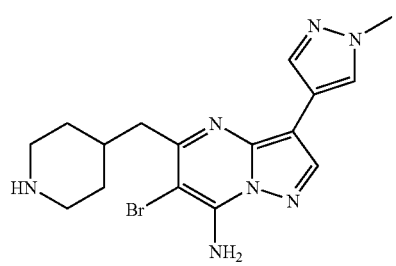
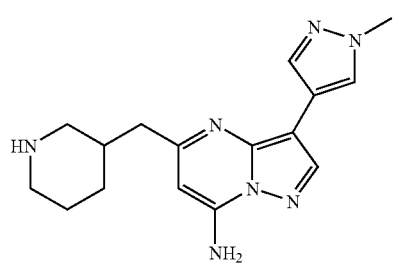
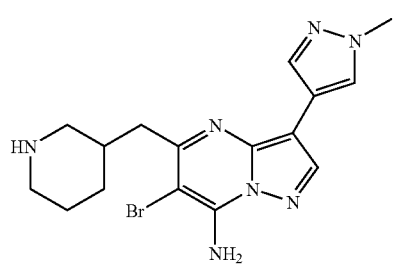
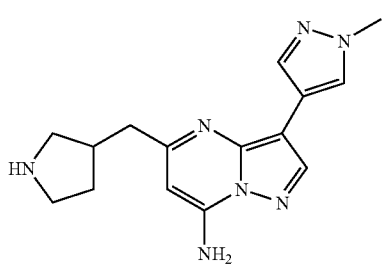

TABLE 1-continued
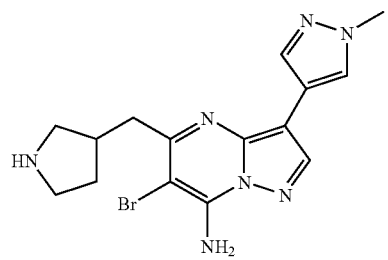
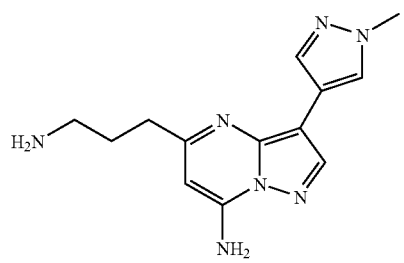
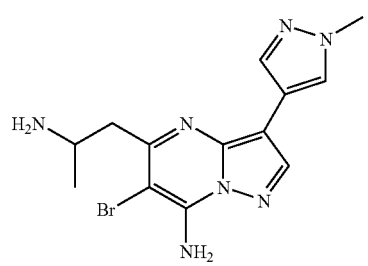
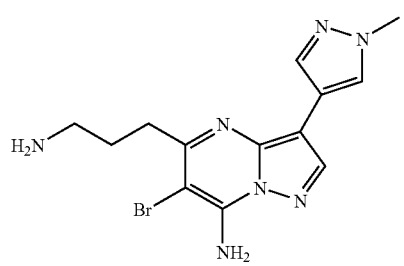
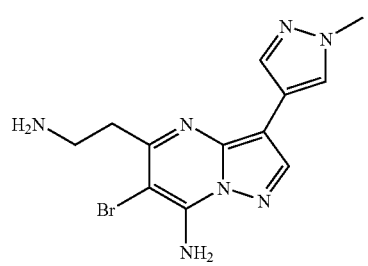
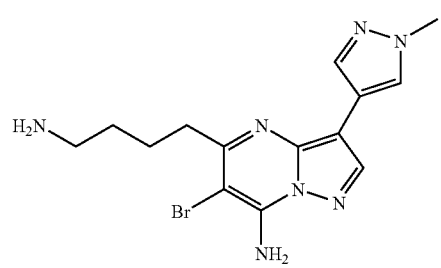

TABLE 1-continued
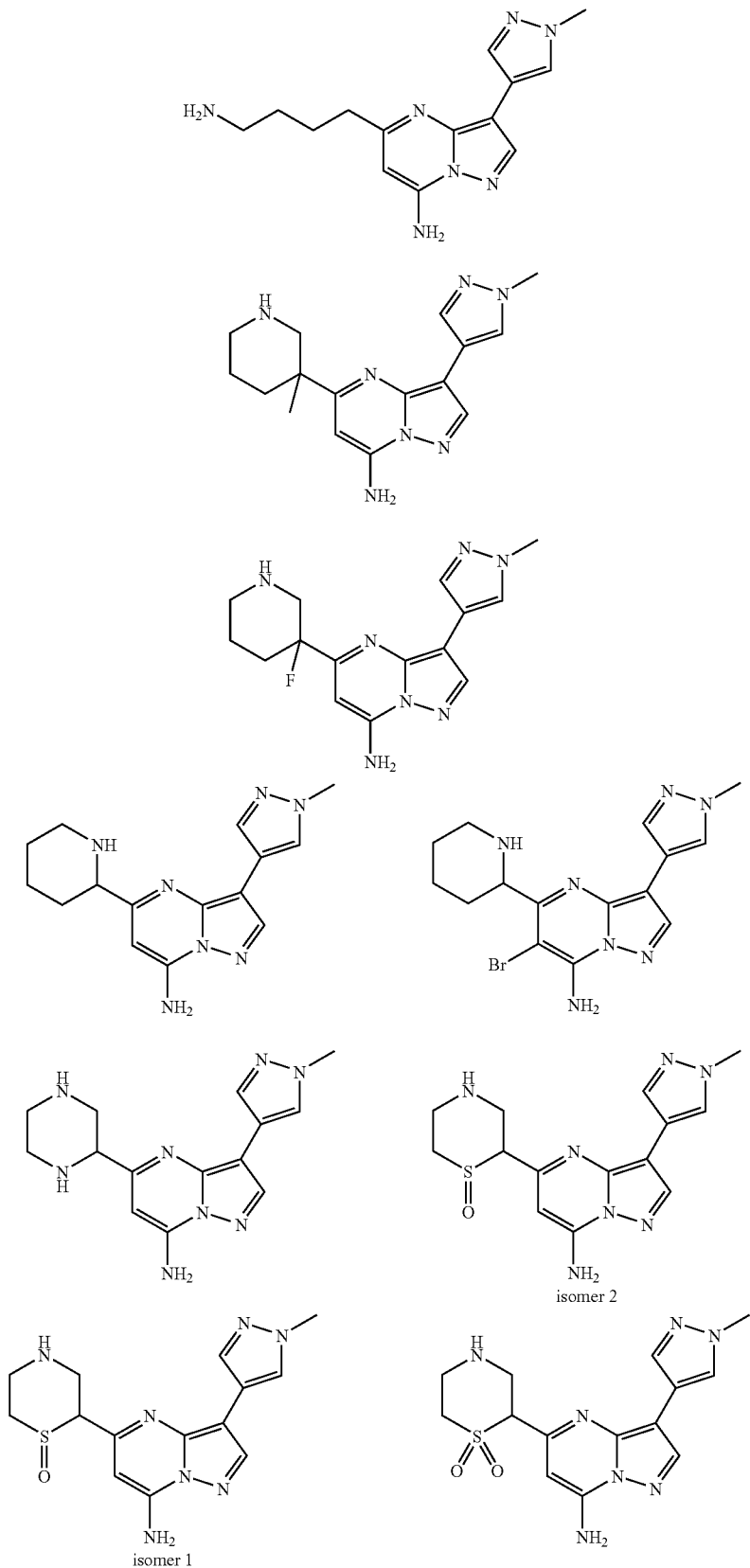

TABLE 1-continued
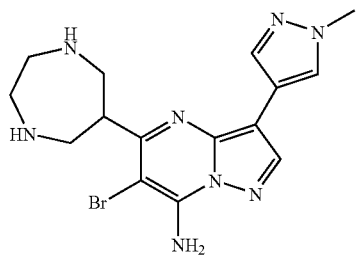 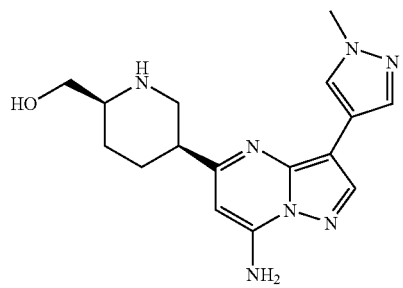
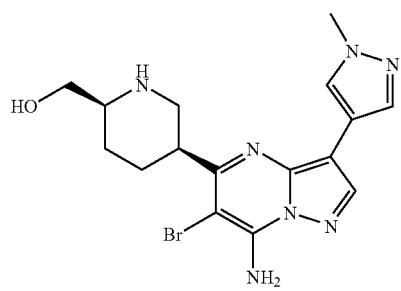 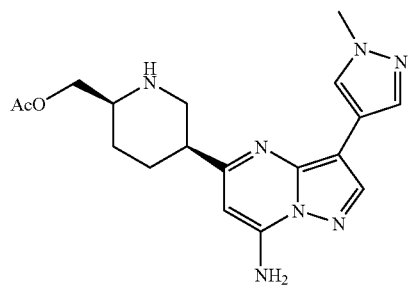
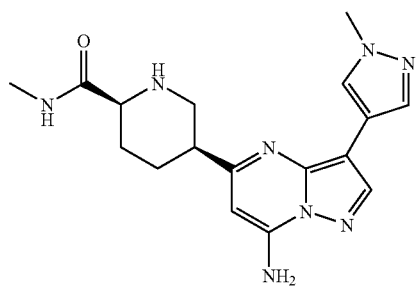
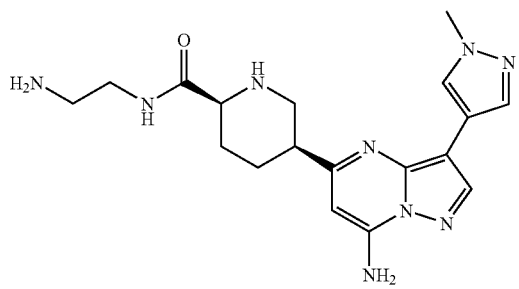
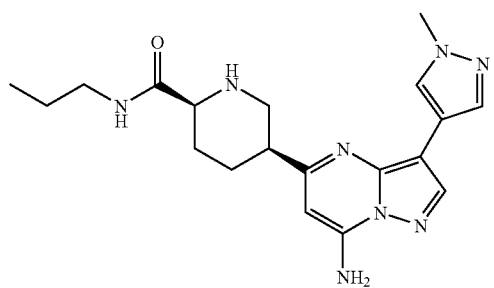

TABLE 1-continued
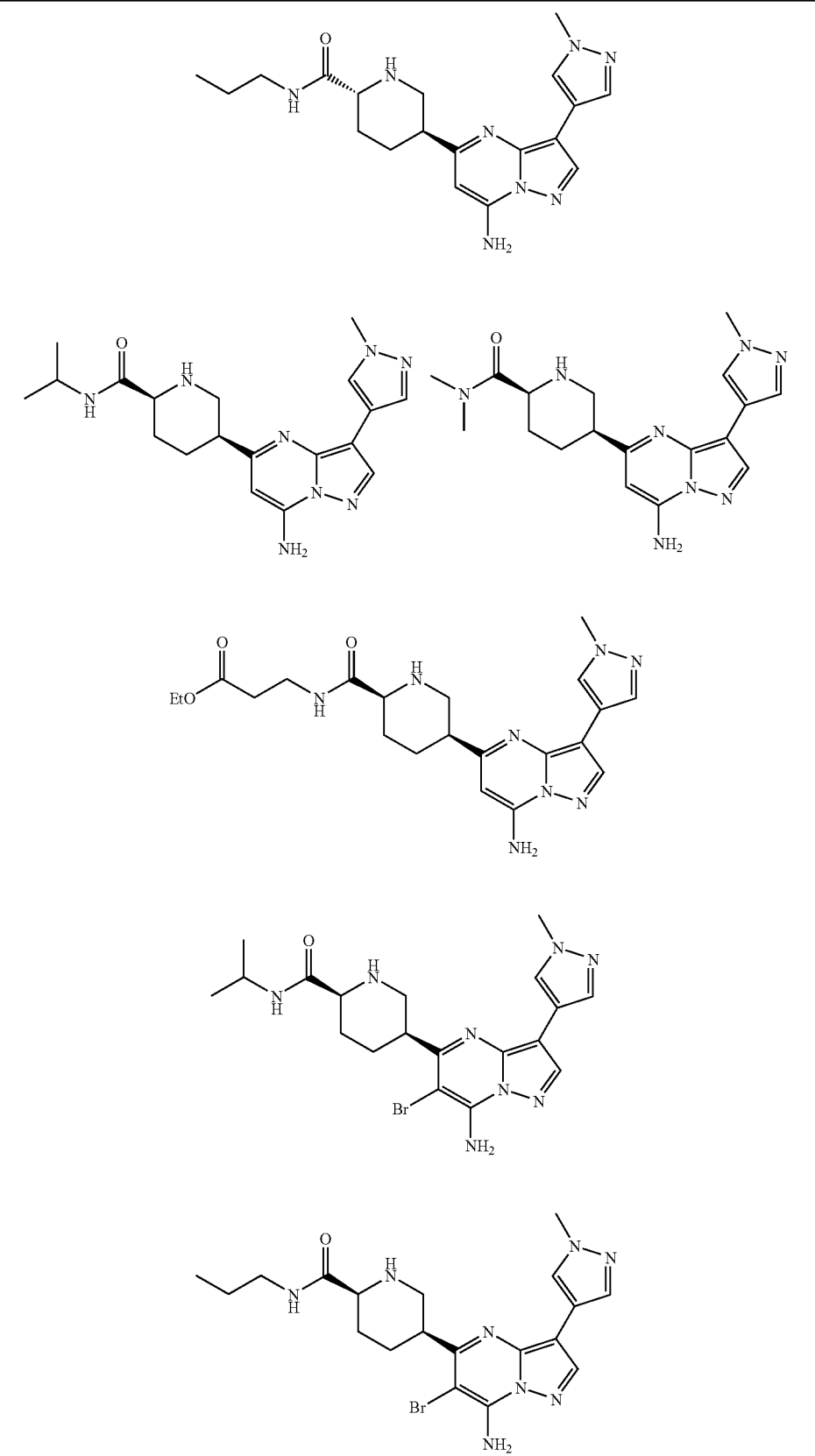

TABLE 1-continued
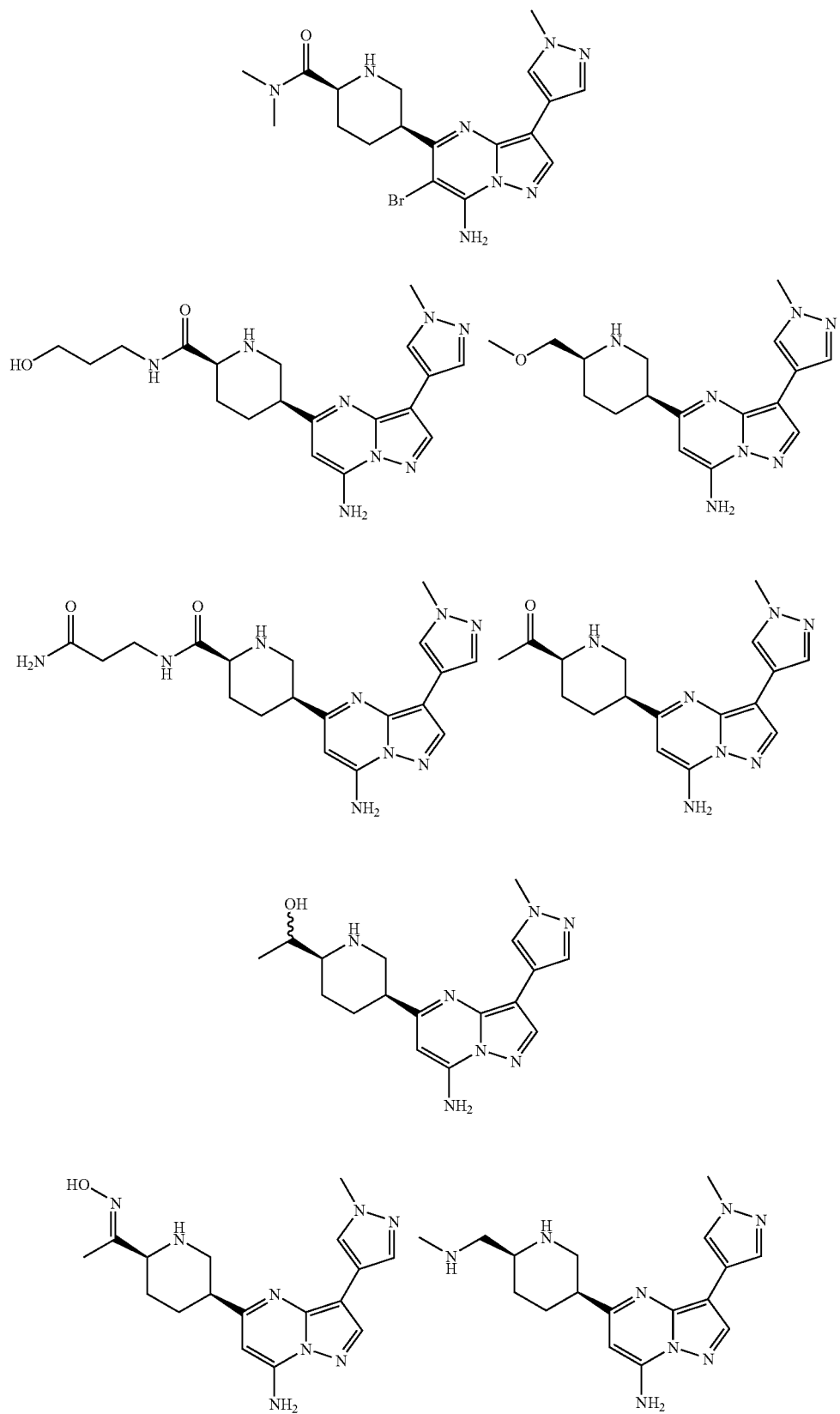

TABLE 1-continued
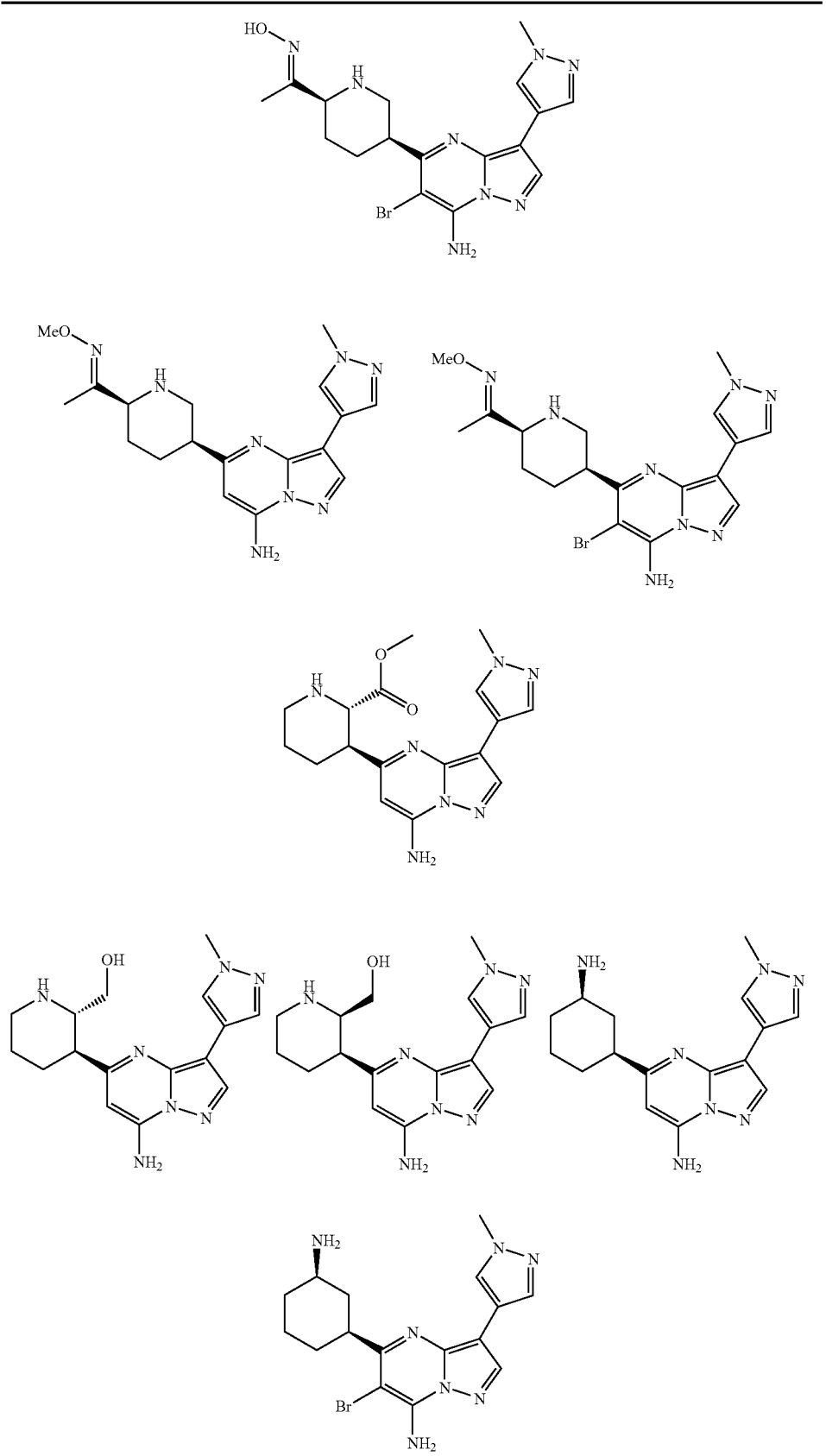

TABLE 1-continued
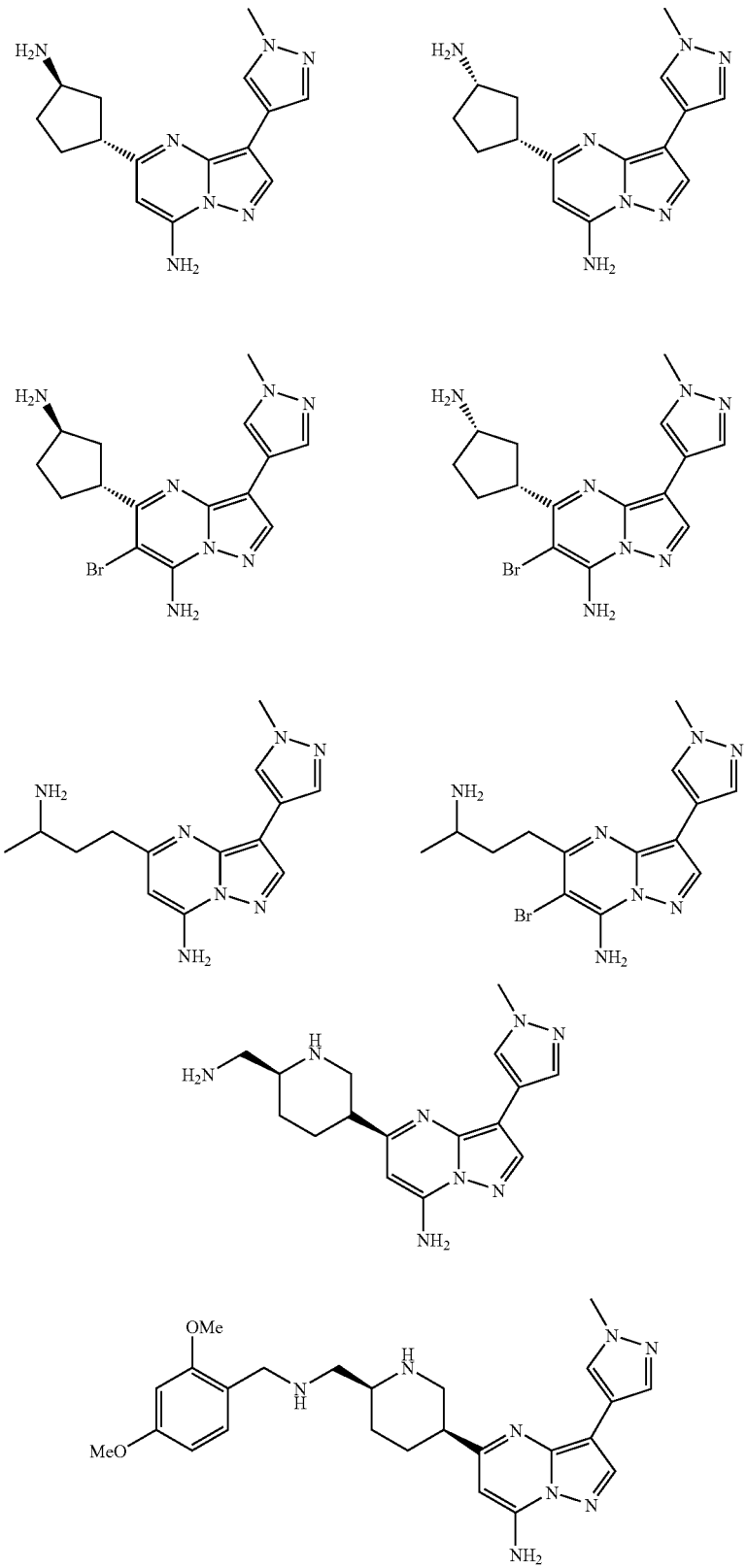

TABLE 1-continued
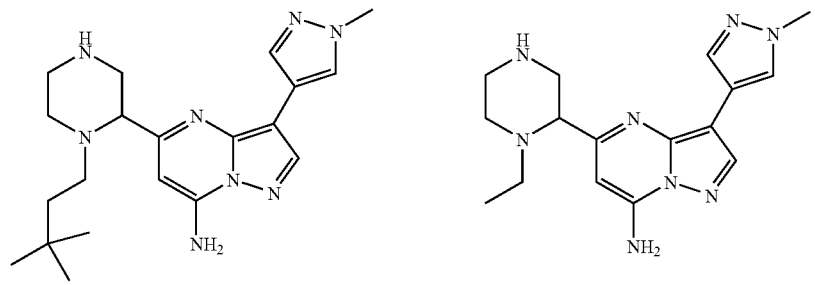
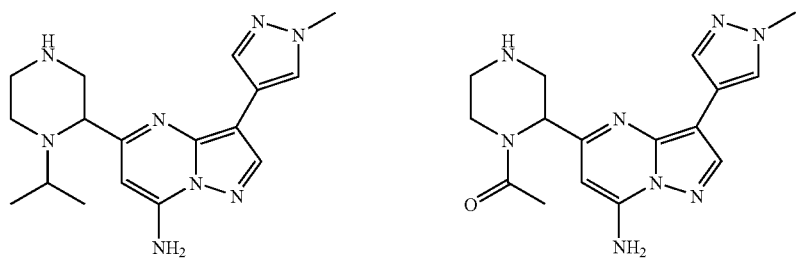
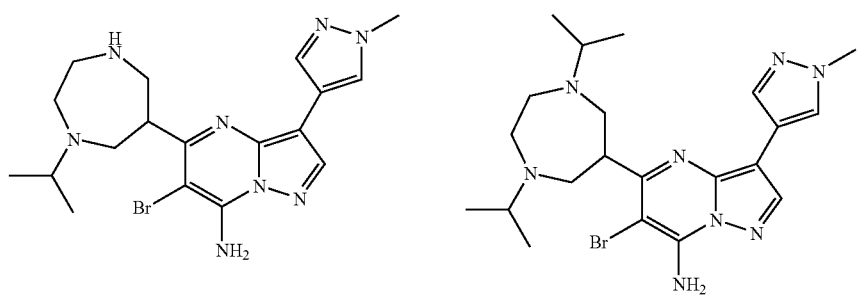
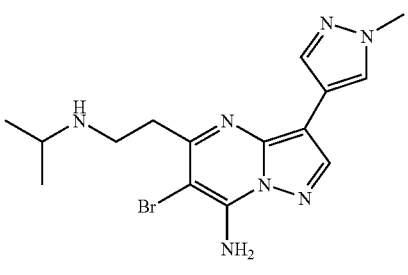
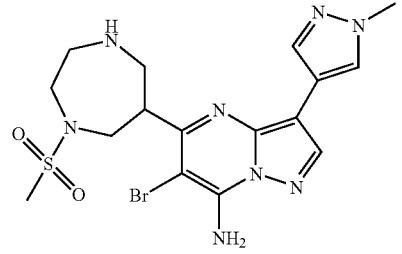

TABLE 1-continued
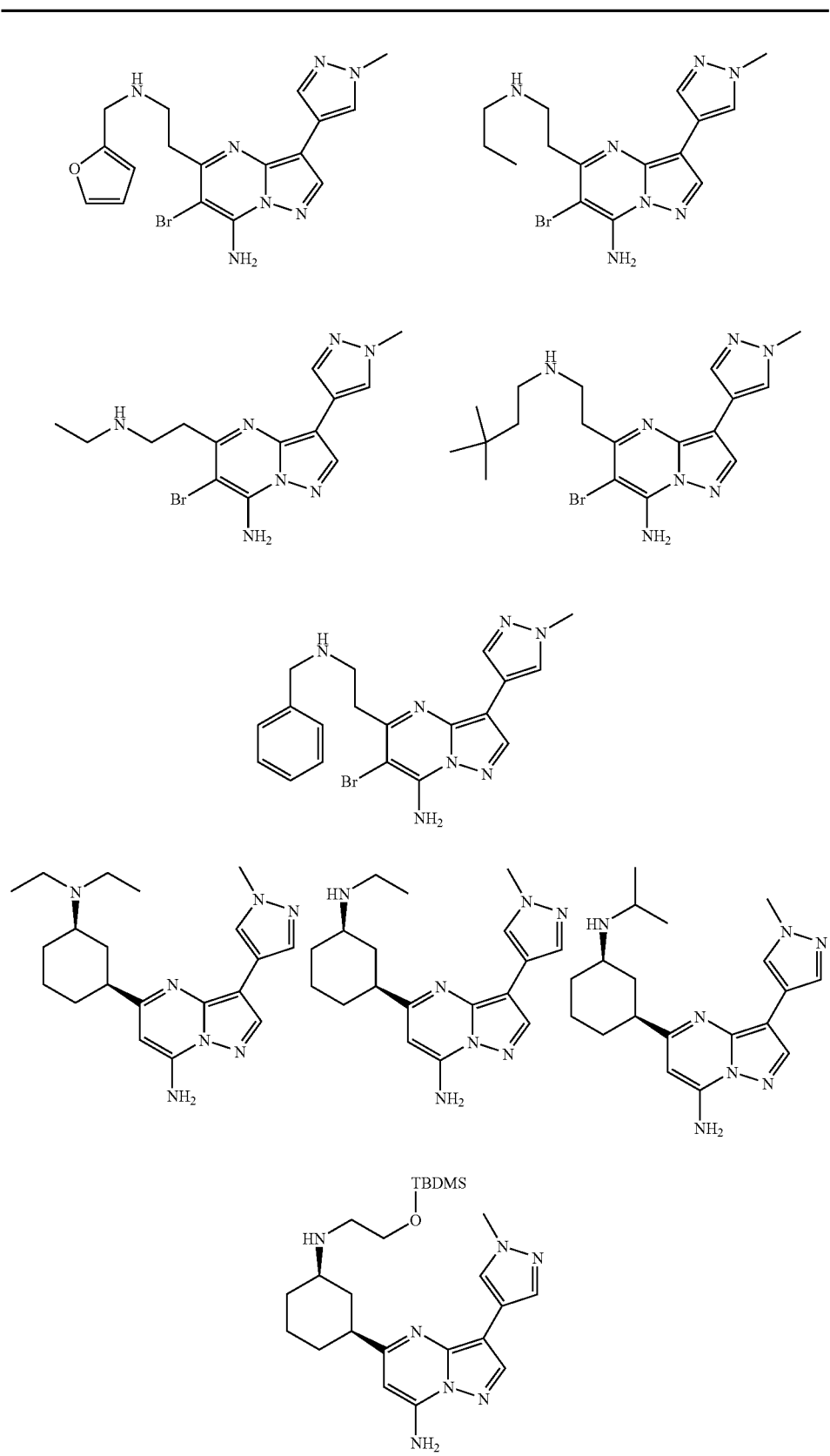

TABLE 1-continued

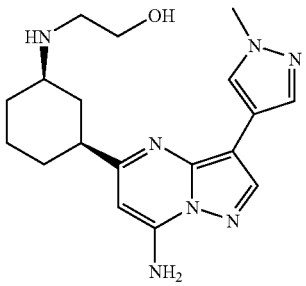

or a pharmaceutically acceptable salt, solvate, ester or prodrug thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (=N—OH), —NH (alkyl), —NH(cycloalkyl), —N(alkyl)$_2$, carboxy and —C(O) O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, oxime (=N—OH), Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

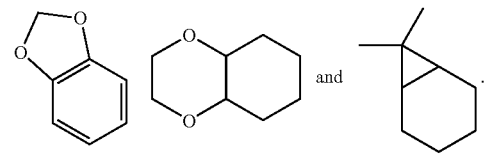

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

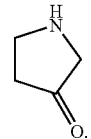

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4- tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

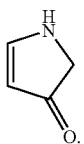

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

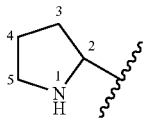

there is no —OH attached directly to carbons marked 2 and 5.

It should also be noted that tautomeric forms such as, for example, the moieties:

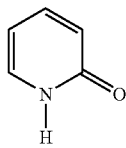 and 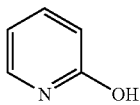

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of The invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Biorversible Carriers in Drug Design, ed. Edward B. Roche, American Pharmaceutical Association and Pergamon Press, 1987.

For example, if a compound of The invention or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C1-C_2)$alkyl, N,N-di $(C1-C_2)$alkylcarbamoyl-$(C_1-C2)$alkyl and piperidino-, pyrrolidino- or morpholino$(C_2-C_3)$ alkyl, and the like.

Similarly, if a compound of The invention contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of The invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of The invention can form salts which are also within the scope of this invention. Reference to a compound of The invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of The invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the The invention may be formed, for example, by reacting a compound of The invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of The invention incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}p$, $^{32}p$, $^{35}S$, $^{18}F$, and $^{36}Cl$, respectively.

Certain isotopically-labelled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds according to the invention have pharmacological properties; in particular, the compounds of the invention can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKs) include, for example, CDC2 (CDK1), CDK2, CDK4, CDK5, CDK6, CDK7 CDK8 and CDK9. The novel compounds of The invention are expected to be useful in the therapy of proliferative diseases such as cancer, autoimmune diseases, viral diseases, fungal diseases, neurological/neurodegenerative disorders, arthritis, inflammation, antiproliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of The invention can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T- cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of The invention may also be useful in the treatment of Alzheimer's disease, as suggested by the recent finding that CDK5 is involved in the phosphorylation of tau protein (*J. Biochem*, (1995) 117, 741-749).

Compounds of The invention may induce or inhibit apoptosis. The apoptotic response is aberrant in a variety of human diseases. Compounds of The invention, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of the invention, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of the invention may also be useful in inhibiting tumor angiogenesis and metastasis.

Compounds of the invention may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of the invention, or a pharmaceutically acceptable salt or solvate of said compound to the mammal.

A preferred dosage is about 0.001 to 500 mg/kg of body weight/day of the compound of the invention. An especially preferred dosage is about 0.01 to 25 mg/kg of body weight/day of a compound of the invention, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxyethyl]-1-piperidinecarboxamide, or SCH 66336 from Schering-Plough Corporation, Kenilworth, N.J.), tipifarnib (Zarnestra® or R115777 from Janssen Pharmaceuticals), L778, 123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225 (or Cetuximab from Merck KGaA, Darmstadt, Germany), and Campath.

The compounds of this invention may specifically be useful in combination (administered together, concurrently or sequentially) with temozolomide and/or radiation therapy.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of The invention may also be administered sequentially with known anticancer or cytotoxic agents when a combination formulation is inappropriate. The invention is not limited in the sequence of administration; compounds of The invention may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of the invention, or a pharmaceutically acceptable salt or solvate thereof, and an amount of one or more anti-cancer treatments and anti-cancer agents listed above wherein the amounts of the compounds/ treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of the invention, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Penn.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of the invention, or a pharmaceutically acceptable salt or solvate of said compound and a pharmaceutically acceptable carrier, vehicle or diluent.

Yet another aspect of this invention is a kit comprising an amount of at least one compound of the invention, or a pharmaceutically acceptable salt or solvate of said compound and an amount of at least one anticancer therapy and/or anticancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33mm×7mm ID; gradient flow: 0 min —10% CH$_3$CN, 5 min-95% CH$_3$CN, 7 min-95% CH$_3$CN, 7.5 min-10% CH$_3$CN, 9 min—stop. The retention time and observed parent ion are given.

The following solvents and reagents may be referred to by their abbreviations in parenthesis:
Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: µl
grams: g
milligrams: mg
room temperature or rt (ambient): about 25° C.
dimethoxyethane: DME

EXAMPLES

Preparative Example 10-C

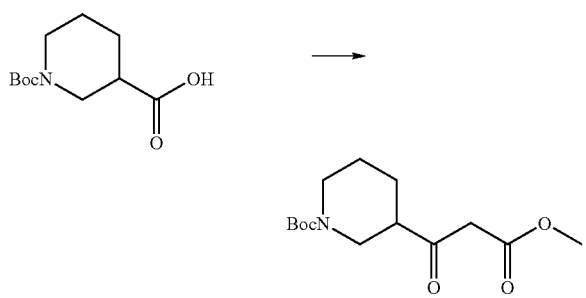

SOCl$_2$ (18.5 mL) was added slowly under N$_2$ to a stirred mixture of the acid (50.0 g, 218 mmol) and pyridine (44.0 mL) in anhydrous CH$_2$Cl$_2$ (300 mL). The mixture was stirred at 25° C for 20 min, then Meldrum's acid (35.0 g, 243 mmol) and DMAP (66.6 g, 546 mmol) were added and the mixture was stirred under N$_2$ for 1 hr. Then Et$_2$O (2 L) was added, the mixture was washed with 1 M HCl (3×500 mL), brine (500 mL), and the organic layer was dried over Na$_2$SO$_4$, filtered, and the solvent was evaporated. The residue was dissolved in MeOH (580 mL), and the mixture was refluxed for 4 hr. The solvent was evaporated and the residue was purified by column chromatography on silica gel with 10:1 CH$_2$Cl$_2$/EtOAc as eluent. Pale yellow oil (26.5 g, 43%) was obtained.

Preparative Example 20-C

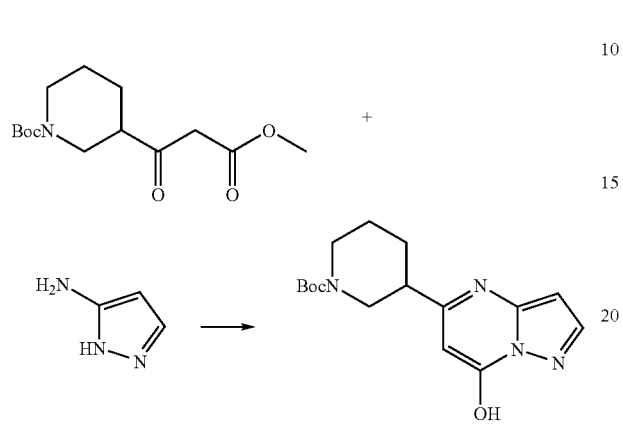

A mixture of the beta-ketoester from Preparative Example 10-C (20.0 g, 70.1 mmol) and 3-aminopyrazole (5.40 g, 65.0 mmol) in anhydrous toluene (60 mL) was stirred and refluxed under N$_2$ for 24 hr. The solvent was evaporated and the residue was purified by column chromatography on silica gel with 20:1 CH$_2$Cl$_2$/MeOH as eluent. White solid (15.0 g, 73%) was obtained. LC-MS: 319 [M+H].

Preparative Example 30-C

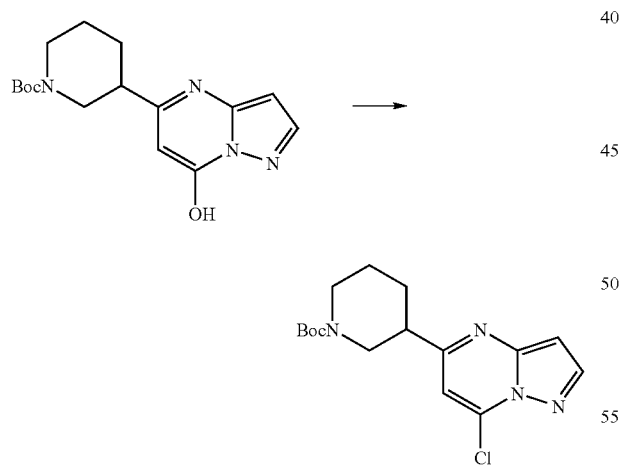

A mixture of the product from Preparative Example 20-C (12.50 g, 39.3 mmol), N,N-dimethylaniline (15.5 mL), and POCl$_3$ (125 mL) was stirred at 25° C. for 4 days. Excess of POCl$_3$ was evaporated and the residue was poured into saturated aqueous NaHCO$_3$ (600 mL). The mixture was extracted with CH$_2$Cl$_2$ (3×200 mL), the combined extracts were dried over Na$_2$SO$_4$, filtered, and the solvent was evaporated. The residue was purified by column chromatography on silica gel with 8:1 CH$_2$Cl$_2$/EtOAc as eluent. Pale yellow wax (9.41 g, 71%) was obtained. LC-MS: 337 [M+].

Preparative Example 40-C

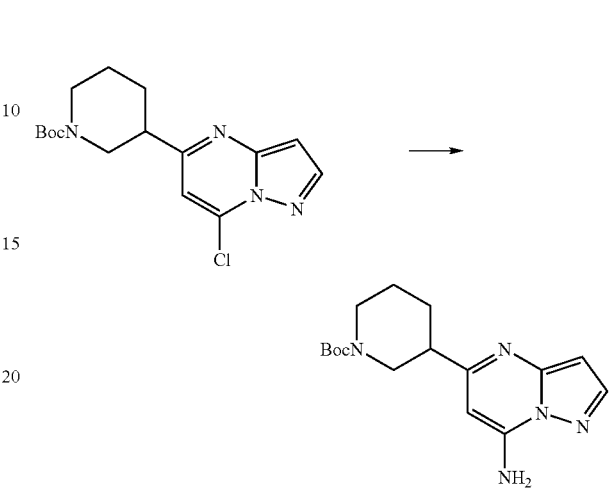

A mixture of the product from Preparative Example 30-C (8.00 g, 23.8 mmol), 2.0 M NH$_3$ in 2-propanol (50 mL), and conc. aqueous NH$_4$OH (5 mL) was stirred in a closed pressure vessel at 70° C. for 28 hr. The solvents were evaporated and the residue was purified by column chromatography on silica gel with 10:1 CH$_2$Cl$_2$/MeOH as eluent. White solid (7.40 g, 98%) was obtained. LC-MS: 318 [M+H].

Preparative Example 50-C

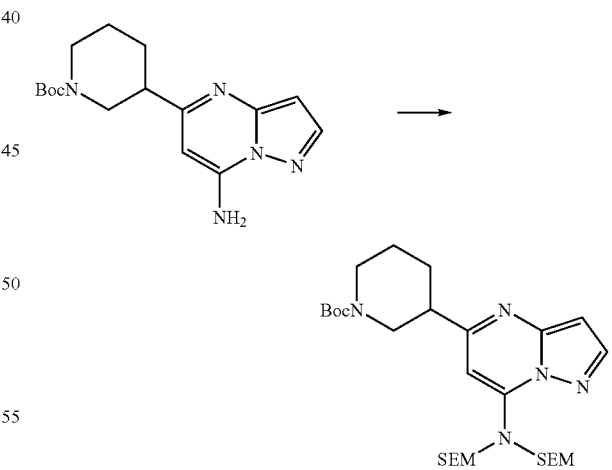

A mixture of the product from Preparative Example 40-C (2.00 g, 6.30 mmol), SEMCI (3.69 g, 22.10 mmol), and diisopropylethylamine (5.70 g, 44.20 mmol) in dry 1,2-dichloroethane (20 mL) and was stirred and refluxed under N$_2$ for 2 hr. The mixture was then poured into saturated aqueous NaHCO$_3$ solution (100 mL), extracted with CH$_2$Cl$_2$ (3×30 mL), dried over Na$_2$SO$_4$, and filtered. The solvents were evaporated and the residue was purified by column chroma-

Preparative Example 60-C

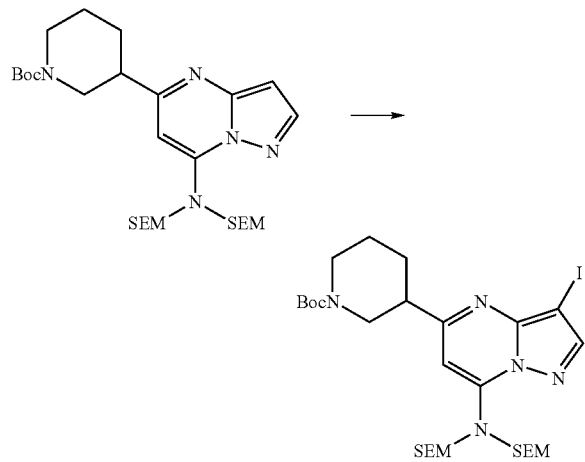

A solution of N-iodosuccinimide (0.90 g, 4.00 mmol) in anhydrous CH$_3$CN (10 mL) was added under N$_2$ to a stirred solution of the product from Preparative Example 50-C (2.50 g, 4.33 mmol) in anhydrous CH$_3$CN (10 mL). The mixture was stirred for 1 hr, the solvents were evaporated, and the residue was purified by column chromatography on silica gel with 40:1 CH$_2$Cl$_2$/EtOAc as eluent. Slightly yellow wax (2.57 g, 92%) was obtained.

Preparative Example 61-C

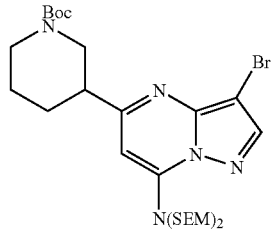

By essentially the same procedure set forth in Preparative Example 60-C only substituting NBS for NIS, the above compound was prepared.

Preparative Example 70-C

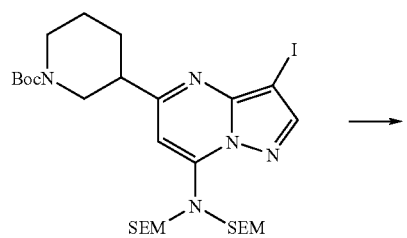

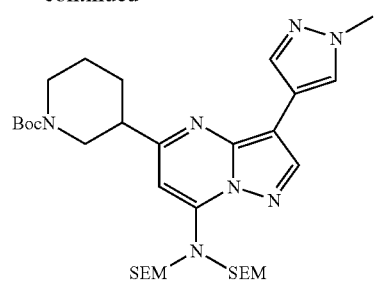

A mixture of the product from Preparative Example 60-C (1.50 g, 2.13 mmol), 1-methyl-4-(4,4,5,5-tetramethyl-1,3,2-dioxaborolan-2-yl)-1H-pyrazole (0.89 g, 4.26 mmol), PdCl$_2$dppf.CH$_2$Cl$_2$ (171 mg, 0.21 mmol), and K$_3$PO$_4$ (1.81 g, 8.52 mmol) in 1,2-dimethoxyethane (30 mL) and H$_2$O (6 mL) was stirred and refluxed under N$_2$ for 3 hr. The solvents were evaporated and the residue was purified by column chromatography on silica gel with 5:1 CH$_2$Cl$_2$/EtOAc as eluent. Yellow wax (1.13 g, 81%) was obtained.

Preparative Example 80-C

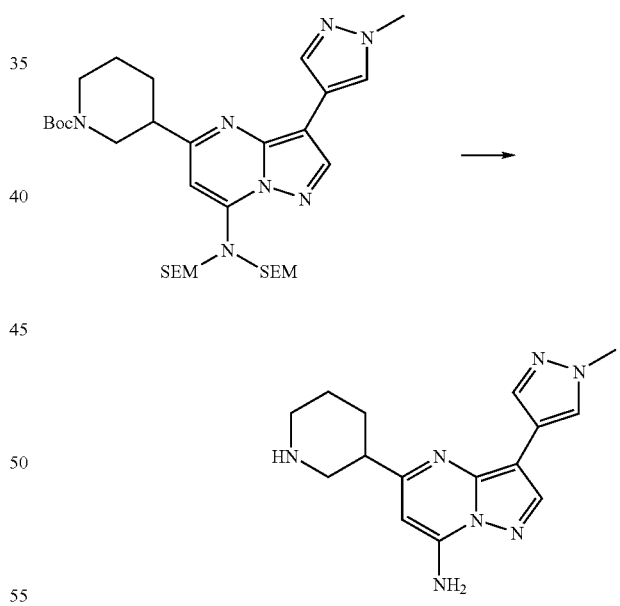

A mixture of the product from Preparative Example 70-C (1.00 g) and 3N aqueous HCl (20 mL) in EtOH (20 mL) was stirred at 60° C. for 1.5 hr. The solvents were evaporated, Na$_2$CO$_3$ (2.0 g) and 6:1 mixture of CH$_2$Cl$_2$/MeOH (20 mL) were added to the residue and the mixture was stirred under N$_2$ for 15 min. Then it was loaded onto a column and it was purified by column chromatography on silica gel with 6:1 CH$_2$Cl$_2$/7N NH$_3$ in MeOH as eluent. White solid (405 mg, 90%) was obtained. LC-MS: 298 [M+H].

Preparative Example 90-C

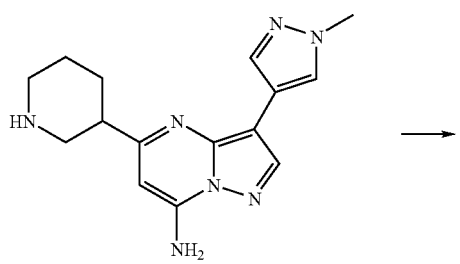

Boc₂O (441 mg, 2.02 mmol) was added to a stirred solution of the product from Preparative Example 80-C (500 mg, 1.68 mmol) and triethylamine (2.0 mL) in anhydrous CH₂Cl₂ (10 mL). The mixture was stirred at 25° C. for 18 hr, then it was poured into saturated aqueous NaHCO₃ solution (60 mL), extracted with CH₂Cl₂ (3×10 mL), dried over Na₂SO₄, and filtered. The solvents were evaporated and the residue was purified by column chromatography on silica gel with 20:1 CH₂Cl₂/MeOH as eluent. Pale yellow solid (670 mg, 100%) was obtained. LC-MS: 398 [M+H].

Preparative Example 100-C

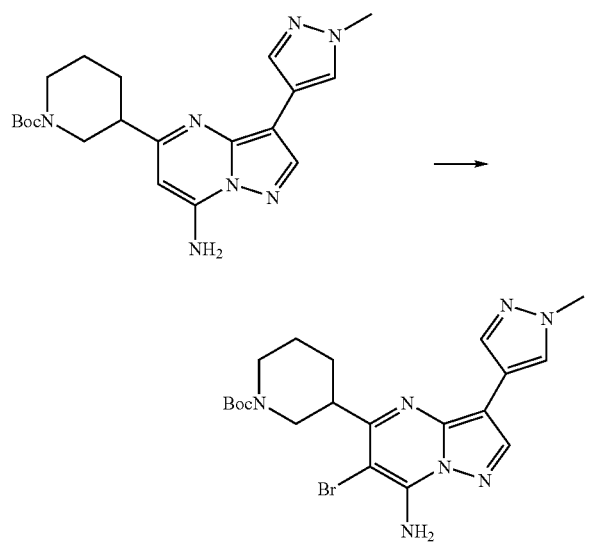

A solution of Br₂ (191 mg, 1.19 mmol) in dry CH₂Cl₂ (4 mL) was added dropwise to a stirred solution of the product from Preparative Example 90-C (500 mg, 1.26 mmol) in tert-BuNH₂ (10 mL) and CH₂Cl₂ (5 mL). The mixture was stirred at 25° C. for 20 hrs, the solvents were evaporated and the residue was purified by column chromatography on silica gel with 1:1 CH₂Cl₂/EtOAc as eluent. White solid (415 mg, 73%) was obtained. LC-MS: 476 [M+].

Preparative Example 110-C

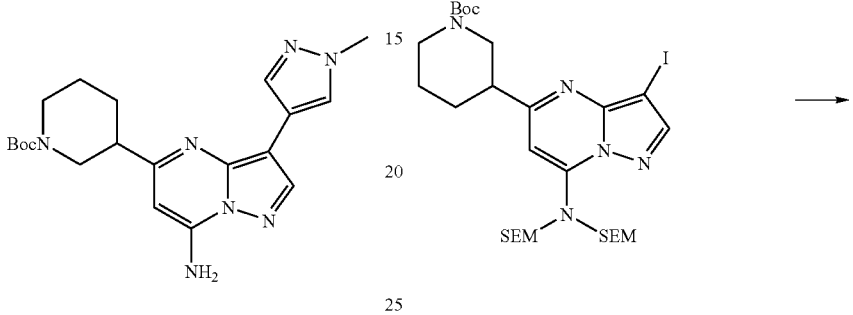

To a solution 3-iodo adduct (0.40 g, 0.57 mmol) from Preparative Example 60-C in a mixture of DME/H₂O (15 mL/3 mL) at rt was added 4-hydroxymethylphenyl boronic acid (0.17 g, 1.14 mmol), Na₂CO₃ (0.18 g, 1.70 mmol), and PdCl₂(dppf) (46 mg, 0.057 mmol). The mixture was degassed under house vacuum 6× and filled with N₂ and was heated to 95° C. The mixture was stirred for 5 h, cooled to rt, and concentrated under reduced pressure. The crude residue was partitioned between CH₂Cl₂ (10 mL) and water (3 mL) and the layers were separated. The aqueous layer was extracted with CH₂Cl₂ (2×10 mL) and the organic layers were combined. The organic layer was dried (Na₂SO₄), filtered and concentrated under reduced pressure. The crude product was purified by preparative thin-layer chromatography (6×1000 μM plates) using a 3:1 mixture of hexanes/EtOAc as eluent to afford (0.38 g, 96% yield) as a yellow semisolid. LC-MS: =684.4 [M+H] 98% purity.

Preparative Examples 120-C-210-C

Following the procedure set forth in Preparative Example 110-C but utilizing the boronic acid/boronates (as indicated) in Table 10-C and commercially available amines, the substituted pyrazolo[1,5-a]pyrimidine adducts were prepared (Products).

TABLE 10-C
| Prep. Ex. | Boronic Acid/Boronate | Product | 1. Yield (%)<br>2. LC-MS |
|---|---|---|---|
| 120-C | 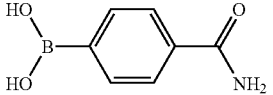 | 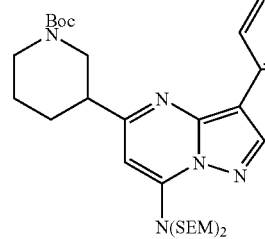 | 1. 88<br>2. 697.5 |
| 130-C | 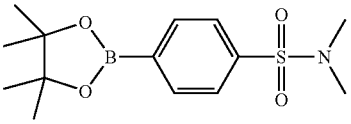 | 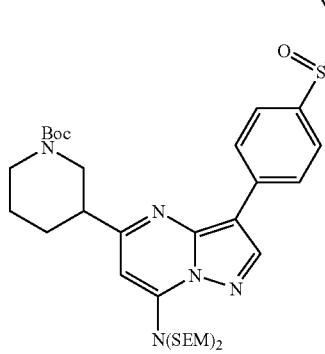 | 1. 88<br>2. 761.5 |
| 140-C | 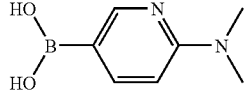 | 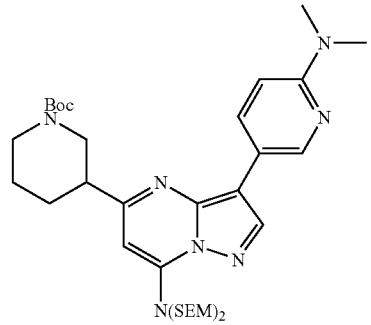 | 1. 60<br>2. 698.5 |
| 150-C | 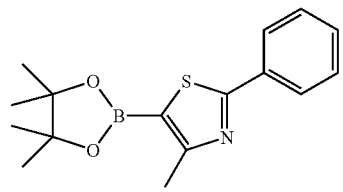 | 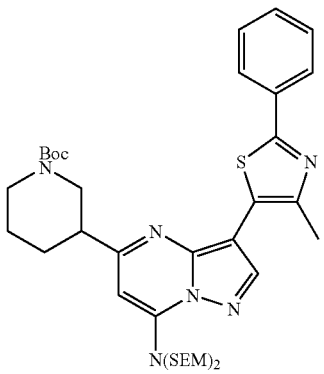 | 1. 71<br>2. 751.2 |

TABLE 10-C-continued

| Prep. Ex. | Boronic Acid/Boronate | Product | 1. Yield (%) 2. LC-MS |
|---|---|---|---|
| 160-C | | | 1. 96 <br> 2. 679.1 |
| 170-C | | | 1. 97 <br> 2. 679.1 |
| 180-C | | | 1. 89 <br> 2. 693.4 |
| 190-C | | | 1. 90 <br> 2. 698.4 |
| 200-C | | | 1. 67 <br> 2. 702.5 |

TABLE 10-C-continued

| Prep. Ex. | Boronic Acid/Boronate | Product | 1. Yield (%)<br>2. LC-MS |
|---|---|---|---|
| 210-C | (structure) | (structure) | 1. 41<br>2. 644.5 |

Preparative Example 220-C

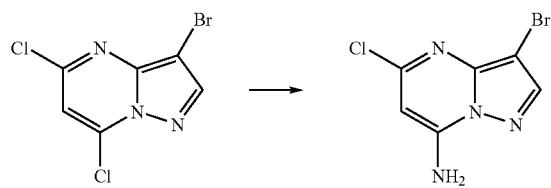

To a pressure tube charged with 3-bromo-5,7-dichloropyrazolo[1,5-a]pyrimidine (3 g, 0.11 mol) from and a stir bar was added conc. NH$_4$OH (~90 mL) at rt. The tube was capped, heated to 85° C., and stirred for 12 h. The mixture was cooled to rt and concentrated under reduced pressure. The crude product was taken up in water (70 mL) and was filtered. The ppt was washed sequentially with water (1×50 mL) and Et$_2$O (1×50 mL). The crude product was placed under high vacuum to afford 2.4 g (88% yield) of a yellow solid. LC-MS: 249.1 [M+H]; 97% purity.

Preparative Example 230-C

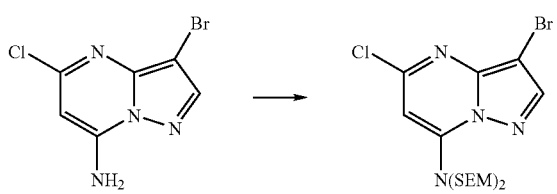

To a mixture of 7-amino adduct (1.0 g, 4.0 mmol) from Preparative Example 220-C in DCE (8 mL) at rt was added DIPEA (4.9 mL, 28.2 mmol) followed by SEMCI (2.2 mL, 12.1 mmol). The resulting mixture was heated to 90° C. and was stirred for 12 h. The mixture was cooled to rt and sat. aq. NaHCO$_3$ (35 mL) was added followed by dilution with CH$_2$Cl$_2$ (50 mL). The layers were separated and the aqueous layer was extracted with CH$_2$Cl$_2$ (3×50 mL). The organic layers were combined, dried (Na$_2$SO$_4$), filtered, and concentrated under reduced pressure. The cured product was purified by flash chromatography using a 7:1 mixture of hexanes/EtOAc to afford 2.0 g (97% yield) of a yellow oil.

Preparative Example 240-C

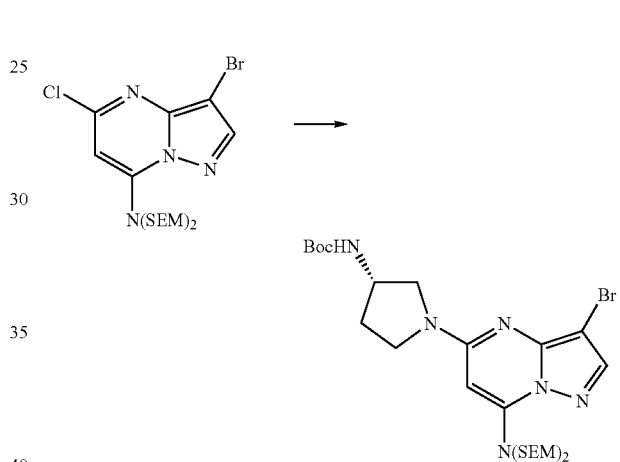

To a mixture of 5-chloro adduct adduct (0.50 g, 0.98 mmol) from Preparative Example 230-C in NMP (3 mL) at rt was added (S)-3-(Boc-amino)pyrrolidine (0.28 g, 1.5 mmol) followed by NaHCO$_3$ (0.19 g, 2.2 mmol). 12.1 mmol). The resulting mixture was heated to 130° C. and was stirred for 12 h. The mixture was concentrated under reduced pressure purified by preparative TLC using 8×1000 µM plates with a 40:1 mixture of CH$_2$Cl$_2$/MeOH as eluent to afford 0.51 g (79% yield) of a light yellow solid. LC-MS: 659.4 [M+H]; 94% purity.

Preparative Example 250-C

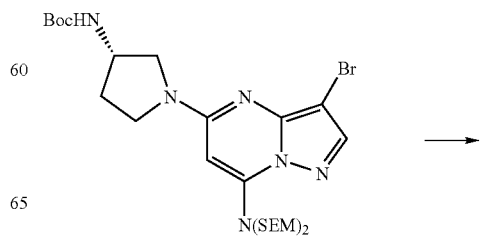

-continued

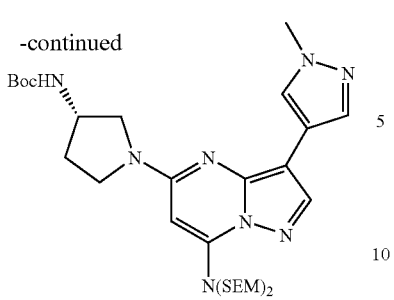

By the same method used in Preparative Example 110-C, the 3-bromo derivative (0.42 g, 0.64 mmol) from Preparative Example 240-C was treated with 1-methyl-4-(4,4,5,5-tetramethyl-1,3,2-dioxaborolan-2-yl)-1H-pyrazole (0.27 g, 1.28 mmol) to afford 0.10 g (24% yield) of a white semisolid. LC-MS: 659.0 [M+H]; 95% purity.

Preparative Example 260-C

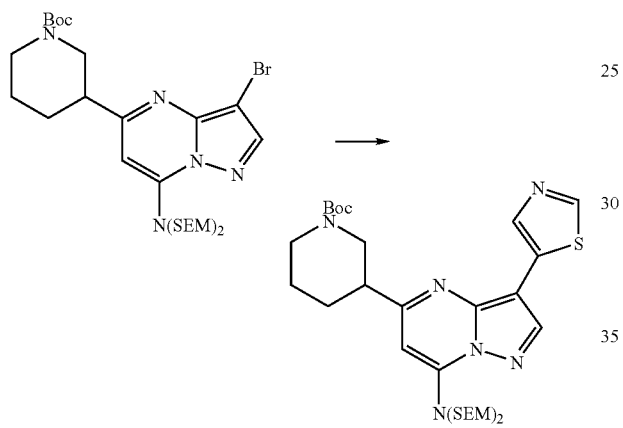

To a solution of 3-Br adduct (0.45 g, 0.69 mmol) from Preparative Example 61-C in CH$_3$CN (4 mL) at rt was 4-tributylstannylthiazole (0.51 g, 1.37 mmol) followed by PdCl$_2$(PPh$_3$)$_2$ (48 mg, 0.069 mmol). The resulting mixture was degassed under aspirator vacuum and filled with N$_2$ six times. The mixture was fitted with a condenser and was heated to 80° C. The mixture was stirred for 12 h, cooled to rt, and diluted with EtOAc (10 mL). The mixture was filtered thru a Celite pad which was washed with CH$_2$Cl$_2$ (1×5 mL) and MeOH (1×5 mL). The resulting filtrate was concentrated under reduced pressure and was placed under high vacuum. The crude product was purified by preparative thin-layer chromatography (6×1000 μM plates) using a 40:1 mixture of CH$_2$Cl$_2$/MeOH as eluent to afford 0.28 g (61% yield) as an orange oil. LC-MS:=661.4 [M+H] 71% purity.

Preparative Example 270-C

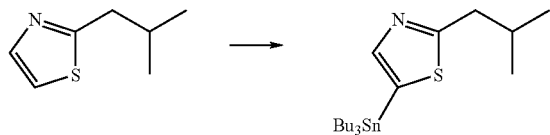

To a solution of 2-isobutylthiazole (5.0 mL, 35.4 mmol) in THF (100 mL) at −78° C. was added a 2 M solution of LDA (21.0 mL, 42.2 mmol) dropwise over 10 min. After 1 h at this temperature, Bu$_3$SnCl (11.5 mL, 42.4 mmol) was added dropwise. The mixture was allowed to gradually warm to rt over about 3 h whereupon the mixture was quenched with sat. aq. NH$_4$Cl (15 mL) and diluted with Et$_2$O (70 mL). The layers were separated and the aqueous layer was extracted with Et$_2$O (2×70 mL). The organic layers were combined, dried (MgSO$_4$), filtered and concentrated under reduced pressure to afford the product as an orange/brown oil. MS:=430.4 The material was taken on crude to the next transformation without purification.

Preparative Example 280-C

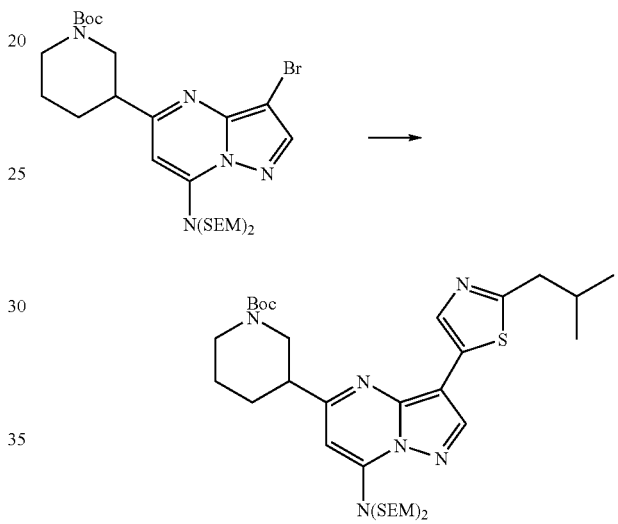

Utilizing the procedure in Preparative Example 260-C, the 3-Br adduct (0.40 g, 0.61 mmol) from Preparative Example 61-C was treated with the tributylstannylthiazole (0.52 g, 1.22 mmol) from Preparative Example 17 to afford 0.34 g (77% yield) of a orange/brown oil. LC-MS:=717.4 [M+H] 62% purity.

Example 10-C

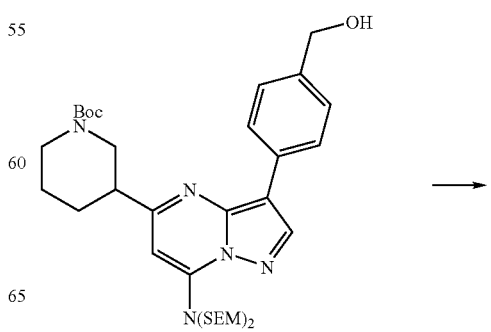

-continued

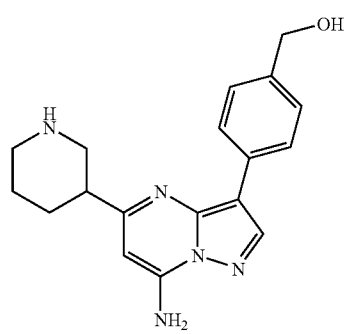

To a solution of adduct (0.25 g, 0.37 mmol) from Preparative Example 110-C in EtOH (3 mL) at rt was added 3M HCl (3 mL). The resulting solution was heated to 60° C. and was stirred for 5 h (until complete by TLC). The mixture was cooled to rt and concentrated under reduced pressure. The crude material was taken up in 7M NH₃ in MeOH (3 mL) and stirred for 3 h. The mixture was concentrated under reduced pressure and was purified by preparative thin-layer chromatography (4×1000 µM plates) using a 10:1 mixture of CH₂Cl₂/MeOH (7M NH₃) as eluent to afford (20 mg, 17% yield) as an off-white solid. LC-MS:=324.2 [M+H] 99% purity.

Examples 20-C-130-C

Following the procedure set forth in Example 10-C, the indicated Preparative Examples in Column 2 of Table 20-C were converted to the substituted pyrazolo[1,5-a]pyrimidine adducts shown in Column 3 of Table 20-C were prepared.

TABLE 20-C

| Ex. | Column 2 | Column 3 | 1. Yield (%) 2. LC-MS 3. mp (° C.) |
|---|---|---|---|
| 20-C | [structure with SEM groups, benzamide] | [structure with NH₂, benzamide] | 1. 12 2. 337.2 3. 134-137 |
| 30-C | [structure with SEM groups, sulfonamide] | [structure with NH₂, sulfonamide] | 1. 11 2. 401.2 3. 167-169 |

TABLE 20-C-continued

| Ex. | Column 2 | Column 3 | 1. Yield (%)<br>2. LC-MS<br>3. mp (° C.) |
|---|---|---|---|
| 40-C | | | 1. 25<br>2. 338.2<br>3. 123-125 |
| 50-C | | | 1. 57<br>2. 391.2<br>3. 165-167 |
| 60-C | | | 1. 42<br>2. 338.2<br>3. 156-160 |
| 70-C | | | 1. 25<br>2. 342.2<br>3. 156-159 |

TABLE 20-C-continued
| Ex. | Column 2 | Column 3 | 1. Yield (%)<br>2. LC-MS<br>3. mp (° C.) |
|---|---|---|---|
| 80-C | 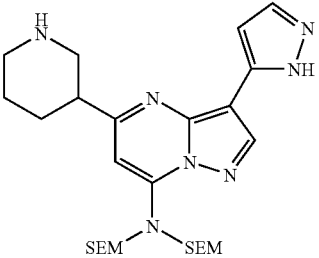 | 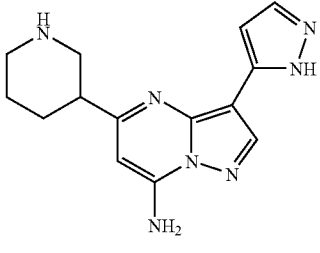 | 1. 48<br>2. 284.2<br>3. 145-147 |
| 90-C | 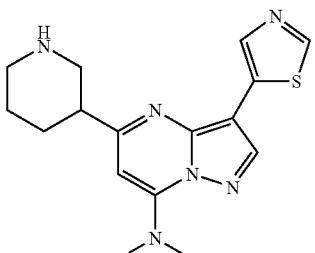 | 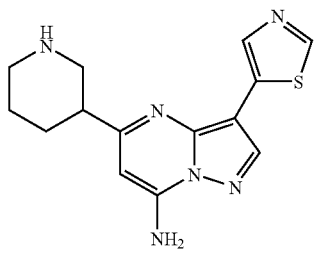 | 1. 70<br>2. 301.2<br>3. 148-150 |
| 100-C | 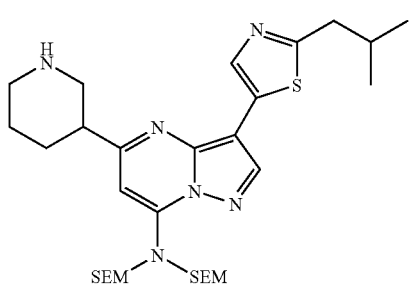 | 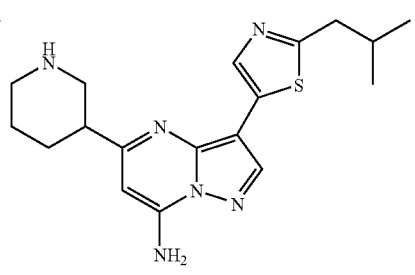 | 1. 27<br>2. 357.2<br>3. 130-132 |
| 110-C | 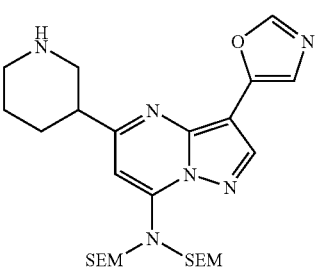 | 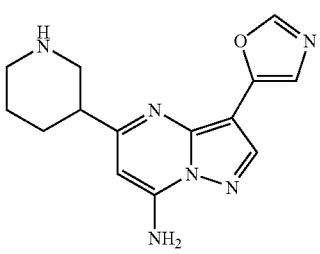 | 1. 45<br>2. 285.2.2<br>3. 167-169 |
| 120-C | 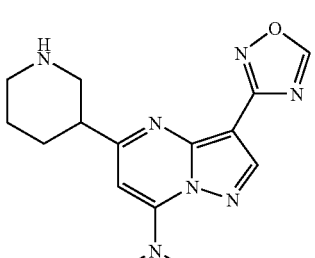 | 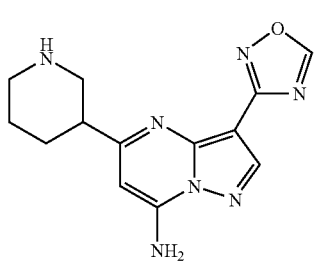 | 1. 85<br>2. 286.2<br>3. 145-148 |

TABLE 20-C-continued

| Ex. | Column 2 | Column 3 | 1. Yield (%) 2. LC-MS 3. mp (° C.) |
|---|---|---|---|
| 130-C | | | 1. 25 2. 299.2 3. 185-187 |

Example 140-C

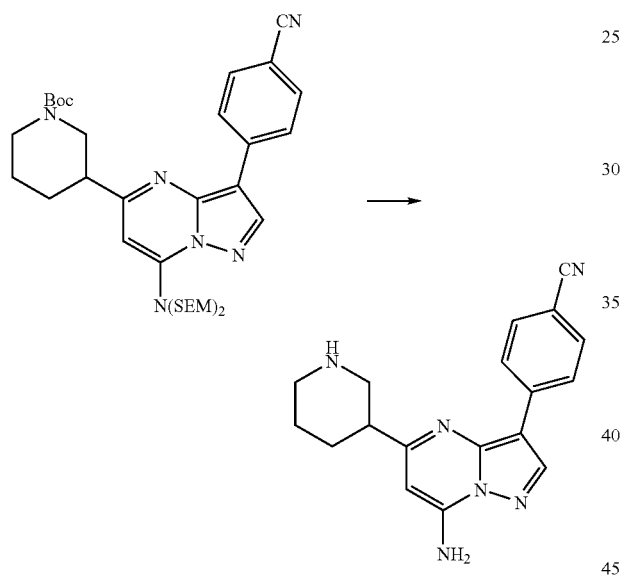

To a solution of adduct (0.28 g, 0.41 mmol) from Preparative Example 170-C in water (4 mL) at rt was added TFA (4 mL). The resulting solution was stirred at rt for 4 h (until complete by TLC) and was concentrated under reduced pressure. The crude material was taken up in 7M NH$_3$ in MeOH (3 mL) and stirred for 3 h. The mixture was concentrated under reduced pressure and was purified by preparative thin-layer chromatography (4×1000 μM plates) using a 10:1 mixture of CH$_2$Cl$_2$/MeOH (7M NH$_3$) as eluent to afford (60 mg, 46% yield) as a yellow solid. mp 167-169° C.; LC-MS:=319.2 [M+H] 99% purity.

Examples 150-C-160-C

Following the procedure set forth in Example 140-C, the compounds in Column 2 of Table 30-C were converted to the substituted pyrazolo[1,5-a]pyrimidine adducts (Column 3) found in Table 30-C.

TABLE 30-C

| Ex. | Column 2 | Column 3 | 1. Yield (%) 2. LC-MS 3. mp (° C.) |
|---|---|---|---|
| 150-C | | | 1. 29 2. 319.4 3. 176-178 |

TABLE 30-C-continued

| Ex. | Column 2 | Column 3 | 1. Yield (%) 2. LC-MS 3. mp (° C.) |
|---|---|---|---|
| 160-C | (BOC-piperidinyl)-pyrazolopyrimidine-NH₂ with 4-CN-phenyl | (H-piperidinyl)-pyrazolopyrimidine-NH₂ with 4-CN-phenyl | 1. 29 2. 333.2 3. 145-147 |

Preparative Example 290-C

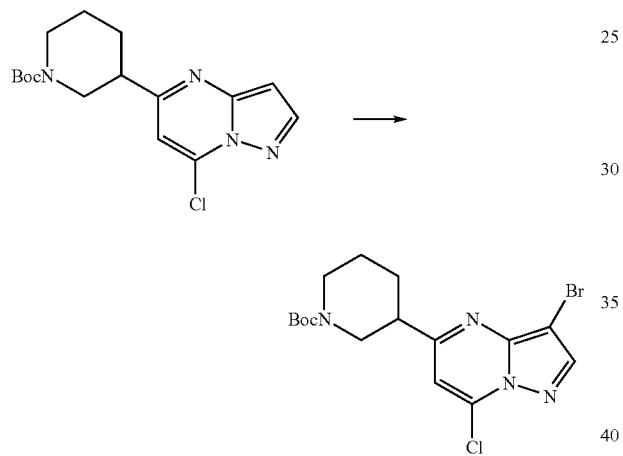

A solution of NBS (4.03 g, 22.7 mmol) in anhydrous CH$_3$CN (40 mL) was added under N$_2$ to a stirred solution of the product from Preparative Example 30-C (7.63 g, 22.7 mmol) in anhydrous CH$_3$CN (60 mL) and CH$_2$Cl$_2$ (20 mL). The mixture was stirred for 2 hr, the solvents were evaporated, and the residue was purified by column chromatography on silica gel with 20:1 CH$_2$Cl$_2$/EtOAc as eluent. Pale yellow solid foam (9.20 g, 97%) was obtained.

Preparative Example 300-C

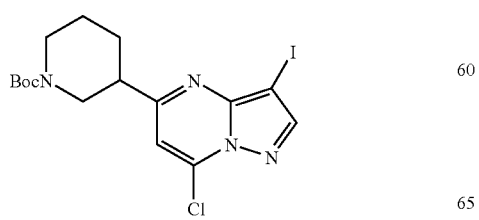

By essentially same procedure set forth in Preparative Example 290-C, reaction of 7-Cl adduct from Preparative Example 30-C with N-iodosuccinimide afforded the title compound.

Preparative Example 310-C

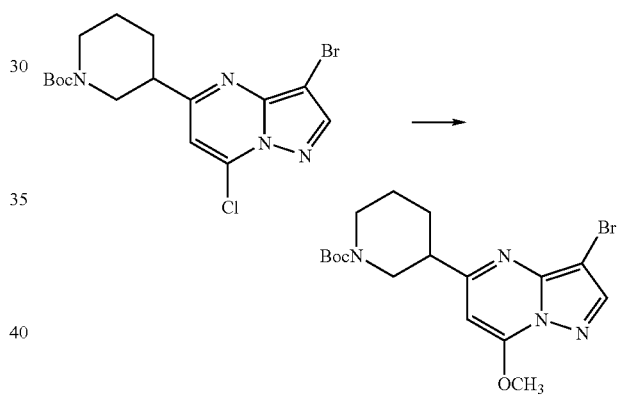

A mixture of the product from Preparative Example 290-C (8.00 g, 19.3 mmol) and MeONa (2.16 g, 40.0 mmol) in anhydrous MeOH (100 mL) was stirred for 20 hr. CH$_2$Cl$_2$ (200 mL) was then added, the mixture was filtered through Celite, the solvent was evaporated, and the residue was purified by column chromatography on silica gel with 2:1 CH$_2$Cl$_2$/EtOAc as eluent. White solid (7.75 g, 98%) was obtained.

Preparative Example 320-C

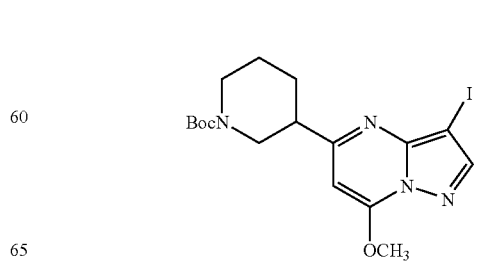

By essentially same procedure set forth in Preparative Example 310-C, starting from the compound from Preparative Example 300-C, the title compound was prepared.

Preparative Example 330-C

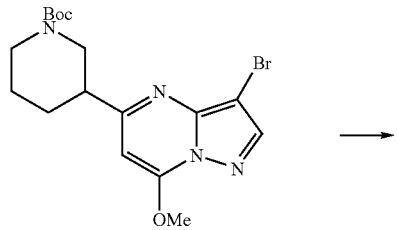

To a solution of 3-Br adduct (0.25 g, 0.61 mmol) from Preparative Example 310-C in CH$_3$CN (3 mL) at rt was 5-tributylstannylthiazole (0.46 g, 1.22 mmol) followed by PdCl$_2$(PPh$_3$)$_2$ (43 mg, 0.069 mmol). The resulting mixture was degassed under aspirator vacuum and filled with N$_2$ six times. The mixture was fitted with a condenser and was heated to 80° C. The mixture was stirred for 12 h, cooled to rt, and diluted with EtOAc (10 mL). The mixture was filtered thru a Celite pad which was washed with EtOAc (3×5 mL), CH$_2$Cl$_2$ (1×5 mL) and MeOH (1×5 mL). The resulting filtrate was concentrated under reduced pressure and was placed under high vacuum. The crude product was purified by preparative thin-layer chromatography (6×1000 μM plates) using a 20:1 mixture of CH$_2$Cl$_2$/MeOH as eluent to afford 0.19 g (75% yield) as a yellow semisolid. LC-MS:=416.2 [M+H] 66% purity.

Preparative Example 340-C

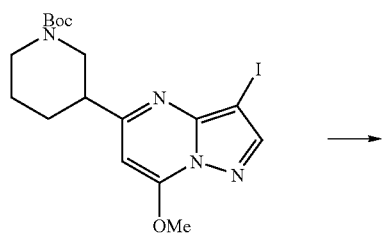

To a solution of 3-I adduct (0.40 g, 0.87 mmol) from Preparative Example 320-C in dioxane (3 mL) at rt was 2-tribu- tylstannylthiazole (0.40 g, 1.09 mmol) followed by Pd(PPh$_3$)$_4$ (63 mg, 0.055 mmol). The mixture was fitted with a condenser and was heated to 90° C. and was stirred at this temperature for 12 h. The mixture was cooled to rt and concentrated under reduced pressure. The crude product was purified by preparative thin-layer chromatography (6×1000 μM plates) using a 20:1 mixture of CH$_2$Cl$_2$/MeOH as eluent to afford 0.16 g (45% yield) as a yellow semisolid. LC-MS:=411.2 [M+H] 84% purity.

Preparative Example 350-C

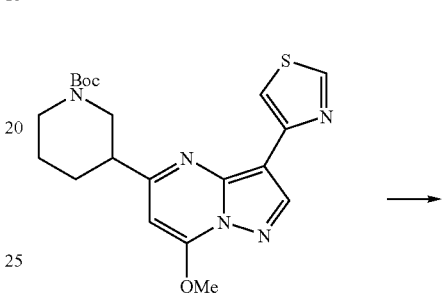

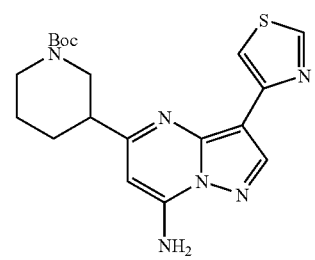

To a pressure tube charged with 7-methoxy adduct (0.18 g, 0.45 mmol) from Preparative Example 330-C and a stir bar was added 7M NH$_3$ in MeOH (5 mL). The tube was capped, heated to 80° C., and stirred for 72 h. The mixture was cooled to rt, concentrated under reduced pressure, and placed under high vacuum. The crude material was purified by preparative thin-layer chromatography (4×1000 μM plates) using a 20:1 mixture of CH$_2$Cl$_2$/MeOH (7M NH$_3$) as eluent to afford 120 mg (66% yield) of a yellow semisolid off-white solid. MS=401.2 [M+H].

Preparative Example 360-C

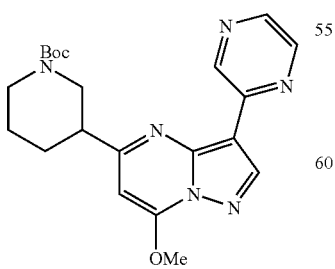

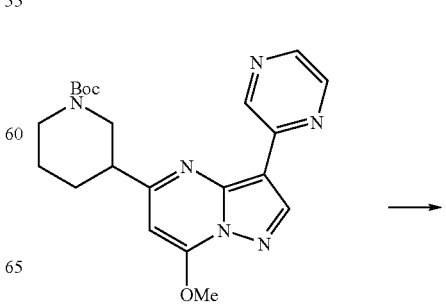

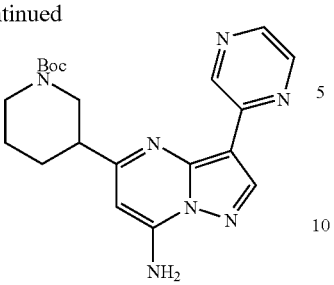

In an analogous fashion as described in Preparative Example 350-C, the 7-methoxy adduct (0.16 g, 0.39 mmol) from Preparative Example 340-C was converted to 52 mg (34% yield) of the title compound. LC-MS:=396.2 [M+H] 74% purity.

Example 170-C

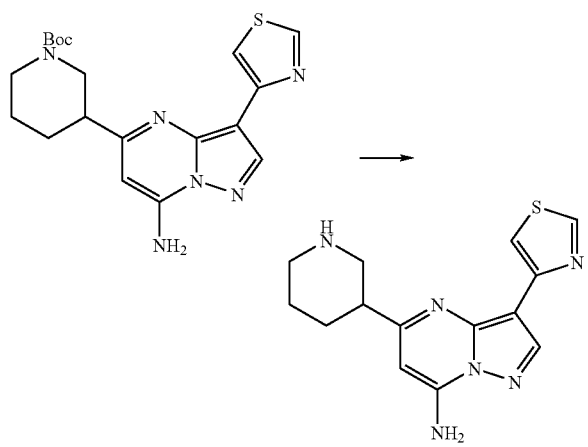

To a mixture of Boc adduct (0.12 g, 0.30 mmol) from Preparative Example 350-C in CH$_2$Cl$_2$ (2 mL) at rt was added TFA (0.4 mL) dropwise. The resulting mixture was stirred for 12 h, concentrated under reduced pressure, and placed under high vacuum to remove trace volatiles. The resulting semi-solid was dissolved in 7M NH$_3$ in MeOH (5 mL), stirred for 4 h, and concentrated under reduced pressure. The crude material was purified by preparative thin-layer chromatography (4×1000 μM plates) using a 6:1 mixture of CH$_2$Cl$_2$/MeOH (7M NH$_3$) as eluent to afford 67 mg (75% yield) of a white solid. mp 162-165° C.; MS =301.2 [M+H].

Example 180-C

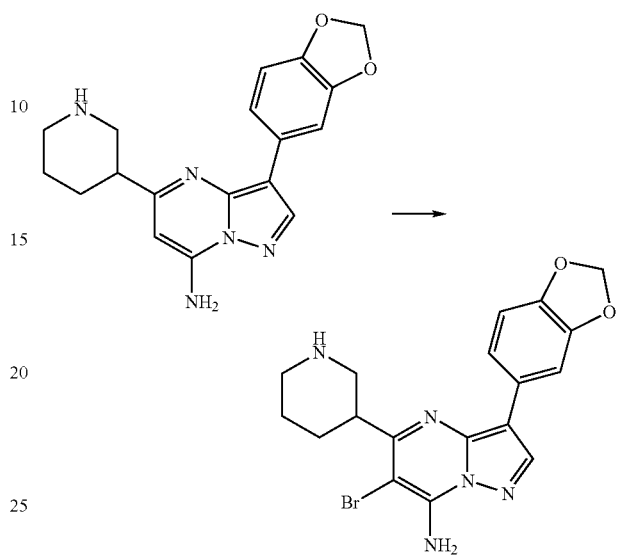

To a mixture of piperidine adduct (41 mg, 0.12 mmol) from Example 170-C in CH$_3$CN (2 mL) at rt was added NBS (22 mg, 0.12 mmol) in one portion. The resulting mixture was stirred for at 0° C. for 2 h and rt for 1 h. The mixture was concentrated under reduced pressure and placed under high vacuum to remove trace volatiles. The crude material was purified by preparative thin-layer chromatography (4×1000 μM plates) using a 12:1 mixture of CH$_2$Cl$_2$/MeOH (7M NH$_3$) as eluent to afford 27 mg (54% yield) of a light tan solid. mp 109-112° C.; MS=418.2 [M+H]; 85% purity.

Examples 190-C-220-C

Following the procedure set forth in Example 180-C utilizing the compounds in Column 2 of Table 40-C the substituted 6-Br pyrazolo[1,5-a]pyrimidine adducts in Column 3 of Table 40-C were prepared.

TABLE 40-C

| Ex. | Column 2 | Column 3 | 1. Yield (%) 2. LC-MS 3. mp (° C.) |
| --- | --- | --- | --- |
| 190-C | ☐ (4-CN phenyl adduct) | ☐ (6-Br, 4-CN phenyl adduct) | 1. 46 2. 397.2 3. 167-169 |

TABLE 40-C-continued
| Ex. | Column 2 | Column 3 | 1. Yield (%) 2. LC-MS 3. mp (° C.) |
|---|---|---|---|
| 200-C | | | 1. 28 2. 381.2 3. 178-180 |
| 210-C | | | 1. 50 2. 381.2 3. 178-182 |
| 220-C | | | 1. 42 2. 379.2 3. 75-77 |
Preparative Example 360-C
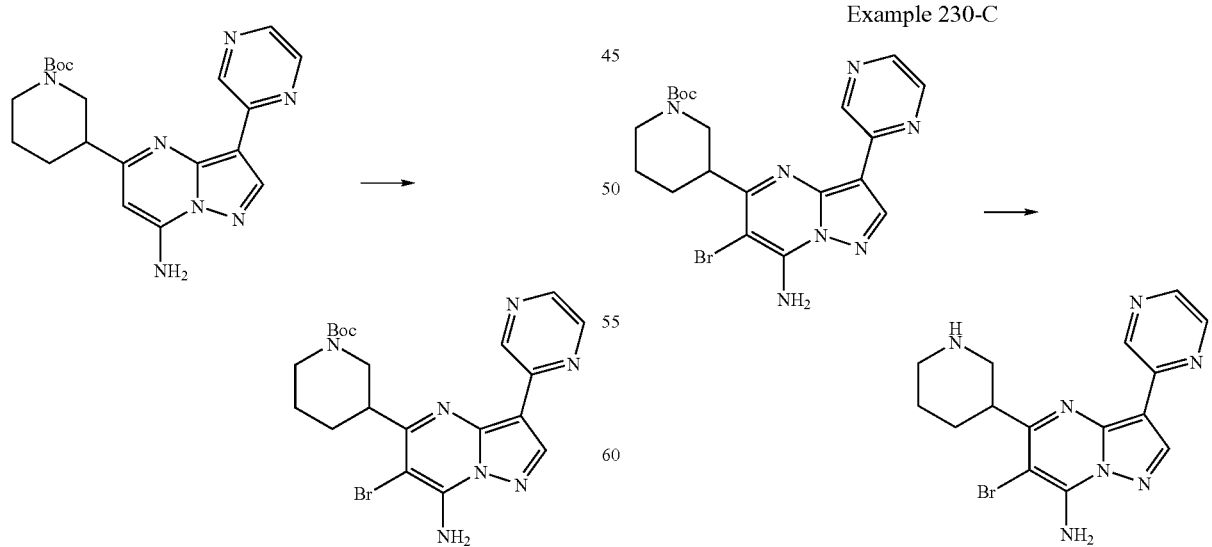
In an analogous fashion as described in Example 180-C, the 7-amino adduct (40 mg, 0.10 mmol) from Preparative Example 360-C was converted to 40 mg (83% yield) of the above compound. LC-MS:=476.3 [M+H] 98% purity.
Example 230-C
In an analogous fashion as described in Example 170-C, the 7-amino adduct (20 mg, 0.10 mmol) from Preparative Example 360-C was converted to 15 mg (94% yield) of a pale yellow solid. mp 144-146° C.; LC-MS:=374.1 [M+H] 90% purity.

Preparative Example 370-C

To a solution of 3-H adduct (0.50 g, 0.87 mmol) from Preparative Example 50-C in DMF (5.4 mL) at 0° C. was added POCl₃ (0.13 mL, 1.39 mmol) dropwise. The resulting solution was stirred at rt for 12 h and then was recooled to 0° C. 1 N NaOH (5 mL) and CH₂Cl₂ (10 mL) were carefully added the layers were separated. The aqueous layer was extracted with CH₂Cl₂ (2×10 mL) and the organic layers were combined. The organic layer was dried (Na₂SO₄), filtered, and concentrated under reduced pressure. The crude material was purified by preparative thin-layer chromatography (6×1000 µM plates) using a 2:1 mixture of hexanes/EtOAc to afford 90 mg (17% yield) of a light yellow semisolid. MS=606.3 [M+H].

Preparative Example 380-C

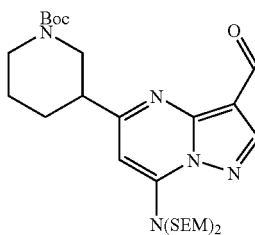

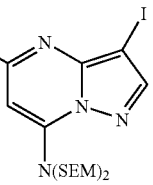

To a solution of 3-formyl adduct (90 mg, 0.15 mmol) from Preparative Example 370-C in MeOH (1.5 mL) at rt was added Tos-Mic (29 mg, 0.15 mmol) and K₂CO₃ (21 mg, 0.15 mmol). The mixture was affixed with a condenser and was heated to reflux. After 4 h, the mixture was cooled to rt and concentrated under reduced pressure. The resultant semisolid was partitioned between CH₂Cl₂ (3 mL) and water (1 mL). The layers were separated and the aqueous layer was extracted with CH₂Cl₂ (2×10 mL). The organic layers were combined and washed with brine (1×5 mL). The organic layer was dried (Na₂SO₄), filtered, and concentrated under reduced pressure. The crude material was purified by preparative thin-layer chromatography (4×1000 µM plates) using a 40:1 mixture of CH₂Cl₂/MeOH (7M NH₃) to afford 67 mg (69% yield) of an orange/brown solid. LC-MS=606.3 [M+H] 93% purity.

Preparative Example 390-C

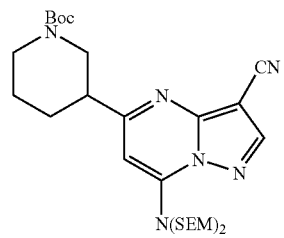

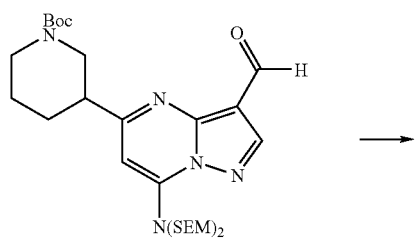

To a round bottom flask charged with 3-I adduct (0.25 g, 0.35 mmol) from Preparative Example 60-C, KCN (26 mg, 0.40 mmol), CuI (20 mg, 0.035 mmol), Pd(PPh₃)₄ (8 mg, 0.035 mmol) and stir bar was added degassed THF (9 mL). The mixture was heated to reflux and was stirred for 5 h (until complete by TLC). The mixture was cooled to rt and diluted with EtOAc (5 mL). The mixture was filtered thru a pad of Celite which was subsequently washed with EtOAc (2×5 mL). The resulting filtrate was washed sequentially with water (2×2 mL) and brine (2×2 mL). The organic layer was dried (Na₂SO₄), filtered, and concentrated under reduced pressure. The crude material was purified by preparative thin-layer chromatography (4×1000 µM plates) using a 50:1 mixture of CH₂Cl₂/MeOH to afford 169 mg (80% yield) of a light yellow semisolid. LC-MS=606.3 [M+H]; 94% purity.

Preparative Example 400-C

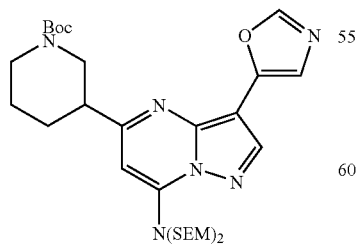

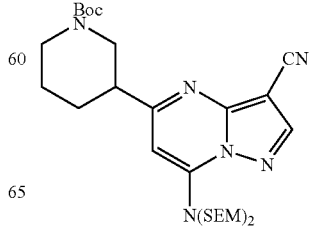

-continued

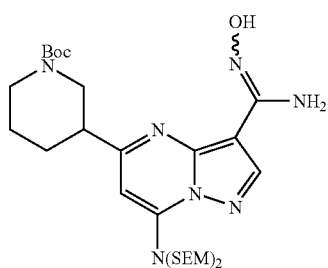

To a solution of 3-CN adduct (0.15 g, 0.25 mmol) from Preparative Example 390-C was added NaHCO₃ (84 mg, 1.0 mmol) and hydroxylamine hydrochloride (35 mg, 0.50 mmol). The mixture was affixed with a condenser and was heated to reflux and stirred for 12 h at this temperature. The mixture was cooled to rt and filtered thru a medium sintered-glass funnel. The resulting ppt was washed with MeOH (2×5 mL) and the resultant filtrate was concentrated under reduced pressure to afford 155 mg (97% yield) of a yellow solid. LC-MS=636.3 [M+H]; 80% purity. This material was carried on without further purification.

Preparative Example 410-C

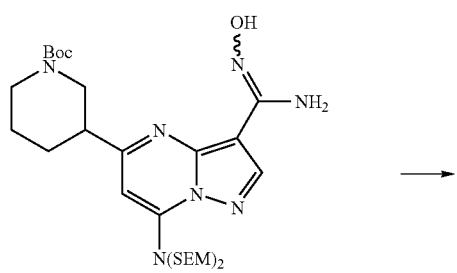

A solution of amidooxime adduct (0.17 g, 0.25 mmol) from Preparative Example 400-C in triethylorthoformate (3 mL) was heated at 80° C. for 12 h. The mixture was cooled to rt whereupon PPTS (94 mg, 0.38 mmol) was added and the mixture was reheated to 80° C. and stirred for 4 h. The mixture was cooled to rt and was concentrated under reduced pressure. The crude material was purified by preparative thin-layer chromatography (6×1000 µM plates) using a 50:1 mix- ture of CH₂Cl₂/MeOH to afford 110 mg (68% yield) of a light yellow semisolid. LC-MS=646.4 [M+H]; 65% purity.

Preparative Example 420-C

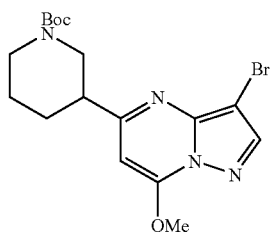 

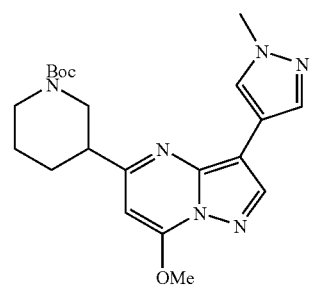

To a mixture of Boc derivative (3.0 g, 7.3 mmol) from Preparative Example 310-C in DME/H₂O (16 mL/4 mL) was added 1-methyl4-(4,4,5,5-tetramethyl-1,3,2-dioxaborolan-2yl)-1H-pyrazole (2.8 g, 13.5 mmol) and Na₂CO₃ (3.9 g, 36.4 mmol). N₂ was bubbled thru the solution for 20 min with stirring whereupon PdCl₂(PPh₃)₂ (0.39 g, 0.47 mmol) was added. The mixture was heated to 110° C. and was stirred for 12 h. The mixture was cooled to rt, concentrated under reduced pressure and placed under high vacuum. The crude product was purified by flash chromatography using a 30:1 mixture of CH₂Cl₂/MeOH as eluent to afford 1.57 g (52% yield) as an orange/brown solid. LC-MS:=413.2 [M+H] 97% purity.

Preparative Example 420-C

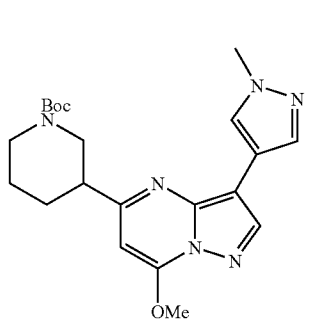 

-continued

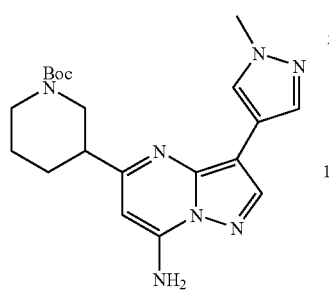

In an analogous fashion as described in Preparative Example 350-C, the 7-methoxy adduct (2.0 g, 4.8 mmol) from Preparative Example 420-C was converted to 600 mg (32% yield) of the title compound. LC-MS:=398.2 [M+H]; 93% purity.

Preparative Example 430-C

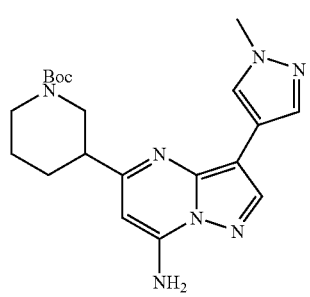

To a solution of Boc adduct (0.60 g, 1.51 mmol) from Preparative Example 420-C in CH₂Cl₂ (10 mL) at rt was added DMAP (0.21 g, 1.7 mmol) followed by Boc₂O (0.36 g, 1.7 mmol). The mixture was allowed to warm to rt and stir for 12 h. The mixture was washed with water (2×3 mL) and brine (2×3 mL). The organic layer was dried (Na₂SO₄), filtered, and concentrated under reduced pressure. The crude material was purified by preparative TLC using 6×1000 mM plates with 20:1 CH₂Cl₂/MeOH (7N NH₃) as eluent to afford 0.35 g (47% yield) as an off-white solid. LC-MS:=498.3 [M+H]; 99% purity.

Preparative Example 440-C

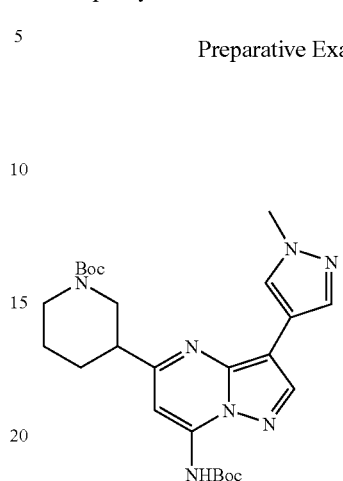

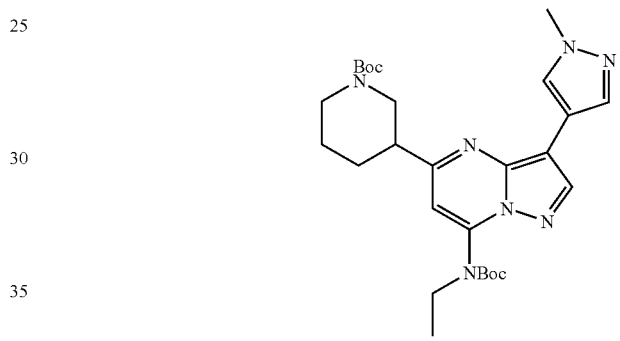

To a solution of Boc adduct (0.10 g, 0.20 mmol) from Preparative Example 430-C in CH₃CN (3 mL) at rt was added K₂CO₃ (55 mg, 0.40 mmol) followed by EtI (24 μL, 0.31 mmol). The mixture stirred at rt for 12 h and was filtered thru a glass-sintered funnel. The ppt was washed with CH₃CN (10 mL) and the filtrate was concentrated under reduced pressure. The crude material was purified by preparative TLC using 2×1000 mM plates with 1:2 hexanes/EtOAc as eluent to afford 70 mg (67% yield) as an off-white solid. LC-MS:=526.3 [M+H]; >85% purity.

Preparative Example 450-C

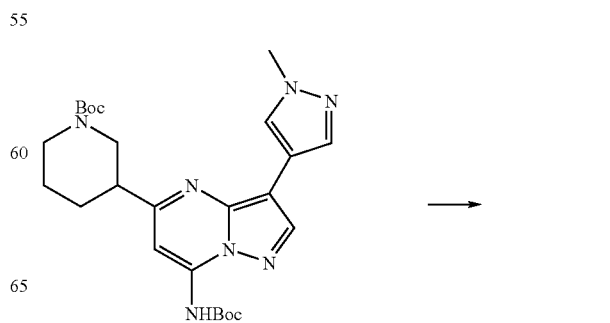

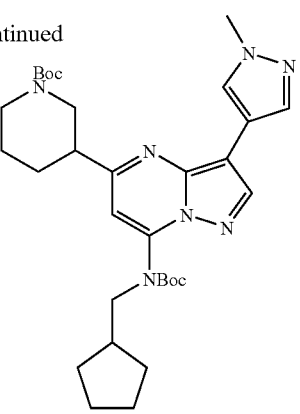

Utilizing the procedure in Preparative Example 440-C, the Boc adduct (0.12 g, 0.24 mmol) from Preparative Example 430-C was treated with cyclopentylmethyl iodide (0.11 g, 0.48 mmol) to afford 50 mg (40% yield) of the title compound. LC-MS:=580.3 [M+H]; 89% purity.

Preparative Example 460-C

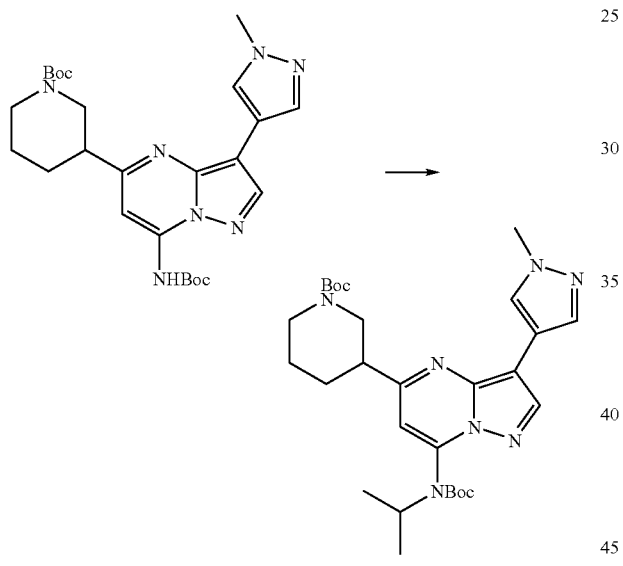

Utilizing the procedure in Preparative Example 440-C, the Boc adduct (0.10 g, 0.20 mmol) from Preparative Example 430-C was treated with 2-iodopropane (30 μL, 0.30 mmol) to afford 75 mg (32% yield) of the title compound. LC-MS:=540.3 [M+H]; 23% purity.

Preparative Example 470-C

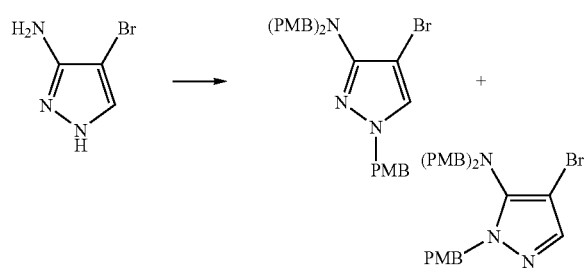

3-Amino4-bromopyrazole (5 g, 30.9 mmol) and 4-methoxybenzyl chloride (21 g, 134 mmol, 4.3 equiv.) were combined in anhydrous DMF (25 mL) and added dropwise to a stirred suspension of sodium hydride (60% dispersion in mineral oil, 6.25 g, 156 mmol, 5 equiv.) in anhydrous DMF (50 mL). The resulting suspension was stirred 2 days at room temperature. Water (300 mL) was added slowly and the resulting mixture was extracted with ether (4×350 mL). The organic layers were combined, washed with brine, dried over anhydrous sodium sulfate and concentrated under reduced pressure. The crude product was dissolved in dichloromethane and purified by silica gel chromatography using a gradient from 10% to 20% ethyl acetate-hexanes. The product, a white solid, is obtained as a 60:40 mixture of the 1-benzylated-1H product and the 2-benzylated-2H product (14.96 g total, 93% yield).

Preparative Example 480-C

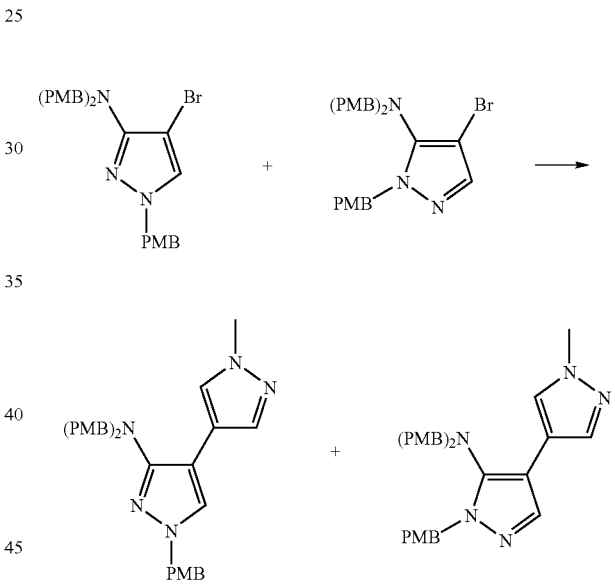

The compound from Preparative Example 470-C (10 g, 19.15 mmol) and 1-methyl-4-(4,4,5,5-tetramethyl-1,3,2-dioxaborolan-2-yl)-1H-pyrazole (11.95 g, 57.42 mmol, 3.0 equiv.) were combined in 120 mL dimethoxyethane. 2M sodium carbonate solution (30 mL, 60 mmol, 3.1 equiv.) was added followed by tetrakis(triphenylphosphine)palladium(0) (2.36 g, 2.04 mmol, 0.11 equiv.). The mixture was stirred 16 hours at 90° C. After cooling to room temperature, water (200 mL) and brine (50 mL) were added and the mixture was extracted with ethyl acetate (2×200 mL). The extracts were combined, washed with brine, dried over anhydrous sodium sulfate and concentrated under reduced pressure. The crude product was dissolved in dichloromethane and purified by silica gel chromatography using a gradient from 33% to 66% ethyl acetate-hexanes. The 1-benzylated-1H product ($R_f$=0.27 in 66% ethyl acetate-hexanes) elutes first, followed by the 2-benzylated-2H-product ($R_f$=0.19 in 66% ethyl acetate-hexanes). The product is obtained as a yellow solid (5.60 g total, 56% yield) with an isomeric ratio of 62:38.

Preparative Example 490-C:

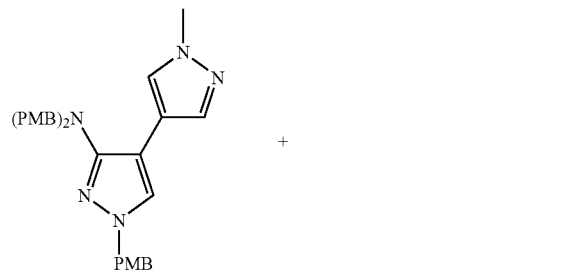

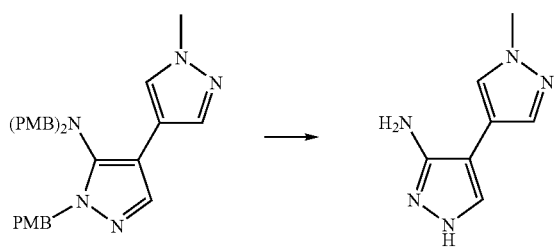

The compound from Preparative Example 480-C (4.3 g, 8.22 mmol) was dissolved in trifluoroacetic acid (70 mL) and stirred 17 hours at reflux. After cooling, the trifluoroacetic acid was removed under reduced pressure. The resulting residue was dissolved in tetrahydrofuran (100 mL), methanol (50 mL) and 4N aqueous sodium hydroxide solution (25 mL, 100 mmol, 12 equiv.). The mixture was stirred 4 hours at 70° C. then cooled to room temperature. The mixture was concentrated and the residue was suspended in brine (100 mL) and water (40 mL). This mixture was extracted with 20% isopropanol in ethyl acetate (8×100 mL). The extracts were combined, dried over anhydrous sodium sulfate, filtered and concentrated under reduced pressure. The crude product was dissolved in 10% methanol in dichloromethane and purified by silica gel chromatography using 10% methanol-dichloromethane followed by 10% 7N ammonia in methanol-dichloromethane. The product is obtained as a tan to brown solid (1.03 g, 77% yield).

Preparative Example 490-C

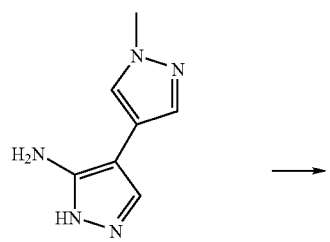

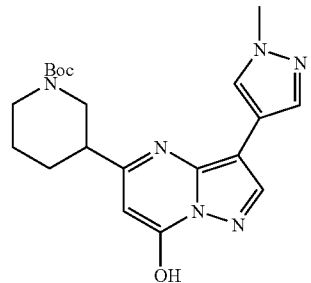

To a solution of aminopyrazole (0.74 g, 4.5 mmol) from Preparative Example 490-C in toluene (40 mL) in a pressure tube at rt was added β-keto ester (1.5 g, 5.0 mmol) from Preparative Example 10-C. The pressure tube was capped and heated to 110° C. and was stirred for 12 h. The mixture was cooled to rt and was concentrated under reduced pressure. The material was taken on crude to the next transformation. LC-MS:=399.2 [M+H]; 70% purity.

Preparative Example 500-C

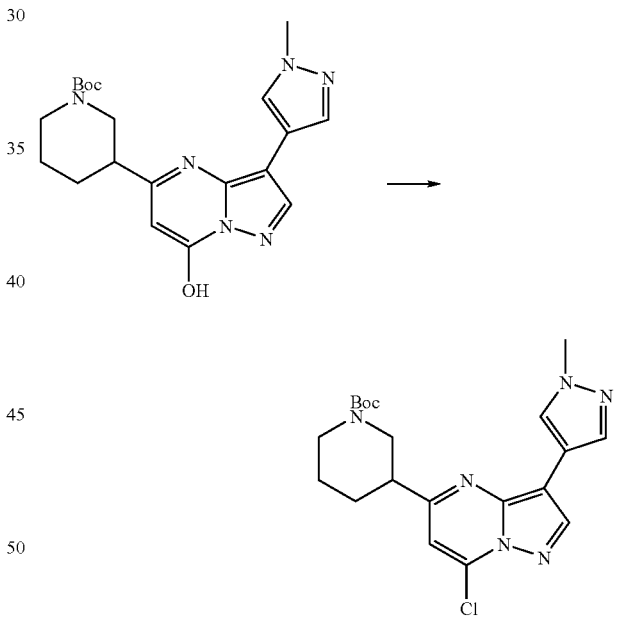

To a solution of 7-hydroxyl adduct (1.84 g, 4.5 mmol) from Preparative Example 490-C in POCl$_3$ (13 mL, 0.14 mol) at rt was added N,N-dimethylaniline (2 mL, 15.8 mmol). The resulting solution was stirred at rt for 12 h (until complete by TLC) and was concentrated under reduced pressure. The crude material was cooled to 0° C. and was treated with CH$_2$Cl$_2$ (50 mL) and sat. aq. NaHCO$_3$ (10 mL). The layers were separated and the aqueous layer was extracted with CH$_2$Cl$_2$ (2×50 mL). The organic layers were combined, dried (Na$_2$SO$_4$), filtered, and concentrated under reduced pressure. The crude product was purified by flash chromatography using a 1:1 mixture of hexanes/CH$_2$Cl$_2$ as eluent to afford 1.4 g (96% yield) of a brown semisolid. LC-MS:=317.2 [M+H]; 95% purity.

Preparative Example 510-C

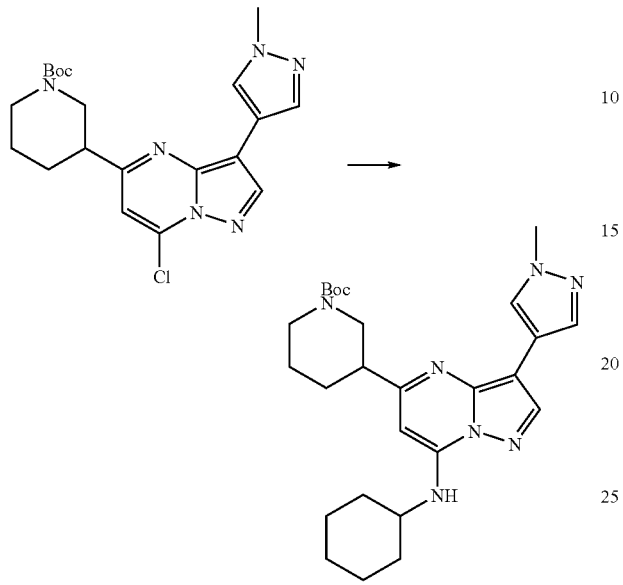

To a solution of 7-chloro adduct (30 mg, 0.072 mmol) from Preparative Example 500-C in dioxane (1 mL) was added DIPEA (25 µL, 0.14 mmol) followed by cyclohexylamine (13 µL, 0.11 mmol). The mixture was heated to 90° C. and stirred for 3 h (until complete by TLC). The mixture was cooled to rt, concentrated under reduced pressure, and placed under high vacuum. The crude product was purified by flash chromatography using a 20:1 mixture of CH$_2$Cl$_2$/MeOH to afford 24 mg (69% yield) of an orange semisolid. MS=480.3 [M+H].

Preparative Examples 520-C-560-C

Following the procedure set forth in Preparative Example 510-C but utilizing the amines in Column 2 of Table 50-C, the substituted pyrazolo[1,5-a]pyrimidine adducts in Column 3 of table 50-C were prepared

TABLE 50-C

| Prep. Ex. | Column 2 | Column 3 | 1. Yield (%) 2. MS |
|---|---|---|---|
| 520-C | | | 1. 80 2. 454.4 |
| 530-C | | | 1. 72 2. 581.6 |
| 540-C | | | 1. 89 2. 466.4 |
| 550-C | | | 1. 79 2. 511.3 |
| 560-C | | | 1. 60 2. 425.5 |

Preparative Example 570-C

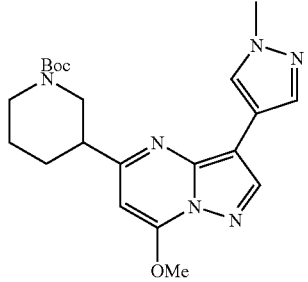

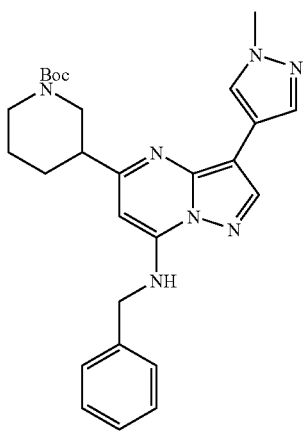

To a solution of 7-methoxy adduct (0.10 g, 0.24 mmol) from Preparative Example 420-C in dioxane (1 mL) was added benzylamine (0.13 mL, 1.2 mmol). The mixture was heated to 90° C. and stirred for 72 h (until complete by TLC). The mixture was cooled to rt, concentrated under reduced pressure, and placed under high vacuum. The crude product was purified by flash chromatography using a 20:1 mixture of CH$_2$Cl$_2$/MeOH to afford 25 mg (21% yield) of an orange semisolid. LC-MS=488.3 [M+H]; 65% purity.

Preparative Example 580-C

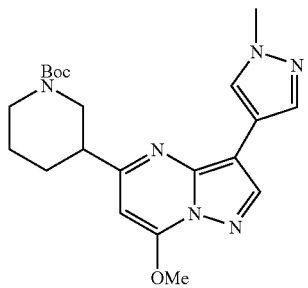

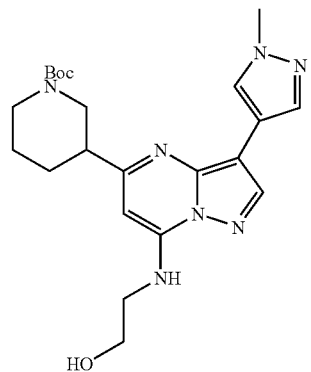

To a soln of ethanolamine (26 μL, 0.44 mmol) in dry DMSO (2 mL) at rt was added 60% NaH in oil (17 mg, 0.44 mmol) in one portion. The resulting mixture was stirred for 15 min at rt where upon the 7-methoxy adduct (0.09 g, 0.22 mmol) from Preparative Example 420-C was added in a single portion. The mixture was stirred for 72 h at rt and quenched with sat. aq. NH$_4$Cl (1 mL). The mixture was extracted with a mixture of 10% IPA/CH$_2$Cl$_2$ (3×5 ml) and the organic layers were combined. The organic layer was washed with brine (1×3 mL), dried (Na$_2$SO$_4$), filtered and concentrated under reduced pressure. The crude product was purified by flash chromatography using a 20:1 mixture of CH$_2$Cl$_2$/MeOH (7M NH$_3$) to afford 120 mg (81% yield) of an orange semisolid. LC-MS=442.2 [M+H]; 85% purity.

Preparative Example 590-C

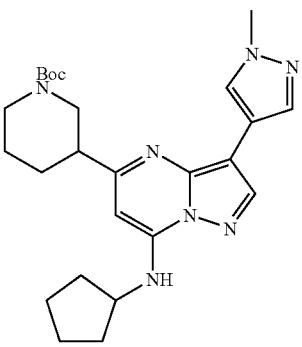

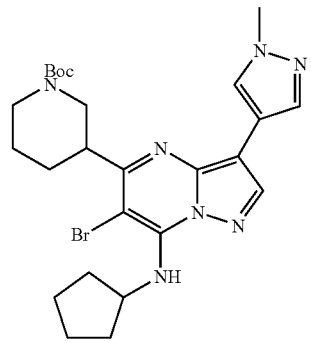

To a solution of Boc adduct (25 mg, 0.054 mmol) from Preparative Example 540-C in CH$_2$Cl$_2$ (5 mL) at rt was added t-BuNH$_2$ (0.17 mL, 1.60 mmol). The mixture was stirred for 15 min whereupon Br$_2$ (2.5 mL, 0.048 mmol) was added dropwise and the reaction was stirred for 10 min (until complete by TLC). The mixture was concentrated to dryness and the crude product was purified by preparative thin-layer chromatography using 2×1000 mM plates with a 99:1 mixture of CH$_2$Cl$_2$/MeOH (7M NH$_3$) as eluent to afford 27 mg (92% yield) of an orange semisolid. LC-MS=545.3 [M+H]; 86% purity.

Preparative Examples 600-C-620-C

Following the procedure set forth in Preparative Example 590-C but utilizing the corresponding Boc precursors in Column 2 of Table 60-C, the substituted pyrazolo[1,5-a]pyrimidine adducts in Column 3 of Table 60-C were prepared.

TABLE 60-C

| Prep. Ex. | Column 2 | Column 3 | 1. Yield (%) 2. LC-MS |
|---|---|---|---|
| 600-C | | | 1. 84 2. 504.4 |
| 610-C | | | 1. 95 2. 558.3 |
| 620-C | | | 1. 87 2. 589.3 |

Example 240-C

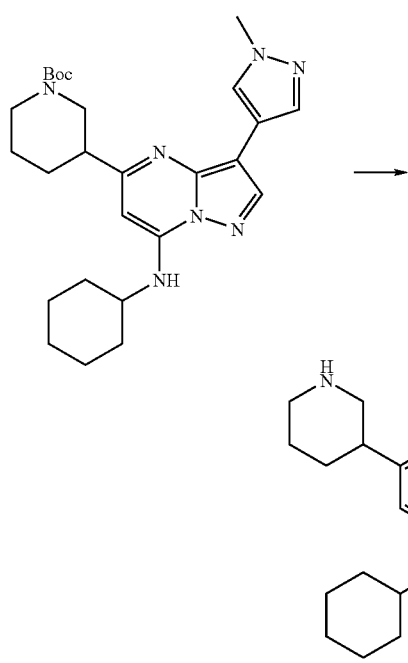

To a mixture of Boc adduct (23 mg, 0.048 mmol) from Preparative Example 520-C in CH$_2$Cl$_2$ (1 mL) at rt was added TFA (0.25 mL) dropwise. The resulting mixture was stirred for 2 h, concentrated under reduced pressure, and placed under high vacuum to remove trace volatiles. The resulting semisolid was dissolved in 7M NH$_3$ in MeOH (5 mL), stirred for 4 h, and concentrated under reduced pressure. The crude material was purified by preparative thin-layer chromatography (4×1000 μM plates) using a 6:1 mixture of CH$_2$Cl$_2$/MeOH (7M NH$_3$) as eluent to afford 14 mg (77% yield) of a pale yellow solid. mp 131-133° C.; MS=380.2 [M+H].

Examples 250-C-370-C

Following the procedure set forth in Example 240-C utilizing the indicated Boc precursors in Column 2 of Table 70-C, the substituted pyrazolo[1,5-a]pyrimidine adducts in Column 3 of Table 70-C were prepared.

TABLE 70-C

| Ex. | Column 2 | Column 3 | 1. Yield (%) 2. LC-MS 3. mp (° C.) |
|---|---|---|---|
| 250-C | | | 1. 99 2. 326.2 3. 121-124 |
| 260-C | | | 1. 86 2. 380.3 3. 118-121 |

TABLE 70-C-continued

| Ex. | Column 2 | Column 3 | 1. Yield (%) 2. LC-MS 3. mp (° C.) |
|---|---|---|---|
| 270-C | | | 1. 94 2. 366.2 3. 128-131 |
| 280-C | | | 1. 65 2. 354.2 3. 116-118 |
| 290-C | | | 1. 34 2. 340.2 3. 165-167 |
| 300-C | | | 1. 12 2. 381.3 3. 166-168 |

US 7,605,155 B2
TABLE 70-C-continued
| Ex. | Column 2 | Column 3 | 1. Yield (%)<br>2. LC-MS<br>3. mp (° C.) |
|---|---|---|---|
| 310-C | 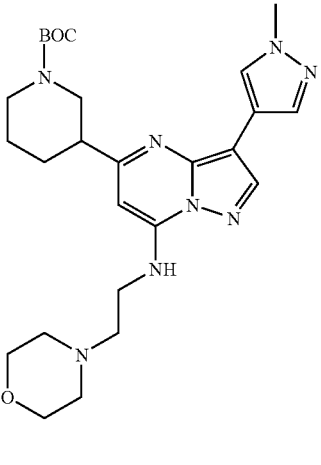 | 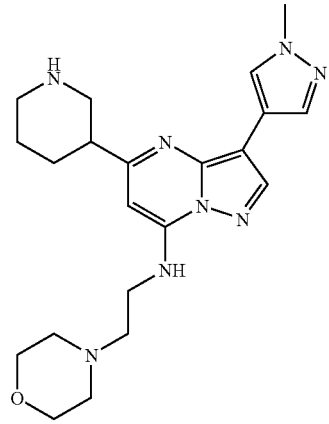 | 1. 99<br>2. 411.3<br>3. 148-151 |
| 320-C | 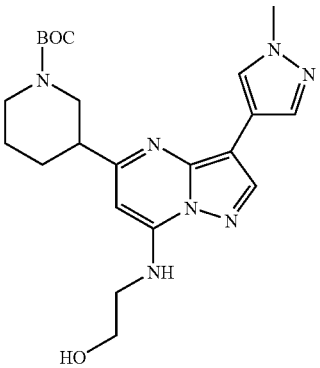 | 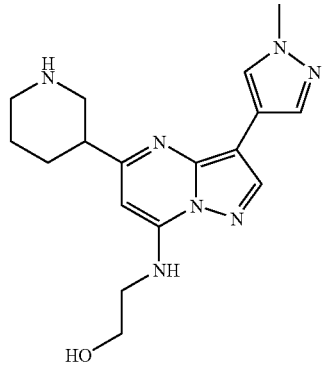 | 1. 42<br>2. 342.2<br>3. 114-116 |
| 330-C | 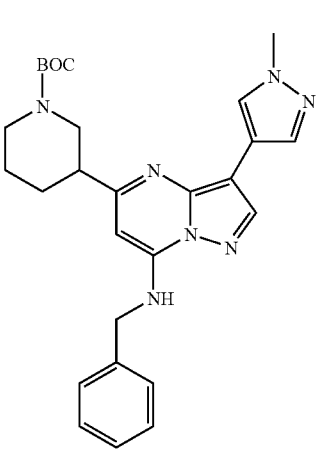 | 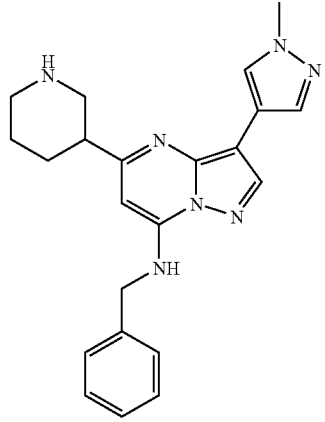 | 1. 36<br>2. 388.3<br>3. 146-148 |

TABLE 70-C-continued

| Ex. | Column 2 | Column 3 | 1. Yield (%) 2. LC-MS 3. mp (° C.) |
|---|---|---|---|
| 340-C | | | 1. 38 2. 444.4 3. 128-131 |
| 350-C | | | 1. 38 2. 404.2 3. 136-138 |
| 360-C | | | 1. 43 2. 458.2 3. 145-148 |
| 370-C | | | 1. 97 2. 489.2 3. 166-168 |

Example 380-C

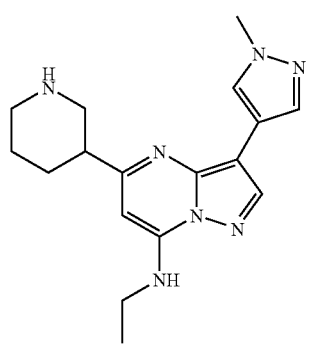

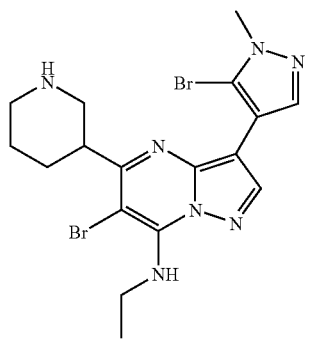

To a mixture of ethyl adduct (65 mg, 0.20 mmol) from Example 24 in CH₃CN (3 mL) at rt was added NBS (32 mg, 0.18 mmol) in a single portion. The resulting mixture was stirred for 1 h, concentrated under reduced pressure, and placed under high vacuum to remove trace volatiles. The crude material was purified by preparative thin-layer chromatography (2×1000 μM plates) using a 10:1 mixture of CH₂Cl₂/MeOH (7M NH₃) as eluent to afford 3 mg (3% yield) of a yellow brown solid. LC-MS=484.3 [M+H]; >80% purity.

Preparative Example 700-C

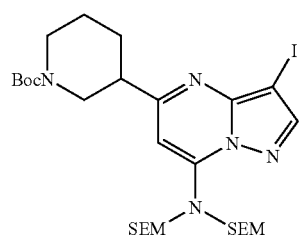

-continued

A mixture of the product from Preparative Example 60-C (1.50 g, 2.13 mmol), 1-methyl-4-(4,4,5,5-tetramethyl-1,3,2-dioxaborolan-2-yl)-1H-pyrazole (0.89 g, 4.26 mmol), PdCl₂dppf.CH₂Cl₂ (171 mg, 0.21 mmol), and K₃PO₄ (1.81 g, 8.52 mmol) in 1,2-dimethoxyethane (30 mL) and H₂O (6 mL) was stirred and refluxed under N₂ for 3 hr. The solvents were evaporated and the residue was purified by column chromatography on silica gel with 5:1 CH₂Cl₂/EtOAc as eluent. Yellow wax (1.13 g, 81%) was obtained.

Preparative Example 710-C

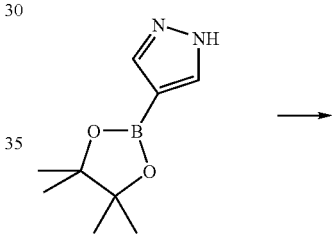

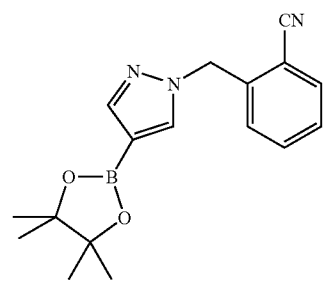

A mixture of 4,4,5,5-tetramethyl-2-(1H-pyrazol-4-yl)-1,3,2-dioxaborolane (0.50 g, 2.58 mmol), 2-(bromomethyl)benzonitrile (0.63 g, 3.21 mmol), and K₂CO₃ (1.06 g, 7.68 mmol) in acetonitrile (60 mL) was stirred and refluxed under N₂ for 72 hr. The solvents were evaporated and the residue was purified by column chromatography on silica gel with 2:1 CH₂Cl₂/EtOAc as eluent. Yellow wax (0.75 g, 94%) was obtained. LC-MS: 310 [M+H].

Preparative Example 720-C-770-C

By essentially same procedures set forth in Preparative Example 710-C only using different alkylating agents given in Column 1, compounds given in Column 2 of Table 100-C were prepared.

TABLE 100-C

| Ex. | Column 1 | Column 2 | Data |
|---|---|---|---|
| 720-C | ethyl 2-chloro-2-phenylacetate | ethyl 2-phenyl-2-[4-(4,4,5,5-tetramethyl-1,3,2-dioxaborolan-2-yl)-1H-pyrazol-1-yl]acetate | LCMS: MH$^+$ = 357 |
| 730-C | 4-(chloromethyl)pyridine ·HCl | 1-(pyridin-4-ylmethyl)-4-(4,4,5,5-tetramethyl-1,3,2-dioxaborolan-2-yl)-1H-pyrazole | LCMS: MH$^+$ = 286 |
| 740-C | 3-(chloromethyl)pyridine ·HCl | 1-(pyridin-3-ylmethyl)-4-(4,4,5,5-tetramethyl-1,3,2-dioxaborolan-2-yl)-1H-pyrazole | LCMS: MH$^+$ = 286 |
| 750-C | 2-(chloromethyl)pyridine ·HCl | 1-(pyridin-2-ylmethyl)-4-(4,4,5,5-tetramethyl-1,3,2-dioxaborolan-2-yl)-1H-pyrazole | LCMS: MH$^+$ = 286 |
| 760-C | 2-iodopropane | 1-isopropyl-4-(4,4,5,5-tetramethyl-1,3,2-dioxaborolan-2-yl)-1H-pyrazole | LCMS: MH$^+$ = 237 |
| 770-C | 2-chloro-N,N-dimethylacetamide | N,N-dimethyl-2-[4-(4,4,5,5-tetramethyl-1,3,2-dioxaborolan-2-yl)-1H-pyrazol-1-yl]acetamide | LCMS: MH$^+$ = 280 |

Example 400-C

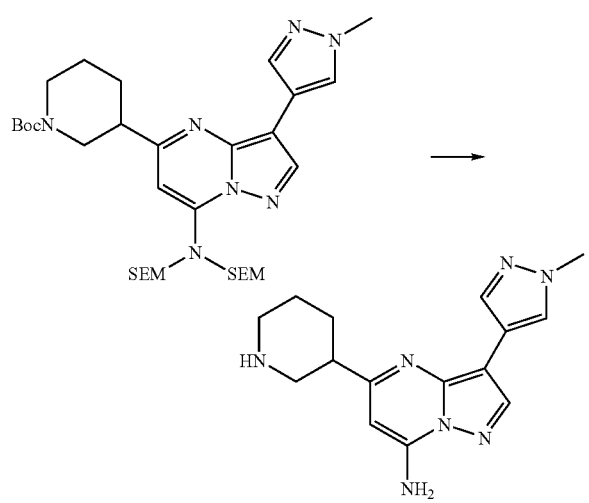

A mixture of the product from Preparative Example 700-C (1.00 g) and 3N aqueous HCl (20 mL) in EtOH (20 mL) was stirred at 60° C. for 1.5 hr. The solvents were evaporated, $Na_2CO_3$ (2.0 g) and 6:1 mixture of $CH_2Cl_2$/MeOH (20 mL) were added to the residue and the mixture was stirred under $N_2$ for 15 min. Then it was loaded onto a column and it was purified by column chromatography on silica gel with 6:1 $CH_2Cl_2$/7N $NH_3$ in MeOH as eluent. White solid (405 mg, 90%) was obtained. LC-MS: 298 [M+H].

Examples 410-C-530-C

By essentially same procedures set forth in Preparative Example 700-C and Example 400-C only using different boron reagents given in Column 1 for the Suzuki couplings with the intermediate from Preparative Example 60-C, compounds given in Column 2 of Table 110-C were prepared.

TABLE 110-C

| Ex. | Column 1 | Column 2 | Data |
|---|---|---|---|
| 410-C | (isoxazole boronic acid pinacol ester) | (piperidinyl-pyrazolopyrimidine with isoxazole) | LCMS: $MH^+ = 285$<br>Mp = 161-164° C. |
| 420-C | (TBS-protected hydroxyethyl pyrazole boronic acid) | (piperidinyl-pyrazolopyrimidine with hydroxyethyl pyrazole) | LCMS: $MH^+ = 328$ |
| 430-C | (5-cyanopyridine-3-boronic acid) | (piperidinyl-pyrazolopyrimidine with cyanopyridine) | LCMS: $MH^+ = 320$ |

TABLE 110-C-continued
| Ex. | Column 1 | Column 2 | Data |
|---|---|---|---|
| 440-C | 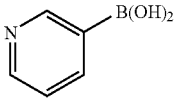 | 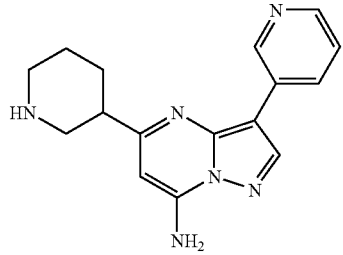 | LCMS: MH$^+$ = 295 |
| 450-C | 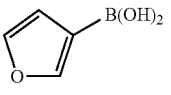 | 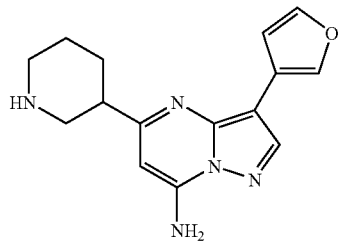 | LCMS: M$^+$ = 284 waxy solid |
| 460-C | 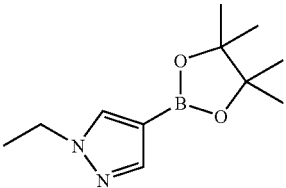 | 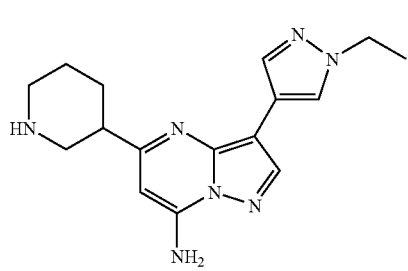 | LCMS: M$^+$ = 390 |
| 470-C | 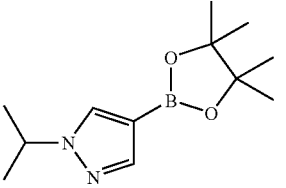 | 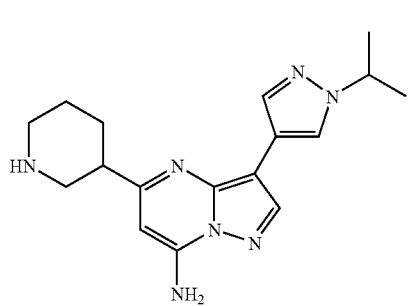 | LCMS: MH$^+$ = 326 wax |
| 480-C | 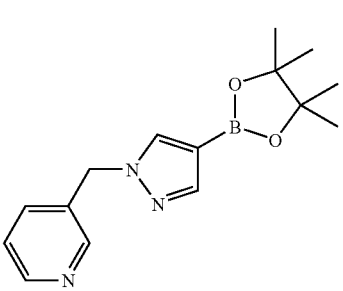 | 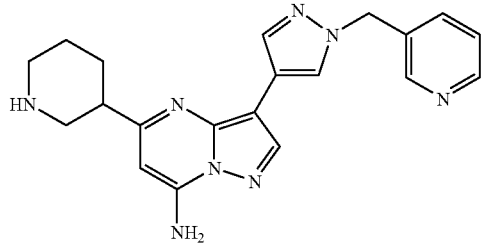 | LCMS: MH$^+$ = 375 wax |

TABLE 110-C-continued

| Ex. | Column 1 | Column 2 | Data |
|---|---|---|---|
| 490-C | | | LCMS: MH⁺ = 375 |
| 500-C | | | LCMS: MH⁺ = 375 |
| 510-C | | | LCMS: MH⁺ = 399 wax |
| 520-C | | | LCMS: MH⁺ = 446 |
| 530-C | | | LCMS: MH⁺ = 369 wax |

Preparative Example 770-C

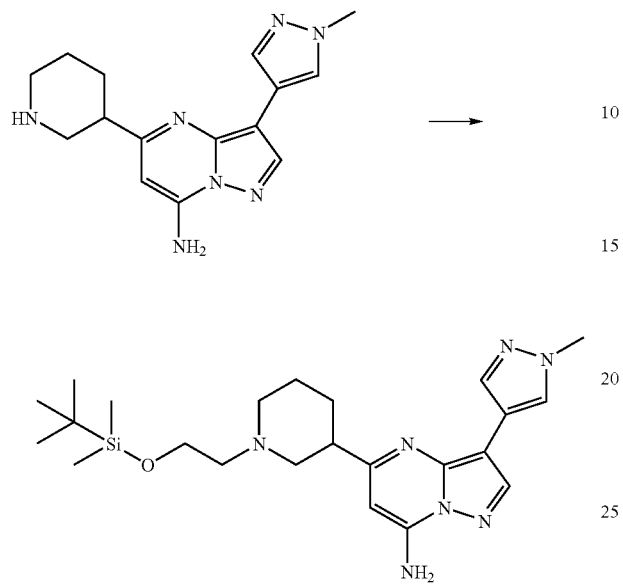

A mixture of the product from Example 400-C (0.30 g, 1.00 mmol) and (tert-butyldimethylsilyloxy)acetaldehyde (0.17 g, 1.00 mmol) in CH2Cl2 (5 mL) and MeOH (1 mL) was stirred at 25° C. for 18 hr. NaBH(OAc)3 (0.36 g, 1.7 mmol) was then added and the mixture was stirred for 1 hr. The solvents were evaporated and the mixture was purified by column chromatography on silica gel with 10:1 $CH_2Cl_2$/MeOH as eluent. Waxy solid (60 mg, 13%) was obtained. LC-MS: 456 [M+].

Example 540-C

By essentially same procedure set forth in Example 400-C, starting from compound from Preparative Example 770-C, the title compound was prepared. Waxy solid. LC-MS: 342 [M+H].

Example 550-C

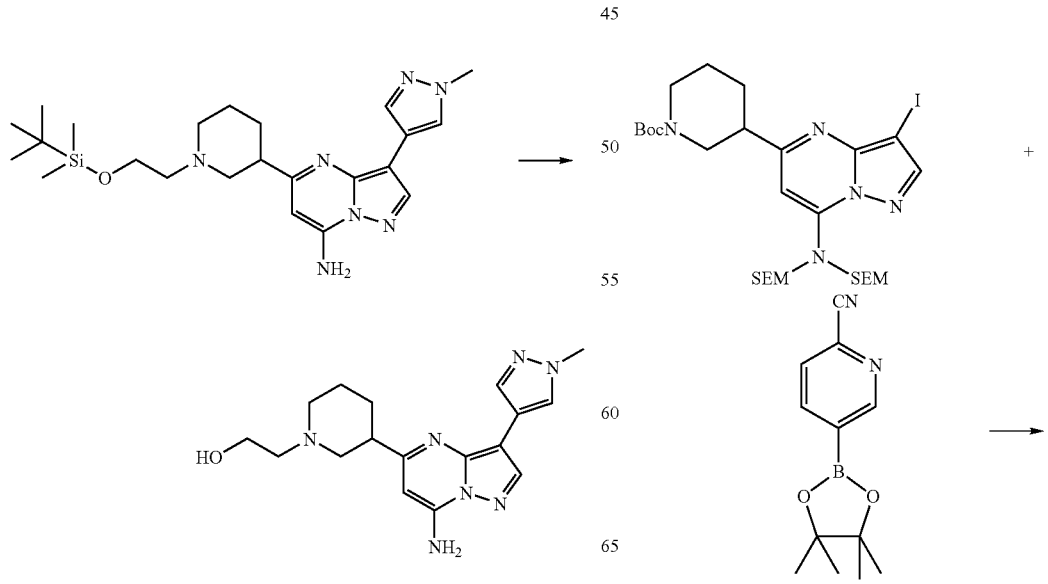

A solution of N-iodosuccinimide (33 mg, 0.15 mmol) in anhydrous $CH_3CN$ (2 mL) was added under $N_2$ to a stirred solution of the product from Example 400-C (50 mg, 0.17 mmol) in anhydrous $CH_3CN$ (3 mL) and $CH_2Cl_2$ (5 mL). The mixture was stirred for 1 hr, the solvents were evaporated, and the residue was purified by column chromatography on silica gel with 15:1 $CH_2Cl_2$/7N $NH_3$ in MeOH as eluent. White solid (52 mg, 83%) was obtained. LC-MS: 424 [M+H]. Mp=99-101° C.

Preparative Example 780-C:

-continued

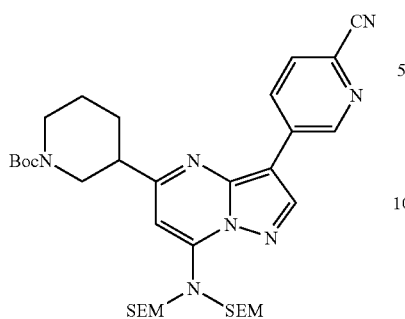

A mixture of the product from Preparative Example 60-C (703 mg, 1.00 mmol), the boronate (299 mg, 1.30 mmol), PdCl₂dppf.CH₂Cl₂ (82 mg, 0.10 mmol), and K₃PO₄ (848 mg, 4.00 mmol) in 1,2-dimethoxyethane (20 mL) and H₂O (4 mL) was stirred and refluxed under N₂ for 3 hr. The solvents were evaporated and the residue was purified by column chromatography on silica gel with 10:1 CH₂Cl₂/EtOAc as eluent. Yellow wax (430 mg, 63%) was obtained. LC-MS: 680 [M+H].

Example 560-C

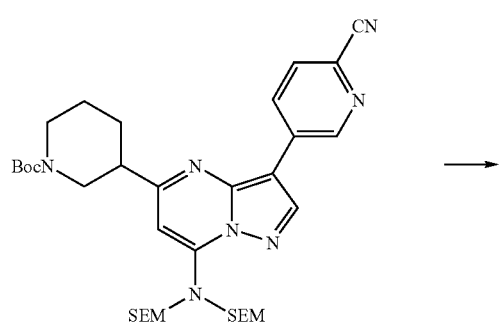

A mixture of the product from Preparative Example 780-C (200 mg) and TFA (5 mL) in H₂O (5 mL) was stirred at 25° C. for 1.5 hr. The solvents were evaporated, Na₂CO₃ (1.0 g) and 6:1 mixture of CH₂Cl₂/MeOH (3 mL) were added to the residue and the mixture was stirred under N₂ for 15 min. Then it was loaded onto a column and it was purified by column chromatography on silica gel with 6:1 CH₂Cl₂/7N NH₃ in MeOH as eluent. White solid (70 mg, 75%) was obtained. Mp=270-272° C. LC-MS: 320 [M+H].

Example 570-C

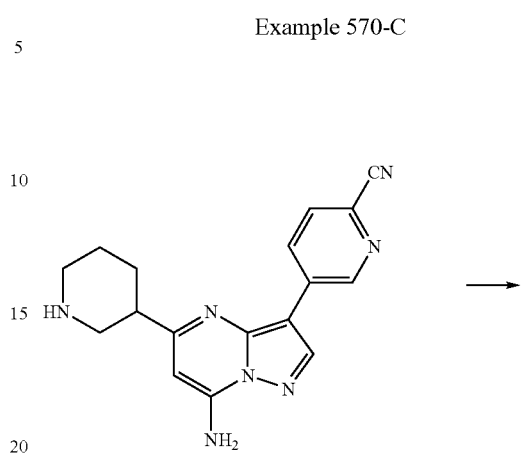

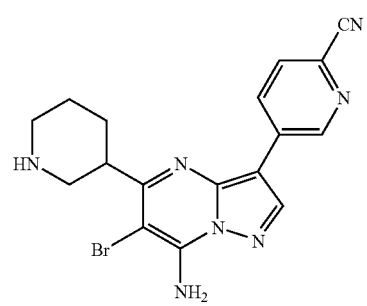

A solution of NBS (32 mg, 0.18 mmol) in anhydrous CH₃CN (3 mL) was added under N₂ to a stirred solution of the product from Example 560-C (65 mg, 0.20 mmol) in anhydrous CH₃CN (3 mL) and MeOH (9 mL). The mixture was stirred for 24 hr, the solvents were evaporated, and the residue was purified by column chromatography on silica gel with 8:1 CH₂Cl₂/7N NH₃ in MeOH as eluent. White solid (27 mg, 38%) was obtained. Mp=200-203° C. LC-MS: 399 [M+H].

Example 580-C

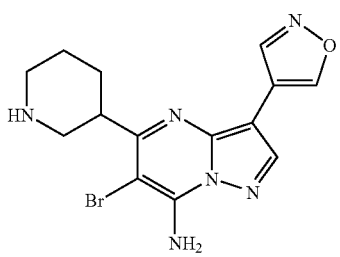

By essentially same procedures set forth in Preparative Example 570-C, starting from the compound from Example 410-C, the compound above was prepared. Pale yellow solid. Mp=64-67° C. LC-MS: 363 [M+H].

Example 590-C

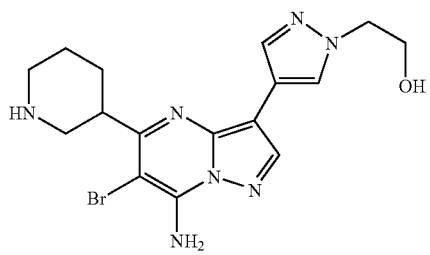

By essentially same procedures set forth in Example 570-C, starting from the compound from Example 420-C, the compound above was prepared. White solid. Mp=66-69° C. LC-MS: 406 [M+].

Examples 590-C-630-C

By essentially same procedure set forth in Example 570-C, starting from the compounds in column 1 of Table 1100, the compounds in column 2 of Table 1100 were prepared.

TABLE 120-C

| Ex. | Column 1 | Column 2 | Data |
|---|---|---|---|
| 590-C | | | LCMS: M+ = 398 |
| 600-C | | | LCMS: M+ = 390 |
| 610-C | | | LCMS: M+ = 453 wax |
| 620-C | | | LCMS: M+ = 447 Mp = 248-250° C. |

TABLE 120-C-continued

| Ex. | Column 1 | Column 2 | Data |
|---|---|---|---|
| 630-C | 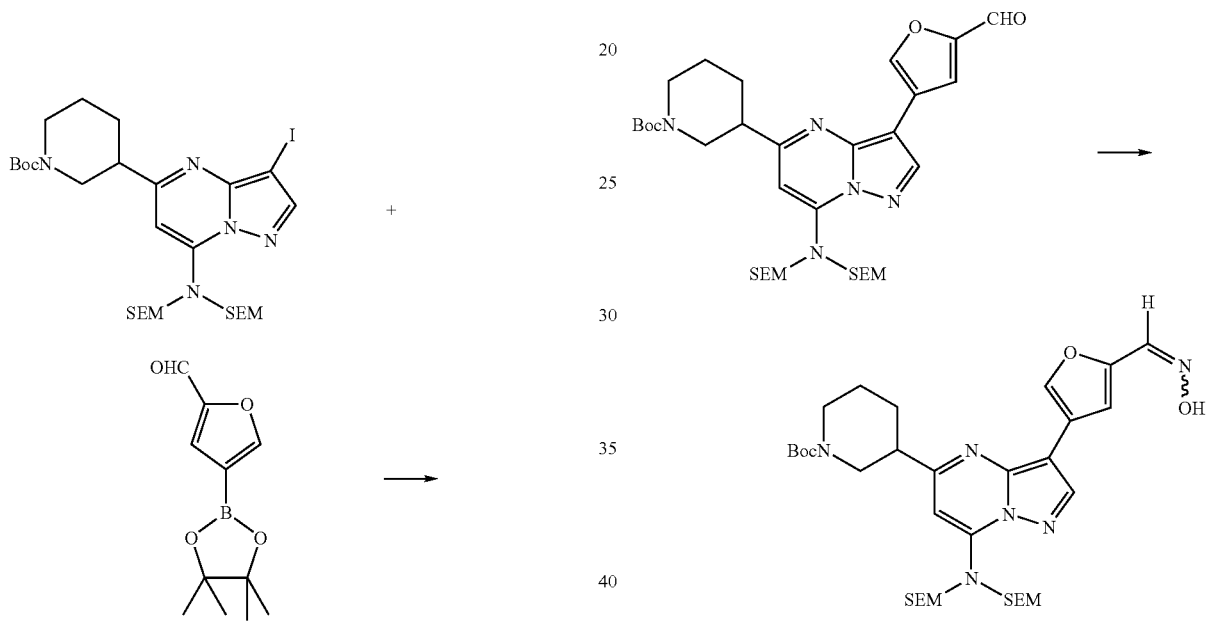 | | LCMS: M+ = 421 wax |

Preparative Example 790-C

Preparative Example 800-C:

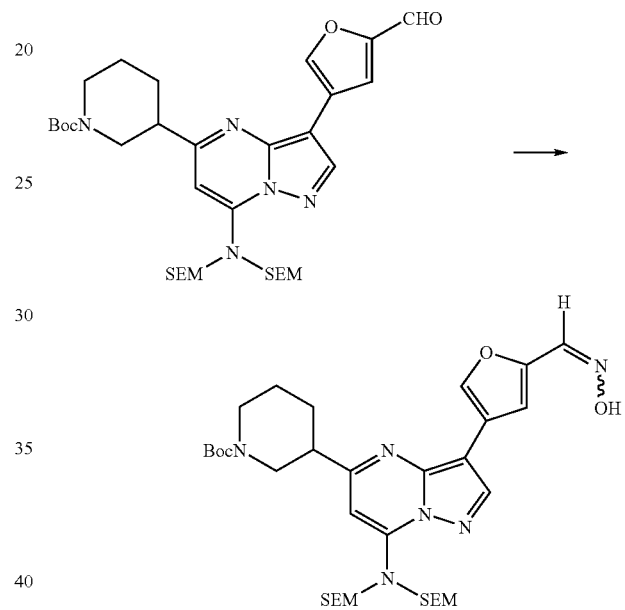

A mixture of the product from Preparative Example 60-C (1.50 g, 2.13 mmol), the formylfuran boronate (0.732 g, 3.30 mmol), PdCl$_2$dppf.CH$_2$Cl$_2$ (171 mg, 0.21 mmol), and K$_3$PO$_4$ (1.81 g, 8.52 mmol) in 1,2-dimethoxyethane (30 mL) and H$_2$O (6 mL) was stirred and refluxed under N$_2$ for 3 hr. The solvents were evaporated and the residue was purified by column chromatography on silica gel with 4:1 hexane/EtOAc as eluent. Yellow wax (890 mg, 62%) was obtained. LC-MS: 672 [M+H].

A mixture of the product from Preparative Example 790-C (440 mg, 0.65 mmol), NH$_2$OH.HCl (50 mg, 0.72 mmol), and triethylamine (1.0 mL) in 1,2-dichloroethane (3 mL) and MeOH (3 mL) was stirred in a closed flask at 25° C. for 1 hr. The solvent was evaporated and the residue was chromatographed on silica gel with 3:1 hexane/EtOAc as eluent. Slightly yellow wax (310 mg, 69%) was obtained. LC-MS: 687 [M+H].

Preparative Example 810-C:

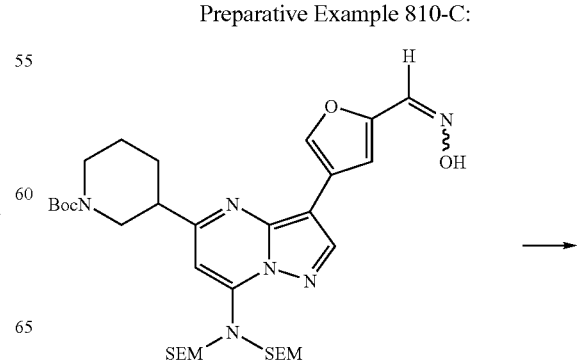

-continued

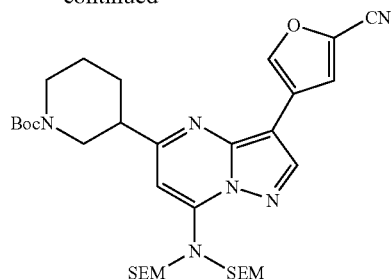

Trifluoroacetic anhydride (92 mg, 0.44 mmol) was added at 0° C. under N₂ to a stirred solution of the product from Preparative Example 800-C (300 mg, 0.44 mmol) in anhydrous CH₂Cl₂ (5 mL) and triethylamine (0.5 mL). The mixture was stirred for 1.5 hr, then it was poured into saturated aqueous NaHCO₃ solution (50 mL), extracted with CH₂Cl₂ (3×10 mL), dried over Na₂SO₄, and filtered. The solvents were evaporated and the residue was purified by column chromatography on silica gel with 7:1 hexane/EtOAc as eluent. Slightly yellow wax (192 mg, 65%) was obtained. LC-MS: 669 [M+H].

Example 640-C

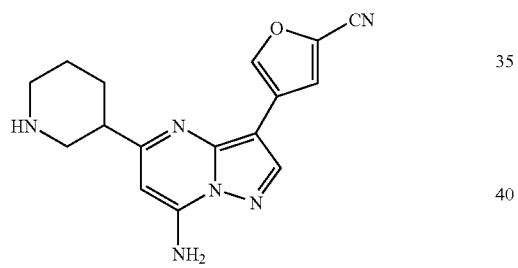

By essentially same procedures set forth in Preparative Example 780-C, starting from the compound from Preparative Example 810-C, the compound above was prepared. White solid. Mp=188-191° C. LC-MS: 309 [M+H].

Example 650-C

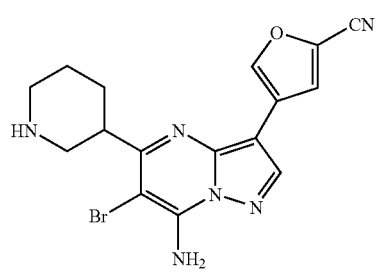

By essentially same procedures set forth in Example 570-C, starting from the compound from Example 640-C, the compound above was prepared. White solid. LC-MS: 387 [M+H].

Example 660-C

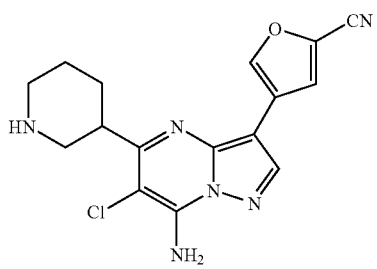

By essentially same procedures set forth in Example 570-C, starting from the compound from Example 640-C and using N-chlorosuccinimide instead of N-bromosuccinimide, the compound above was prepared. White solid. LC-MS: 343 [M+H].

Example 670-C

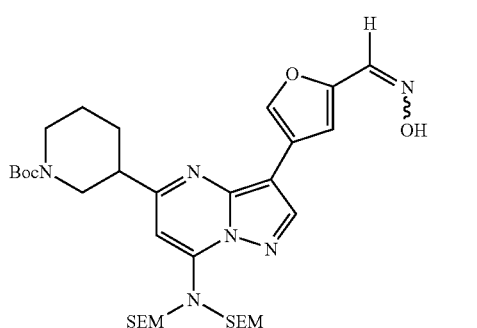

By essentially same procedures set forth in Preparative Example 560-C, starting from the compound from Preparative Example 800-C, the compound above was prepared. White solid. LC-MS: 327 [M+H].

Example 680-C

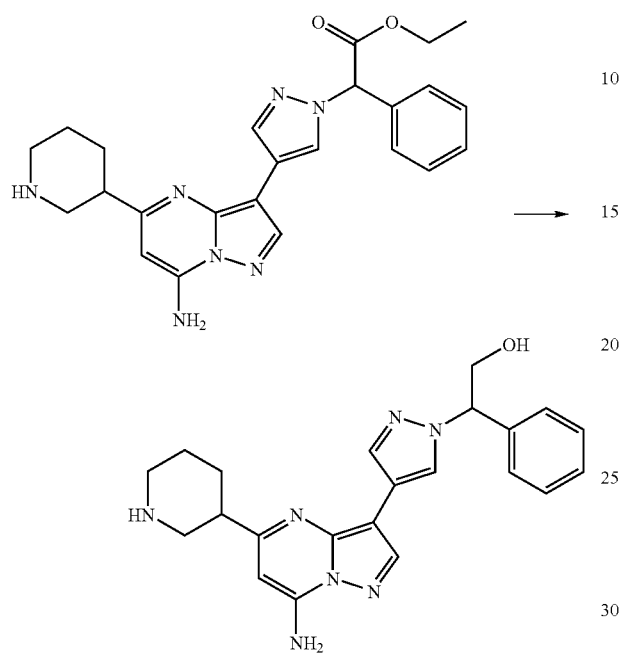

A solution of LiAlH₄ (1.0 M, 1.5 mL, 1.5 mmol) in THF was added under N₂ to a stirred solution of the product from Preparative Example 520-C (70 mg, 0.16 mmol) in anhydrous THF (5 mL). The mixture was stirred for 24 hr, and then MeOH (0.5 mL) was added. The solvents were evaporated and the residue was purified by column chromatography on silica gel with 5:1 CH₂Cl₂/7N NH₃ in MeOH as eluent. Yellow wax (22 mg, 35%) was obtained. LC-MS: 404 [M+H].

Preparative Example 820-C

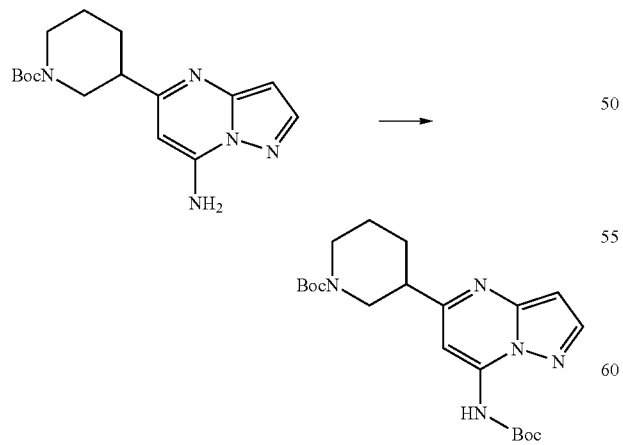

A mixture of the product from Preparative Example 40-C (1.00 g, 3.15 mmol), Boc₂O (0.757 g, 3.47 mmol), 4-dimethylaminopyridine (0.040 g, 0.33 mmol) and TEA (2.0 mL) in dry CH₂Cl₂ (20 mL) and was stirred under N₂ for 2 hr. The mixture was then poured into saturated aqueous NaHCO₃ solution (100 mL), extracted with CH₂Cl₂ (3×30 mL), dried over Na₂SO₄, and filtered. The solvents were evaporated and the residue was purified by column chromatography on silica gel with 2:1 hexane/EtOAc as eluent. White solid (0.94 g, 71%) was obtained. LC-MS: 418 [M+H].

Preparative Example 830-C

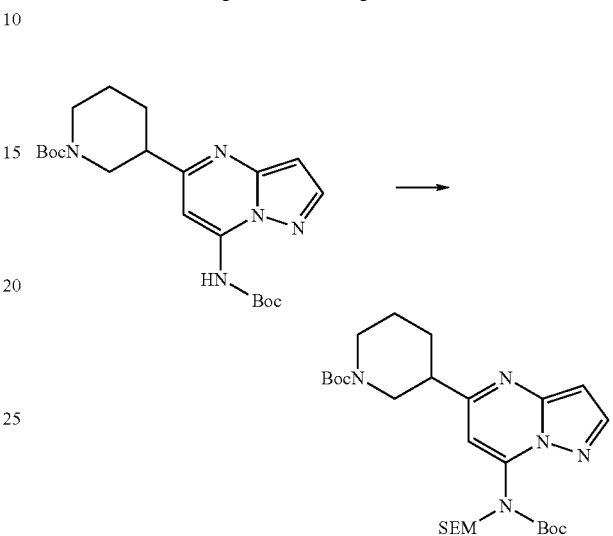

A mixture of the product from Preparative Example 820-C (460 mg, 1.10 mmol), SEMCl (276 mg, 1.65 mmol), and diisopropylethylamine (426 mg, 3.30 mmol) in dry 1,2-dichloroethane (5 mL) and was stirred and refluxed under N₂ for 2 hr. The mixture was then poured into saturated aqueous NaHCO₃ solution (50 mL), extracted with CH₂Cl₂ (3×10 mL), dried over Na₂SO₄, and filtered. The solvents were evaporated and the residue was purified by column chromatography on silica gel with 2:1 hexane/EtOAc as eluent. Slightly yellow wax (500 mg, 83%) was obtained. LC-MS: 548 [M+H].

Preparative Example 840-C

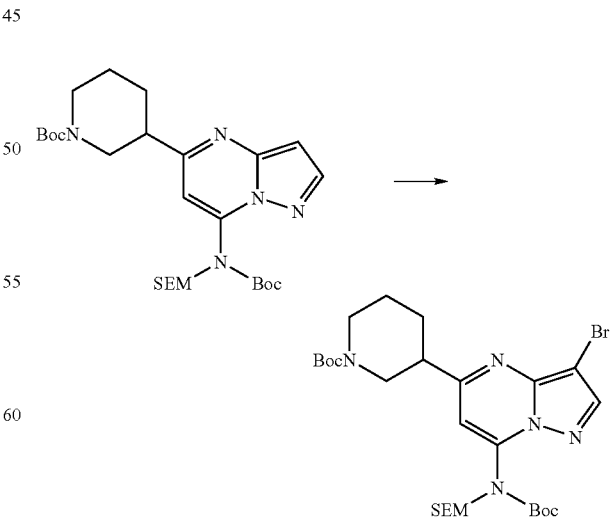

A solution of NBS (71 mg, 0.40 mmol) in anhydrous CH₃CN (2 mL) was added under N₂ to a stirred solution of the product from Preparative Example 830-C (240 mg, 0.44 mmol) in anhydrous $CH_3CN$ (3 mL). The mixture was stirred for 1 hr, the solvents were evaporated, and the residue was purified by column chromatography on silica gel with 5:1 hexane/EtOAc as eluent. Colorless waxy solid (231 mg, 92%) was obtained. LC-MS: 628 [M+H].

Preparative Example 850-C

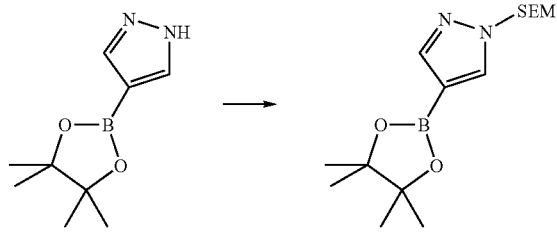

A mixture of 4,4,5,5-tetramethyl-2-(1H-pyrazol4-yl)-1,3,2-dioxaborolane (5.48 g), SEMCl (5.2 mL), and $K_2CO_3$ (5.85 g) in NMP (50 mL) was stirred under $N_2$ for 1 hr. The reaction mixture was diluted with EtOAc, rinsed with $H_2O$, brine, and dried over $Na_2SO_4$. The mixture was filtered, the solvents were evaporated and the residue was used directly in the next step.

Preparative Example 860-C

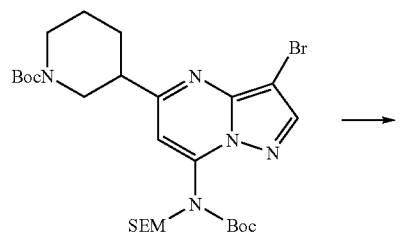

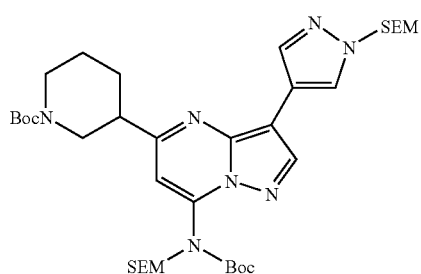

A mixture of the product from Preparative Example 850-C (774 mg, 1.23 mmol), the boronate from Preparative Example 1650 (520 mg, 1.60 mmol), $PdCl_2dppf.CH_2Cl_2$ (100 mg, 0.123 mmol), and $K_3PO_4$ (1.04 g, 4.92 mmol) in 1,2-dimethoxyethane (18 mL) and $H_2O$ (6 mL) was stirred and refluxed under $N_2$ for 5 hr. The solvents were evaporated and the residue was purified by column chromatography on silica gel with 4:1 hexane/EtOAc as eluent. Yellow wax (528 mg, 58%) was obtained. LC-MS: 744 [M+H].

Example 690-C

A mixture of the product from Preparative Example 860-C (520 mg) and 3N aqueous HCl (6 mL) in EtOH (12 mL) was stirred at 60° C. for 1.5 hr. The solvents were evaporated, $NaHCO_3$ (1.0 g) and 6:1 mixture of $CH_2Cl_2/MeOH$ (10 mL) were added to the residue and the mixture was stirred under $N_2$ for 15 min. Then it was loaded onto a column and it was purified by column chromatography on silica gel with 2:1 $CH_2Cl_2$/7N $NH_3$ in MeOH as eluent. White solid (60 mg, 30%) was obtained. LC-MS: 284 [M+H].

Example 700-C and 710-C isomer 1 + isomer 2

Racemic product from Preparative Example 690-C was separated on a semipreparative Chiralcel AD column. Chromatography with mobile phase 80:20 hexane/2-propanol with 0.2% diethylamine afforded two isomers: Example 700-

C: fast eluting (isomer 1): white solid; LC-MS: 284 [M+H] Example 710-C: slow eluting (isomer 2): white solid; LC-MS: 284 [M+H].

Example 720-C

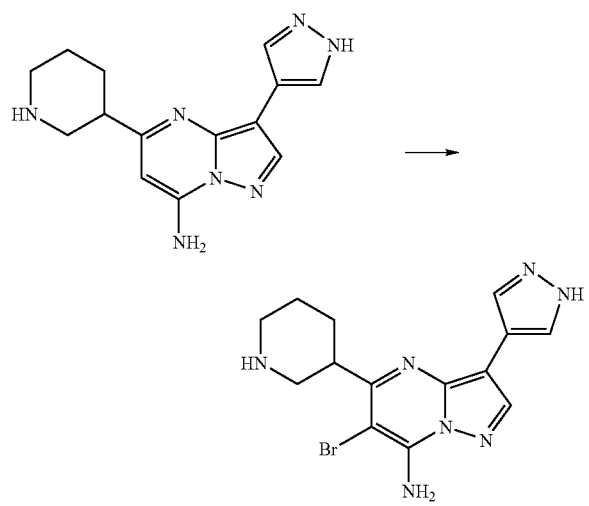

A solution of NBS (3.7 mg, 0.021 mmol) in anhydrous CH$_3$CN (0.2 mL) was added under N$_2$ to a stirred solution of isomer 2 from Example 710-C (7 mg, 0.024 mmol) in anhydrous MeOH (2 mL). The mixture was stirred for 18 hr, the solvents were evaporated, and the residue was purified by preparative thin layer chromatography on silica gel with 7:1 CH$_2$Cl$_2$/7N NH$_3$ in MeOH as eluent. White solid (3.5 mg, 46%) was obtained. LC-MS: 362 [M+H].

Preparative Example 800-C

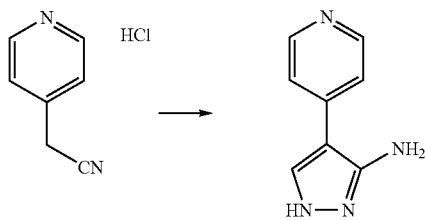

Sodium hydride (60% dispersion in mineral oil, 1.57 g, 39.3 mmol, 3.04 equiv.) was suspended in anhydrous ethyl ether (60 mL) and cooled to 0° C. To this suspension was added ethyl formate (1.55 mL, 19.19 mmol, 1.48 equiv.) and ethanol (1.50 mL, 25.72 mmol, 1.99 equiv.), followed by solid 4-pyridylacetonitrile hydrochloride (2.00 g, 12.95 mmol) in small portions over several minutes. The suspension was then stirred 16 hours, warming to room temperature. Ethanol (3 mL) was added to quench the reaction, and the resulting suspension was filtered and washed with ethyl ether. After drying under vacuum, a light pink solid was obtained (2.7211 g). This solid was suspended in ethanol (30 mL) and acetic acid (3 mL) and hydrazine monohydrate (2.0 mL, 41.23 mmol, 3.18 equiv.) was added. The mixture was then heated to reflux overnight. After cooling, the heterogeneous mixture was concentrated under reduce pressure and the crude solid was suspended in 6.5% methanol-dichloromethane, loaded on a silica gel chromatography column and purified using 6.5% to 20% methanol-dichloromethane. An orange oily solid was obtained (0.645 g, 31% yield).

Preparative Example 810-C

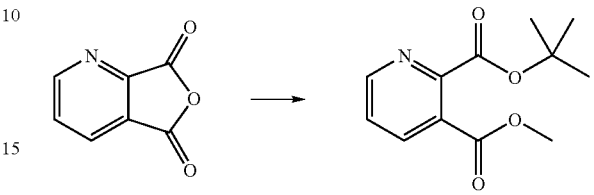

Pyridine-2,3-dicarboxylic anhydride (24 g, 161 mmol) was suspended in anhydrous pyridine (20 mL) and tert-butanol (30 mL) and stirred at 40° C. for 16 hours. After cooling, the suspension was concentrated under reduced pressure at 50° C. for at least 30 minutes, and was then dried under vacuum for 3 hours. The crude intermediate (53 g), which includes pyridine (21 wt %) and tert-butanol (8 wt %), is dissolved in methanol (300 mL) and dichloromethane (100 mL) and treated with trimethylsilyldiazomethane (2M solution in hexanes, 165 mL, 330 mmol, 2.05 equiv.). The resulting orange solution is stirred 16 hours at room temperature, concentrated at reduced pressure (50° C.), and the crude product is dissolved in dichloromethane (120 mL) and purified on an Isco Redisep 330g chromatography column eluting with 75% ethyl acetate-hexanes. The product, a brown oil (21.3 g, 56% yield), consists of 80% 2-tert-butyl, 3-methyl pyridine-2,3-dicarboxylate and 20% 3-tert-butyl, 2-methyl pyridine-2,3-dicarboxylate.

Preparative Example 820-C

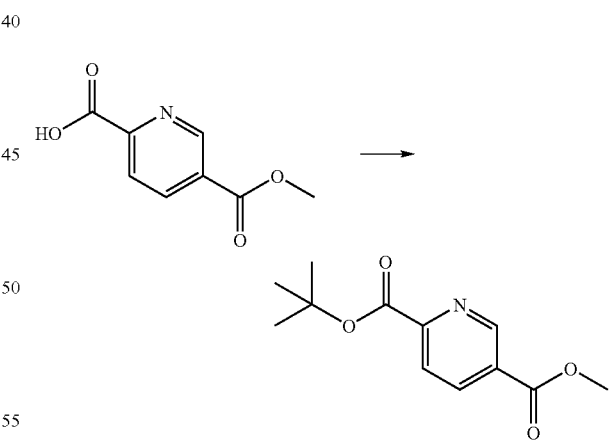

4-(Methoxycarbonyl)pyridine-2-carboxylic acid (24.63 g, 136 mmol) was suspended in tert-butanol (250 mL) and pyridine (75 mL) and cooled in an ice-water bath. 4-Toluenesulfonyl chloride (62.11 g, 326 mmol, 2.39 equiv.) was added in one portion and the mixture was stirred 30 minutes in the ice-water bath then 2 hours at room temperature. The mixture was then slowly poured in a stirring mixture of saturated aqueous sodium bicarbonate (1 L) and ethyl ether (500 mL). The resulting two-phase mixture was then extracted with ethyl ether (3×1 L). The extracts were combined, washed with brine, dried with anhydrous sodium sulfate, filtered and concentrated under reduced pressure. The crude product (25.37 g, 79%) yield was used without further purification.

Preparative Example 830-C

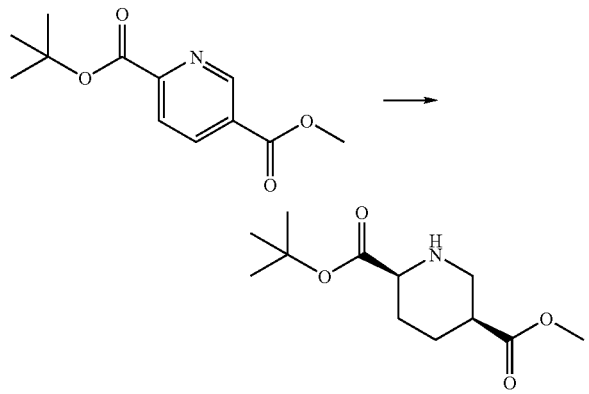

The compound from Preparative Example 820-C (25.36 g, 107 mmol) was dissolved in glacial acetic acid (120 mL) and hydrogenated at 40-50 psi for 3 days with 10% palladium on carbon catalyst (2.50 g, 2.34 mmol, 0.022 equiv.). The mixture was filtered through a pad of Celite which was then washed with methanol. The combined filtrates were concentrated under reduced pressure until only excess acetic acid remained. The residue was dissolved in water (500 mL) and solid sodium carbonate (55 g) was added to bring the pH to 8. This solution was extracted with dichloromethane (2×500 mL), and the extracts were combined, washed with brine, dried with anhydrous sodium sulfate, filtered and concentrated under reduced pressure to yield a yellow oil (25.98 g, 100% yield).

Preparative Example 840-C

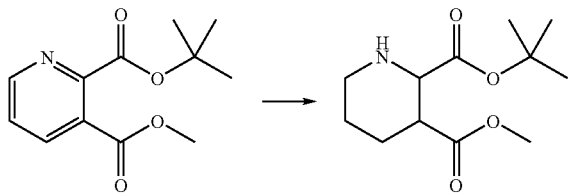

By essentially the same procedure as set forth in Preparative Example 830-C, only utilizing the compound from Preparative Example 810-C, the above compound was prepared in 96% yield (80:20 mixture of isomers).

Preparative Example 850-C

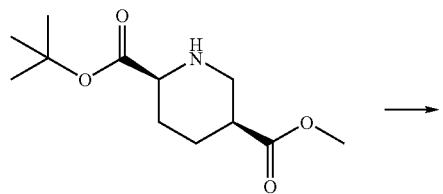

-continued

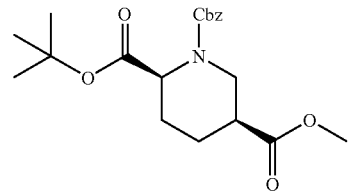

The compound from Preparative Example 830-C (25.97 g, 106.9 mmol) and triethylamine (20 mL, 143 mmol, 1.34 equiv.) were combined in dichloromethane (200 mL) and cooled to 0° C. Benzyl chloroformate (18.5 mL, 130 mmol, 1.21 equiv.) was slowly added and the mixture was stirred 2 days at room temperature. The mixture was diluted with water (200 mL) and extracted with dichloromethane (2×200 mL). The combined extracts were washed with brine, dried with anhydrous sodium sulfate, filtered and concentrated under reduced pressure. The crude product (41.69 g) was loaded on an Isco Redisep 750-gram chromatography column and purified using the ISCO Combiflash Companion XL system, running a gradient from 10% to 20% ethyl acetate-hexanes. A colorless oil (19.66 g, 49% yield) was obtained.

Preparative Example 860-C

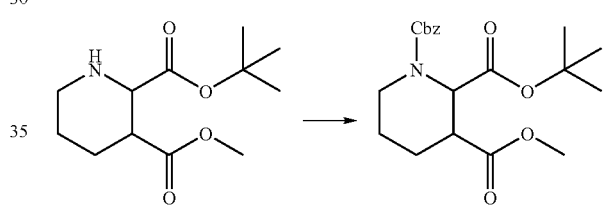

By essentially the same procedure as set forth in Preparative Example 850-C, only utilizing the compound from Preparative Example 840-C, the above piperidine was prepared in 82% yield.

Preparative Example 870-C

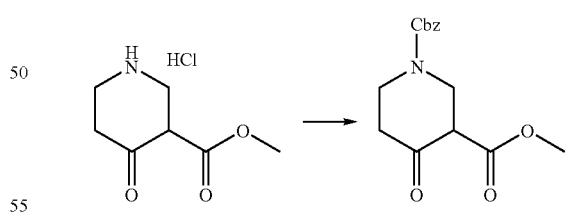

Methyl 4-oxo-piperidinecarboxylate hydrochloride (7.51 g, 38.79 mmol) was suspended in dichloromethane (100 mL) and cooled to 0C. Triethylamine (19 mL, 136 mmol, 3.5 equiv.) was slowly added followed by benzyl chloroformate (11 mL, 77 mmol, 1.99 equiv.). The mixture was stirred 3 days at room temperature, and was then diluted with water (100 mL) and the two phases were separated. The aqueous phase was then extracted with dichloromethane (100 mL), the two organic extracts were combined and washed with brine, dried with anhydrous sodium sulfate, filtered and concentrated under reduced pressure. The resulting yellow oil was purified by chromatography on an Analogix SF40-240 column using an Analogix Intelliflash 280 system running a gradient from 15% to 30% ethyl acetate-hexanes. The product was obtained as a colorless oil (6.40 g, 57% yield).

Preparative Example 880-C

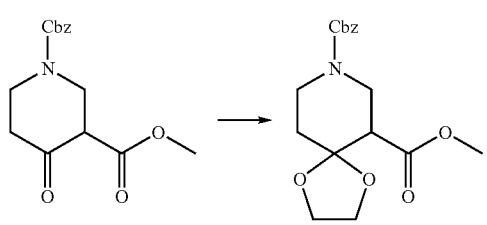

The keto ester from Preparative Example 870-C (6.39 g, 22.0 mmol), ethylene glycol (12 mL, 215 mmol, 9.8 equiv.) and 4-toluenesulfonic acid monohydrate (0.640 g, 3.36 mmol, 0.15 equiv.) were heated together in benzene (90 mL) at reflux with a Dean-Stark trap for 12 hours. After cooling, saturated aqueous sodium bicarbonate (75 mL) was added and the two phases were mixed and separated. The aqueous phase was extracted with ethyl ether (75 mL), and the ether and benzene layers were combined and washed with brine, dried with anhydrous sodium sulfate, filtered and concentrated under reduced pressure. A colorless oil (7.17 g, 98% yield) was obtained, which was used without further purification.

Preparative Example 890-C

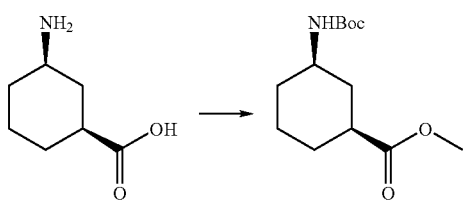

3-Amino-1-cyclohexanecarboxylic acid (1.503 g, 10.50 mmol, 87% cis by NMR) was suspended in anhydrous methanol (20 mL) and thionyl chloride (0.80 mL, 10.99 mmol, 1.05 equiv.) was added dropwise over 3 minutes, resulting in a slightly yellow homogeneous solution. After stirring 1 hour at room temperature, the solution was concentrated under reduced pressure to yield a colorless, viscous oil. This oil was dissolved in anhydrous dichloromethane (20 mL) and triethylamine (3.70 mL, 26.55 mmol, 2.53 equiv.) was added, followed by di-tert-butyldicarbonate (2.78 g, 12.74 mmol, 1.21 equiv.). The resulting suspension was stirred 15 hours at room temperature and was then diluted with water (20 mL), mixed and separated into two phases. The aqueous phase was further extracted with ethyl acetate (2×20 mL). The organic phases were combined, washed with brine, dried with anhydrous sodium sulfate, filtered and concentrated under reduced pressure. The product is obtained as a white solid (2.607 g, 97% yield) which is 90% cis by NMR.

Preparative Example 900-C

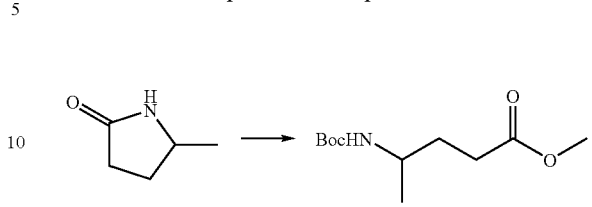

5-Methyl-2-pyrrolidinone (5.09 g, 51.35 mmol) was stirred 15 hours in 6N aqueous hydrochloric acid (75 mL) at 100° C. The solution was concentrated under reduced pressure to yield a white solid that was redissolved in methanol (100 mL) to which thionyl chloride (3.75 mL, 51.54 mmol, 1.00 equiv.) was slowly added. After 1 hour at room temperature, the solution was concentrated under reduced pressure and the resulting crude ester was redissolved in anhydrous dichloromethane (100 mL). Triethylamine (21.5 mL, 154 mmol, 3.00 equiv.) was added, followed by di-tert-butyldicarbonate (16.88 g, 77.3 mmol, 1.51 equiv.), and the resulting solution was stirred 2 days at room temperature. The opaque yellow solution was diluted with water (100 mL), and the two phases were mixed and separated. The aqueous phase was extracted with dichloromethane (2×100 mL), and the combined extracts were washed with brine, dried with anhydrous sodium sulfate, filtered and concentrated under reduced pressure to yield an orange oil (11.13 g, 94% yield.)

Preparative Example 910-C

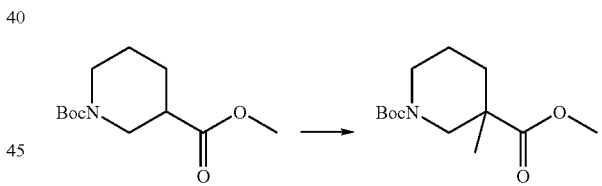

A solution of ester (1.23 g, 5.05 mmol) in THF (20 mL) at −78° C. was treated with LIHMDS (6.1 mL of a 1.0M solution in THF, 1.2 equiv.) dropwise. The solution was stirred at −78° C. for 1 h and treated with $CH_3I$ (0.38 mL, 1.2 equiv.) dropwise. The solution was stirred at −78° C. for 2 h. and at 25° C. for 1 h. The solution was quenched by the addition of saturated $NH_4Cl$ (100 mL). The aqueous layer was extracted with $Et_2O$ (3×25 mL). The combined organic layer was dried ($MgSO_4$), filtered and concentrated under reduced pressure. The residue was purified by an Analogix purification system using a RediSep 40 g column (25% ethyl acetate-hexanes) to provide (1.08 g, 83%) a white solid.

Preparative Example 920-C-930-C

By essentially same procedure set forth in Preparative Example 910-C, the compounds given in Column 2 of Table 200-C were prepared.

TABLE 200-C

| Prep. Ex. | Column 2 |
|---|---|
| 920-C | 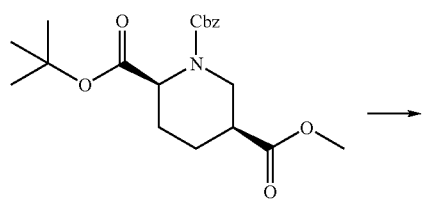 |
| 930-C | |

Preparative Example 940-C

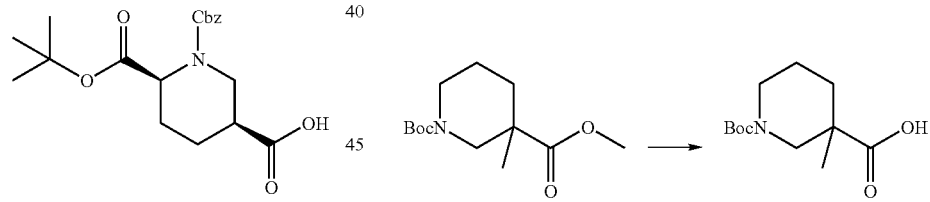

The compound from Preparative Example 850-C (2.024 g, 5.37 mmol) was stirred 16 hours at room temperature in a mixture of 2N aqueous sodium hydroxide (6.5 mL, 13 mmol, 2.42 equiv.), methanol (8 mL) and tetrahydrofuran (15 mL). 4N aqueous hydrochloric acid (3 mL) was then added to bring the pH to 2-3, the mixture was diluted with water (50 mL) and extracted with ethyl acetate (3×50 mL). The combined extracts were washed with brine, dried with anhydrous sodium sulfate, filtered and concentrated under reduced pressure to yield a light yellow oil (1.857 g, 95% yield).

Preparative Example 950-C-980-C

By essentially same procedure set forth in Preparative Example 940-C, the compounds given in Column 2 of Table 210-C were prepared.

TABLE 210-C

| Prep. Ex. | Column 2 |
|---|---|
| 950-C | |
| 960-C | |
| 970-C | |
| 980-C | |

Preparative Example 990-C

A solution of ester from Preparative Example 910-C (1.08 g, 4.20 mmol) in EtOH (16.8 mL) at 25° C. was treated with NaOH (.050 g, 3 equiv.). The solution was heated at 70° C. for 3 h. The solution was cooled to 25° C. and concentrated under reduced pressure. The residue was dissolved in $H_2O$ (50 mL). The aqueous layer was washed with $Et_2O$ (2×30 mL). The aqueous layer was acidified to pH=1 with 1M HCl. The aqueous layer was extracted with $Et_2O$ (2×30 mL) and the organic layer was dried ($MgSO_4$), filtered and concentrated under reduced pressure. The residue was used directly in the next reaction.

Preparative Example 1000-C and 1010-C

By essentially same procedure set forth in Preparative Example 990-C, the compounds given in Column 2 of Table 220-C were prepared.

TABLE 220-C

| Prep. Ex. | Column 2 |
|---|---|
| 1000-C | 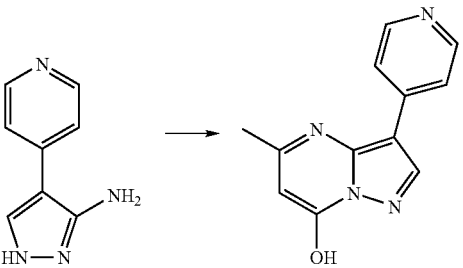 |
| 1010-C | |

Preparative Example 1020-C

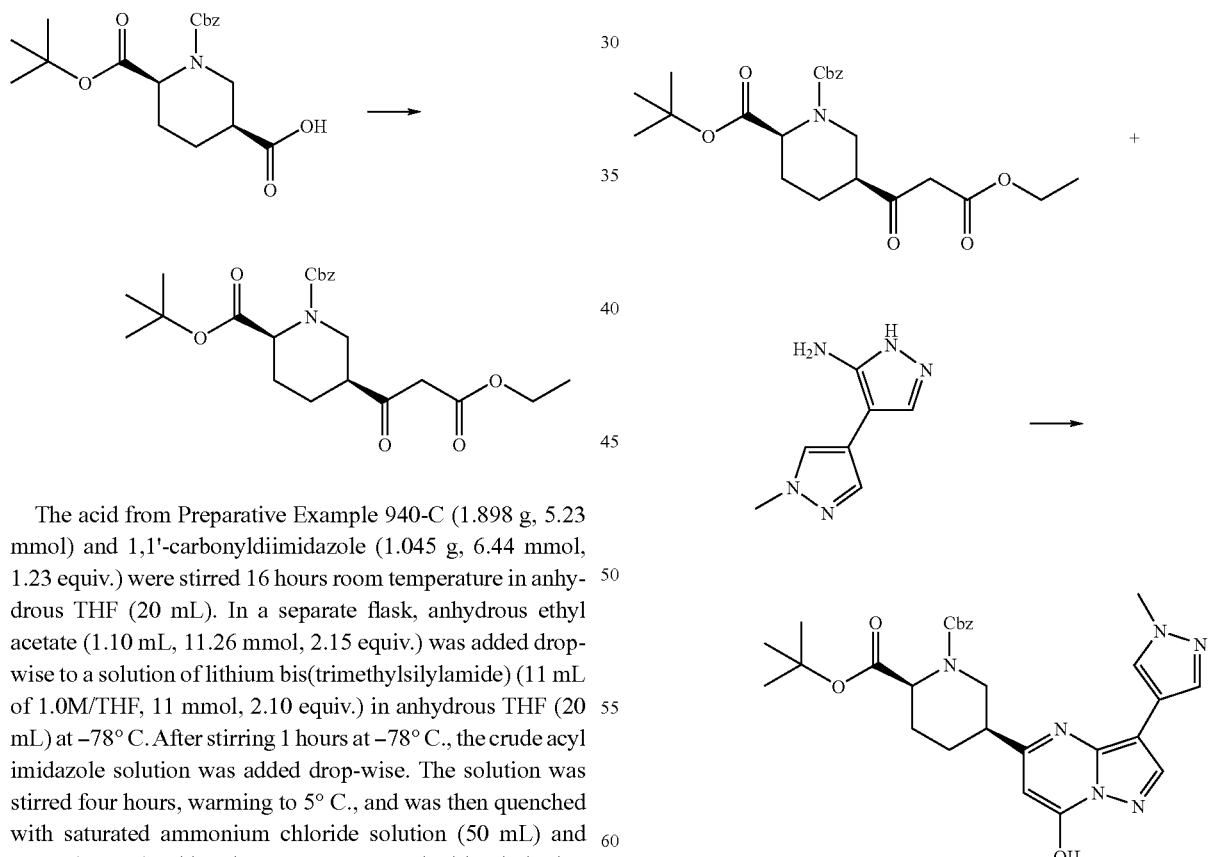

The acid from Preparative Example 940-C (1.898 g, 5.23 mmol) and 1,1'-carbonyldiimidazole (1.045 g, 6.44 mmol, 1.23 equiv.) were stirred 16 hours room temperature in anhydrous THF (20 mL). In a separate flask, anhydrous ethyl acetate (1.10 mL, 11.26 mmol, 2.15 equiv.) was added drop-wise to a solution of lithium bis(trimethylsilylamide) (11 mL of 1.0M/THF, 11 mmol, 2.10 equiv.) in anhydrous THF (20 mL) at −78° C. After stirring 1 hours at −78° C., the crude acyl imidazole solution was added drop-wise. The solution was stirred four hours, warming to 5° C., and was then quenched with saturated ammonium chloride solution (50 mL) and water (10 mL). This mixture was extracted with ethyl ether (2×60 mL), and the combined extracts were washed with saturated sodium bicarbonate, washed with brine, dried with anhydrous sodium sulfate, filtered, and concentrated under reduced pressure. The crude product (2.17 g) was used without further purification.

Preparative Example 1030-C

The aminopyrazole from Preparative Example 800-C (2.39 g, 14.94 mmol) and ethyl acetoacetate (2.50 mL, 19.61 mmol, 1.31 equiv.) were combined in glacial acetic acid (15 mL) and stirred 14 hours at reflux. After cooling, the thick suspension was diluted with ethyl ether, filtered and the resulting solid was washed with additional ethyl ether. After drying under vacuum overnight at 55° C., an orange solid was obtained (2.687 g, 80% yield).

Preparative Example 1040-C

The β-keto ester from Preparative Example 1020-C (1.516 g, 3.50 mmol) and pyrazole XY (0.457 g, 2.80 mmol) were stirred for 24 hours in a sealed tube heated to 115° C. After cooling to room temperature, the dark brown solution was concentrated under reduced pressure a crude product (1.8434 g, ~80% pure) that was used without purification.

Preparative Example 1050C

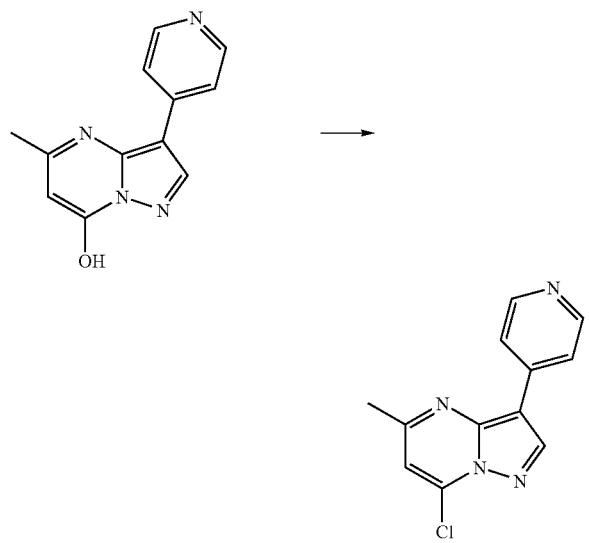

Phosphorus oxychloride (25 mL) was added to the compound from Preparative Example 1030-C (2.683 g, 11.87 mmol) to give a green suspension, to which N,N-dimethylaniline (6.25 mL, 49.31 mmol, 4.15 equiv.) was added resulting in a yellow-brown suspension. This suspension was heated at 105° C. for 1.5 hours then cooled to room temperature. The reaction was quenched by slowing adding it to a vigorously stirring mixture of ice (200 g), water (100 mL) and sodium carbonate (90 g). After the ice had finished melting, the resulting dark red suspension was extracted with ethyl acetate (200 mL). The organic extract was then washed with water (200 mL) and with brine (100 mL), and then dried with anhydrous sodium sulfate, filtered and concentrated under reduced pressure. The crude red solid thus obtained was dissolved in dichloromethane and purified by chromatography on silica gel using a gradient from 0% to 100% ethyl-acetate-dichloromethane followed by 0.5% to 5% methanol-ethyl acetate. A yellow-brown solid (1.014 g, 35% yield) was obtained.

Preparative Example 1060C

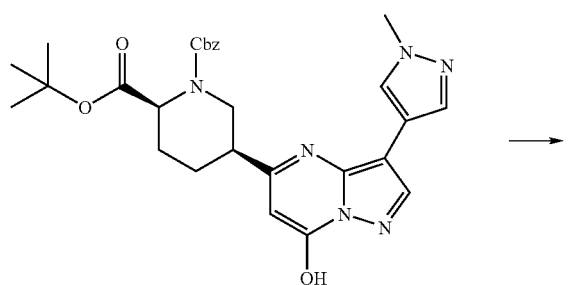

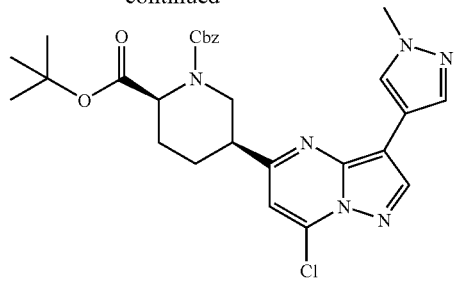

Phosphorus oxychloride (10 mL) was added to crude compound from Preparative Example 1020-C (0.861 g, 1.40 mmol) to give a green suspension, to which N,N-dimethylaniline (0.55 mL, 4.34 mmol, 3.10 equiv.) was added resulting in a dark brown suspension. This suspension was stirred 2 days at room temperature, and was then diluted with dichloromethane and concentrated under reduced pressure. The residue was redissolved in ethyl acetate (10 mL) and added to a stirring mixture of ice (75 g), 2M aqueous sodium carbonate (75 mL) and ethyl acetate (25 mL). After the ice had finished melting, the resulting dark red suspension was extracted with ethyl acetate (3×100 mL). The combined extracts were then washed with water (200 mL) and with brine (100 mL), and then dried with anhydrous sodium sulfate, filtered and concentrated under reduced pressure. The crude red oil thus obtained was dissolved in dichloromethane and purified by chromatography on silica gel using a gradient from 33% to 100% ethyl-acetate-hexane. An orange oil (0.395 g, 51% yield) was obtained.

Preparative Example 1070-C

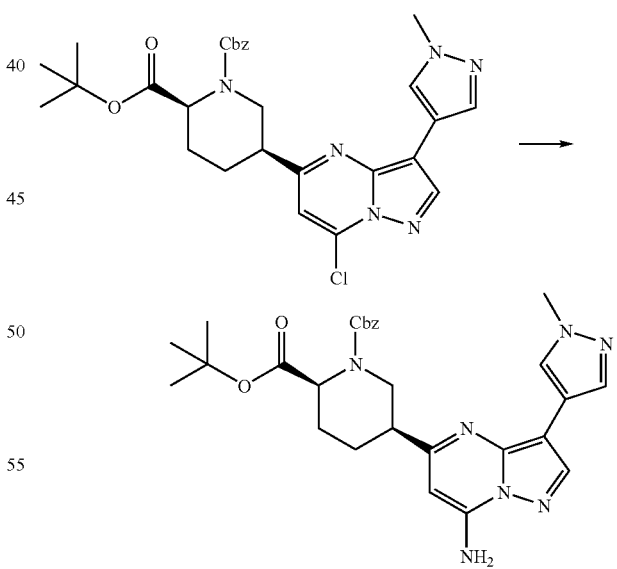

The chloro compound from Preparative Example 1060-C (0.397 g, 0.721 mmol) in 7N ammonia in methanol (8 mL) was stirred for 16 hours in a sealed tube at 55° C. and then 21 hours at 80° C. Upon cooling, a white precipitate forms and this dissolves upon addition of dichloromethane (5 mL). The solution was concentrated and the resulting yellow solid was dissolved in 20% acetonitrile-dichloromethane and purified by silica gel chromatography using a gradient from 20% to 75% acetonitrile-dichloromethane. A white solid (0.282 g, 74% yield) was obtained.

Preparative Example 1080C

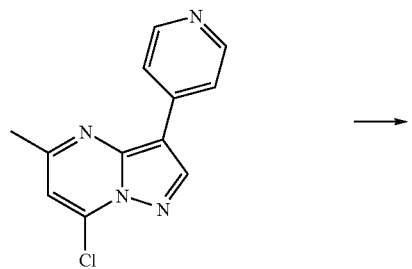

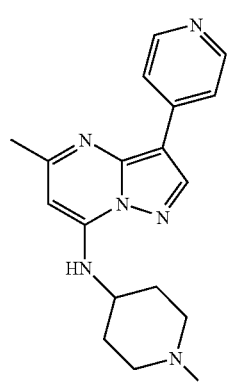

The chloro compound from Preparative Example 1050-C (0.100 g, 0.410 mmol), 4-amino-1-Boc-piperidine (0.137 g, 0.684 mmol, 1.67 equiv.) and triethylamine (0.25 mL, 1.79 mmol, 4.37 equiv.) were dissolved in anhydrous 1,4-dioxane (5 mL) and the resulting solution was stirred 15 hours at 95° C. After cooling, the solution was concentrated under reduced pressure to yield a yellow solid. This solid was dissolved in dichloromethane and purified by silica gel chromatography using 5% methanol-dichloromethane. A yellow solid (0.1145 g, 68% yield) was obtained. LCMS: 409 [MH+]. $^{13}$C NMR (CDCl$_3$) δ 161.14, 154.58, 149.49, 146.33, 145.27, 141.64, 140.97, 119.79, 105.65, 86.68, 80.10, 67.07, 49.42, 31.72, 28.39, 25.52.

Preparative Example 1090-C

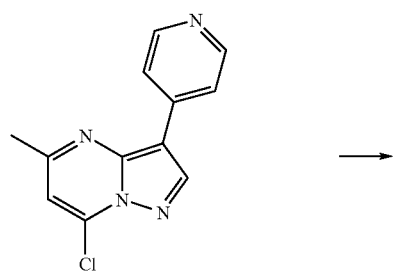

-continued

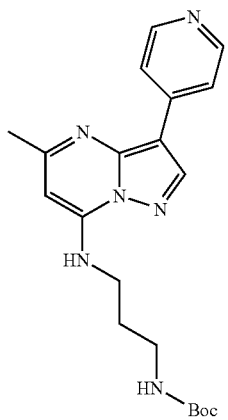

By essentially the same procedure as set forth in Preparative Example 1080-C, the above was prepared, using N-Boc-propanediamine.

Preparative Example 100-C and 1110-C

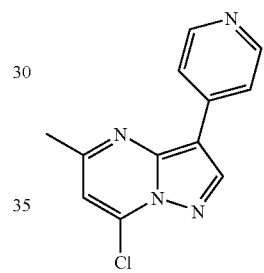

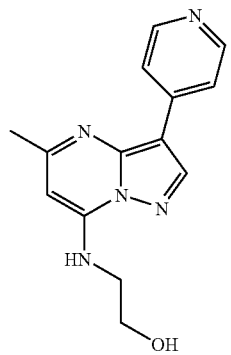

+

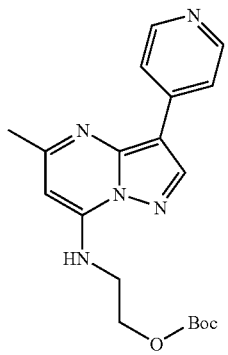

By essentially the same procedure as set forth in Preparative Example 1080-C, using N-Boc-ethanolamine, the above compounds, Preparative Example 1100-C and Preparative Example 1110-C were both prepared. 1100-C LCMS: 270 [MH+]. $^{13}$C NMR (CD$_3$OD) δ 162.51, 149.43, 148.26, 147.47, 142.95, 121.03, 105.46, 87.73, 60.84, 44.92, 25.33. XXb: LCMS: 370 [MH+]. $^{13}$C NMR (CDCl$_3$) δ 161.25, 153.31, 149.37, 146.32, 141.79, 141.06, 119.91, 105.55, 86.51, 83.13, 64.29, 41.26, 27.66, 25.52.

Preparative Example 1120-C

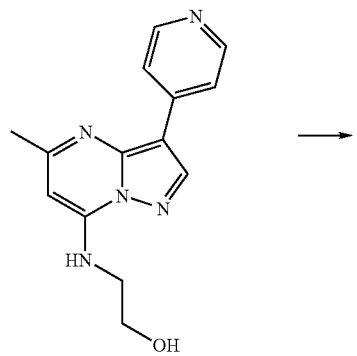

The compound from Preparative Example 1100-C (0.031 g, 0.115 mmol) was dissolved in anhydrous dichloromethane (3 mL) and triethylamine (0.10 mL, 0.717 mmol, 6.23 equiv.) and acetic anhydride (0.03 mL, 0.32 mmol, 2.78 equiv.) were added. The solution was stirred 2 days at room temperature and was then concentrated under reduced pressure to yield a yellow solid that was dissolved in dichloromethane and purified by silica gel chromatography using a gradient from 5% to 10% methanol-dichloromethane. A yellow solid (0.034 g, 95% yield) was obtained. LCMS: 312 [MH+]. $^{13}$C NMR (CDCl$_3$) δ 170.97, 161.18, 149.63, 146.29, 141.79, 140.75, 119.98, 105.66, 86.46, 62.09, 41.12, 25.50, 20.79.

Preparative Example 1130-C

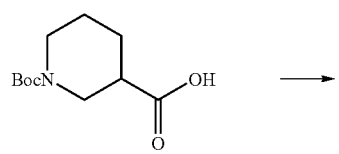

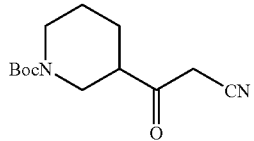

A solution of acid (10.0 g, 43.62 mmol) in THF (132 mL) was treated with 1,1'-carbonyldiimidazole (7.78 g, 1.1 equiv.). The solution was stirred at 25° C. for 18 hrs. In a separate flask was added LiHMDS (96 mL of a 1.0M solution in THF, 2.2 equiv.) in THF (132 mL). The solution was cooled to −78° C. and treated with CH$_3$CN (5.0 mL, 2.2 equiv.) dropwise. The solution was stirred at −78° C. for 1 h. To this solution was added the solution of acyl imidazole dropwise over 10 minutes. The solution was stirred at −78° C. for 2 h. and allowed to warm to 25° C. and stirring was continued for 15 h. The solution was quenched by the addition of saturated NH$_4$Cl (500 mL). The aqueous layer was extracted with Et$_2$O (3×100 mL). The combined organic layer was dried (MgSO$_4$), filtered and concentrated under reduced pressure. The residue was purified by an Analogix purification system using a RediSep 40 g column (0-50% ethyl acetate-hexanes gradient) to provide XX (4.4 g, 40%) as a pale yellow oil.

Preparative Example 1140-C-1350-C

By essentially same procedure set forth in Preparative Example 1130-C, the compounds given in Column 2 of Table 230-C were prepared.

TABLE 230-C

| Prep. Ex. | Column 2 |
|---|---|
| 1140-C | ![structure] |
| 1150-C | ![structure] |
| 1160-C | ![structure] |
| 1170-C | ![structure] |
| 1180-C | ![structure] |

TABLE 230-C-continued
| Prep. Ex. | Column 2 |
|---|---|
| 1190-C | |
| 1200-C | |
| 1210-C | |
| 1220-C | |
| 1230-C | |
| 1240-C | |
| 1250-C | |
| 1260-C | |
| 1270-C | |
| 1280-C | |
| 1290-C | |
TABLE 230-C-continued
| Prep. Ex. | Column 2 |
|---|---|
| 1300-C | |
| 1310-C | |
| 1320-C | |
| 1330-C | |
| 1340-C | |
| 1350-C | |
Preparative Example 1360-C
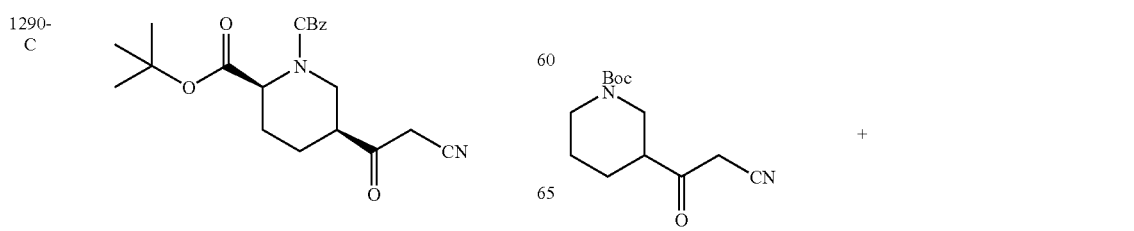

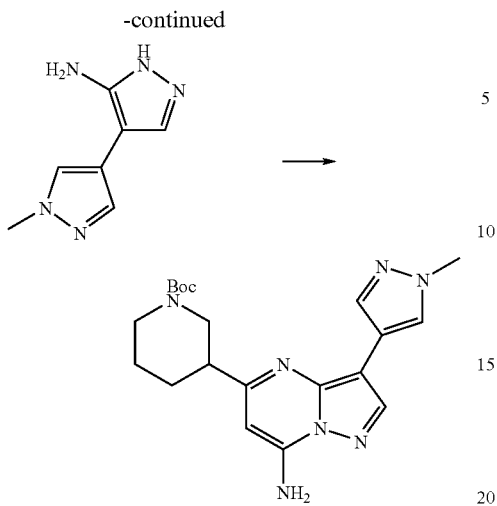

A solution of beta-ketonitrile from Preparative Example 1130-C (7.96 g, 22.11 mmol) and bispyrazole from Preparative Example 490-C(3.87 g, 23.73 mmol) in toluene (50 mL) was heated at 115° C. for 40 h. The solution was cooled to 25° C. and MeOH was added to solubilize the precipitate. The solution was concentrated under reduced pressure. Purification by an Analogix purification system using an Analogix SF40-240g column (0-50% acetone-CH$_2$Cl$_2$ gradient) afforded (7.17 g, 82%) a pale yellow solid.

Preparative Example 1370-C-1540-C

By essentially same procedure set forth in Preparative Example 1360-C, the compounds given in Column 2 of Table 240-C were prepared.

TABLE 240-C-continued

| Prep. Ex. | Column 2 |
|---|---|
| 1440-C | |
| 1450-C | |
| 1460-C | |
| 1470-C | |
| 1480-C | |
| 1490-C | |
| 1500-C | |
| 1510-C | |
| 1520-C | |
| 1530-C | |

TABLE 240-C-continued

| Prep. Ex. | Column 2 |
|---|---|
| 1540-C | 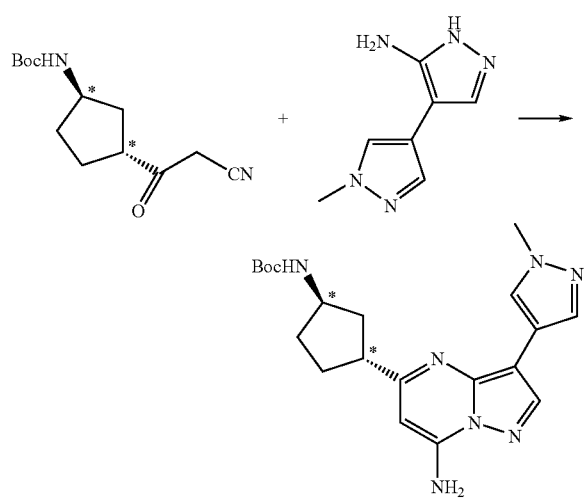 |

Preparative Example 1550-C

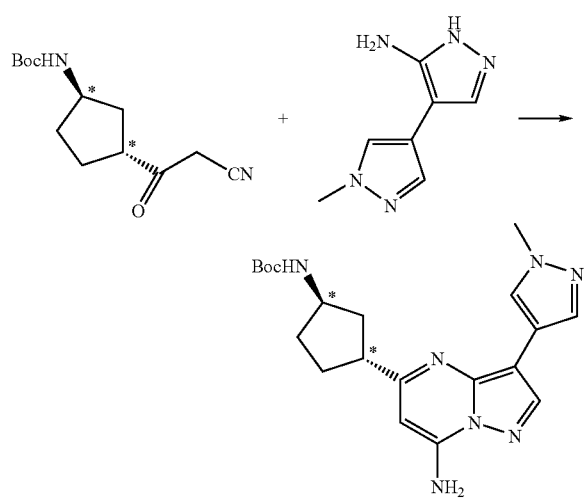

The β-Keto nitrile from Preparative Example 1330-C (0.638 g, 2.53 mmol), bispyrazole from Preparative Example 490-C (0.414 g, 2.54 mmol, 1.00 equiv.), and anhydrous magnesium sulfate (0.4965 g, 4.14 mmol, 1.63 equiv.) were combined in methanol (5 mL) and the resulting suspension was stirred vigorously for two days at room temperature. The suspension was then diluted with dichloromethane, filtered to remove the magnesium sulfate, and the filtrate was concentrated under reduced pressure to yield a tan solid. This was suspended in dichloromethane and loaded on an Isco Redisep RS-40 column using an Analogix DASI-65-Si-50 silica module to retain the undissolved solids from the column. The product was purified using an Analogix Intelliflash 280 system running a gradient from 10% to 70% acetone-dichloromethane. The product was obtained as an off-white solid (0.725 g, 72% yield).

Preparative Example 1560-C and 1570-C

Using essentially the same procedure as set forth in Preparative Example 1550-C only substituting the appropriate β-keto nitrites, the compounds shown in Column 2 of Table 250-C were prepared.

TABLE 250-C

| Prep. Ex. | Column 2 |
|---|---|
| 1560-C | 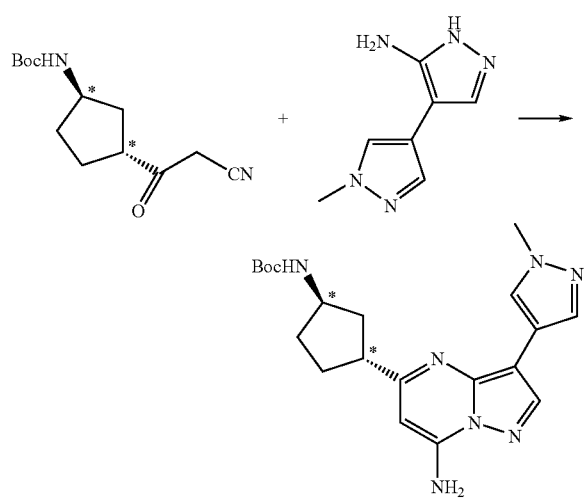 |
| 1570-C | 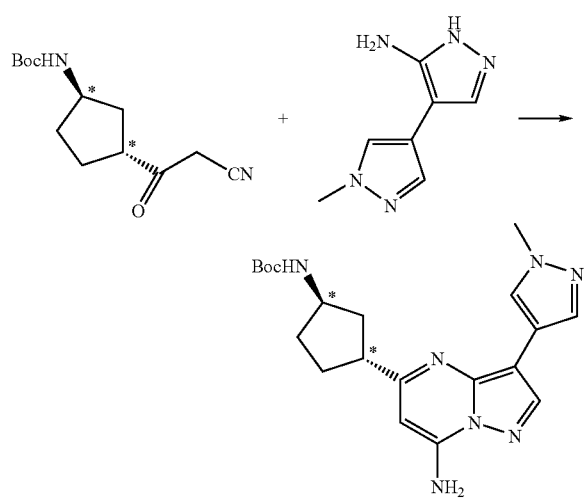 |

Example 800-C

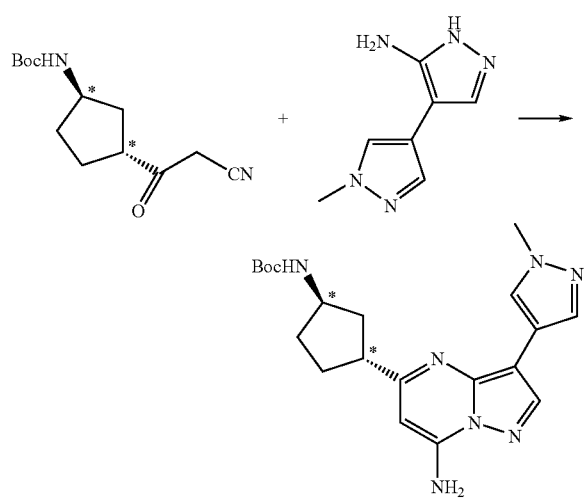

The compound from Preparative Example 1500-C (0.116 g, 0.218 mmol) was dissolved in 50% ethanol-ethyl acetate (5 mL) and hydrogenated using the Thales Nanotechnology H-Cube hydrogenation reactor with a 10% palladium-on-carbon catalyst cartridge at 1 mL/minute, 50 bar hydrogen pressure and room temperature. The product solution was concentrated and purified by silica gel chromatography using a gradient from 4% to 7.5% 7N ammonia in methanol-dichloromethane. A white solid (0.040 g, 46% yield) is obtained. LCMS: 398 [MH$^+$]. $^{13}$C NMR (CDCl$_3$) δ 172.61, 164.07, 147.21, 144.47, 140.72, 135.93, 127.30, 113.39, 101.40, 87.21, 81.50, 57.10, 46.98, 40.44, 38.44, 27.96, 27.85, 25.28.

Example 810-C

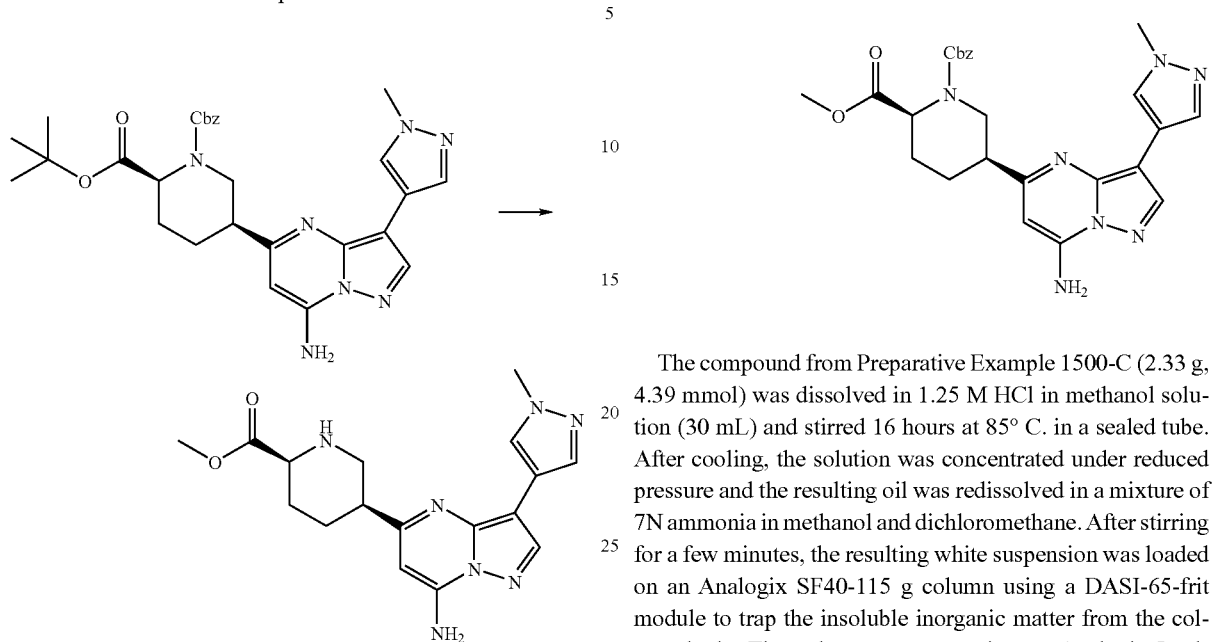

The compound from Preparative Example 1500-C (0.120 g, 0.226 mmol) was stirred in 1.25 M HCl/methanol (10 mL) in a sealed tube at 85° C. for 24 hours. After cooling, the solution was concentrated and the resulting oil was redissolved in methanol (4 mL). Half of this solution was then diluted with glacial acetic acid (0.5 mL) and hydrogenated using the Thales Nanotechnology H-Cube hydrogenation reactor with a 10% palladium-on-carbon catalyst cartridge at 1 mL/minute, 50 bar hydrogen pressure and room temperature. The product solution was concentrated and the residue was redissolved in 7N ammonia in methanol (5 mL) and concentrated again. The resulting white solid was loaded on an Isco Redisep 5-gram chromatography column and purified using an Analogix Intelliflash 280 system running a gradient from 0% to 10% methanol-dichloromethane followed by 5% to 15% 7N ammonia in methanol-dichloromethane. The product was a colorless oil (0.018 g, 46% yield). LCMS: 356 [MH+]. $^{13}$C NMR (CDCl$_3$) δ 171.15, 162.63, 147.89, 143.87, 141.23, 136.15, 127.26, 112.96, 101.37, 87.03, 55.95, 52.63, 46.45, 38.43, 37.77, 27.35, 23.67.

Preparative Example 1580-C

-continued

The compound from Preparative Example 1500-C (2.33 g, 4.39 mmol) was dissolved in 1.25 M HCl in methanol solution (30 mL) and stirred 16 hours at 85° C. in a sealed tube. After cooling, the solution was concentrated under reduced pressure and the resulting oil was redissolved in a mixture of 7N ammonia in methanol and dichloromethane. After stirring for a few minutes, the resulting white suspension was loaded on an Analogix SF40-115 g column using a DASI-65-frit module to trap the insoluble inorganic matter from the column body. The column was run using an Analogix Intelliflash-280 system running a gradient from 0% to 5% methanol-dichloromethane. The product was obtained as a light brown solid (1.838 g, 85% yield).

Preparative Example 1590-C

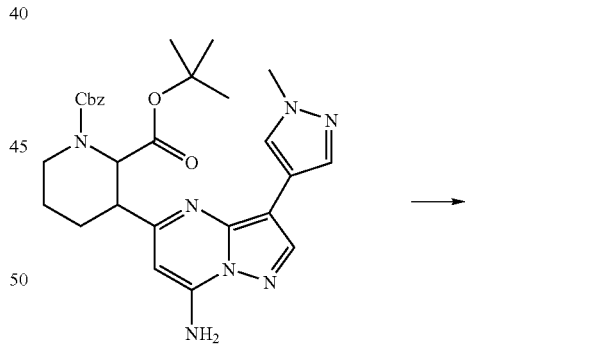

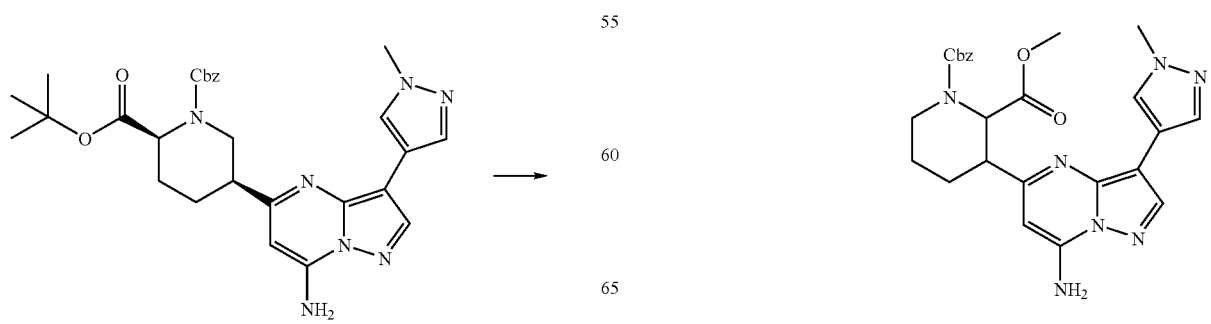

By essentially the same procedure as set forth in Preparative Example 1580-C, only substituting the methyl ester from Preparative Example 1520-C the tert-butyl ester was prepared in 70% yield.

Preparative Example 1600-C

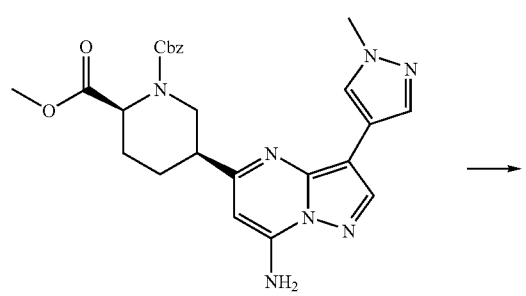

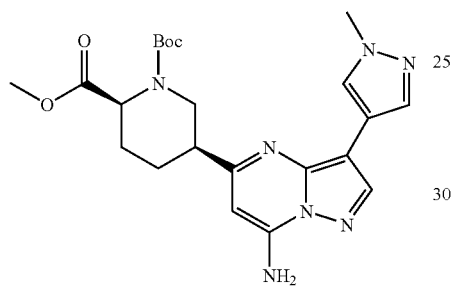

The compound from Preparative Example 1520-C (1.894 g, 3.874 mmol) was dissolved in methanol (75 mL) to which di-tert-butyldicarbonate (2.535 g, 11.62 mmol, 3.00 equiv.) and 10% palladium on carbon (1.220 g, 1.15 mmol, 0.30 equiv.) were then added. The mixture was hydrogenated in a Parr vessel for 3 days at 52 psi. After filtering through Celite and washing with methanol then dichloromethane, the combined filtrates were combined and concentrated under reduced pressure. The residue was dissolved in methanol and purified on an Analogix SF40-150 column using the Analogix Intelliflash-280 running a gradient from 0% to 10% methanol-dichloromethane. The product was obtained as a yellow solid (1.510 g, 86% yield).

Preparative Example 1610-C

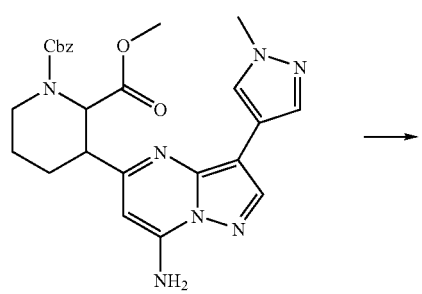

-continued

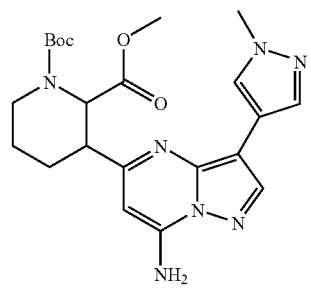

By essentially the same procedure as set forth in Preparative Example 1600-C, only substituting the methyl ester from Preparative Example 1590-C the above compound was prepared in 81% yield.

Preparative Example 1620-C

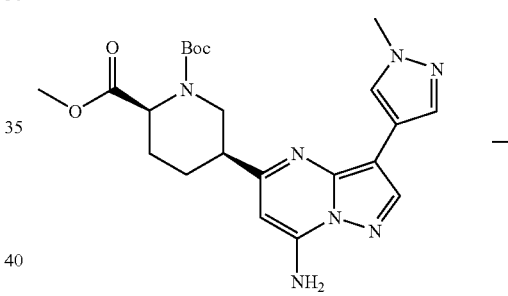

The ester from Preparative Example 1600-C (0.356 g, 0.781 mmol) in anhydrous THF (6 mL) was treated with lithium triethylborohydride (1M solution in THF, 4.6 mL, 4.6 mmol, 5.89 equiv.) and stirred 14 hours at room temperature. The solution was then diluted with methanol and concentrated. The residue was suspended in dichloromethane, loaded on an Isco Redisep-40 gram column and purified with an Analogix Intelliflash-280 system running a gradient from 0% to 5% methanol-dichloromethane. The product is obtained as a white solid (0.282 g, 85% yield).

Preparative Example 1630-C

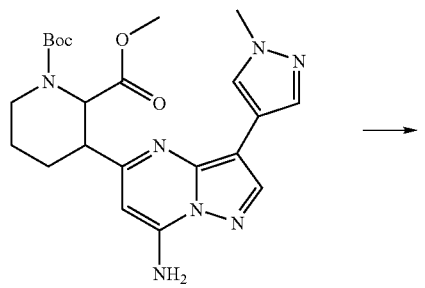

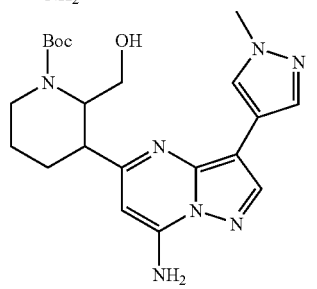

+

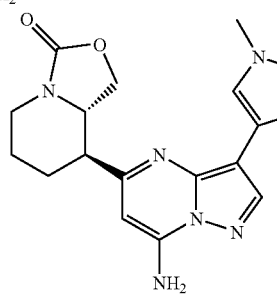

By essentially the same procedure as set forth in Preparative Example 1620-C, two products were obtained from the methyl ester from Preparative Example 1610-C. The alcohol (53% yield) was obtained as a mixture of cis and trans isomers, while the cyclic carbamate (18% yield) consisted only of trans isomer. LCMS 354 [MH⁺]. ¹H NMR (CDCl₃) δ 8.16 (s, 1H), 7.93 (s, 1H), 7.86 (s, 1H), 5.99 (s, 1H), 5.96 (s, 2H), 4.48 (t, J=8.8 Hz, 1H), 4.25 (m, 1H), 4.06 (m, 1H), 3.98 (s, 3H), 3.95 (m, 1H), 2.90 (m, 1H), 2.65 (m, 1H), 2.18 (m, 1H), 1.6-1.9 (m, 3H).

Preparative Example 1640-C

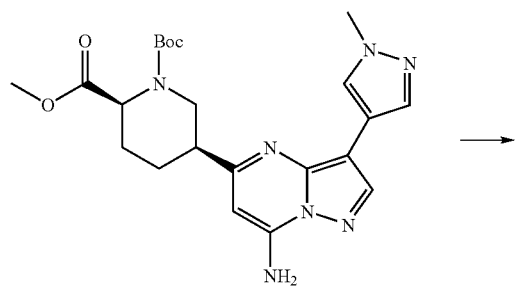

-continued

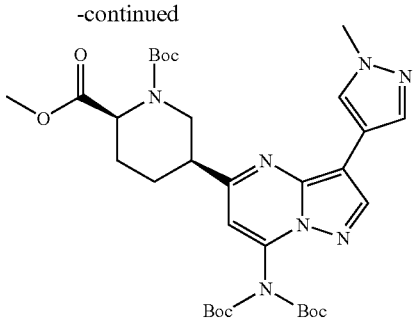

The ester from Preparative Example 1600-C (0.182 g, 0.400 mmol), di-tert-butyl dicarbonate (0.263 g, 1.20 mmol, 3 equiv.) and N,N-dimethylaminopyridine (0.149 g, 1.22 mmol, 3 equiv.) were stirred together in THF (2 mL) at room temperature for 14 hours. The resulting solution was then concentrated under reduced pressure, and the residue was dissolved in dichloromethane and purified by chromatography on an Isco Redisep-12 gram column using an Analogix Intelliflash 280 system running 1% methanol-dichloromethane. A yellow oil (0.245 g, 94% yield) was obtained.

Preparative Example 1650-C

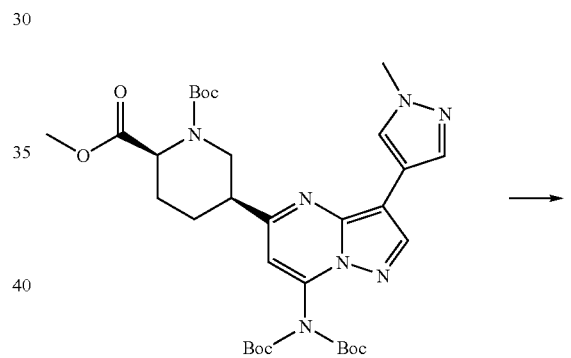

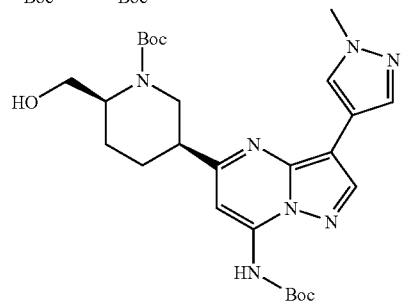

The ester from Preparative Example 1640-C (0.255 g, 0.374 mmol) in anhydrous THF (5 mL) was treated with lithium triethylborohydride (1M solution in THF, 2.5 mL, 2.5 mmol, 6.68 equiv.) and stirred 14 hours at room temperature. The solution was then diluted with saturated aqueous ammonium chloride (10 mL) and water (1 mL) and extracted with ethyl acetate (2×15 mL). The combined extracts were washed with brine, dried with anhydrous sodium sulfate, filtered and concentrated under reduced pressure. The resulting yellow solid was suspended in dichloromethane, loaded on an Isco Redisep-4 gram column and purified using an Analogix Intelliflash-280 system running a gradient from 0% to 30% methanol-dichloromethane. The product is obtained as a yellow oil (0.172 g, 87% yield).

Preparative Example 1660-C

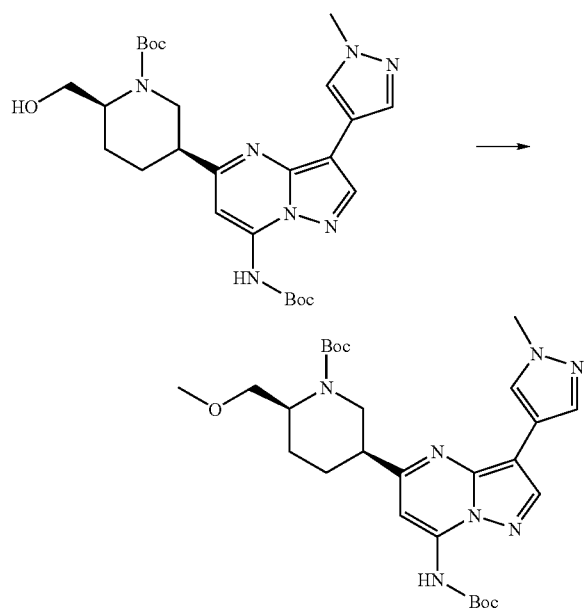

The alcohol from Preparative Example 1650-C (0.086 g, 0.162 mmol) was dissolved in anhydrous THF (1 mL) and sodium hydride (60% dispersion in mineral oil, 0.019 g, 0.475 mmol, 2.93 equiv.) was added. The resulting suspension was stirred 1.5 hours at room temperature, then iodomethane (0.11 mL, 0.161 mmol, 0.99 equiv.) was added, the mixture was stirred 16 hours at room temperature. Water (3 mL) and brine (1 mL) were added, and the mixture was extracted with ethyl acetate (3×3 mL). The combined extracted were concentrated under reduced pressure, and the residue was dissolved in dichloromethane and purified by chromatography on an Analogix SF12-4 column using an Analogix Intelliflash 280 system running a gradient from 10% to 50% acetone-dichloromethane. The product was obtained as a yellow oil (0.018 g, 21% yield).

Preparative Example 1670-C

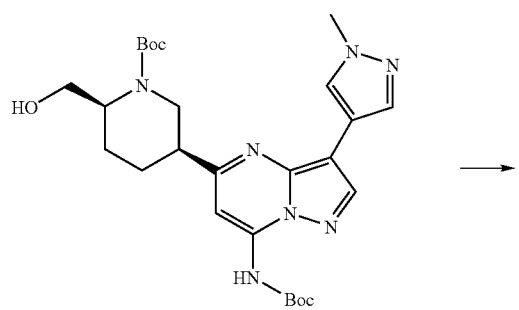

-continued

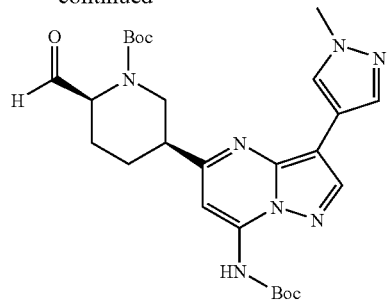

The alcohol from Preparative Example 1660-C (0.160 g, 0.298 mmol) in dichloromethane (5 mL) was slowly added to a suspension Dess-Martin periodinane (0.267 g, 0.629 mmol, 2.11 equiv.) in dichloromethane (2 mL). The resulting solution was stirred 2.5 hours at room temperature before it was quenched by adding 2N aqueous sodium hydroxide (10 mL) and ethyl ether (10 mL). The two-phase mixture was stirred vigorously for 1 hour, and then the two layers were separated, and the aqueous phase was extracted with ethyl ether (10 mL). The ether extracts were combined, washed with brine, dried with anhydrous sodium sulfate, filtered, and concentrated under reduced pressure to yield a yellow solid (0.091 g, 57% yield) which was used without further purification.

Preparative Example 1680-C

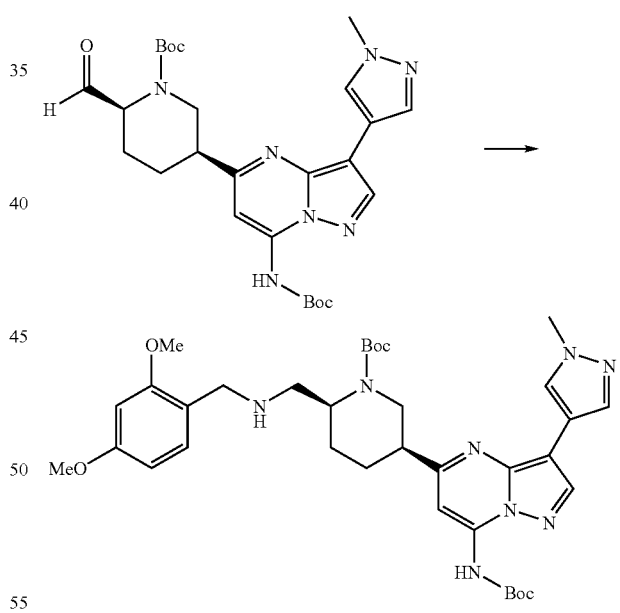

The aldehyde fro Preparative Example 1670-C (0.086 g, 0.164 mmol), 2,4-dimethoxybenzylamine (0.05 mL, 0.333 mmol, 2.03 equiv.), and sodium cyanoborohydride (0.031 g, 0.493 mmol, 3.01 equiv.) were combined in methanol (2 mL) and acetic acid (0.025 mL, 0.440 mmol, 2.66 equiv.) was added to achieve a pH of 5 to 6. The resulting solution was stirred 3 days at room temperature. Water (10 mL) and saturated aqueous potassium carbonate (1 mL) were added, and the mixture was extracted with dichloromethane (3×10 mL). The extracts were combined and concentrated under reduced pressure to yield a crude oil that was purified by chromatography on an Isco Redisep 4-gram column using an Analogix Intelliflash 280 system running a gradient from 0% to 10% methanol-dichloromethane. The product was obtained as a yellow oil (0.090 g, 82% yield)

Preparative Example 1690-C

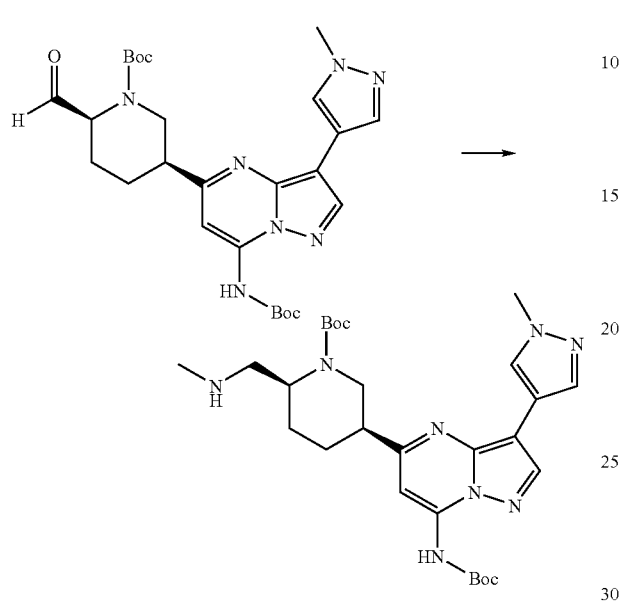

By essentially the same procedure set forth in Preparative Example 1680-C, the above secondary amine was prepared using methylamine (2M solution in THF, 3.67 equiv.). The product was obtained as a yellow solid (0.014 g, 22% yield).

Preparative Example 1700-C

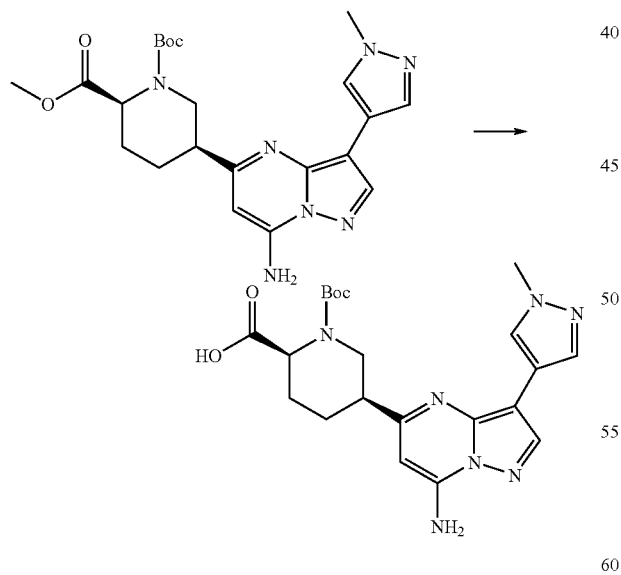

The ester from Preparative Example 1600-C (0.125 g, 0.275 mmol) was stirred for 4.5 hours at room temperature in a mixture of THF (2 mL), methanol (1 mL) and 2N aqueous sodium hydroxide (0.50 mL, 1.0 mmol, 3.6 equiv.). After adding 2N aqueous hydrochloric acid (0.50 mL) and water (5 mL), the mixture was extracted with ethyl acetate (6×5 mL). The combined extracts were dried with anhydrous sodium sulfate, filtered and concentrated under reduced pressure to yield a yellow solid (0.116 g, 92% yield).

Preparative Example 1710-C

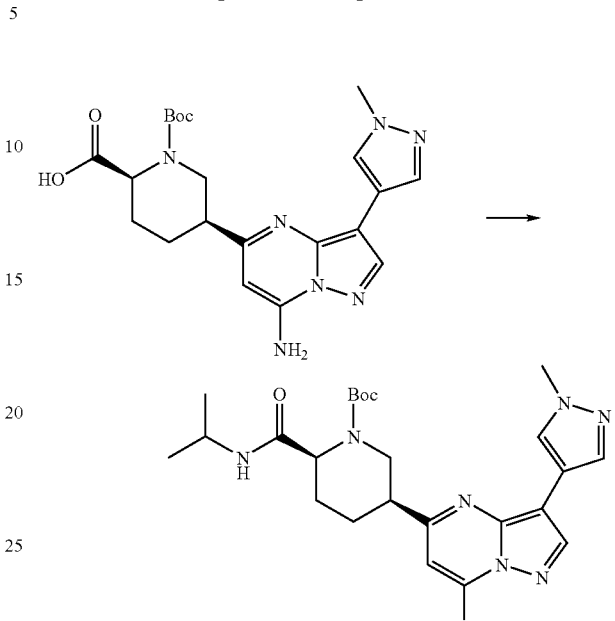

The acid from Preparative Example 1700-C (0.114 g, 0.258 mmol), N-(3-dimethylaminopropyl)-N'-ethylcarbodiimide hydrochloride (0.075 g, 0.391 mmol, 1.52 equiv.), 1-hydroxybenzotriazole (0.056 g, 0.411 mmol, 1.59 equiv.), triethylamine (0.12 mL, 0.861 mmol, 3.34 equiv.) and isopropylamine (0.04 mL, 0.467 mmol, 1.81 equiv.) were combined in anhydrous dichloromethane (5.0 mL) and anhydrous DMF (0.12 mL) and stirred at room temperature for 16 hours. The crude reaction mixture was then loaded directly on an Isco Redisep 4-gram chromatography column and purified using an Analogix Intelliflash 280 system running a gradient from 0% to 3% methanol-dichloromethane. The product was obtained as a yellow oil (0.100 g, 81% yield).

Preparative Example 1720-C-1760-C

By essentially the same procedure as set forth in Preparative Example 1710-C, the compounds given in Column 2 of Table 260-C were prepared.

TABLE 260-C

| Prep. Ex. | Column 2 |
|---|---|
| 1720-C | |

TABLE 260-C-continued

| Prep. Ex. | Column 2 |
|---|---|
| 1730-C | 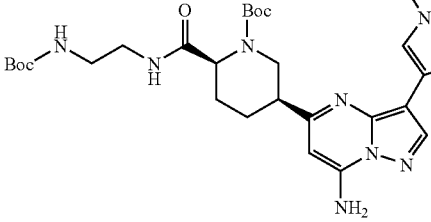 |
| 1740-C | 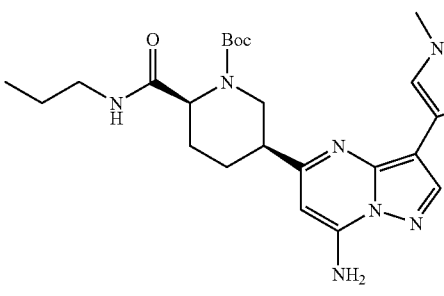 |
| 1750-C | 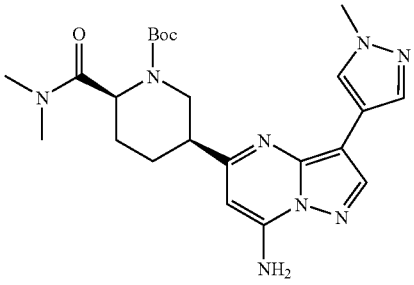 |
| 1760-C | 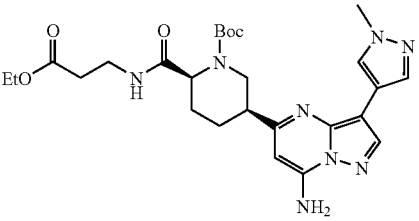 |

Preparative Example 1770-C

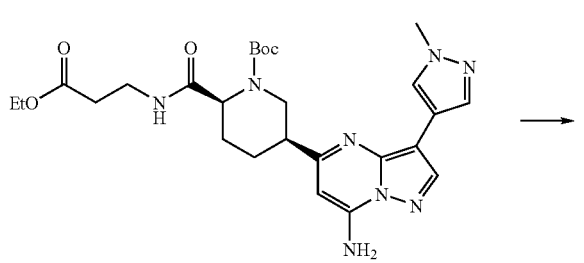

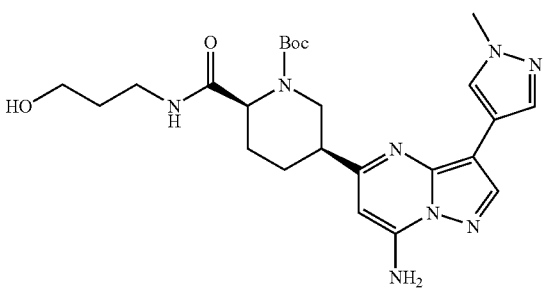

By essentially the same procedure as set forth in Preparative Example 1620-C, only utilizing the compound from Preparative Example 1760-C (0.037 g, 0.069 mmol) the above alcohol was obtained as a colorless oil (0.025 g, 72% yield).

Preparative Example 1780-C

The ester from Preparative Example 1760-C (0.037 g, 0.069 mmol) was stirred for 15 hours at 95° C. in a sealed tube with 7N ammonia in methanol (3 mL). After cooling, the solution was concentrated under reduced pressure and the purified by chromatography on an Isco Redisep-4 gram column using an Analogix Intelliflash 280 system running a gradient from 0% to 10% methanol-dichloromethane. The product was obtained as a yellow solid (0.024 g, 70% yield).

Preparative Example 1790-C

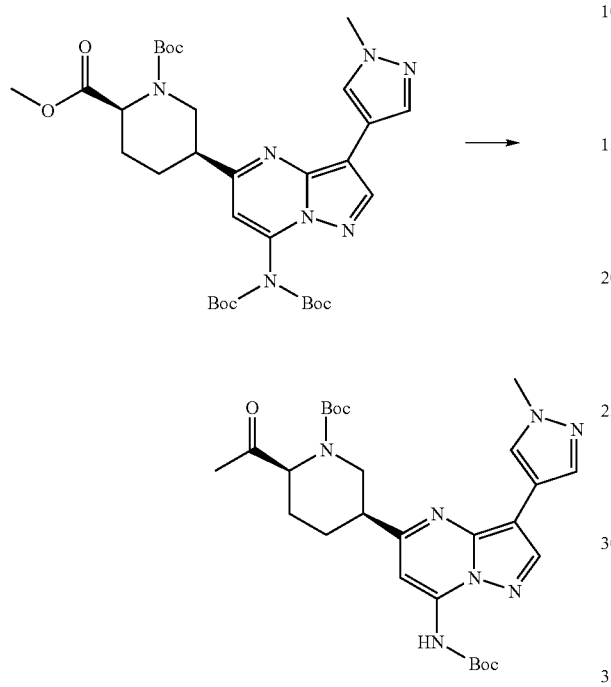

The ester from Preparative Example 1640-C (0.211 g, 0.322 mmol) was dissolved anhydrous THF (3.5 mL) and cooled to −20° C. N,O-dimethylhydroxylamine hydrochloride (0.043 g, 0.441 mmol, 1.37 equiv.) in one portion followed by methylmagnesium chloride (3M solution in THF, 0.35 mL, 1.05 mmol, 3.26 equiv.) slowly via syringe. After stirring for 1 hour, warming to −5° C., additional methylmagnesium chloride (3M solution in THF, 0.70 mL, 2.10 mmol, 6.52 equiv.) was added, and the mixture was stirred 15 hours warming to room temperature. At this point, TLC (20% methanol-dichloromethane) indicated the continued presence of starting material. An additional portion of N,O-dimethylhydroxylamine hydrochloride (0.052 g, 0.533 mmol, 1.66 equiv.) followed by methylmagnesium chloride (3M solution in THF, 0.40 mL, 1.20 mmol, 3.73 equiv.). After stirring 1.5 hours at room temperature, additional methylmagnesium chloride (3M solution in THF, 0.70 mL, 2.10 mmol, 6.52 equiv.) was added. The mixture was stirred 3 hours at room temperature and was then quenched with saturated aqueous ammonium chloride (10 mL) and water (2 mL) and extracted with ethyl acetate (3×15 mL). The combined extracts were washed with brine, dried with anhydrous sodium sulfate, filtered and concentrated. The crude material was purified by chromatography on an Isco Redisep-12g column using an Analogix Intelliflash 280 system running a gradient from 0% to 20% acetone-dichloromethane. The product was obtained as an partially solidified yellow oil (0.113 g, 66% yield).

Preparative Example 1800-C

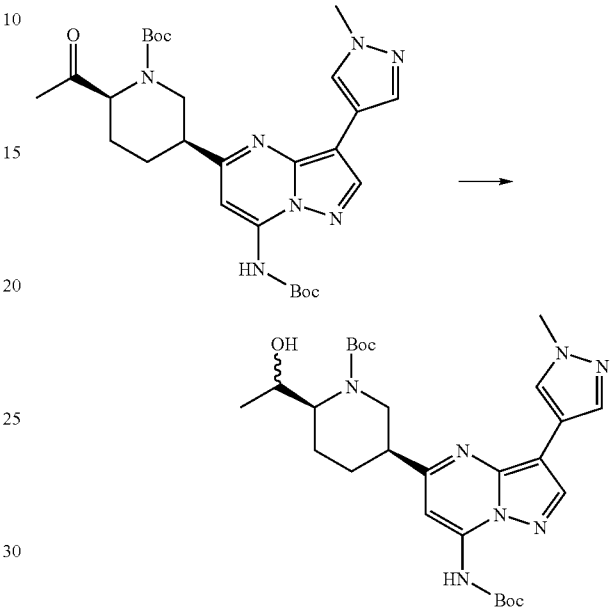

The ketone from Preparative Example 1790-C (0.056 g, 0.104 mmol) in anhydrous THF (3 mL) was treated with lithium triethylborohydride (1 M solution in THF, 0.35 mL, 0.35 mmol, 3.37 equiv.) and stirred 15 hours at room temperature. Water was then added (2 mL) and the resulting solution was concentrated under reduced pressure. The resulting oily residue was dissolved in methanol and concentrated again to yield a yellow solid. This was suspended in 10% methanol-dichloromethane (1.5 mL), loaded on an Isco Redisep-4 g chromatography column and purified using an Analogix Intelliflash 280 system running a gradient from 0% to 35% acetone-dichloromethane. The product was obtained as a yellow oil (0.048 g, 85% yield).

Preparative Example 1810-C

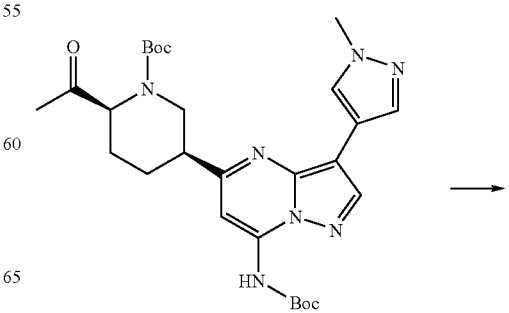

-continued

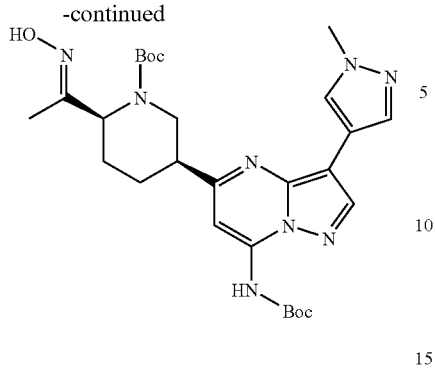

The ketone from Preparative Example 1790-C (0.066 g, 0.122 mmol), hydroxylamine hydrochloride (0.023 g, 0.334 mmol, 2.74 equiv.) and sodium acetate (0.023 g, 0.274 mmol, 2.25 equiv.) were stirred 15 hours in ethanol (5 mL) at 70° C. After cooling, the mixture was concentrated under reduced pressure, and the crude solid was suspended in dichloromethane and purified by chromatography on an Isco Redisep-4 g column using an Analogix Intelliflash 280 system running gradient from 0% to 20% acetone-dichloromethane. The product was obtained as a yellow oil (0.0566 g total, 84% yield) in an E:Z ratio of 87:13, of which 0.037 g was obtained as pure E isomer.

Preparative Example 1820-C

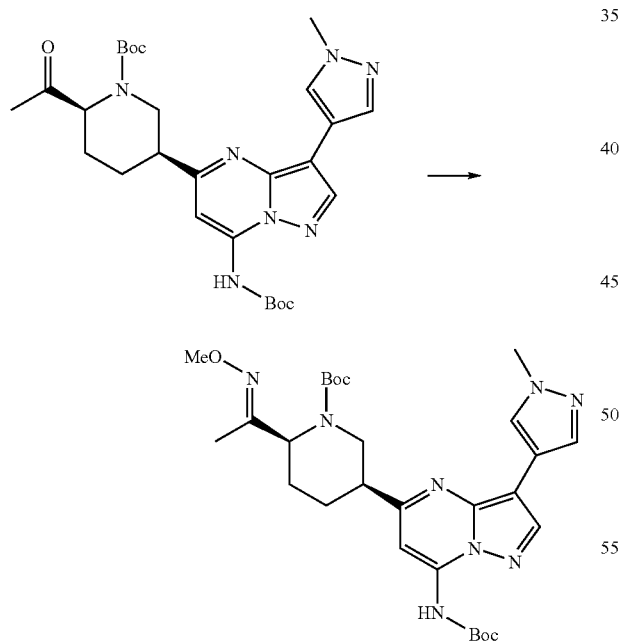

By essentially the same procedure set forth in Preparative Example 1810-C, methyl oxime was prepared using methoxylamine hydrochloride. The product was obtained as a yellow oil in 81% yield that consisted of a 90:10 ration of E to Z product. This mixture was used without further purification in the next step.

Example 820-C

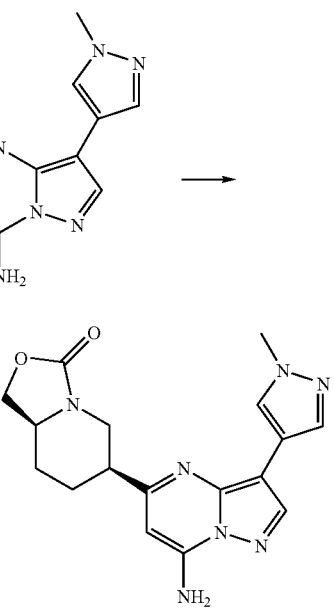

The alcohol from Preparative Example 1650-C (0.067 g, 0.156 mmol) in anhydrous dichloromethane (2 mL) was treated with triethylamine (0.025 mL, 0.179 mmol, 1.15 equiv.) and methanesulfonyl chloride (0.03 mL, 0.388 mmol, 2.49 equiv.) and stirred 14 hours at room temperature. The resulting yellow-white suspension was treated with additional triethylamine (0.10 mL, 0.717 mmol, 4.60 equiv.), at which point it became homogenous, and was then heated for 4 hours at 40° C. After cooling, the solution was diluted with water (7 mL) and extracted with ethyl acetate (3×7 mL). The combined extracts were dried with anhydrous sodium sulfate, filtered and concentrated under reduced pressure. The crude orange solid was dissolved in dichloromethane and purified by chromatography on an Isco Redisep 4-gram column using an Analogix Intelliflash 280 system running 5% methanol-dichloromethane. The product was obtained as a yellow oil (0.023 g, 41% yield). LCMS: 354 [MH$^+$]. $^{13}$C NMR (CDCl$_3$) δ 161.74, 157.61, 147.16, 144.96, 136.56, 127.12, 113.82, 102.53, 86.95, 69.05, 54.49, 43.62, 42.79, 38.76, 30.67, 26.68.

Preparative Example 1830-C

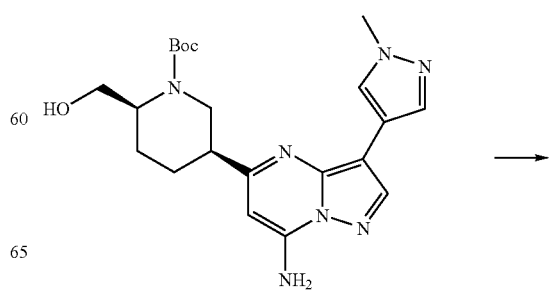

-continued

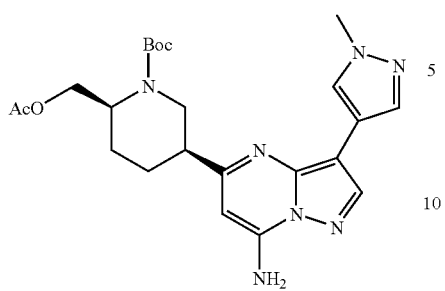

The alcohol from Preparative Example 1650-C(0.050 g, 0.117 mmol) was dissolved in anhydrous dichloromethane (1 mL) and triethylamine (0.04 mL, 0.287 mmol, 2.45 equiv.) and acetic anhydride (0.015 mL, 0.159 mmol, 1.35 equiv.) were added. The solution was 15 hours at room temperature. The solution was then concentrated under reduced pressure to yield a yellow solid that was dissolved in dichloromethane and purified by chromatography on an Isco Redisep 4-gram column using an Analogix Intelliflash 280 system running a gradient from 0% to 5% methanol-dichloromethane. A yellow oil (0.051 g, 94% yield) was obtained.

Example 830-C

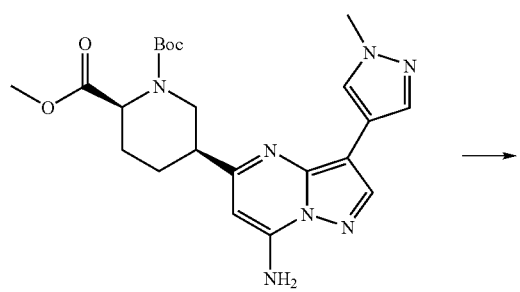

The ester from Preparative Example 1640-C (0.103 g, 0.227 mmol) was dissolved in 7N ammonia in methanol (10 mL) in a sealed tube and stirred 15 hours at 120° C. followed by 22 hours at 160° C. After cooling, the solution was concentrated under reduced pressure to yield an orange gummy solid which was dissolved in 25% acetonitrile-water (1.0 mL) and purified by reverse-phase HPLC on a Waters PrepLC 25mm column running a gradient from 5% to 50% acetonitrile-water. The product was obtained as a yellow oil (0.024 g, 26% yield). LCMS 341 [MH$^+$]. $^{13}$C NMR (CD$_3$OD) δ 161.70, 149.97, 146.25, 142.43, 137.51, 128.49, 115.42, 102.33, 87.25, 58.67, 47.92, 41.75, 38.87, 30.35, 28.61.

Example 840-C

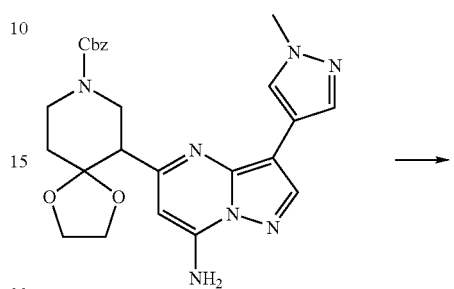

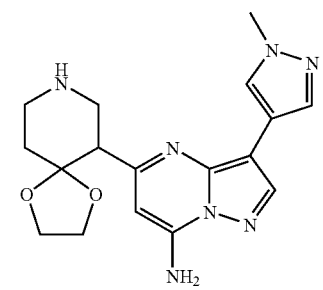

The ketal from Preparative Example 1510-C (0.075 g, 0.153 mmol) hydrogenated at 55 psi for 20 hours in methanol (20 mL) with 10% palladium on carbon (0.055 g, 0.052 mmol, 0.34 equiv.) added. The suspension was filtered through Celite, the Celite was washed with methanol and dichloromethane, and the combined filtrates were concentrated under reduced pressure. The crude residue was dissolved in 5% methanol-dichloromethane and purified by chromatography on an Isco Redisep-4g column using an Analogix Intelliflash 280 system running a gradient from 0% to 10% 7N ammonia in methanol-dichloromethane. The product was obtained as a colorless oil (0.0125 g, 23% yield). LCMS: 356 [MH$^+$]. $^{13}$C NMR (CDCl$_3$) δ 160.09, 146.21, 144.36, 140.83, 136.27, 126.88, 113.56, 108.44, 101.81, 89.65, 64.82, 64.52, 51.60, 49.33, 48.49, 44.10, 38.81.

Preparative Example 1840-C

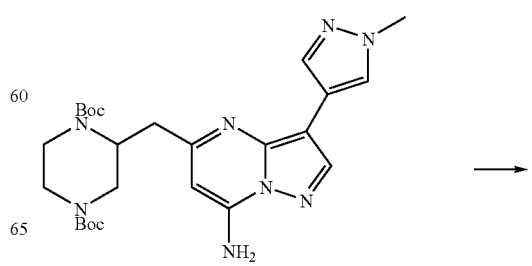

-continued

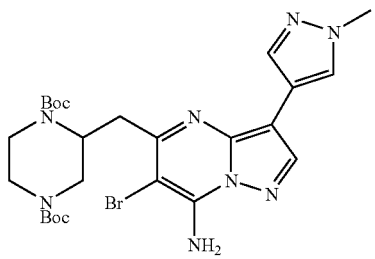

N-Bromosuccinimide (0.017 g, 1.0 equiv.) in CH$_3$CN (0.5 mL) was added dropwise to a solution of the compound from Preparative Example 1570-C (0.050 g, 0.097 mmol) in anhydrous acetonitrile (0.5 mL) and CH$_2$Cl$_2$ (0.5 mL) and the mixture was stirred for 0.5 hours at 25° C. The solution was concentrated and purified by preparative chromatography (20%acetone-CH$_2$Cl$_2$) to give (0.054 g, 94.4%) of a cream solid.

Preparative Example 1850-C-2030-C

By essentially the same procedure as set forth in Preparative Example 1840-C, the compounds given in Column 2 of Table 270-C were prepared.

TABLE 270-C

| Prep. Ex. | Column 2 |
|---|---|
| 1850-C | 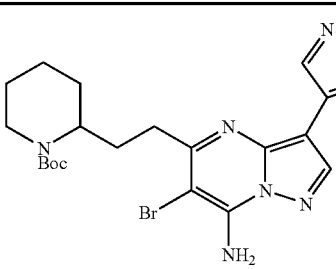 |
| 1860-C | 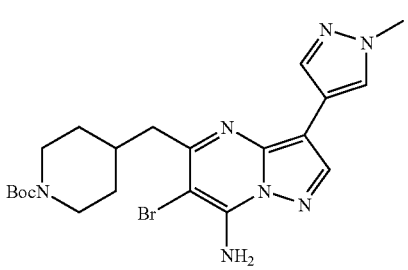 |
| 1870-C | 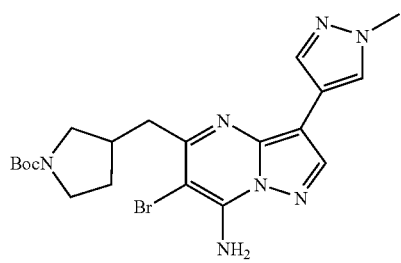 |

TABLE 270-C-continued

| Prep. Ex. | Column 2 |
|---|---|
| 1880-C | 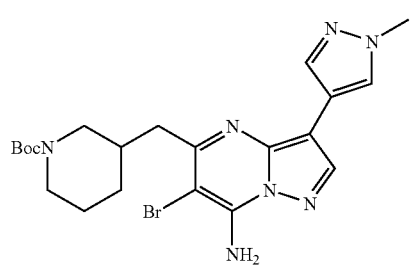 |
| 1890-C | 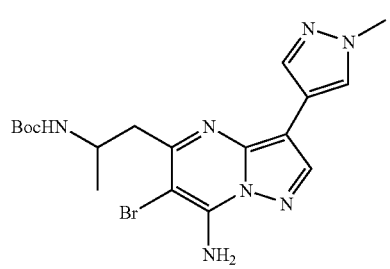 |
| 1900-C | 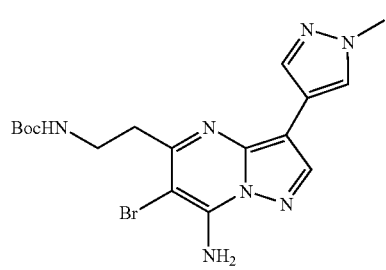 |
| 1910-C | 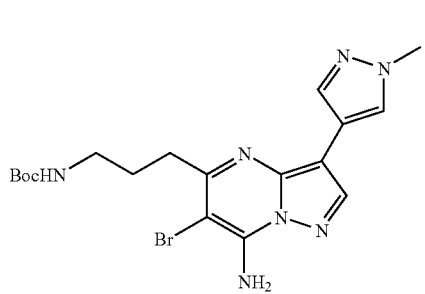 |
| 1920-C | 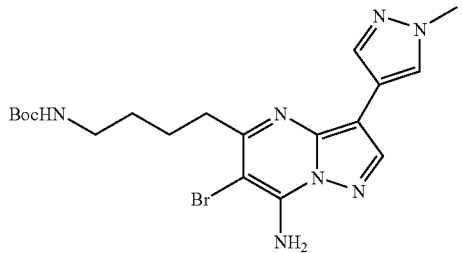 |

TABLE 270-C-continued
| Prep. Ex. | Column 2 |
|---|---|
| 1930-C | 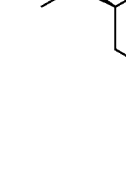 |
| 1940-C | |
| 1950-C | |
| 1960-C | |
| 1970-C | |
| 1980-C | 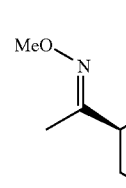 |
| 1990-C | |
| 2000-C | |
| 2010-C | |
| 2020-C | |

TABLE 270-C-continued

| Prep. Ex. | Column 2 |
|---|---|
| 2030-C | 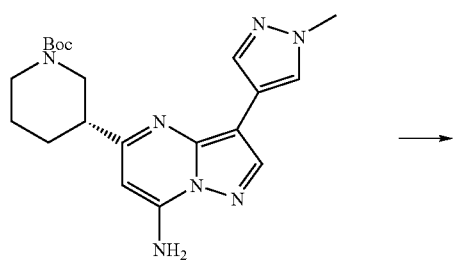 |
| Example 850-C | |

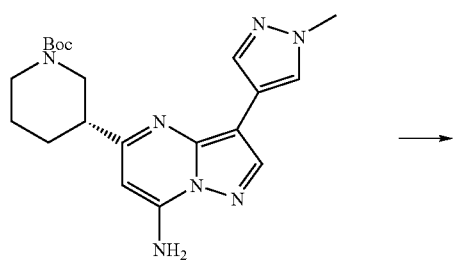

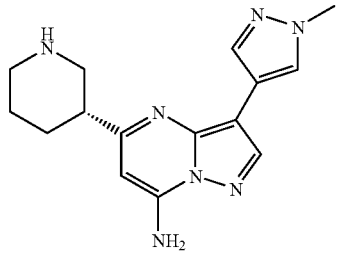

A solution of the compound from Preparative Example 1360-C (0.25 g, 0.63 mmol) in CH$_2$Cl$_2$ (6 mL) and trifluoroacetic acid (2 ml) was stirred at 25° C. for 1 h. The solution was concentrated under reduced pressure and the residue was diluted with CH$_2$Cl$_2$ (10 mL), 1N NaOH (1 mL) and saturated aqueous K$_2$CO$_3$ (30 mL). The aqueous layer was further extracted with CH$_2$Cl$_2$ (3×10 mL). The combined organic layer was dried (Na$_2$SO$_4$), filtered and concentrated under reduced pressure. Purification by preparative thin layer chromatography (10% 7N NH$_3$ in MeOH—CH$_2$Cl$_2$) afforded XX (0.16 g, 85%) as a white solid. $^1$H NMR (CD$_3$OD) δ 8.20 (s, 1H), 8.05 (s, 1H), 7.96 (s, 1H), 6.06 (s, 1H), 3.94 (s, 3H), 3.29-3.22 (m, 1H), 3.10-3.03 (m, 1H), 2.99-2.93 (m, 1H), 2.88-2.80 (m, 1H), 2.73-2.66 (m, 1H), 2.14-2.09 (m, 1H), 1.89-1.79 (m, 2H), 1.71-1.60 (m, 1H); MH$^+$=298.

Example 860-C-1600-C

By essentially the same procedure as set forth in Example 850-C, the compounds given in Column 2 of Table 280-C were prepared.

TABLE 280-C

| Ex. | Column 2 | $^1$H or $^{13}$C NMR, LCMS [MH$^+$] |
|---|---|---|
| 860-C | | $^{13}$C NMR (DMSO-d$_6$) δ 160.45, 149.53, 146.17, 145.56, 141.76, 140.34, 118.94, 103.43, 86.67, 49.72, 44.98, 32.30, 24.85; MH$^+$ = 309 |
| 870-C | | $^{13}$C NMR (DMSO-d$_6$) δ 160.30, 149.51, 146.54, 146.03, 141.85, 140.38, 118.91, 103.37, 86.30, 31.36, 24.86, MH$^+$ = 283 |

TABLE 280-C-continued
| Ex. | Column 2 | $^1$H or $^{13}$C NMR, LCMS [MH$^+$] |
|---|---|---|
| 880-C | 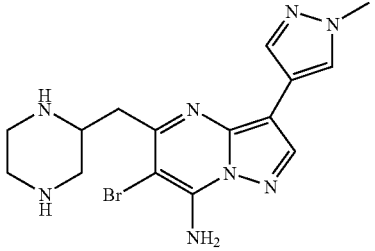 | $^1$H NMR (CD$_3$OD) δ 8.20 (s, 1H), 8.07 (s, 1H), 7.95 (s, 1H), 3.95 (s, 3H), 3.48-3.39 (m, 1H), 3.07-2.86 (m, 6H), 2.81-2.75 (m, 1H), 2.65-2.60 (m, 1H); MH$^+$ = 391/393. |
| 890-C | 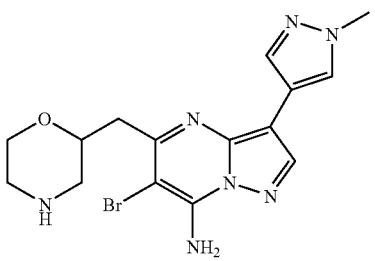 | $^1$H NMR (CD$_3$OD) δ 8.21 (s, 1H), 8.08 (s, 1H), 7.96 (s, 1H), 4.25-4.19 (m, 1H), 3.95 (s, 3H), 3.88-3.84 (m, 1H), 3.70-3.63 (m, 1H), 3.23-3.17 (m, 1H), 3.07-2.96 (m, 2H), 2.89-2.78 (m, 2H), 2.73-2.67 (m, 1H); MH$^+$ = 392/394. |
| 900-C | 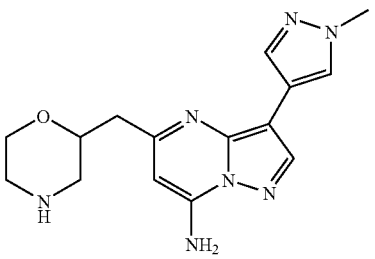 | $^1$H NMR (CD$_3$OD) δ 8.19 (s, 1H), 8.05 (s, 1H), 7.92 (s, 1H), 6.10 (s, 1H), 4.03-3.96 (m, 1H), 3.94 (s, 3H), 3.85-3.82 (m, 1H), 3.65-3.58 (m, 1H), 2.99-2.95 (m, 1H), 2.88-2.75 (m, 4H), 2.65-2.59 (m, 1H); MH$^+$ = 314. |
| 1000-C | 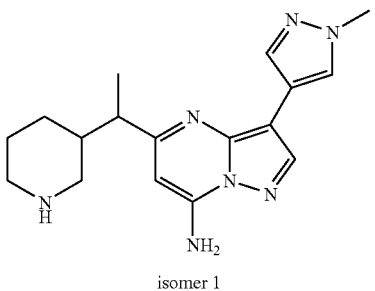  isomer 1 | $^1$H NMR (CD$_3$OD) δ 8.19 (s, 1H), 8.05 (s, 1H), 7.95 (s, 1H), 6.03 (s, 1H), 3.94 (s, 3H), 3.04-3.01 (m, 1H), 2.87-2.84 (m, 1H), 2.61-2.55 (m, 1H), 2.42-2.36 (m, 1H), 2.12-2.09 (m, 1H), 2.02-1.94 (m, 1H), 1.83-1.79 (m, 1H), 1.64-1.54 (m, 1H), 1.33-1.17 (m, 4H); MH$^+$ = 326. |
| 1010-C | 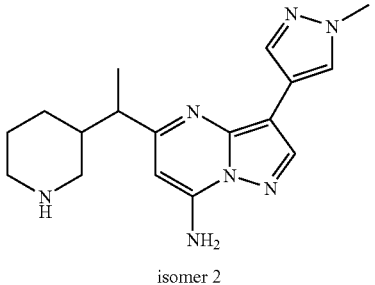  isomer 2 | $^1$H NMR (CD$_3$OD) δ 8.19 (s, 1H), 8.04 (s, 1H), 7.96 (s, 1H), 6.04 (s, 1H), 3.94 (s, 3H), 3.38-3.34 (m, 1H), 3.07-3.04 (m, 1H), 2.681-2.50 (m, 3H), 2.03-1.98 (m, 1H), 1.72-1.64 (m, 2H), 1.55-1.45 (m, 1H), 1.34-1.28 (m, 4H); MH$^+$ = 326. |

TABLE 280-C-continued

| Ex. | Column 2 | $^1$H or $^{13}$C NMR, LCMS [MH$^+$] |
|---|---|---|
| 1020-C | 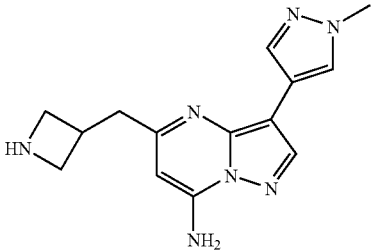 | $^1$H NMR (CD$_3$OD) δ 8.19 (s, 1H), 8.01 (s, 1H), 7.94 (s, 1H), 6.02 (s, 1H), 3.94 (s, 3H), 3.92-3.88 (m, 2H), 3.73-3.69 (m, 2H), 3.39-3.33 (m, 1H), 3.05-3.03 (d, J=8.05 Hz, 2H); MH$^+$ = 284. |
| 1030-C | 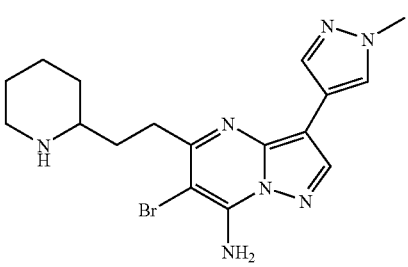 | $^1$H NMR (CD$_3$OD) δ 8.19 (s, 1H), 8.05 (s, 1H), 7.95 (s, 1H), 3.93 (s, 3H), 3.03-3.00 (m, 3H), 2.61-2.55 (m, 2H), 1.91-1.76 (m, 4H), 1.62-1.59 (m, 1H), 1.51-1.33 (m, 2H), 1.25-1.15 (m, 1H); MH$^+$ = 404/406. |
| 1040-C | 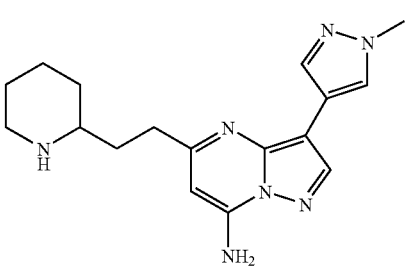 | $^1$H NMR (CD$_3$OD) δ 8.18 (s, 1H), 8.03 (s, 1H), 7.93 (s, 1H), 6.07 (s, 1H), 3.94 (s, 3H), 3.06-3.04 (m, 1H), 2.81-2.77 (m, 2H), 2.66-2.60 (m, 2H), 1.93-1.80 (m, 4H), 1.65-1.62 (m, 1H), 1.52-1.15 (m, 2H), 0.91-0.85 (m, 1H); MH$^+$ = 326. |
| 1050-C | 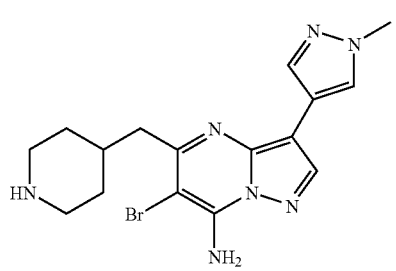 | $^1$H NMR (CD$_3$OD) δ 8.19(s, 1H), 8.03 s, 1H), 7.96(s, 1H), 3.94 (s, 3H), 3.10-3.04 (m, 2H), 2.90-2.88 (d, J=6.59 Hz, 2H), 2.67-2.60 (m, 2H), 2.24-2.13 (m, 1H), 1.831-1.75 (m, 2H), 1.42-1.31 (m, 2H); MH$^+$ = 390/392. |
| 1060-C | 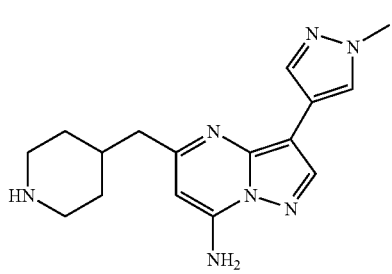 | $^1$H NMR (CD$_3$OD) δ 8.18 (s, 1H), 8.01 (s, 1H), 7.92 (s, 1H), 6.04 (s, 1H), 3.94 (s, 3H), 3.11-3.08 (m, 2H), 2.70-2.64 (m, 4H), 2.10-2.01 (m, 1H), 1.83-1.76 (m, 2H), 1.38-1.28 (m, 2H); MH$^+$ = 312. |
| 1070-C | 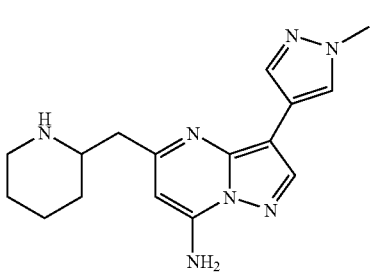 | $^1$H NMR (CD$_3$OD) δ 8.19 (s, 1H), 8.03 (s, 1H), 7.93 (s, 1H), 6.04 (s, 1H), 3.93 (s, 3H), 3.10-3.02 (m, 2H), 2.77-2.75 (m, 2H), 2.68-2.62 (m, 1H), 1.83-1.73 (m, 2H), 1.66-1.62 (m, 1H), 1.54-1.24 (m, 3H); MH$^+$ = 312. |

TABLE 280-C-continued
| Ex. | Column 2 | $^1$H or $^{13}$C NMR, LCMS [MH$^+$] |
|---|---|---|
| 1080-C | 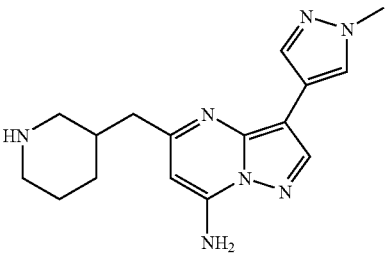 | $^1$H NMR (CD$_3$OD) δ 8.18 (s, 1H), 8.03 (s, 1H), 7.91 (s, 1H), 6.02 (s, 1H), 3.94 (s, 3H), 3.05-2.97 (m, 2H), 2.60-2.52 (m, 3H), 2.41-2.35 (m, 1H), 2.14-2.02 (m, 1H), 1.89-1.86 (m, 1H), 1.73-1.68 (m, 1H), 1.59-1.47 (m, 1H), 1.30-1.18 (m, 1H); MH$^+$ = 312. |
| 1090-C | 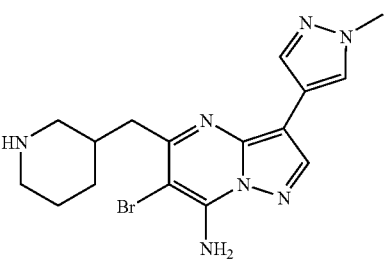 | $^1$H NMR (CD$_3$OD) δ 8.19 (s, 1H), 8.05 (s, 1H), 7.94 (s, 1H), 3.94 (s, 3H), 3.09-3.06 (m, 1H), 2.99-2.96 (m, 1H), 2.88-2.78 (m, 2H), 2.60-2.53 (m, 1H), 2.43 (t, J=11 Hz, 1H), 2.27-2.17 (m, 1H), 1.98-1.87 (m, 1H), 1.74-1.69 (m, 1H), 1.60-1.48 (m, 1H), 1.34-1.24 (m, 1H); MH$^+$ = 390/392. |
| 1100-C | 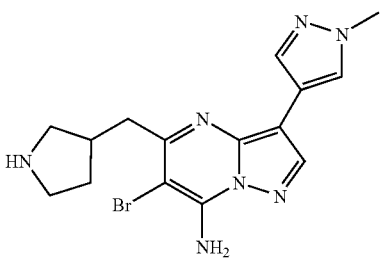 | $^1$H NMR (CD$_3$OD) δ 8.19 (s, 1H), 8.03 (s, 1H), 7.96 (s, 1H), 3.94 (s, 3H), 3.24-3.19 (m, 1H), 3.11-2.95 (m, 4H), 2.88-2.81 (m, 1H), 2.77-2.72 (m, 1H), 2.14-2.06 (m, 1H), 1.70-1.61 (m, 1H), MH$^+$ = 376/378. |
| 1110-C | 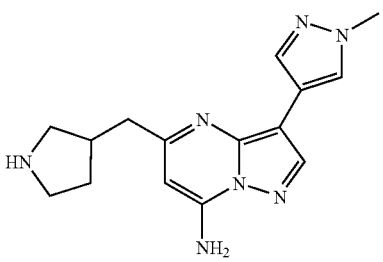 | $^1$H NMR (CD$_3$OD) δ 8.19 (s, 1H), 8.02 (s, 1H), 7.94 (s, 1H), 6.07 (s, 1H), 3.94 (s, 3H), 3.27-3.23 (m, 1H), 3.19-3.13 (m, 1H), 3.08-3.01 (m, 1H), 2.88-2.71 (m, 4H), 2.14-2.06 (m, 1H), 1.71-1.62 (m, 1H); MH$^+$ = 298. |
| 1120-C | 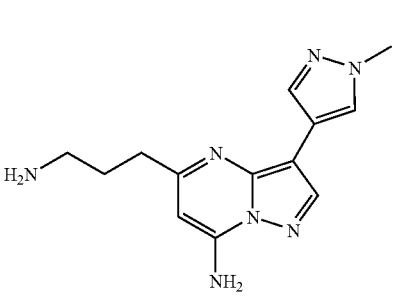 | $^1$H NMR (CD$_3$OD) δ 8.18 (s, 1H), 8.03 (s, 1H), 7.92 (s, 1H), 6.07 (s, 3H), 3.94 (s, 3H), 2.79-2.74 (m, 4H), 2.00-1.93 (m, 2H), MH$^+$ = 272. |

TABLE 280-C-continued

| Ex. | Column 2 | ¹H or ¹³C NMR, LCMS [MH⁺] |
|---|---|---|
| 1130-C | | ¹H NMR (CD₃OD) δ 8.19 (s, 1H), 8.05 (s, 1H), 7.95 (s, 1H), 3.94 (s, 3H), 3.00 (t, J=6.6 Hz, 1H), 2.80 (t, J=6.6 Hz, 1H), 2.05 (m, 1H); MH⁺ = 350/352. |
| 1140-C | | ¹H NMR (CD₃OD) δ 8.21 (s, 1H), 8.05 (s, 1H), 7.94 (s, 1H), 3.94 (s, 3H), 3.67-3.59 (m, 1H), 3.06 (dd, J=15.2 Hz, J=4.8 Hz, 1H), 2.91 (dd, J=15.2 Hz, J=8.4 Hz, 1H), 1.25 (d, J=6.6 Hz, 3H); MH⁺ = 350/352. |
| 1150-C | | ¹H NMR (CD₃OD) δ 8.20 (s, 1H), 8.05 (s, 1H), 7.94 (s, 1H), 3.94 (s, 3H), 2.97 (t, J=7.3 Hz, 2H), 2.75 (t, J=7.3 Hz, 1H), 1.92-1.85 (m, 2H), 1.69-1.61 (m, 2H); MH⁺ = 364/366. |
| 1160-C | | ¹H NMR (CD₃OD) δ 8.19 (s, 1H), 8.05 (s, 1H), 7.95 (s, 1H), 3.94 (s, 3H), 2.19 (t, J=5.8 Hz, 2H), 2.75 (t, J=5.8 Hz, 2H); MH⁺ = 336/338. |
| 1170-C | | ¹H NMR (CD₃OD) δ 8.17 (s, 1H), 8.03 (s, 1H), 7.91 (s, 1H), 6.06 (s, 1H), 3.94 (s, 3H), 2.75-2.67 (m, 4H), 1.86-1.79 (m, 2H), 1.61-1.54 (m, 2H); MH⁺ = 286. |
| 1180-C | | ¹H NMR (CD₃OD) δ 8.23 (s, 1H), 8.03 (s, 1H), 7.96 (s, 1H), 6.23 (s, 1H), 3.93 (s, 3H), 3.87-3.84 (m, 1H), 2.99-2.94 (m, 1H), 2.74-2.65 (m, 2H), 2.39-2.30 (m, 1H), 1.93 (s, 3H), 1.80-1.73 (m, 1H), 1.62-1.56 (m, 1H), 1.44-1.32 (m, 1H); MH⁺ = 312. |

TABLE 280-C-continued
| Ex. | Column 2 | $^1$H or $^{13}$C NMR, LCMS [MH$^+$] |
|---|---|---|
| 1190-C | 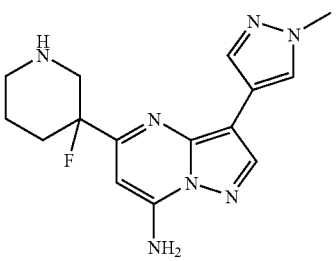 | $^1$H NMR (CD$_3$OD) δ 8.25 (s, 1H), 8.05 (s, 1H), 7.96 (s, 1H), 6.39 (d, J=2.2 Hz, 1H), 3.95 (s, 3H), 3.43-3.34 (m, 1H), 3.15-3.07 (m, 2H), 2.85-2.74 (m, 1H), 2.47-2.30 (m, 1H), 2.11-2.06 (m, 1H), 2.00-1.88 (m, 4H), 1.74-1.69 (m, 1H); MH$^+$ = 316. |
| 1200-C | 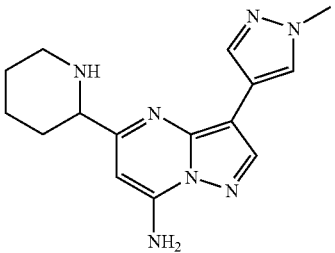 | $^1$H NMR (CDCl$_3$) δ 8.12 (s, 1H), 8.01 (s, 1H), 7.89 (s, 1H), 6.20 (s, 1H), 5.93-5.80 (br s, 2H), 3.96 (s, 3H), 3.75-3.72 (m, 1H), 3.29-3.27 (m, 2H), 2.85-2.79 (m, 1H), 2.55-2.38 (m, 3H), 2.04-1.93 (m, 1H), 1.68-1.51 (m, 4H); MH$^+$ = 298. |
| 1210-C | 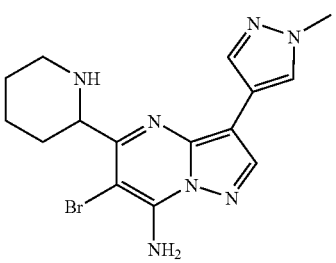 | $^1$H NMR (CD$_3$OD) δ 8.25 (s, 1H), 8.24 (s, 1H), 7.99 (s, 1H), 4.25-4.21 (m, 1H), 3.96 (s, 3H), 3.35-3.31 (m, 1H), 2.88-2.82 (m, 1H), 2.18-2.13 (m, 1H), 1.78-1.59 (m, 2H), 1.49-1.39 (m, 1H); M$^+$ = 376/378. |
| 1220-C | 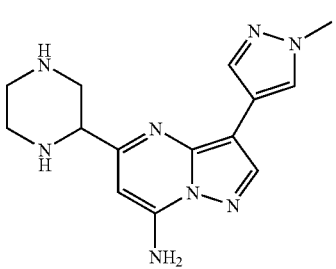 | $^1$H NMR (CD$_3$OD) δ 8.23 (s, 1H), 8.17 (s, 1H), 7.98 (s, 1H), 6.16 (s, 1H), 3.94 (s, 3H), 3.87-3.84 (m, 1H), 3.27-3.23 (m, 1H), 3.16-3.09 (m, 1H), 2.98-2.91 (m, 2H), 2.85-2.78 (m, 2H); MH$^+$ = 299. |
| 1230-C | 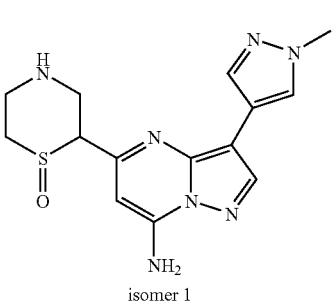<br>isomer 1 | $^1$H NMR (CD$_3$OD) δ 8.23-8.21 (m, 1H), 8.02-8.01 (m, 1H), 7.95-7.94 (m, 1H), 6.20-6.19 (m, 1H), 4.00-3.98 (m, 1H), 3.93-3.92 (m, 3H), 3.69-3.62 (m, 1H), 3.58-3.53 (m, 1H), 3.48-3.42 (m, 1H), 3.31-3.30 (m, 1H), 3.18-3.07 (m, 1H), 2.92-2.85 (m, 1H); MH$^+$ = 332. |

TABLE 280-C-continued
| Ex. | Column 2 | $^1$H or $^{13}$C NMR, LCMS [MH$^+$] |
|---|---|---|
| 1240-C | 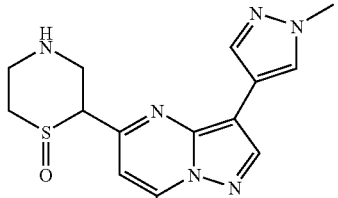 isomer 2 | $^1$H NMR (CD$_3$OD) δ 8.20-8.18 (m, 1H), 7.99-7.98 (m, 1H), 7.95-7.92 (m, 1H), 6.17-6.13 (m, 1H), 3.91-3.90 (m, 3H), 3.88-3.85 (m, 1H), 3.60-3.3 (m, 2H), 3.35-3.28 (m, 1H), 3.15-2.99 (m, 2H), 2.86-2.80 (m, 1H); MH$^+$ = 332. |
| 1250-C | 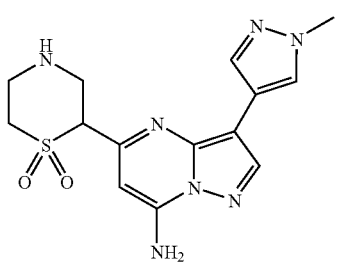 | $^1$H NMR (CD$_3$OD) δ 8.26 (s, 1H), 8.04 (s, 1H), 7.95 (s, 1H), 6.33 (s, 1H), 4.36-3.32 (m, 1H), 3.95 (s, 3H), 3.75-3.69 (m, 1H), 3.62-3.57 (m, 1H), 3.44-3.35 (m, 3H), 3.21-3.15 (m, 1H), MH$^+$ = 348. |
| 1260-C | 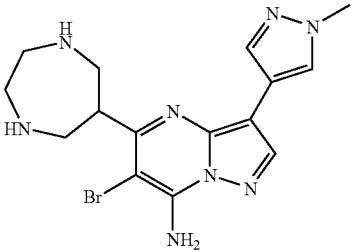 | $^1$H NMR (CD$_3$OD) δ 8.20 (s, 1H), 8.05 (s, 1H), 7.93 (s, 1H), 3.94 (s, 3H), 3.79-3.72 (m, 1H), 3.38-3.33 (m, 2H), 3.23-3.17 (m, 2H), 3.05-2.97 (m, 4H); MH$^+$ = 391/393. |
| 1270-C | 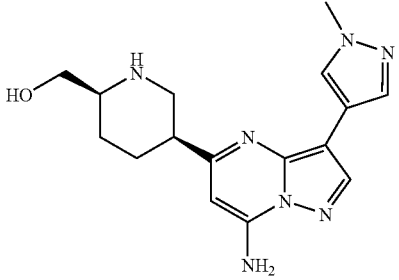 | $^{13}$C NMR (DMSO-d$_6$) δ 147.83, 143.91, 140.64, 135.60, 126.38, 113.24, 100.26, 86.18, 62.20, 56.05, 46.56, 38.43, 26.71, 23.42; MH$^+$ = 328. |
| 1280-C | 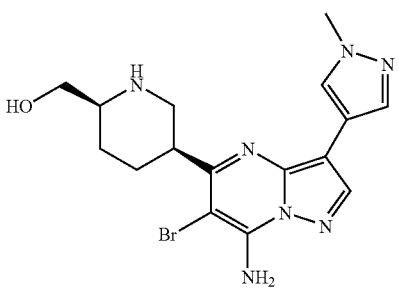 | $^{13}$C NMR (CD$_3$OD) δ 160.54, 148.14, 143.80, 143.10, 137.94, 129.35, 114.28, 103.23, 83.34, 62.38, 58.71, 47.86, 38.94, 36.41, 26.47, 22.13; MH$^+$ = 406/408. |

TABLE 280-C-continued

| Ex. | Column 2 | ¹H or ¹³C NMR, LCMS [MH⁺] |
|---|---|---|
| 1290-C | | ¹³C NMR (CD₃OD) δ 171.99, 163.62, 150.60, 144.98, 143.20, 137.46, 128.69, 115.13, 102.28, 64.65, 56.51, 48.20, 39.01, 37.10, 28.55, 22.27, 19.97; MH⁺ = 370. |
| 1300-C | | ¹³C NMR (CD₃OD) δ 164.20, 150.50, 144.92, 143.23, 137.59, 129.63, 114.46, 102.70, 87.83, 58.92, 47.34, 38.85, 37.07, 28.70, 26.40, 24.64; MH⁺ = 355. |
| 1310-C | | ¹³C NMR (CD₃OD) δ 171.65, 164.17, 150.54, 144.88, 143.24, 137.78, 129.40, 114.55, 102.61, 87.84, 58.92, 47.39, 38.93, 38.30, 36.90, 28.69, 24.38; MH⁺ = 385. |
| 1320-C | | ¹³C NMR (CD₃OD) δ 170.35, 164.24, 150.43, 144.90, 143.14, 137.53, 129.61, 114.46, 102.65, 87.85, 58.95, 47.29, 42.33, 38.83, 37.14, 28.73, 24.84, 23.61, 11.70; MH⁺ = 383. |
| 1330-C | | ¹³C NMR (CD₃OD) δ 171.52, 162.70, 149.90, 146.32, 142.12, 137.51, 128.47, 115.47, 102.23, 87.27, 58.60, 43.85, 42.32, 38.86, 30.58, 29.47, 25.31, 23.63, 11.68; MH⁺ = 383. |

TABLE 280-C-continued

| Ex. | Column 2 | ¹H or ¹³C NMR, LCMS [MH⁺] |
|---|---|---|
| 1340-C | | ¹³C NMR (CD$_3$OD) δ 169.33, 164.22, 150.46, 144.88, 143.17, 137.54, 129.66, 114.44, 102.68, 87.86, 58.98, 58.98, 47.25, 43.00, 68.83, 37.01, 28.72, 24.72, 22.50; MH⁺ = 383. |
| 1350-C | | ¹³C NMR (CD$_3$OD) δ 170.08, 164.43, 150.47, 144.89, 143.20, 137.55, 129.88, 114.39, 102.74, 87.87, 57.19, 47.16, 38.83, 36.94, 36.85, 35.96, 28.58, 23.07. MH⁺ = 369. |
| 1360-C | | ¹³C NMR (CD$_3$OD) δ 173.25, 171.02, 164.42, 150.38, 145.02, 143.08, 137.52, 129.56, 114.54, 102.63, 87.85, 61.79, 58.83, 47.44, 38.89, 37.60, 36.53, 24.86, 28.77, 24.97, 14.48; MH⁺ = 441. |
| 1370-C | | ¹³C NMR (CD$_3$OD) δ 169.19, 160.32, 148.04, 143.66, 142.87, 137.76, 129.86, 113.87, 103.38, 83.40, 58.75, 47.15, 42.99, 38.89, 35.95, 26.44, 24.65, 22.53; MH⁺ = 461/463. |
| 1380-C | | ¹³C NMR (CD$_3$OD) δ 170.07, 160.36, 148.12, 143.73, 142.93, 137.82, 129.86, 113.92, 103.41, 83.39, 58.79, 47.21, 42.36, 38.89, 35.99, 26.47, 24.71, 23.59, 11.70; MH⁺ = 461/463. |

TABLE 280-C-continued

| Ex. | Column 2 | ¹H or ¹³C NMR, LCMS [MH⁺] |
|---|---|---|
| 1390-C | | ¹³C NMR (CD₃OD) δ 169.97, 160.54, 148.11, 143.74, 142.90, 137.82, 130.10, 113.84, 103.46, 83.39, 56.97, 47.13, 38.89, 36.95, 35.97, 35.78, 26.28, 22.99; MH⁺ = 447/449. |
| 1400-C | | ¹³C NMR (CD₃OD) δ 170.46, 164.24, 150.46, 144.93, 143.18, 137.56, 129.62, 114.46, 102.68, 87.85, 60.33, 58.91, 47.30, 38.88, 37.68, 37.14, 33.13, 28.73, 24.78; MH⁺ = 399. |
| 1410-C | | ¹³C NMR (CD₃OD) δ 163.89, 150.50, 145.03, 143.22, 137.72, 128.81, 115.02, 102.38, 87.60, 72.82, 59.55, 57.04, 47.82, 38.98, 37.17, 28.71, 22.35; MH⁺ = 342. |
| 1420-C | | ¹³C NMR (CD₃OD) δ 193.34, 170.43, 164.21, 150.48, 144.91, 143.20, 137.58, 129.69, 114.44, 102.68, 87.84, 58.84, 47.28, 38.91, 37.05, 37.03, 35.75, 28.70, 24.73; MH⁺ = 412. |
| 1430-C | | ¹³C NMR (CD₃OD) δ 205.83, 164.03, 150.53, 144.87, 143.23, 137.60, 129.10, 114.54, 102.47, 87.85, 64.38, 47.35, 38.95, 37.05, 28.85, 22.95; MH⁺ = 340. |

TABLE 280-C-continued
| Ex. | Column 2 | $^1$H or $^{13}$C NMR, LCMS [MH$^+$] |
|---|---|---|
| 1440-C | 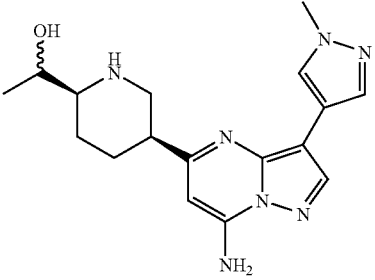 | $^{13}$C NMR (CD$_3$OD) δ 163.90, 150.48, 145.09, 143.16, 137.66, 129.00, 114.88, 102.41, 87.65, 68.07, 62.83, 47.82, 38.93, 37.43, 28.53, 23.23, 20.54; MH$^+$ = 342. |
| 1450-C | 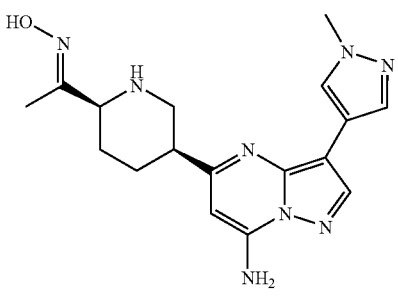 | $^{13}$C NMR (CD$_3$OD) δ 164.29, 154.15, 150.54, 143.32, 137.79, 128.94, 114.99, 87.78, 59.95, 48.19, 39.06, 37.39, 29.12, 25.14, 11.68; MH$^+$ = 355. |
| 1460-C | 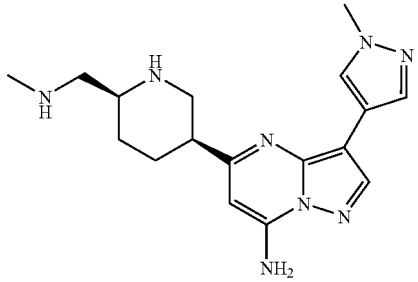 | $^1$H NMR (CD$_3$OD) δ 8.24 (s, 1H), 8.00 (s, 1H), 7.95 (s, 1H), 6.13 (s, 1H), 3.94 (s, 3H), 3.75 (m, 1H), 3.25 (m, 2H), 3.13 (m, 1H), 2.85-2.95 (m, 2H), 2.53 (s, 3H), 2.05-2.12 (m, 2H), 1.58-1.80 (m, 2H); MH$^+$ = 341. |
| 1470-C | 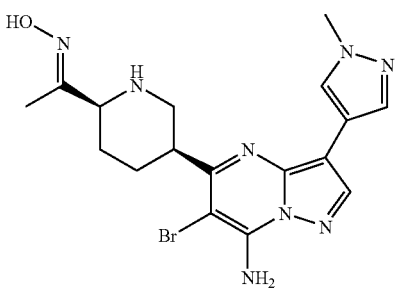 | $^{13}$C NMR (CD$_3$OD) δ 160.51, 154.07, 148.14, 143.74, 143.09, 137.83, 129.24, 114.47, 102.97, 83.42, 59.73, 48.14, 39.10, 36.52, 26.84, 25.13, 11.73; MH$^+$ = 433/435. |
| 1480-C | 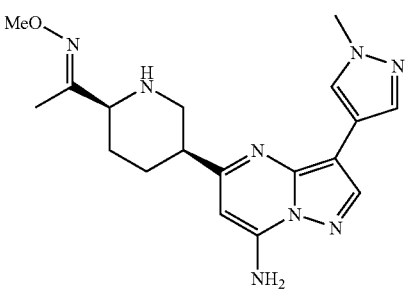 | $^{13}$C NMR (CD$_3$OD) δ 163.77, 154.83, 150.57, 144.95, 143.25, 137.73, 128.81, 115.05, 102.47, 87.59, 62.45, 59.16, 47.75, 38.99, 37.14, 29.20, 25.30, 12.32; MH$^+$ = 368. |

TABLE 280-C-continued
| Ex. | Column 2 | $^1$H or $^{13}$C NMR, LCMS [MH$^+$] |
|---|---|---|
| 1490-C | 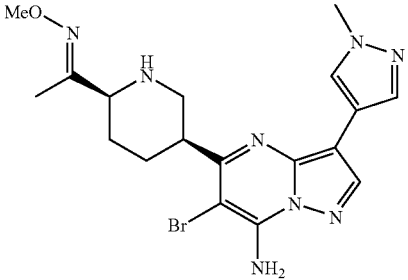 | $^{13}$C NMR (CD$_3$OD) δ 160.15, 154.81, 148.24, 143.76, 143.01, 137.80, 129.03, 114.58, 103.16, 83.21, 62.41, 59.11, 48.02, 39.04, 36.63, 26.77, 25.51, 12.40; MH$^+$ = 447/449. |
| 1500-C | 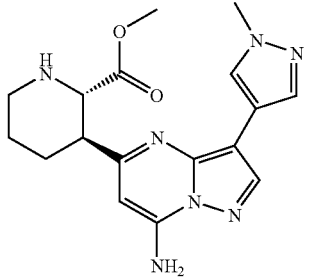 | $^{13}$C NMR (CD$_3$OD) δ 170.23, 161.12, 150.05, 145.97, 142.52, 137.50, 128.61, 115.33, 102.43, 87.43, 61.11, 53.46, 45.63, 45.05, 38.87, 29.78, 22.78; MH$^+$ = 356. |
| 1510-C | 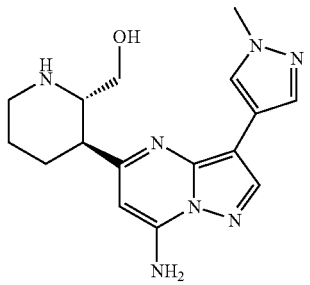 | $^{13}$C NMR (CD$_3$OD) δ 161.79, 149.98, 146.40, 142.54, 137.47, 128.59, 115.37, 102.26, 88.25, 61.78, 60.99, 45.39, 44.98, 38.86, 31.16, 23.50; MH$^+$ = 383. |
| 1520-C | 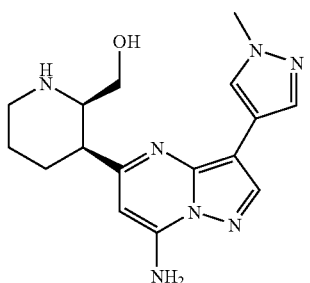 | $^{13}$NMR (CD$_3$OD) δ 158.35, 153.81, 149.08, 141.20, 136.81, 133.15, 100.35, 86.30, 56.24, 55.52, 43.77, 42.08, 39.23, 21.26, 19.35; MH$^+$ = 383. |
| 1530-C | 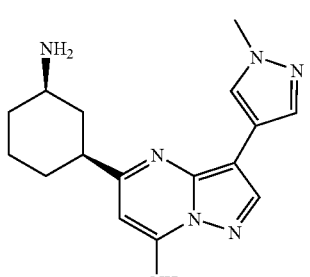 | $^{13}$C NMR (CD$_3$OD) δ 165.74, 149.84, 146.31, 142.37, 137.58, 128.53, 115.57, 101.90, 87.07, 51.53, 45.47, 38.86, 36.94, 32.44, 31.54, 25.12; MH$^+$ = 312. |

TABLE 280-C-continued

| Ex. | Column 2 | ¹H or ¹³C NMR, LCMS [MH⁺] |
|---|---|---|
| 1540-C | | ¹³C NMR (CD$_3$OD) δ 161.51, 146.99, 144.33, 142.42, 137.51, 128.39, 115.22, 102.84, 84.24, 51.45, 43.67, 38.92, 35.99, 31.61, 31.47, 25.09; MH⁺ = 390/392. |
| 1550-C | | ¹³C NMR (CD$_3$OD) δ 165.58, 149.58, 146.48, 142.26, 137.47, 128.36, 115.64, 101.92, 87.46, 53.14, 46.43, 38.86, 37.79, 32.38, 32.58; MH⁺ = 298. |
| 1560-C | | ¹³C NMR (CD$_3$OD) δ 166.79, 150.01, 146.48, 143.54, 138.11, 129.14, 115.05, 101.47, 88.00, 53.49, 46.64, 38.97, 38.23, 32.44, 32.83; MH⁺ = 298. |
| 1570-C | | ¹³C NMR (CD$_3$OD) δ 161.77, 146.95, 144.09, 142.47, 137.39, 128.34, 115.19, 102.83, 84.45, 53.23, 44.97, 38.92, 37.04, 32.14, 31.43; MH⁺ = 376/378. |
| 1580-C | | ¹³C NMR (CD$_3$OD) δ 162.23, 147.26, 144.21, 143.26, 137.93, 128.94, 114.79, 102.59, 84.41, 53.38, 45.53, 38.97, 37.31, 31.87, 31.51; MH⁺ = 376/378. |

TABLE 280-C-continued

| Ex. | Column 2 | $^{1}$H or $^{13}$C NMR, LCMS [MH$^{+}$] |
|---|---|---|
| 1590-C | | $^{13}$C NMR (CD$_3$OD) δ 161.79, 150.40, 144.83, 143.41, 137.92, 129.11, 114.54, 101.53, 88.56, 48.69, 38.92, 34.78, 34.05, 18.71; MH$^{+}$ = 286. |
| 1600-C | | $^{13}$C NMR (CD$_3$OD) δ 158.88, 147.07, 144.17, 142.66, 137.57, 128.61, 115.01, 102.73, 84.48, 48.62, 38.91, 34.37, 33.46, 18.78; MH$^{+}$ = 364/366. |

Example 1610-C and 1620-C

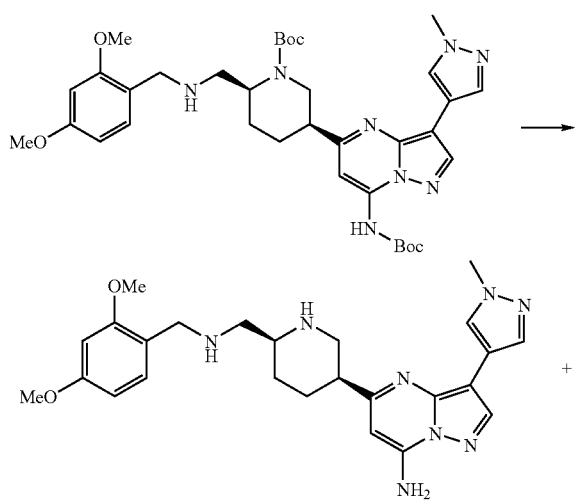

The compound from Preparative Example 1680-C (0.094 g, 0.139 mmol) was stirred 15 hours at room temperature in dichloromethane (3 mL) and trifluoroacetic acid (3 mL). A portion of this solution (0.4 mL) was removed, concentrated under reduced pressure and purified by reverse-phase HPLC on a Waters PrepLC 25mm column running a gradient from 5% to 50% acetonitrile-water. Example 1610-C, the DMB-protected amine, was obtained as a yellow oil (0.012 g, 18% yield). LCMS 477 [MH$^{+}$]. $^{13}$C NMR (CD$_3$OD) δ 163.71, 163.03, 160.26, 150.27, 145.53, 142.89, 137.63, 132.48, 128.70, 116.99, 115.20, 105.75, 102.40, 99.46, 87.46, 55.99, 55.10, 49.93, 47.39, 38.96, 28.14, 24.93.

The remainder of the deprotection reaction was heated to 60° C. for 15 hours with an additional quantity of trifluroacetic acid (2 mL) added. After cooling, this solution was also concentrated and purified by reverse-phase HPLC as above. Example 1620-C, the fully deprotected amine, was obtained as a yellow oil (0.026 g, 57% yield). LCMS 327 [MH$^{+}$]. $^{13}$C NMR (CD$_3$OD) δ 162.30, 150.42, 145.51, 142.96, 137.59, 128.83, 115.12, 102.45, 87.24, 54.77, 47.50, 42.50, 41.64, 38.94, 38.16, 27.13, 24.51.

Preparative Example 2040-C

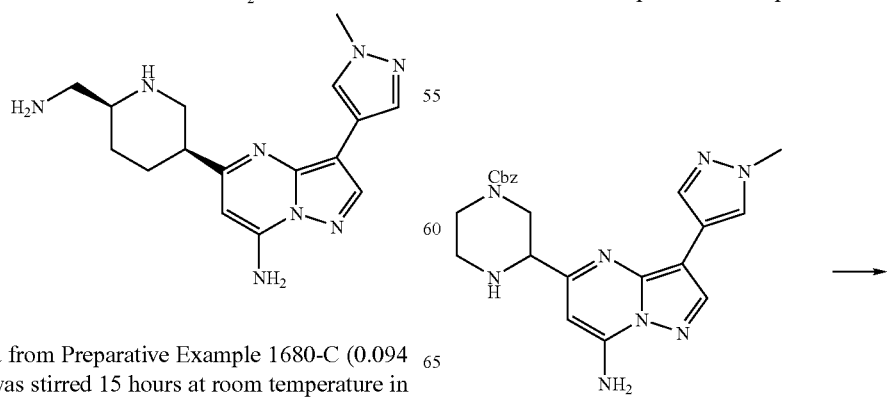

-continued

A solution of the monoprotected piperazine (0.075 g, 0.17 mmol) in CH$_2$Cl$_2$ (1.6 mL) and acetic acid (0.1 mL) at 25° C. was treated with 3,3-dimethyl butyraldehyde (0.03 mL, 3 equiv.) followed by sodium triacetoxyborohydride (0.11 g, 3 equiv.). The solution was stirred at 25° C. overnight. The solution was concentrated and purified by preparative chromatography (5% MeOH-EtOAc) to yield pure product (0.050 g, 56%).

Preparative Example 2050-C and 2060-C

By essentially the same procedure as set forth in Preparative Example 2040-C, the compounds given in Column 2 of Table 300-C were prepared.

TABLE 300-C

| Prep. Ex. | Column 2 |
|---|---|
| 2050-C | |
| 2060-C | |

Preparative Example 2070-C

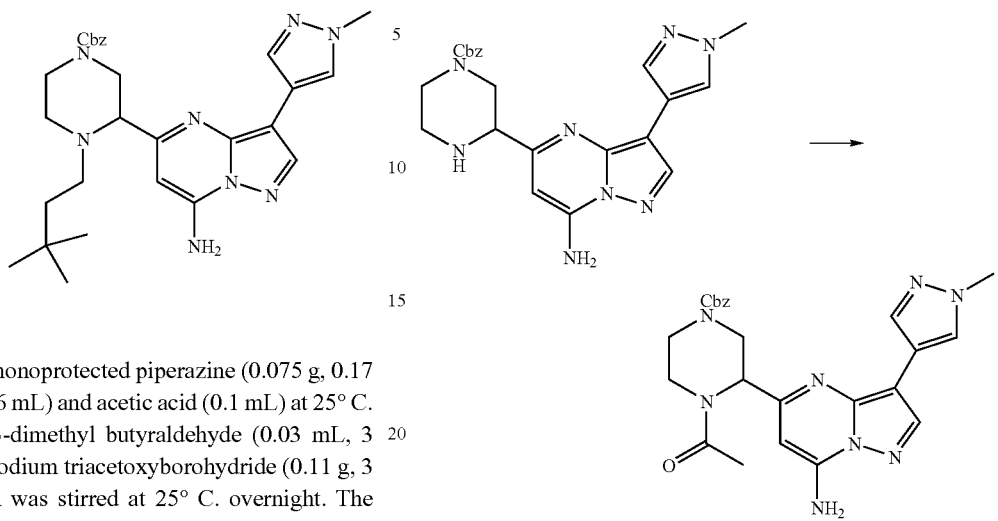

A solution of the monoprotrected piperazine (0.067 g, 0.15 mmol) in THF (1.5 mL) at 25° C. was treated with triethylamine (0.043 mL, 2.0 equiv.) followed by acetyl chloride (0.014 mL, 1.3 equiv.). The solution was stirred at 25° C. overnight. The solution was concentrated and purified by preparative chromatography (5% MeOH-EtOAc) to give pure product (0.058 g, 79%).

Example 1630-C

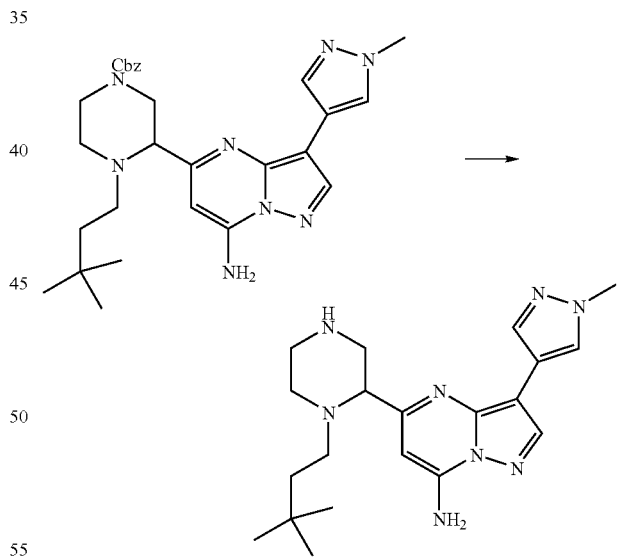

A mixture of the compound from Preparative Example 2040-C (0.050 g, 0.097 mmol) in EtOAc (1 ml) and MeOH (1 mL) was treated with Pd/C and stirred under a hydrogen atmosphere overnight. The mixture was filtered through a pad of Celite and concentrated. Purification by preparative chromatography (10% 7N NH$_3$ in MeOH-EtOAc) yielded product (0.032 g, 87%). $^1$H NMR (CD$_3$OD) δ 8.22 (s, 1H), 8.14 (s, 1H), 7.96 (s, 1H), 6.31 (s, 1H), 3.94 (s, 3H), 3.39 (dd, J=10.2 Hz, J=2.9 Hz, 1H), 3.16-2.78 (m, 5H), 2.65-2.58 (m, 1H), 2.35-2.28 (m, 1H), 2.21-2.13 (m, 1H), 1.62-1.54 (m, 1H), 1.40-1.33 (m, 1H), 0.75 (s, 9H); MH$^+$=383.

Example 1640-C-1660-C

By essentially the same procedure as set forth in Example 1630-C, the compounds given in Column 2 of Table 310-C were prepared.

TABLE 310-C

| Ex. | Column 2 | $^1$H or $^{13}$C NMR, LCMS [MH$^+$] |
|---|---|---|
| 1640-C | (structure) | $^1$H NMR (CD$_3$OD) δ 8.21 (s, 1H), 8.13 (s, 1H), 7.94 (s, 1H), 6.31 (s, 1H), 3.94 (s, 3H), 3.37 (dd, J=10.4 Hz, J=3.7 Hz, 1H), 3.17-2.81 (m, 5H), 2.70-2.61 (m, 1H), 2.34-2.18 (m, 1H), 1.05 (t, J=6.6 Hz, 3H); MH$^+$ = 327. |
| 1650-C | (structure) | $^1$H NMR (CD$_3$OD) δ 8.21 (s, 1H), 8.10 (s, 1H), 7.95 (s, 1H), 6.33 (s, 1H), 3.94 (s, 3H), 3.72-3.69 (m, 1H), 3.09-2.83 (m, 6H), 2.53-2.46 (m, 1H); MH$^+$ = 341. |
| 1660-C | (structure) | |

Example 1670-C-1700-C

By essentially the same procedure as set forth in Preparative Example 2040-C, only utilizing the appropriate amine, the compounds given in Column 2 of Table 320-C were prepared.

TABLE 320-C

| Ex. | Column 2 | $^1$H or $^{13}$C NMR, LCMS [MH$^+$] |
|---|---|---|
| 1670-C | (structure) | |

TABLE 320-C-continued

| Ex. | Column 2 | ¹H or ¹³C NMR, LCMS [MH⁺] |
|---|---|---|
| 1680-C | | ¹H NMR (CDCl₃) δ 8.11 (s, 1H), 7.96 (s, 1H), 7.92 (s, 1H), 6.06 (br s, 2H), 3.97 (s, 3H), 3.21-2.73 (m, 11H), 1.12-1.08 (m, 12H); MH⁺ = 475/477. |
| 1690-C | | ¹H NMR (CD₃OD) δ 8.21 (s, 1H), 8.03 (s, 1H), 7.96 (s, 1H), 3.94 (s, 3H), 3.20-3.17 (m, 4H), 3.06-2.99 (m, 1H), 1.15 (s, 3H), 1.14 (s, 3H); M⁺ = 378/380. |
| 1700-C | | ¹H NMR (CD₃OD) δ 8.21 (s, 1H), 8.03 (s, 1H), 7.96 (s, 1H), 3.94 (s, 3H), 3.26-3.17 (m, 5H), 1.99-1.90 (m, 2H), 1.74-1.53 (m, 4H), 1.44-1.35 (m, 2H); M⁺ = 404/406. |

Example 1710-C

By essentially the same procedure as set forth in Example 2070-C, the compounds given in Column 2 of Table 330-C were prepared.

TABLE 330-C

| Ex. | Column 2 | ¹H or ¹³C NMR, LCMS [MH⁺] |
|---|---|---|
| 1710-C | 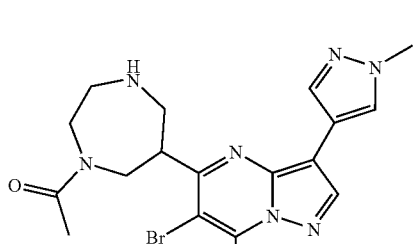 | |

Example 1720-C

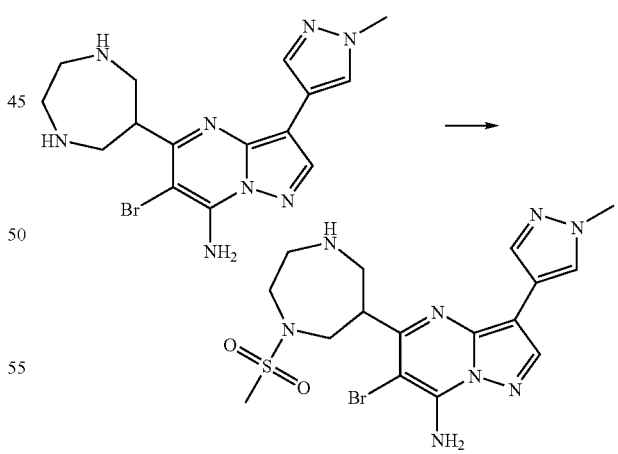

A solution of the compound from Example 1260-C (0.075 g, 0.19 mmol) in DMF (3.8 mL) was treated with triethylamine (0.054 mL, 2.0 equiv.) followed by methanesulfonyl chloride 0.015 mL, 1.0 equiv.). The solution was stirred at 25° C. for 19 h. The solution was concentrated under reduced pressure and purified by preparative chromatography (10% 7N NH₃ in MeOH—CH₂Cl₂) to yield product (0.0135 g, 14%).

Example 1730-C

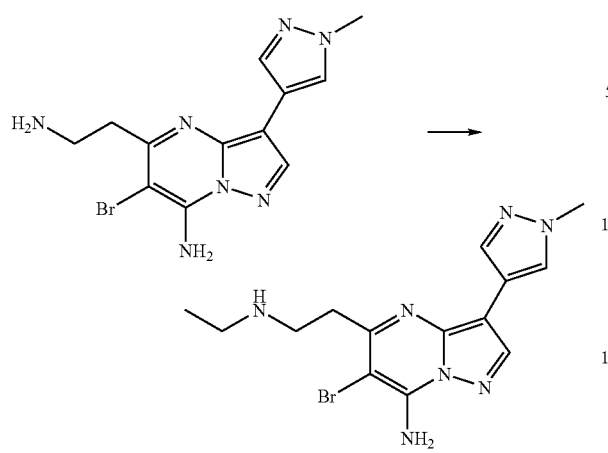

A solution of the compound from Example 1150-C (0.050 g, 0.14 mmol) in CH$_2$Cl$_2$ (0.75 mL) and MeOH (0.75 mL) was stirred at 25° C. for 3 h. NaBH$_4$ (0.01 g, 1.1. equiv.) was added and stirring was continued for 17 h. The solution was concentrated and purified by preparative chromatography (10% 7N NH$_3$ in MeOH—CH$_2$Cl$_2$) to yield (0.035 g, 65%) a light orange solid. $^1$H NMR (CD$_3$OD) δ 8.21 (s, 1H), 8.03 (s, 1H), 7.96 (s, 1H), 3.94 (s, 3H), 3.19-3.17 (m, 4H), 2.75 (q, J=15.4 Hz, J=6.8 Hz, 2H), 1.92-1.85 (t, J=7.2 Hz, 3H) ; MH$^+$=364/366.

Examples 1740-C-1770-C

By essentially the same procedure as set forth in Example 1730-C, the compounds given in Column 2 of Table 400-C were prepared.

TABLE 400-C

| Ex. | Column 2 | $^1$H NMR, LCMS [MH$^+$] |
|---|---|---|
| 1740-C | | $^1$H NMR (CD$_3$OD) δ 8.21 (s, 1H), 8.04 (s, 1H), 7.96 (s, 1H), 3.94 (s, 3H), 3.19-3.17 (m, 4H), 2.76-2.70 (m, 2H), 1.47-1.41 (m, 2H), 0.92 (s, 9H); M$^+$ = 420/422. |
| 1750-C | | $^1$H NMR (CD$_3$OD) δ 8.20 (s, 1H), 8.02 (s, 1H), 7.94 (s, 1H), 7.41-7.40 (m, 1H), 6.34-6.33 (m, 1H), 6.28-6.27 (d, J=3.2 Hz, 1H) 3.92 (s, 3H), 3.87 (s, 2H), 3.15-3.13 (m, 4H); M$^+$ = 416/418. |
| 1760-C | | $^1$H NMR (CD$_3$OD) δ 8.21 (s, 1H), 8.03 (s, 1H), 7.96 (s, 1H), 3.94 (s, 3H), 3.17-3.14 (m, 4H), 2.70 (t, J=7.2 Hz, 2H), 1.61-1.50 (m, 2H), 0.93 (t, J= 7.2 Hz, 1H); M$^+$ = 378/380. |
| 1770-C | | $^1$H NMR (CD$_3$OD) δ 8.20 (s, 1H), 7.97 (s, 1H), 7.93 (s, 1H), 7.38-7.33 (m,, 5H), 4.05-4.00 (m, 2H), 3.89 (s, 3H), 3.38-3.23 (m, 4H); M$^+$ = 426/428. |

Example 1780-C and 1790-C

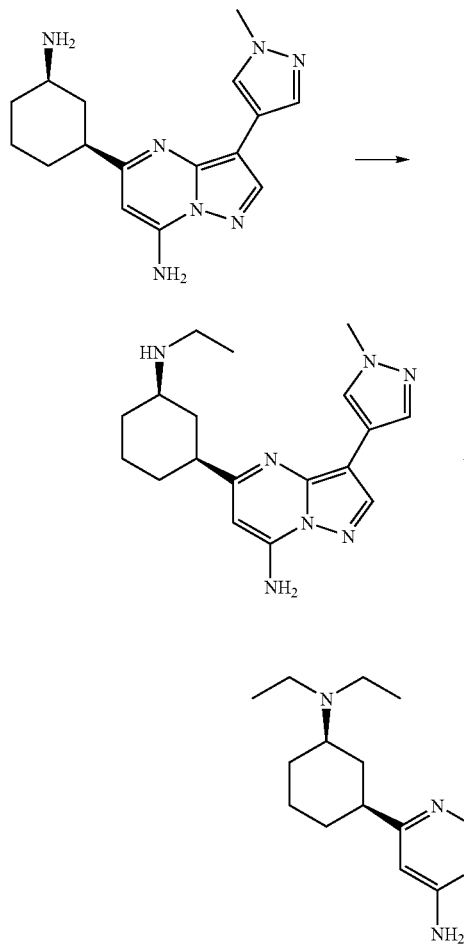

The compound from Example Compound 1530-C (0.047 g, 0.151 mmol), sodium cyanoborohydride (0.019 g, 0.302 mmol, 2 equiv.) and acetaldehyde (0.01 mL, 0.178 mmol, 1.18 equiv.) were dissolved in methanol (5 mL), and acetic acid (2 drops) was added to reach a pH of about 6. The mixture was stirred 15 hours at room temperature in a sealed vial. The mixture was concentrated under a stream of nitrogen to a volume of about 1 mL, diluted with dichloromethane (6 mL) and loaded on an Isco Redisep 12-gram column, and partially purified using an Analogix Intelliflash 280 running a gradient from 5% to 50% 7N ammonia in methanol-dichloromethane. Fractions containing the products were combined, concentrated under reduced pressure then purified by reverse-phase HPLC on a Waters PrepLC 25 mm column running a gradient from 5% to 20% acetonitrile-water. Example 1780-C (0.031 g, 61% yield) and Example 1790-C (0.015 g, 26% yield) were obtained as colorless oils. LCMS 340 [MH$^+$], $^{13}$C NMR (CD$_3$OD) δ 165.74, 149.77, 146.51, 142.31, 137.56, 128.48, 115.57, 101.94, 87.15, 57.89, 45.52, 41.09, 38.89, 35.52, 32.64, 29.99, 25.10, 11.82; and LCMS 368 [MH$^+$], $^{13}$C NMR (CD$_3$OD) δ 165.63, 149.82, 146.49, 142.38, 128.56, 115.52, 101.97, 87.05, 63.16, 46.60, 46.00, 38.88, 33.30, 32.43, 27.36, 25.44, 10.70, respectively.

Examples 1800-C and 1810-C

By essentially the same procedure as set forth in Example 1780-C, the compounds in Column 2 of Table 410-C were prepared from compound BOB by employing acetone and 2-(tert-butyldimethylsilyloxy)acetaldehyde, respectively.

| Ex. | Column 2 | $^{13}$C NMR and LCMS [MH$^+$] |
|---|---|---|
| 1800-C | 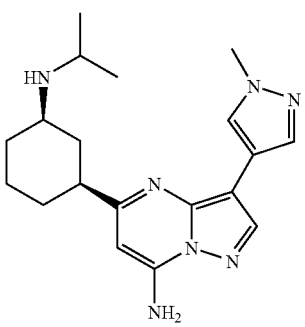 | $^{13}$C NMR (CD$_3$OD) δ 165.75, 149.79, 146.52, 142.32, 137.59, 128.45, 115.61, 101.93, 87.10, 55.00, 48.12, 45.50, 38.87, 35.59, 32.70, 30.02, 25.11, 19.39; MH$^+$ = 354. |

| Ex. | Column 2 | 13C NMR and LCMS [MH+] |
|---|---|---|
| 1810-C | (structure with TBDMS, pyrazolopyrimidine, cyclohexyl-NH-CH2CH2-O-TBDMS, N-methylpyrazole, NH2) | 13C NMR (CD3OD) δ 166.90, 158.24, 149.74, 142.26, 137.52, 128.61, 115.54, 101.85, 86.98, 62.01, 58.11, 48.90, 46.32, 38.86, 38.13, 33.08, 32.21, 26.41, 25.68, 5.17, −5.24; MH+ = 470. |

Example 1820-C

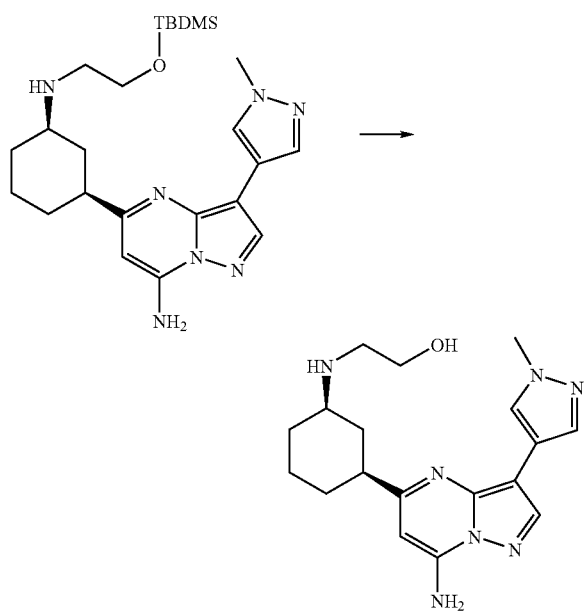

The compound from Example 1810-C (0.060 g, 0.128 mmol) in anhydrous THF (3 mL) was treated with tetrabutylammonium fluoride (1 M solution in THF, 0.25 mL, 0.25 mmol, 1.95 equiv.) and the solution was stirred 12 hours at room temperature. The solution was then diluted with methanol and dichloromethane and concentrated under reduced pressure. The colorless oil that resulted was purified reverse-phase HPLC on a Waters PrepLC 25 mm column running a gradient from 5% to 20% acetonitrile-water. The product was obtained as a white solid (0.038 g, 83% yield). LCMS 356 [MH+]. 13C NMR (CD3OD) δ 165.80, 149.78, 146.50, 142.29, 137.55, 128.51, 115.55, 101.94, 87.08, 58.22, 58.18, 47.84, 45.66, 38.87, 35.33, 32.63, 29.78, 25.20.

Assay:

BACULOVIRUS CONSTRUCTIONS: Cyclins A and E were cloned into pFASTBAC (Invitrogen) by PCR, with the addition of a GluTAG sequence (EYMPME) at the amino-terminal end to allow purification on anti-GluTAG affinity columns. The expressed proteins were approximately 46 kDa (cyclin E) and 50 kDa (cyclin A) in size. CDK2 was also cloned into pFASTBAC by PCR, with the addition of a haemaglutinin epitope tag at the carboxy-terminal end (YD-VPDYAS). The expressed protein was approximately 34 kDa in size.

ENZYME PRODUCTION: Recombinant baculoviruses expressing cyclins A, E and CDK2 were infected into SF9 cells at a multiplicity of infection (MOI) of 5, for 48 hrs. Cells were harvested by centrifugation at 1000 RPM for 10 minutes. Cyclin-containing (E or A) pellets were combined with CDK2 containing cell pellets and lysed on ice for 30 minutes in five times the pellet volume of lysis buffer containing 50 mM Tris pH 8.0, 0.5% NP40, 1 mM DTT and protease/phosphatase inhibitors (Roche Diagnostics GmbH, Mannheim, Germany). Mixtures were stirred for 30-60 minutes to promote cyclin-CDK2 complex formation. Mixed lysates were then spun down at 15000 RPM for 10 minutes and the supernatant retained. 5 ml of anti-GluTAG beads (for one liter of SF9 cells) were then used to capture cyclin-CDK2 complexes. Bound beads were washed three times in lysis buffer. Proteins were competitively eluted with lysis buffer containing 100-200 ug/mL of the GluTAG peptide. Eluate was dialyzed overnight in 2 liters of kinase buffer containing 50 mM Tris pH 8.0, 1 mM DTT, 10 mM MgCl2, 100 uM sodium orthovanadate and 20% glycerol. Enzyme was stored in aliquots at −70° C.

IN VITRO KINASE ASSAY: CDK2 kinase assays (either cyclin A or E-dependent) were performed in low protein binding 96-well plates (Corning Inc, Corning, N.Y.). Enzyme was diluted to a final concentration of 50 μg/ml in kinase buffer containing 50 mM Tris pH 8.0, 10 mM MgCl2, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μl of the 50 μg/ml enzyme solution (1 μg of enzyme) and 20 μl of the 1 μM substrate solution were mixed, then combined with 10 μl of diluted compound in each well for testing. The kinase reaction was started by addition of 50 μl of 4 μM ATP and 1 μCi of 33P-ATP (from Amersham, UK). The reaction was allowed to run for 1 hour at room temperature. The reaction was stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ DETERMINATION: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis. The thus-obtained $IC_{50}$ values for a non-limiting, illustrative, group of compounds of the invention are shown in Table 2 below. These kinase activities were generated by using cyclin A or cyclin E using the above-described assay.

TABLE 2

| CMPD | $IC_{50}$ (µM) |
|---|---|
| 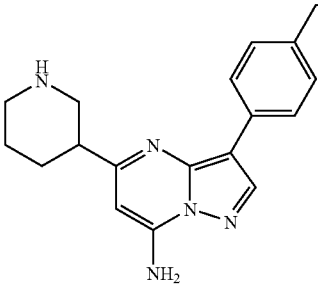 | 1.4 |
| 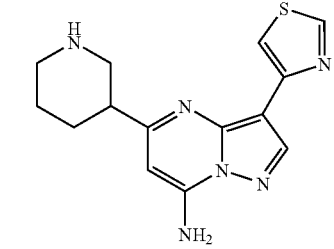 | 0.21 |
| 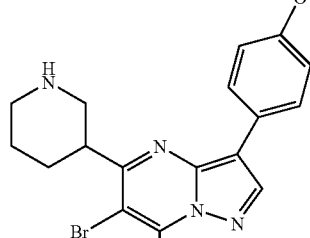 | 1.3 |
| 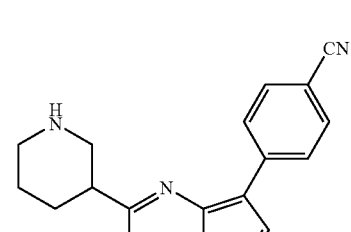 | 2.5 |

TABLE 2-continued

| CMPD | $IC_{50}$ (µM) |
|---|---|
| 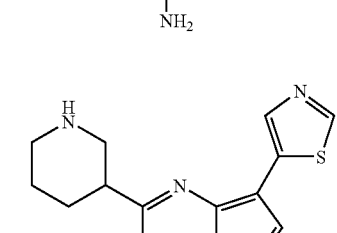 | 12 |
| 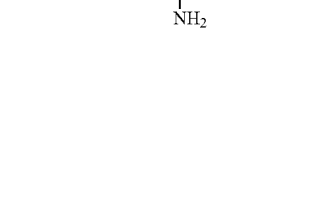 | 10 |
| 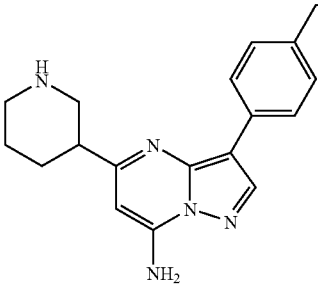 | 0.57 |
| 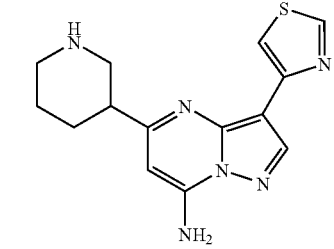 | 0.24 |
| 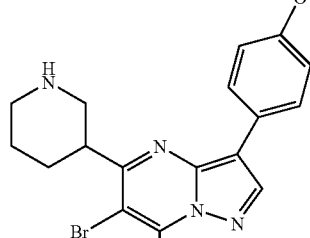 | 0.096 |

TABLE 2-continued
| CMPD | IC$_{50}$ (μM) |
|---|---|
| 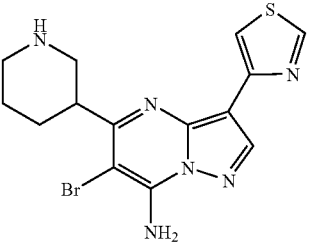 | 5.8 |
| 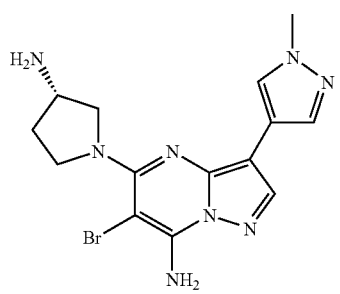 | 1.2 |
| 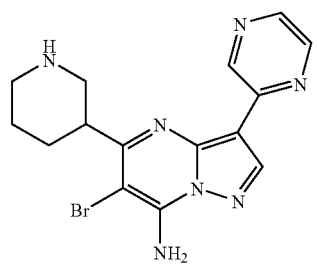 | 4.7 |
| 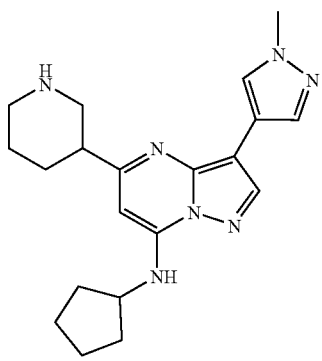 | 25 |
TABLE 2-continued
| CMPD | IC$_{50}$ (μM) |
|---|---|
| 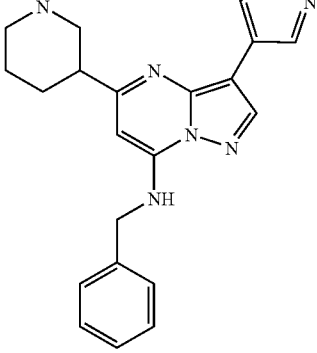 | 31 |
| 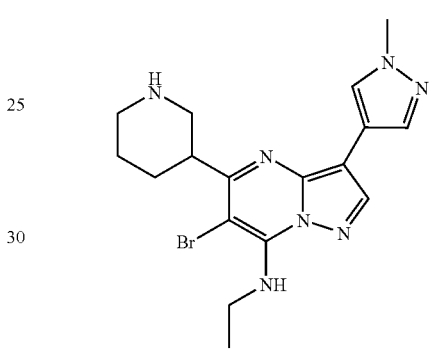 | 5.7 |
| 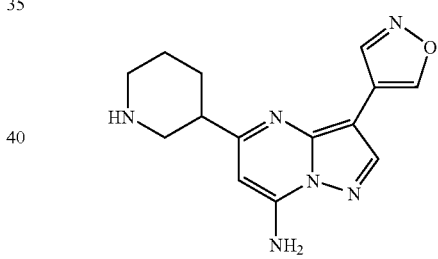 | 0.79 |
| 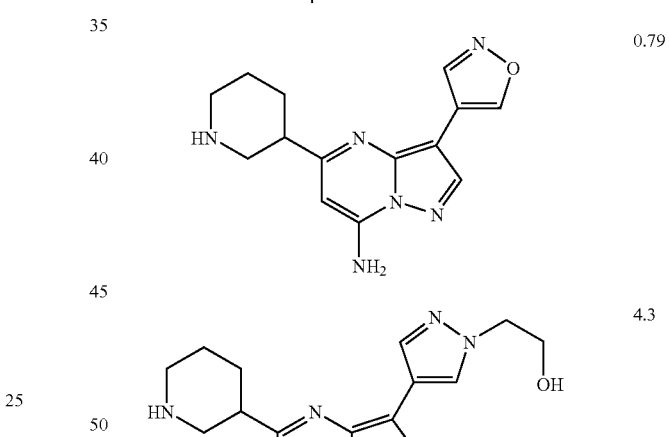 | 4.3 |
| 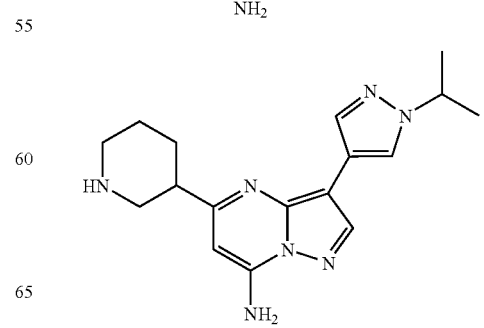 | 8.3 |

TABLE 2-continued
| CMPD | IC$_{50}$ (μM) |
|---|---|
| 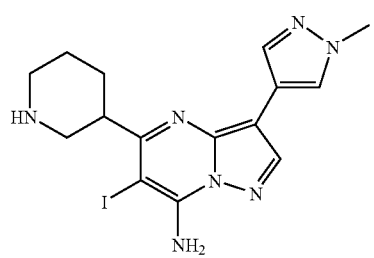 | 0.02 |
| 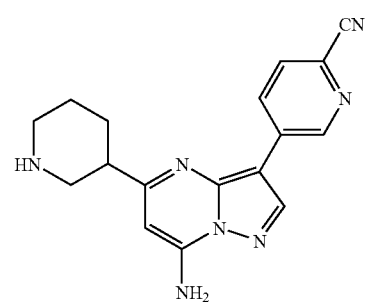 | 2.3 |
| 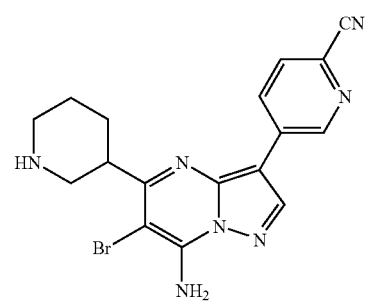 | 0.88 |
| 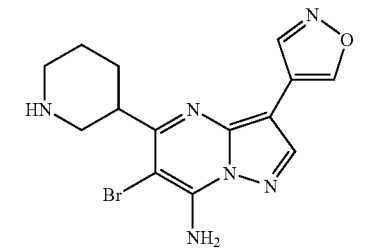 | 0.16 |
| 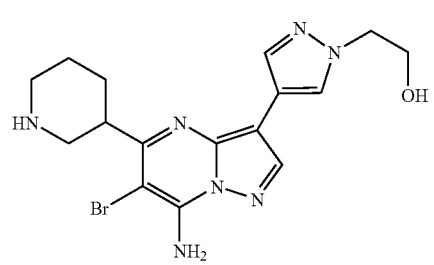 | 0.2 |
TABLE 2-continued
| CMPD | IC$_{50}$ (μM) |
|---|---|
| 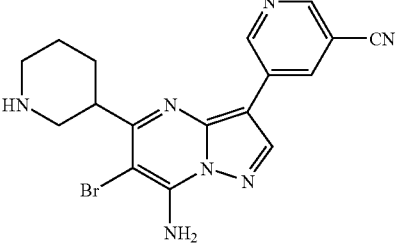 | 5.8 |
| 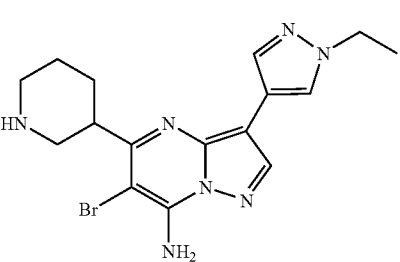 | 0.41 |
| 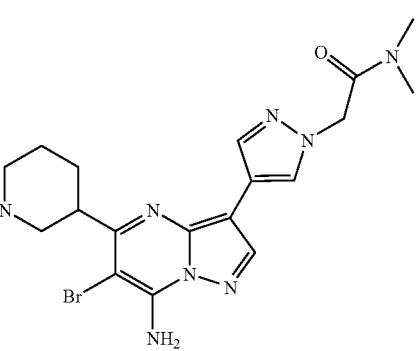 | 1.4 |
| 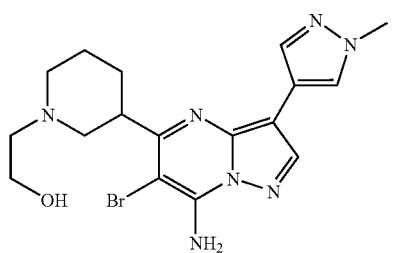 | 1.75 |
| 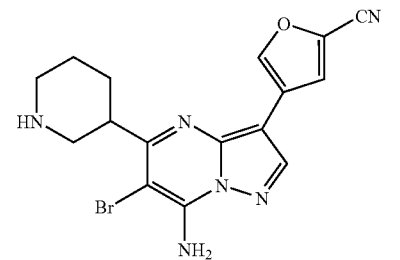 | 0.14 |

TABLE 2-continued

| CMPD | IC$_{50}$ (μM) |
|---|---|
| (structure) | 0.21 |
| (structure) | 0.04 |
| (structure) | 1.5 |
| (structure) | 14 |
| (structure) | 6.1 |
| (structure) | 5.7 |
| (structure) | 2.4 |
| (structure) | 0.84 |
| (structure) | 0.92 |
| (structure) | 6.0 |
| (structure) | 28 |

TABLE 2-continued
| CMPD | IC$_{50}$ (μM) |
|---|---|
| 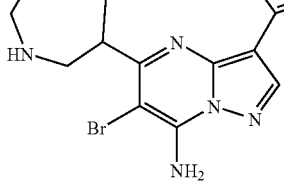 | 0.72 |
| | 12 |
| | 0.52 |
| | 0.44 |
| | 5.6 |
TABLE 2-continued
| CMPD | IC$_{50}$ (μM) |
|---|---|
| 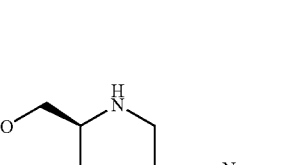 | 3.7 |
| | 0.12 |
| | 0.24 |
| | 1.2 |
| | 2.6 |

TABLE 2-continued

| CMPD | IC$_{50}$ (μM) |
|---|---|
| (structure) | 2.6 |
| (structure) | 3.1 |
| (structure) | 3.7 |

As demonstrated above by the assay values, the compounds of the present invention exhibit excellent CDK inhibitory properties.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound selected from the group consisting of the compounds of the formula:

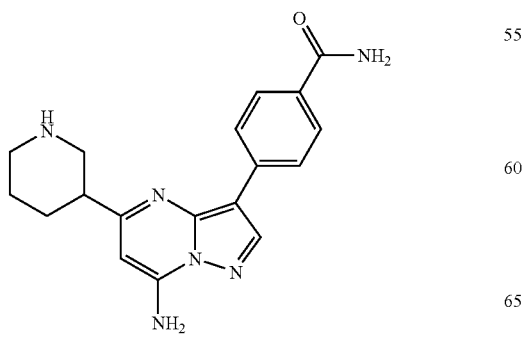

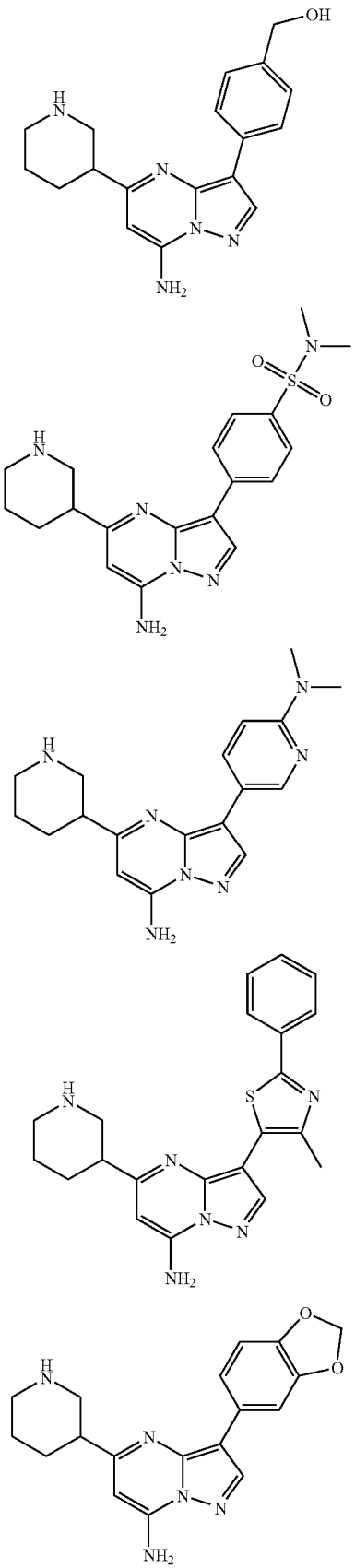

-continued
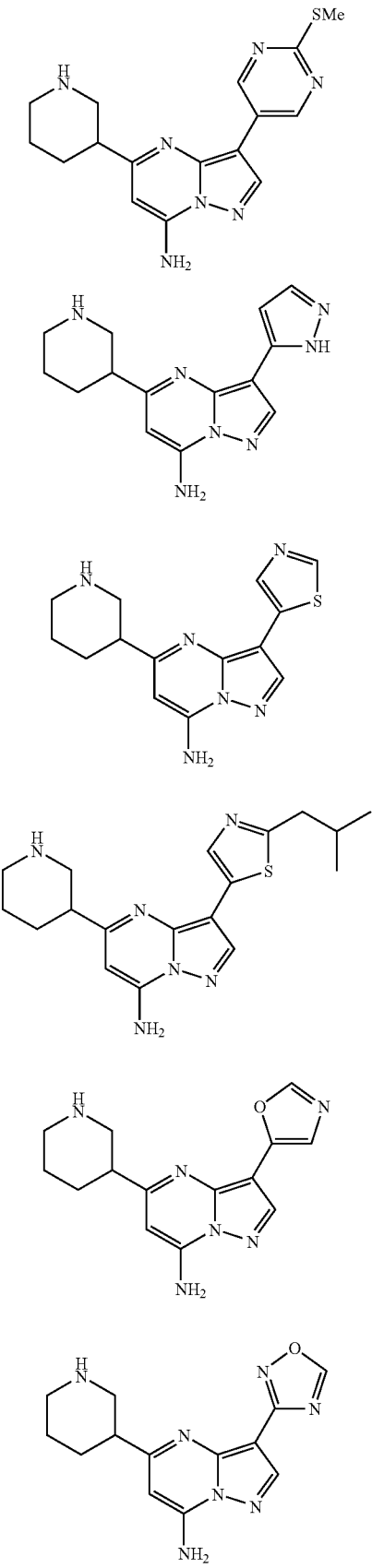
-continued
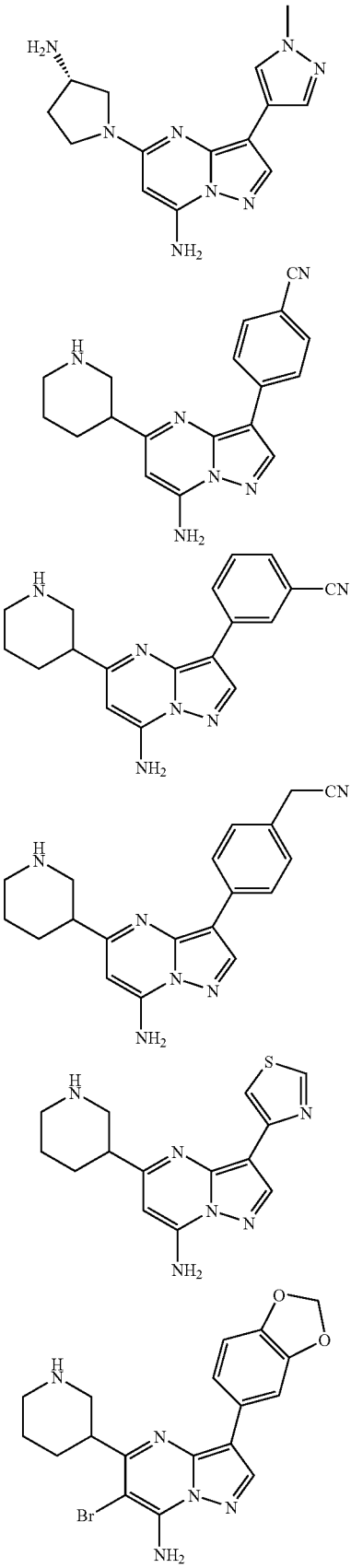

-continued
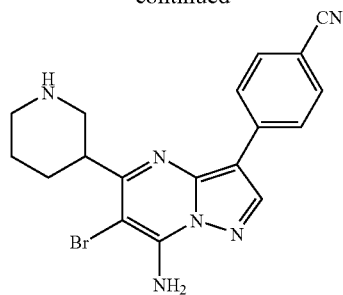
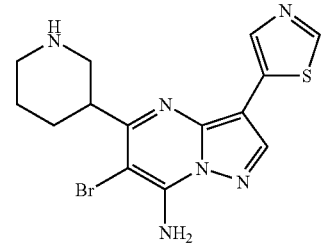
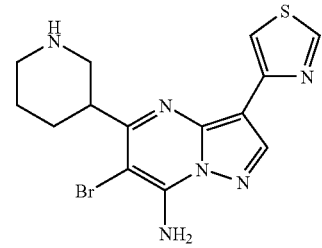
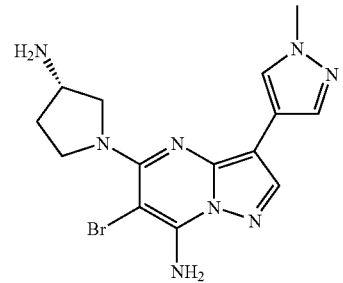
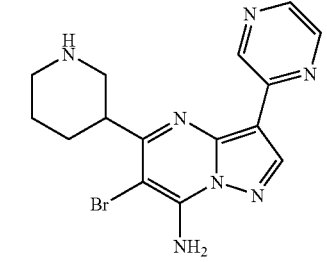
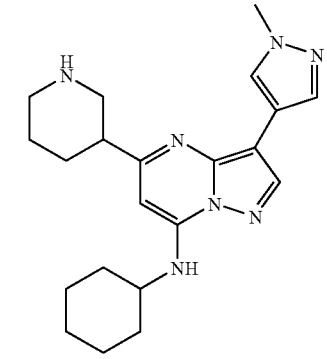
-continued
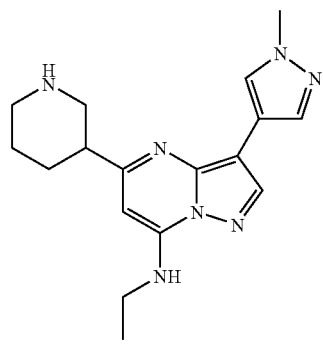
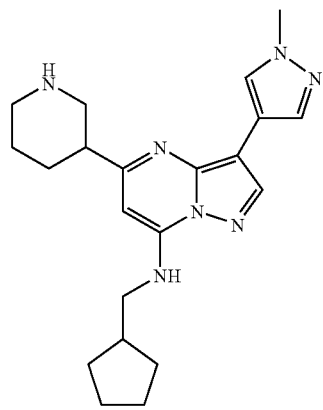
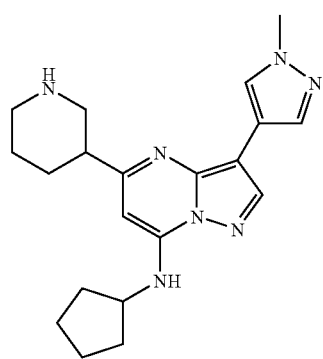
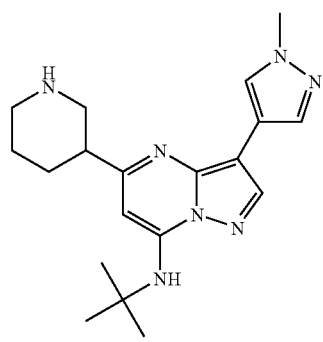

-continued
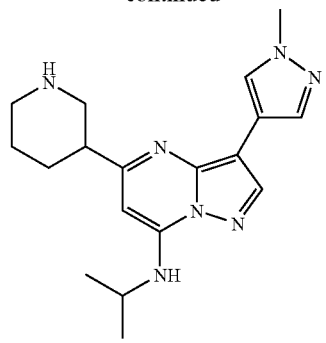
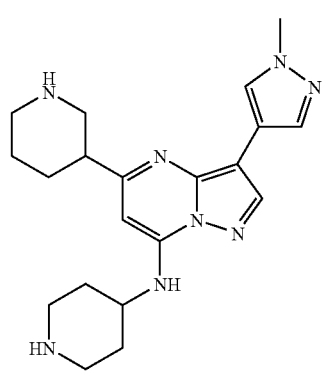
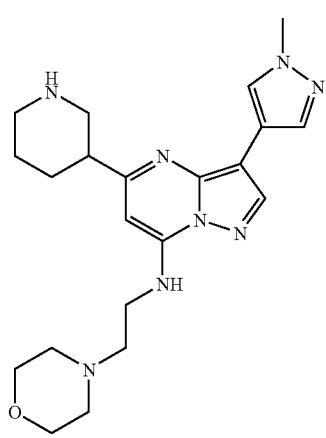
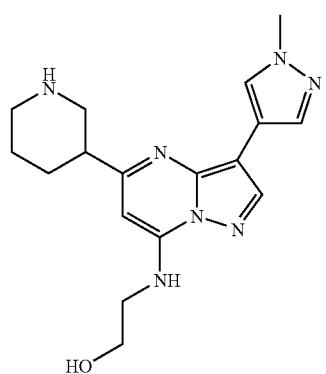
-continued
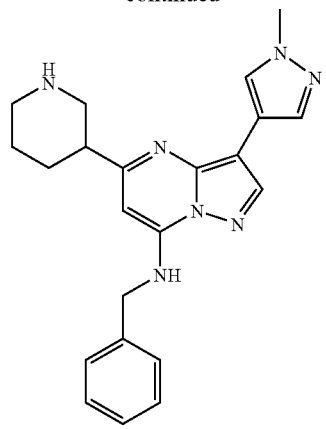
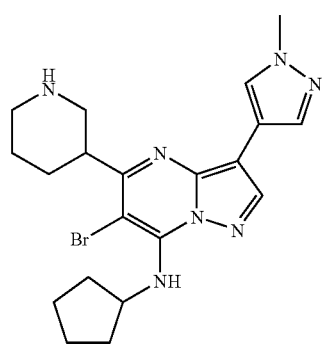
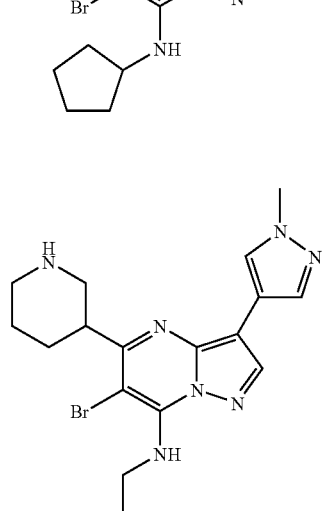
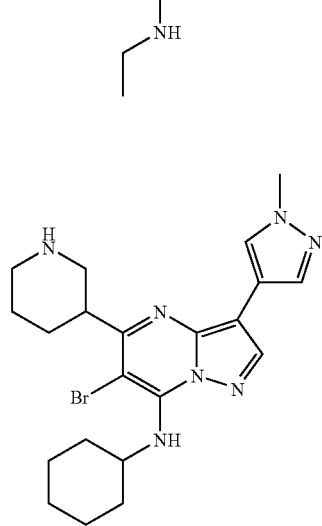

-continued
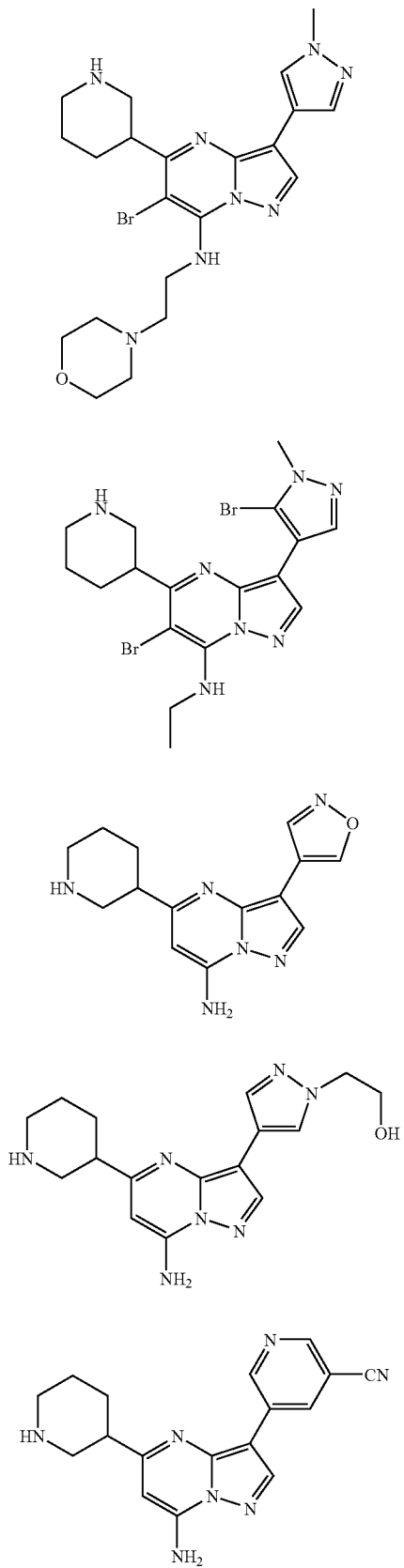
-continued
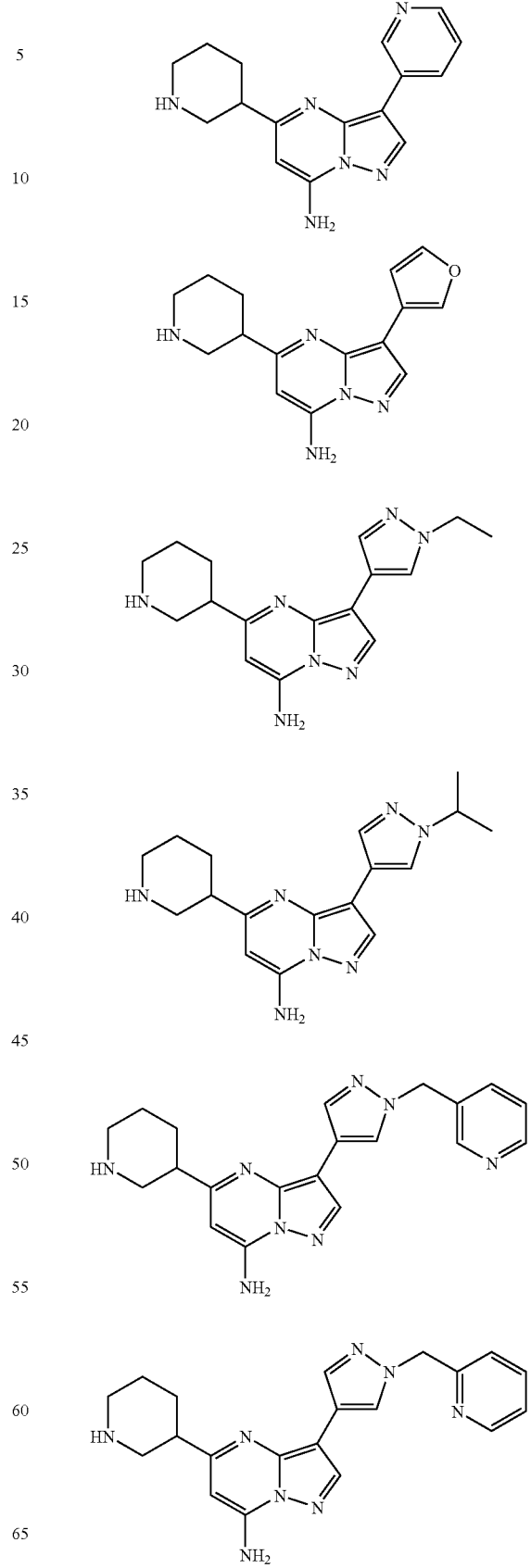

249
-continued
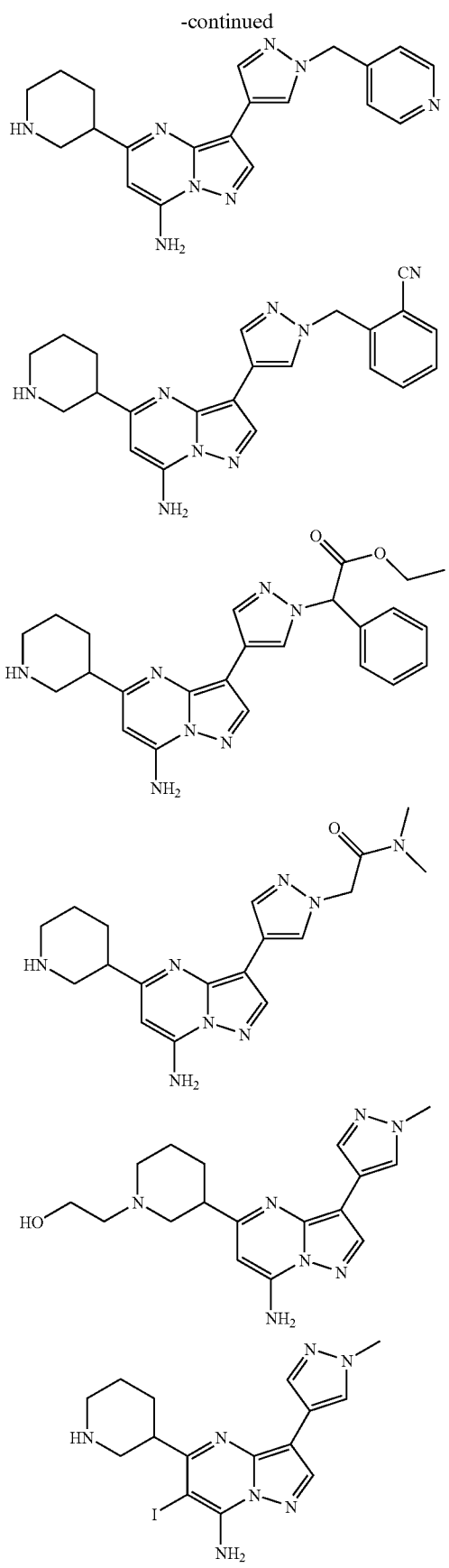
250
-continued
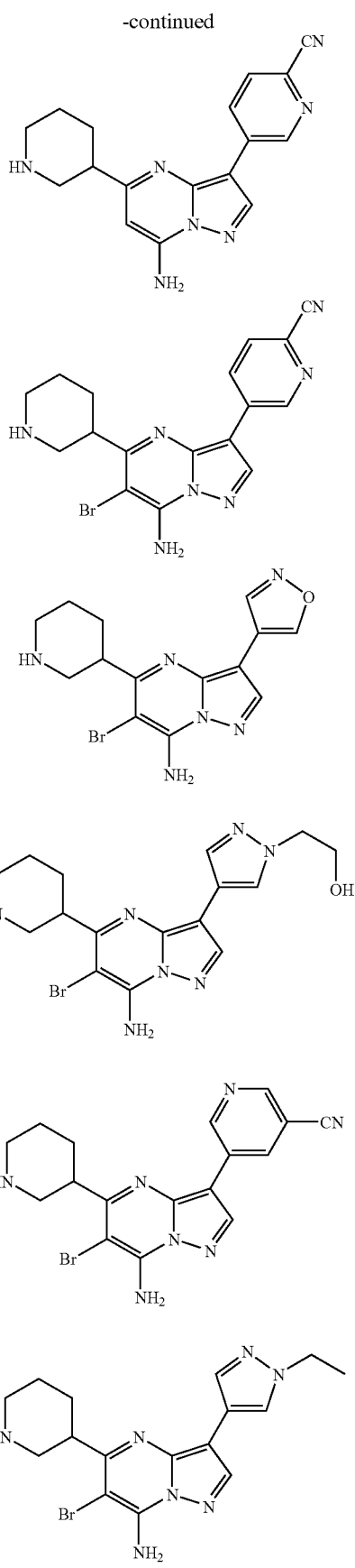

251
-continued
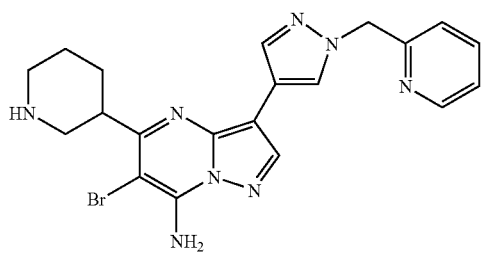
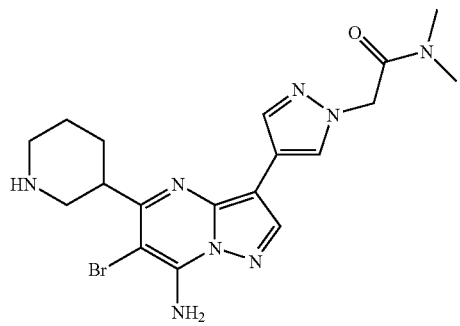
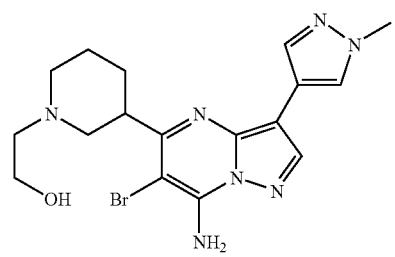
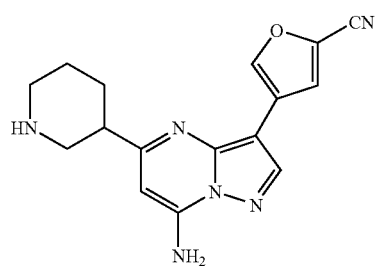
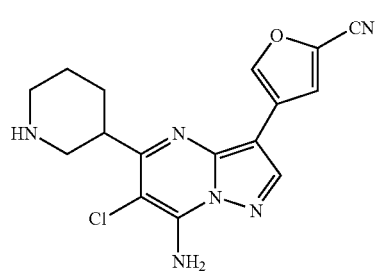
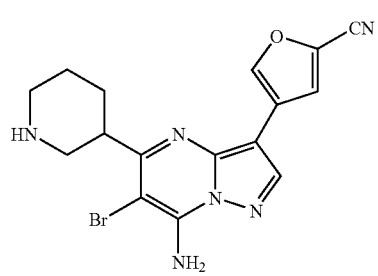
252
-continued
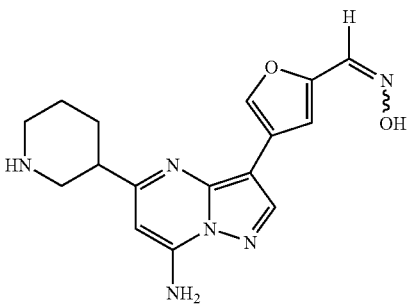
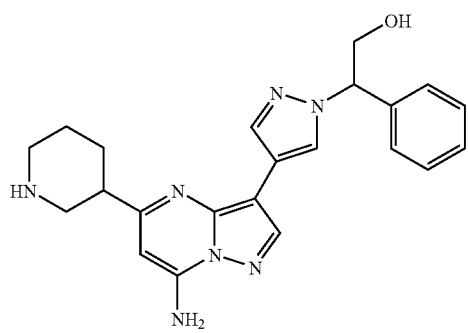
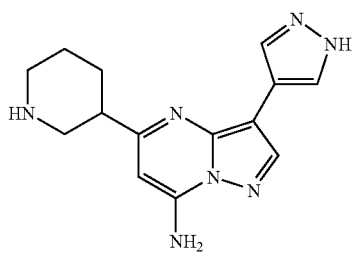
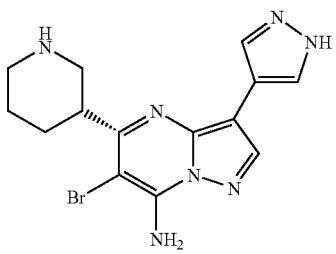
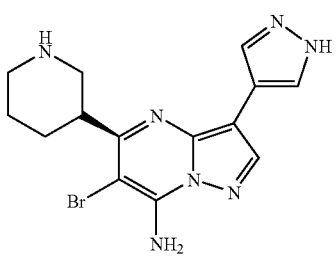
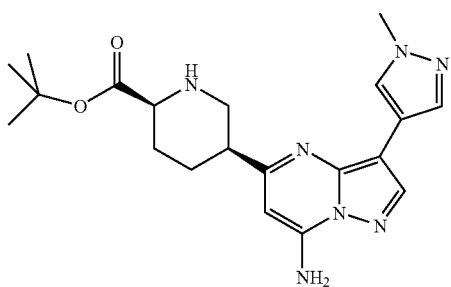

-continued
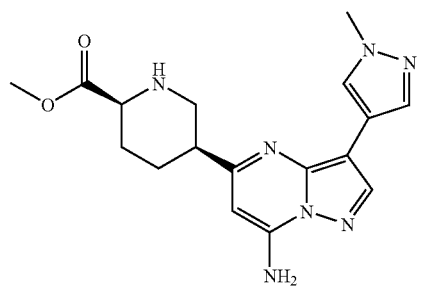
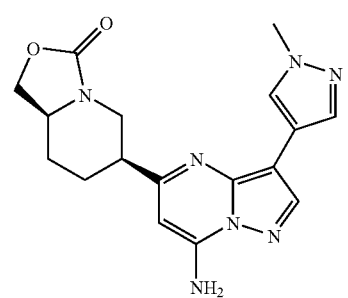
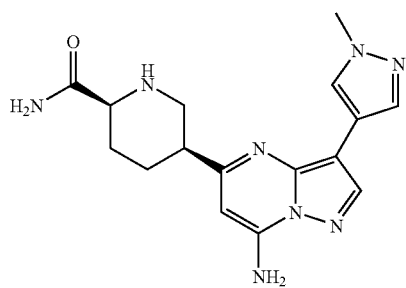
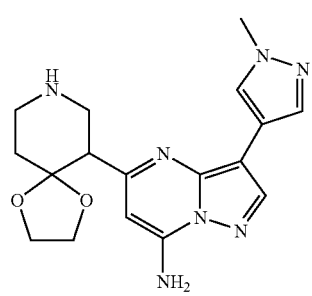
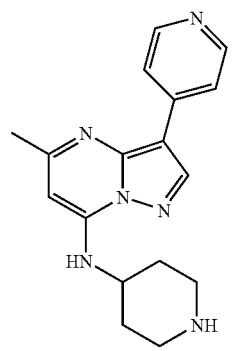
-continued
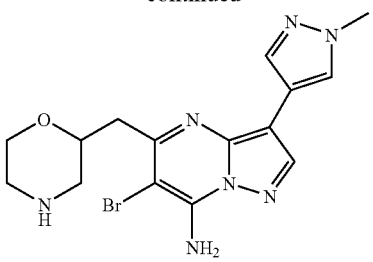
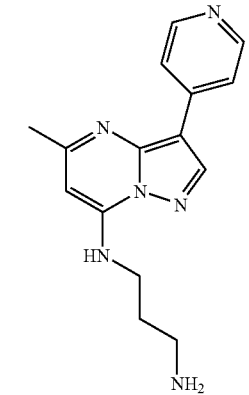
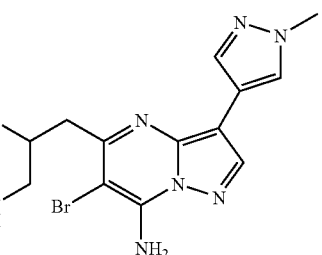
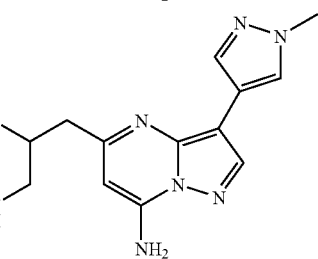
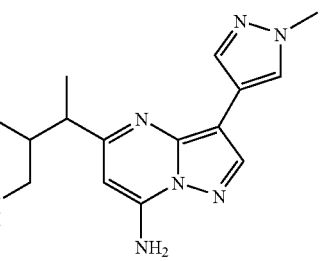
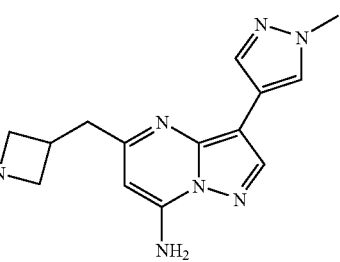

-continued
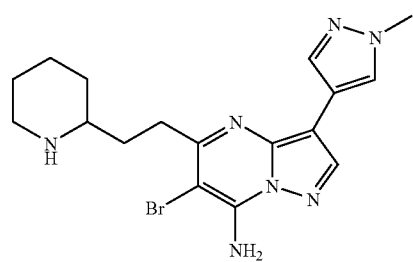
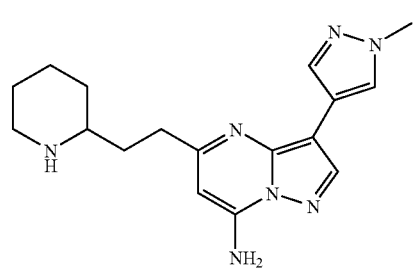
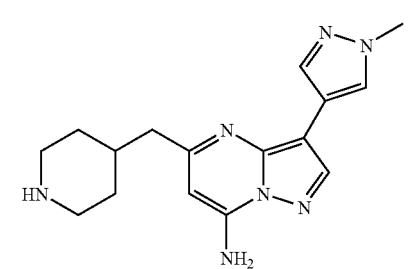
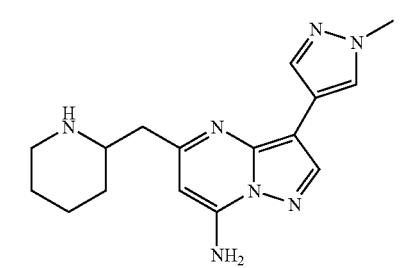
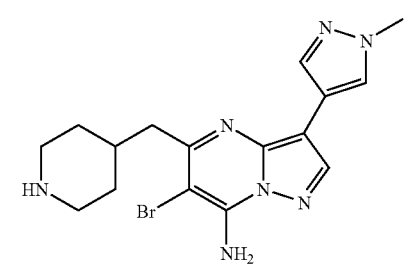
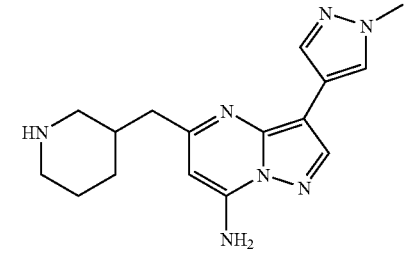
-continued
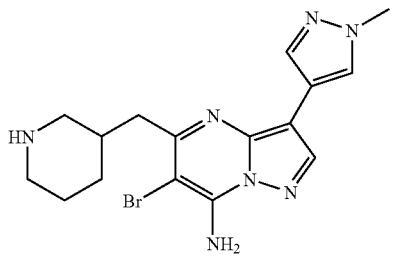
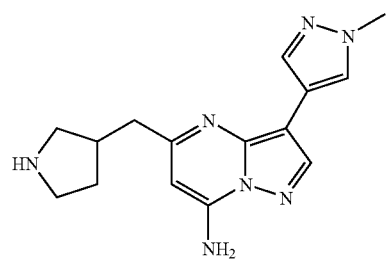
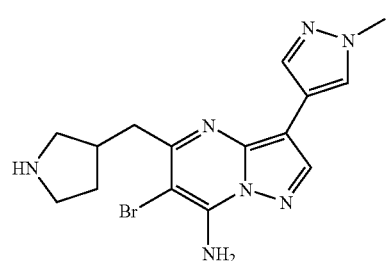
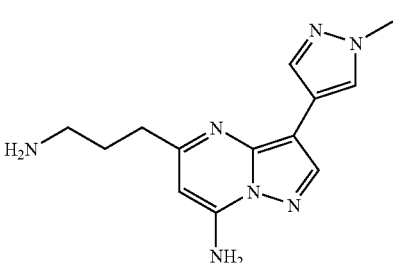
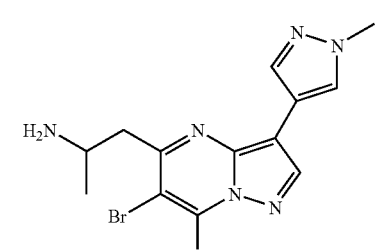
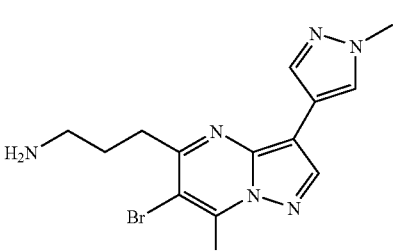

-continued
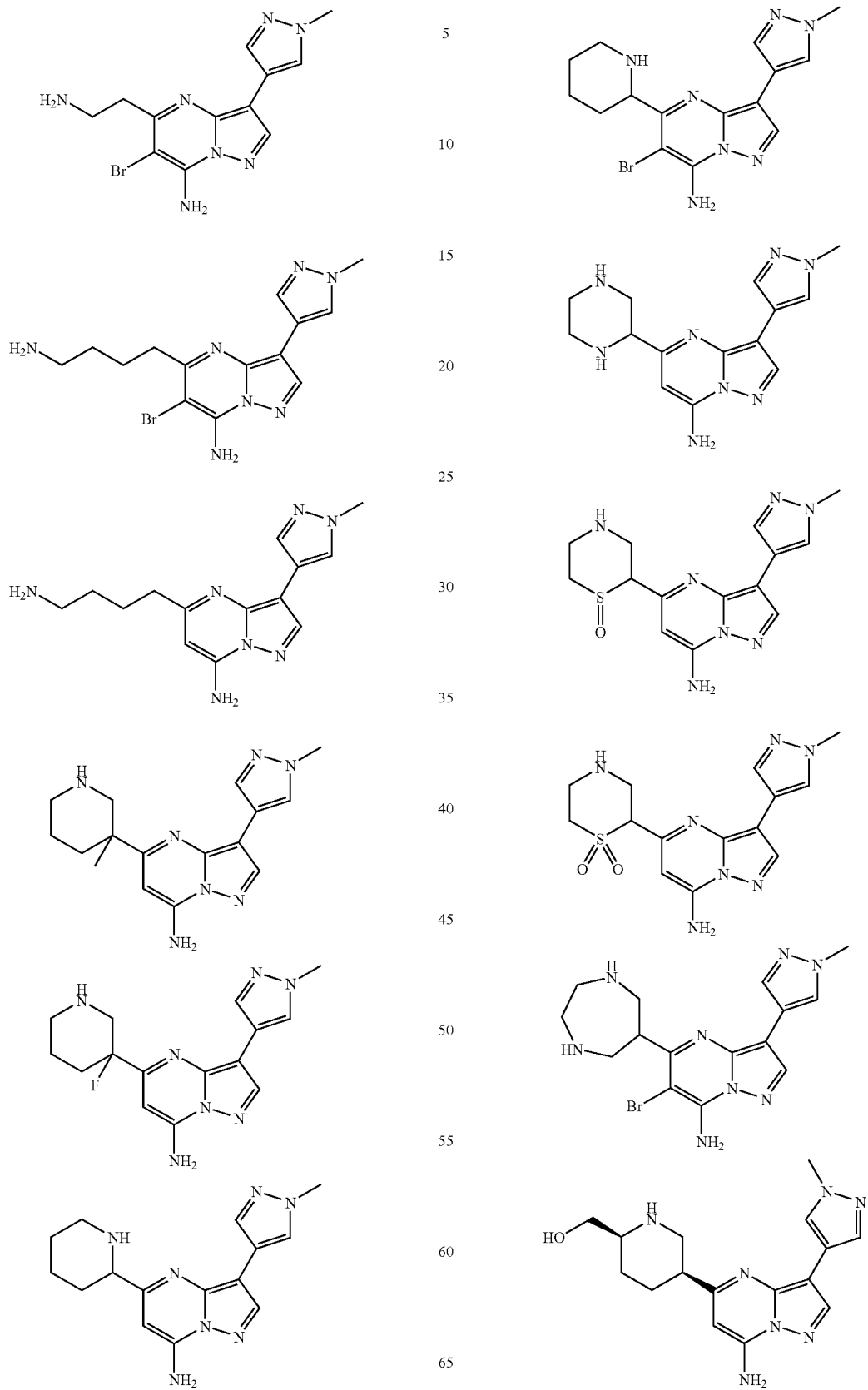

259
-continued
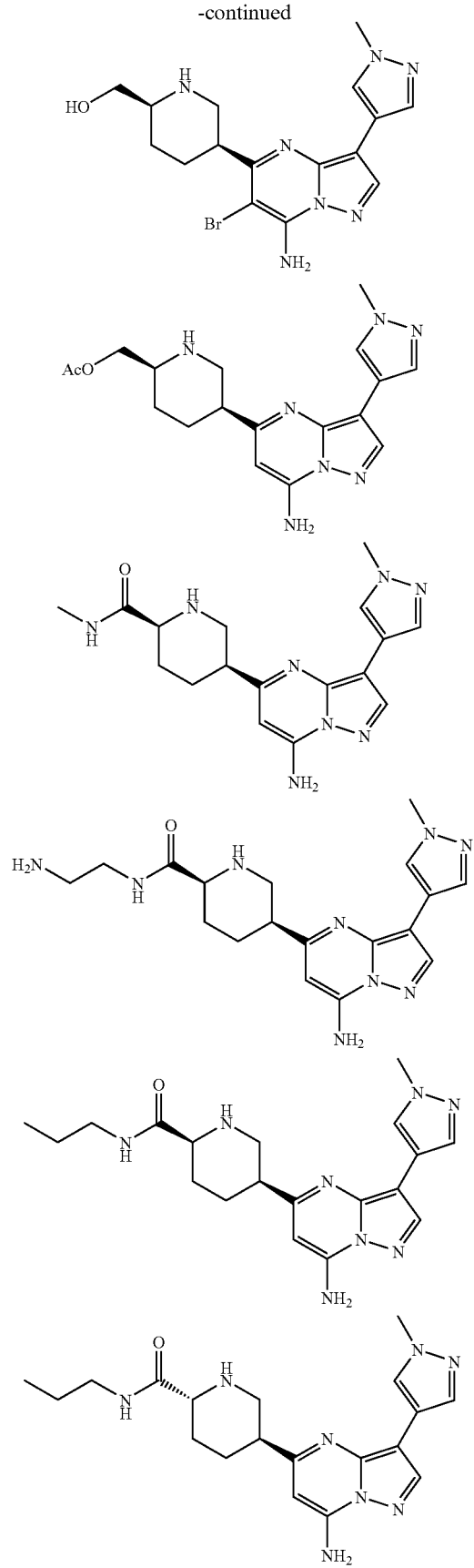
260
-continued
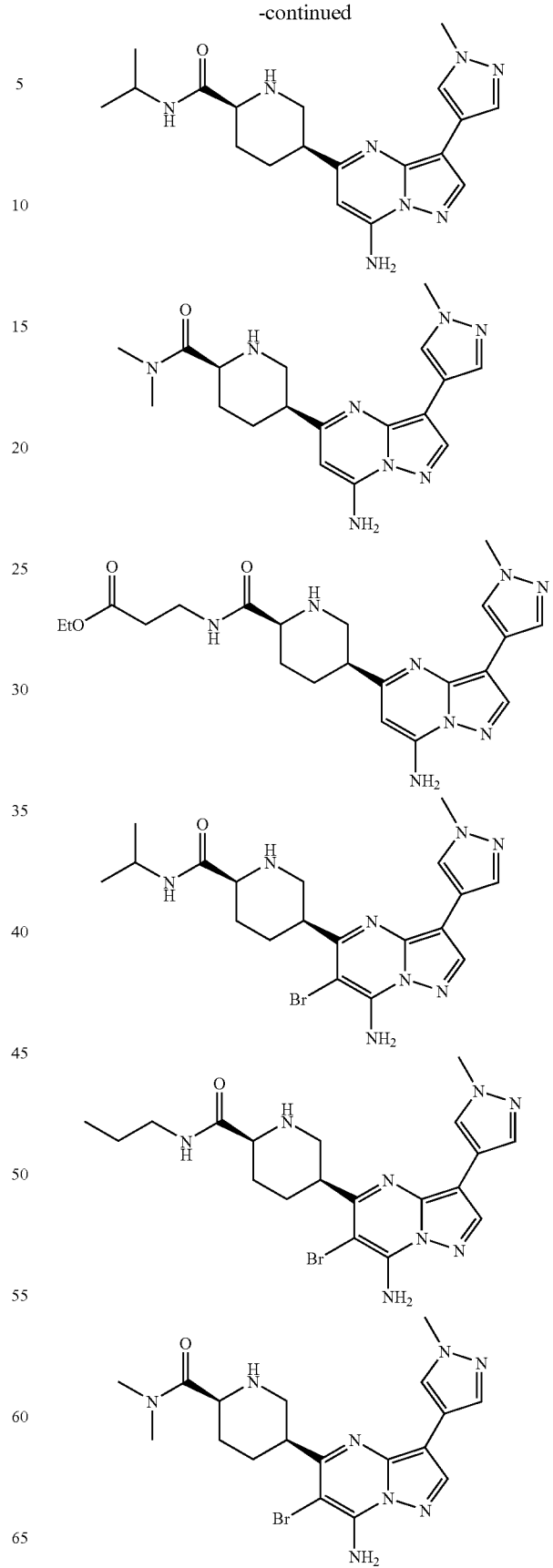

-continued
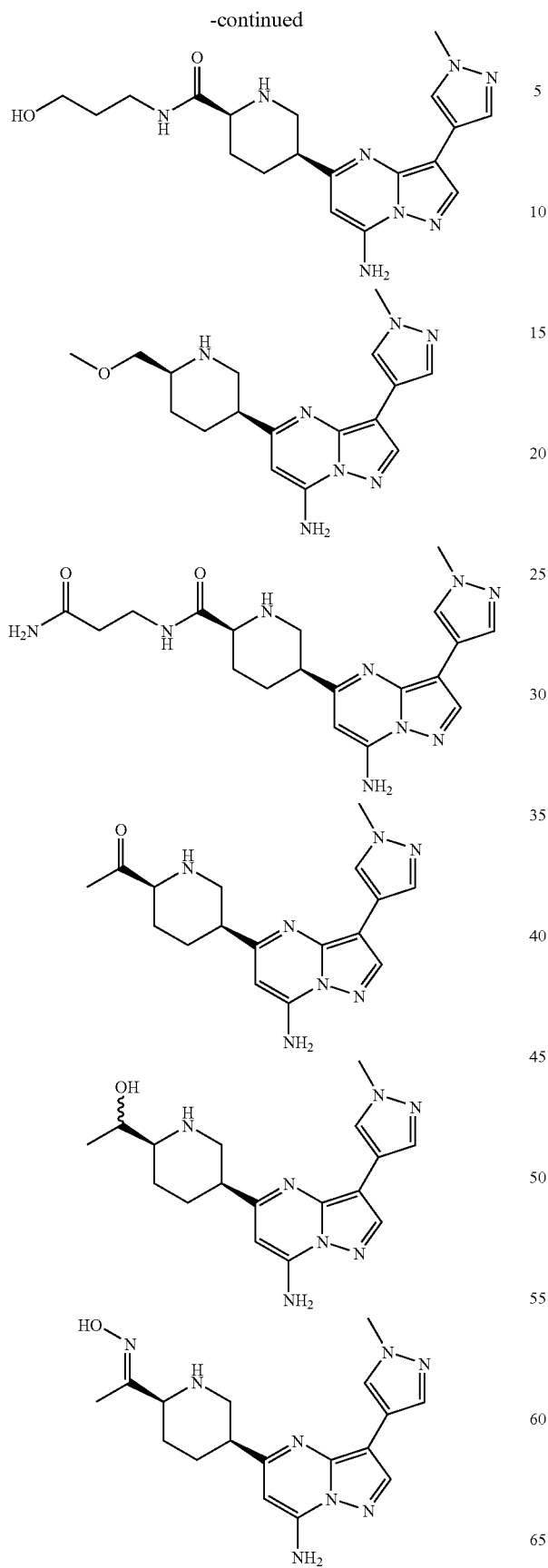
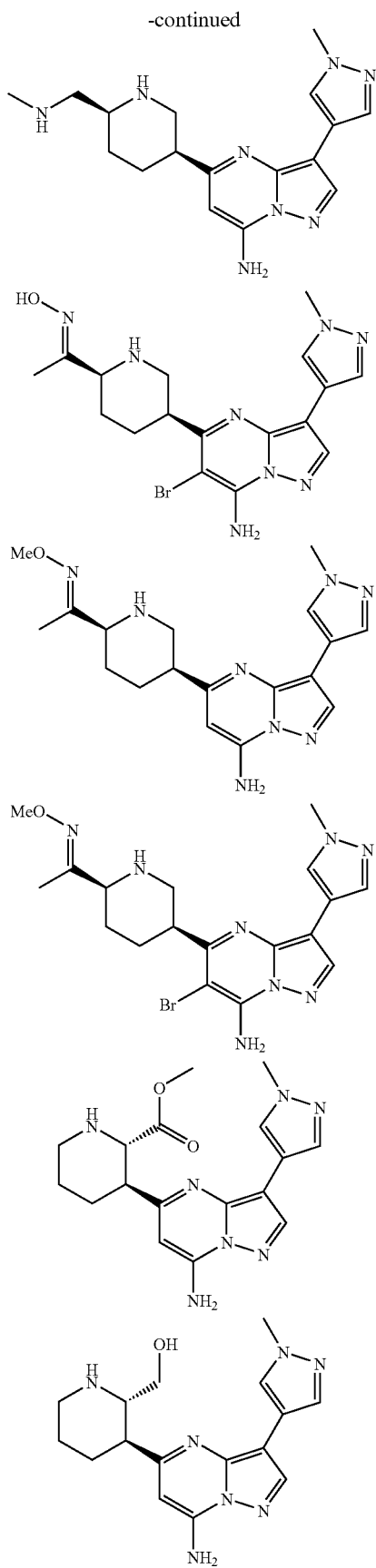

-continued
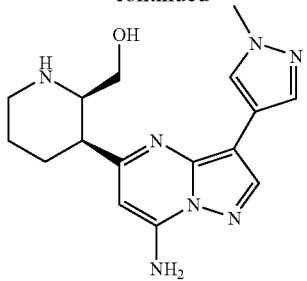
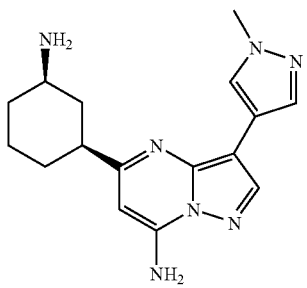
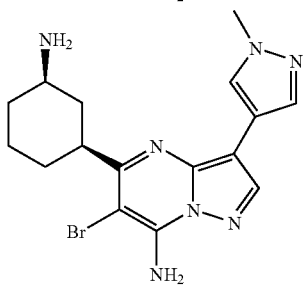
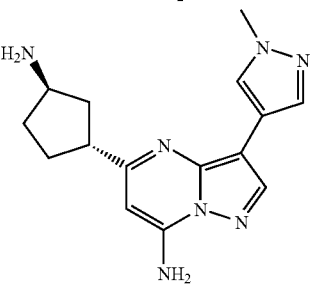
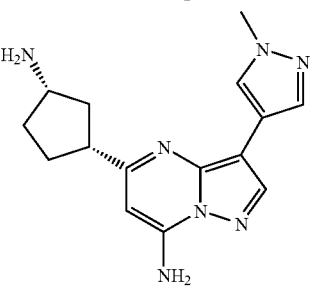
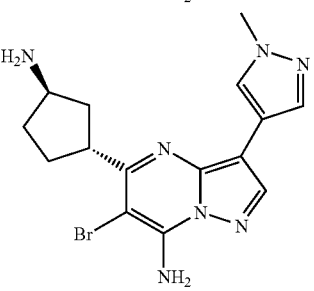
-continued
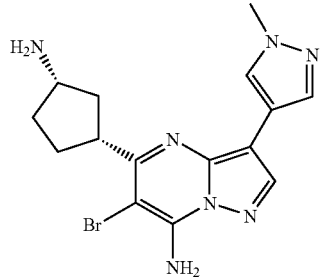
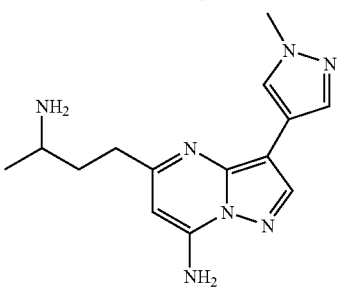
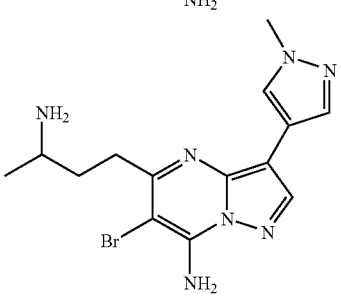
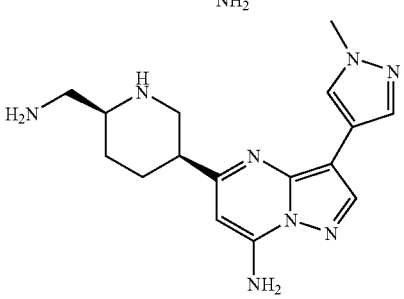
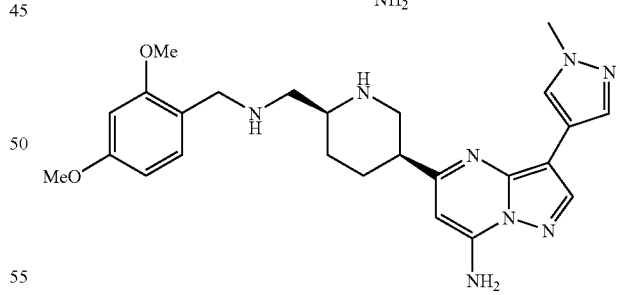
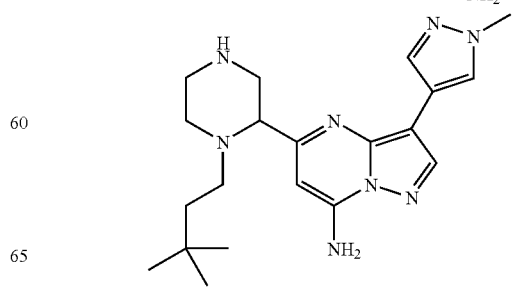

265
-continued
266
-continued
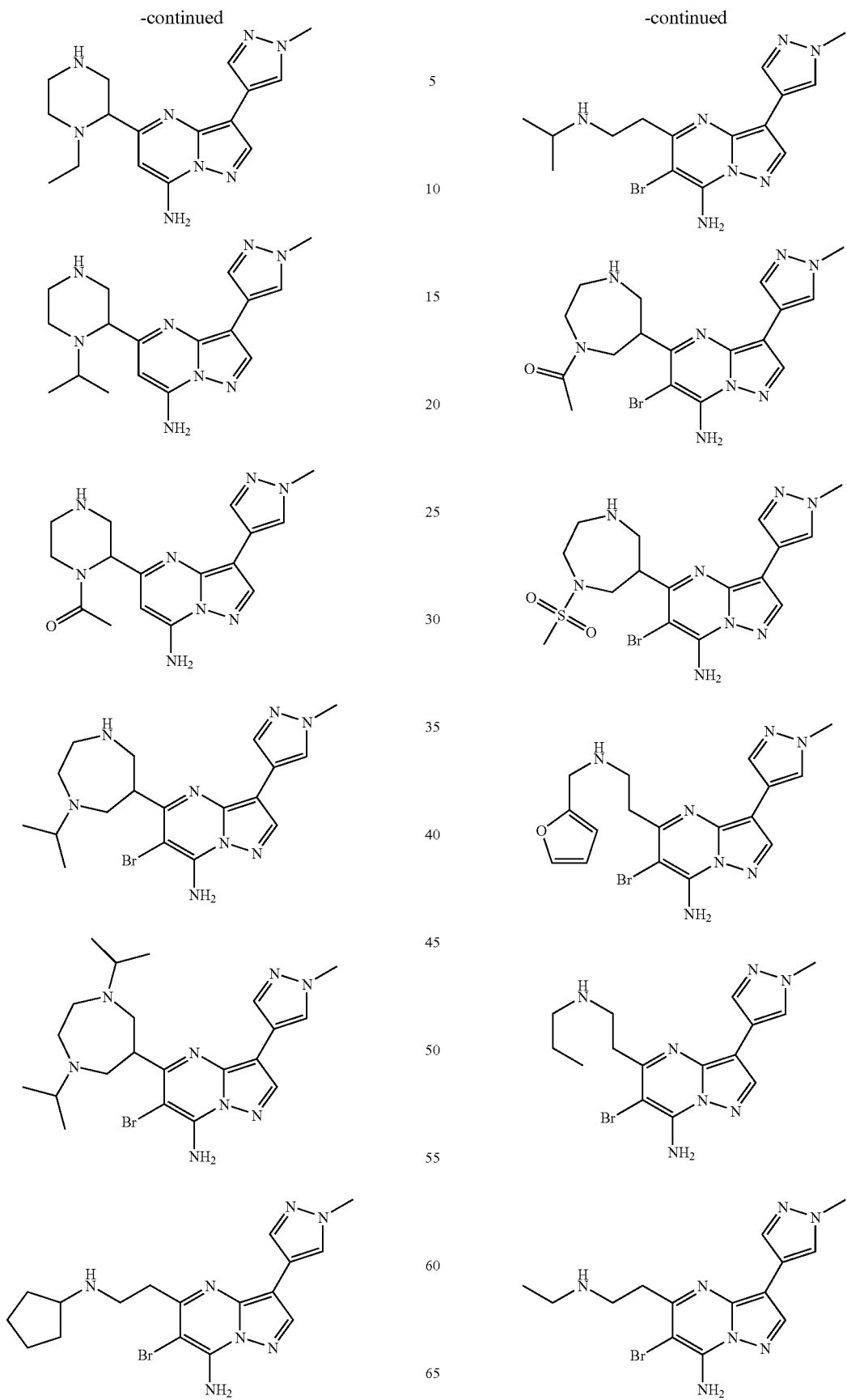

-continued

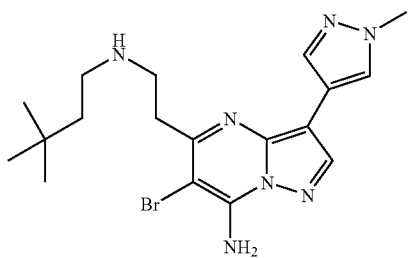

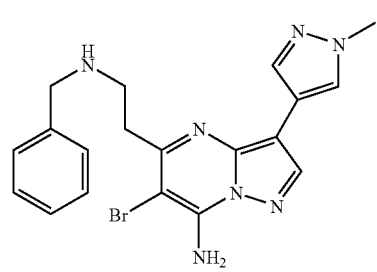

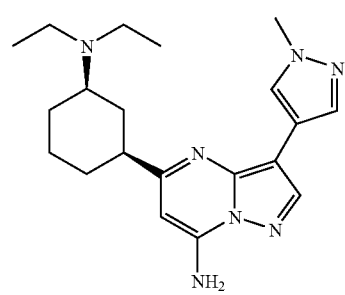

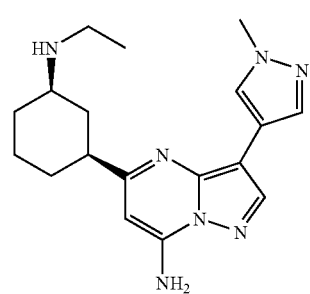

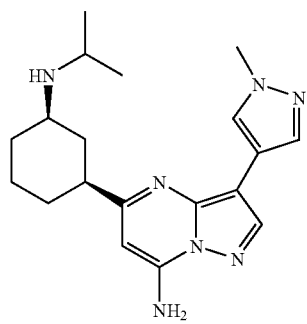

-continued

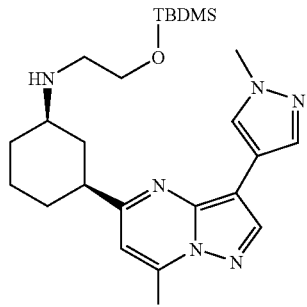

and

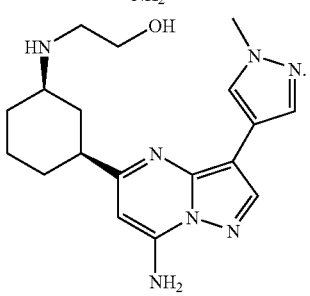

or a pharmaceutically acceptable salt, solvate, ester or prodrug thereof.

2. A pharmaceutical composition comprising a therapeutically effective amount of at least one compound of claim 1, or a pharmaceutically acceptable salt thereof, in combination with at least one pharmaceutically acceptable carrier.

3. A compound of the formula:

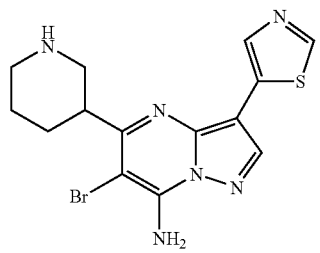

or a pharmaceutically acceptable salt thereof.

4. A compound of the formula:

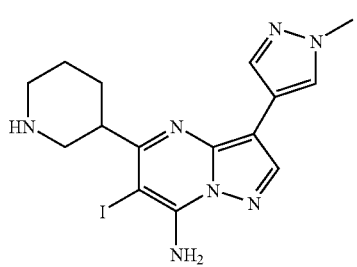

or a pharmaceutically acceptable salt thereof.

5. A compound of the formula:

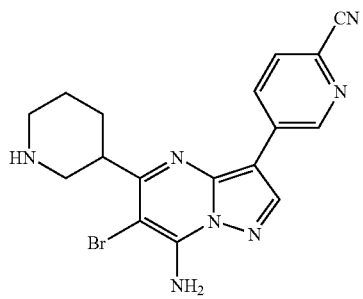

or a pharmaceutically acceptable salt thereof.

6. A compound of the formula:

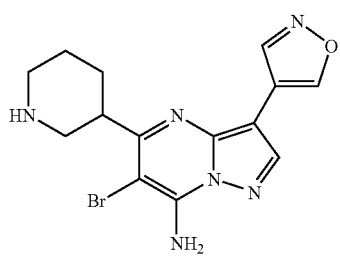

or a pharmaceutically acceptable salt thereof.

7. A compound of the formula:

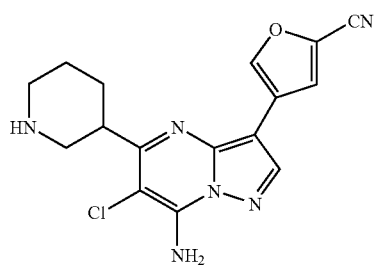

or a pharmaceutically acceptable salt thereof.

8. A compound of the formula:

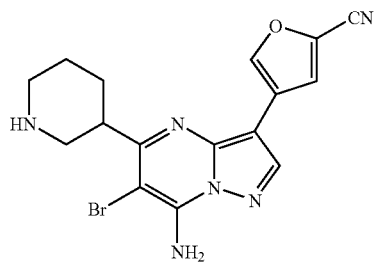

or a pharmaceutically acceptable salt thereof.

9. A compound of the formula:

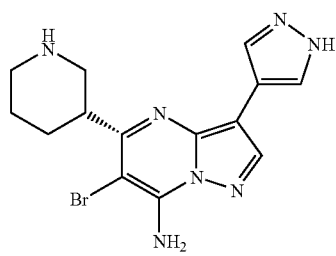

or a pharmaceutically acceptable salt thereof.

10. A compound of the formula:

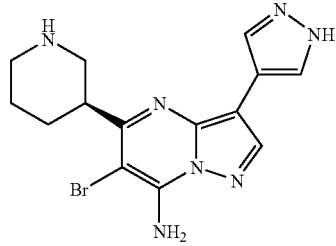

or a pharmaceutically acceptable salt thereof.

11. A compound of the formula:

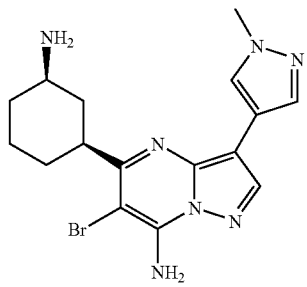

or a pharmaceutically acceptable salt thereof.

12. A compound of the formula:
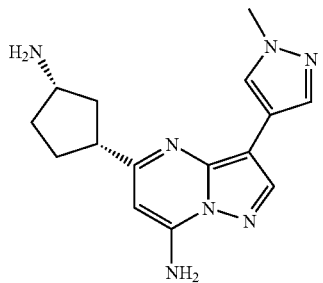
or a pharmaceutically acceptable salt thereof.
13. A compound of the formula:
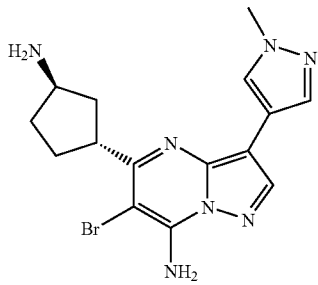
or a pharmaceutically acceptable salt thereof.
14. A compound of claim 1 in purified and isolated form.
* * * * *